(12) United States Patent
Li et al.

(10) Patent No.: US 10,294,474 B2
(45) Date of Patent: May 21, 2019

(54) TARGETING LIGANDS

(71) Applicant: Arrowhead Pharmaceuticals, Inc., Pasadena, CA (US)

(72) Inventors: Zhen Li, Monona, WI (US); Tao Pei, Middleton, WI (US); Agnieszka Glebocka, Madison, WI (US); Michael Lawler, Mequon, WI (US); Fred Fleitz, Germantown, WI (US); Erich Altenhofer, Madison, WI (US); Pankaj Kumar, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 15/452,324

(22) Filed: Mar. 7, 2017

(65) Prior Publication Data

US 2018/0064819 A1  Mar. 8, 2018

Related U.S. Application Data

(60) Provisional application No. 62/456,339, filed on Feb. 8, 2017, provisional application No. 62/383,221, filed on Sep. 2, 2016.

(51) Int. Cl.
| | |
|---|---|
| *A61K 31/7008* | (2006.01) |
| *C12N 15/113* | (2010.01) |
| *A61K 31/711* | (2006.01) |
| *C07H 21/02* | (2006.01) |
| *A61K 31/7105* | (2006.01) |
| *C07H 5/06* | (2006.01) |
| *C07H 21/04* | (2006.01) |
| *A61K 31/713* | (2006.01) |
| *A61K 47/54* | (2017.01) |

(52) U.S. Cl.
CPC ........ *C12N 15/113* (2013.01); *A61K 31/7008* (2013.01); *A61K 31/711* (2013.01); *A61K 31/713* (2013.01); *A61K 31/7105* (2013.01); *A61K 47/549* (2017.08); *C07H 5/06* (2013.01); *C07H 21/02* (2013.01); *C07H 21/04* (2013.01); *C12N 2310/14* (2013.01); *C12N 2310/31* (2013.01); *C12N 2310/315* (2013.01); *C12N 2310/317* (2013.01); *C12N 2310/321* (2013.01); *C12N 2310/322* (2013.01); *C12N 2310/332* (2013.01); *C12N 2310/3515* (2013.01); *C12N 2310/3517* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,469,863 | A | 9/1984 | Ts'o et al. |
| 4,751,219 | A | 6/1988 | Kempen |
| 5,885,968 | A | 3/1999 | Biessen et al. |
| 5,994,517 | A | 11/1999 | Ts'o et al. |
| 5,998,203 | A | 12/1999 | Matulic-Adamic |
| 6,300,319 | B1 | 10/2001 | Manoharan |
| 6,383,812 | B1 | 5/2002 | Chen et al. |
| 6,525,031 | B2 | 2/2003 | Manoharan |
| 6,620,916 | B1 | 9/2003 | Takahara et al. |
| 6,660,720 | B2 | 12/2003 | Manoharan et al. |
| 6,906,182 | B2 | 6/2005 | Ts'o et al. |
| 6,908,903 | B1 | 6/2005 | Theodore et al. |
| 7,109,165 | B2 | 9/2006 | Matulic-Adamic et al. |
| 7,262,177 | B2 | 8/2007 | Ts'o et al. |
| 7,439,043 | B2 | 10/2008 | DeFrees et al. |
| 7,491,805 | B2 | 2/2009 | Vargeese et al. |
| 7,582,744 | B2 | 9/2009 | Manoharan et al. |
| 7,723,509 | B2 | 5/2010 | Manoharan et al. |
| 7,833,992 | B2 | 11/2010 | Vargeese et al. |
| 7,851,615 | B2 | 12/2010 | Manoharan et al. |
| 7,964,578 | B2 | 6/2011 | Vargeese et al. |

(Continued)

FOREIGN PATENT DOCUMENTS

| | | |
|---|---|---|
| WO | 1997020563 A1 | 6/1997 |
| WO | 1997046098 A1 | 12/1997 |

(Continued)

OTHER PUBLICATIONS

Chen et al., "Synthesis of Antisense Oligonucleotide-Peptide Conjugate Targeting to GLUT-1 in HepG-2 and MCF-7 Cells" Bioconjugate Chemistry (2002) vol. 13 pp. 525-529 (Year: 2002).*

(Continued)

*Primary Examiner* — Eric Olson
(74) *Attorney, Agent, or Firm* — Fish & Richardson P.C.

(57) ABSTRACT

Described are novel targeting ligands that may be linked to compounds, such therapeutic compounds that are useful in directing the compounds to the in vivo target. The targeting ligands disclosed herein can serve to target expression-inhibiting oligomeric compounds, such as RNAi agents, to liver cells to modulate gene expression. The targeting ligands disclosed herein, when conjugated to a therapeutic compound, may be used in a variety of applications, including use in therapeutic, diagnostic, target validation, and genomic discovery applications. Compositions including the targeting ligands disclosed herein when linked to expression-inhibiting oligomeric compounds are capable of mediating expression of target nucleic acid sequences in liver cells, such as hepatocytes, which may be useful in the treatment of diseases or conditions that respond to inhibition of gene expression or activity in a cell, tissue, or organism.

50 Claims, 23 Drawing Sheets

Specification includes a Sequence Listing.

(56) References Cited

U.S. PATENT DOCUMENTS

| | | |
|---|---|---|
| 8,106,022 B2 | 1/2012 | Manoharan et al. |
| 8,137,695 B2 | 3/2012 | Rozema et al. |
| 8,158,601 B2 | 4/2012 | Chen et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,426,377 B2 | 4/2013 | Manoharan et al. |
| 8,435,491 B2 | 5/2013 | Wang et al. |
| 8,450,467 B2 | 5/2013 | Manoharan et al. |
| 8,501,930 B2 | 8/2013 | Rozema et al. |
| 8,541,548 B2 | 9/2013 | Rozema |
| 8,552,163 B2 | 10/2013 | Lee et al. |
| 8,828,956 B2 | 9/2014 | Manoharan et al. |
| 8,877,917 B2 | 11/2014 | Forst et al. |
| 9,127,276 B2 | 9/2015 | Prakash et al. |
| 9,181,549 B2 | 11/2015 | Prakash et al. |
| 9,290,760 B2 | 3/2016 | Rajeev et al. |
| 9,309,513 B2 | 4/2016 | Bhat et al. |
| 9,352,048 B2 | 5/2016 | Manoharan et al. |
| 9,540,639 B2 | 1/2017 | Tellers et al. |
| 2002/0086356 A1 | 7/2002 | Tuschl et al. |
| 2003/0119724 A1 | 6/2003 | Ts'o et al. |
| 2003/0143732 A1 | 7/2003 | Fosnaugh et al. |
| 2003/0148928 A1 | 8/2003 | Beigelman et al. |
| 2004/0110296 A1 | 6/2004 | Vargeese et al. |
| 2004/0259247 A1 | 12/2004 | Tuschl et al. |
| 2005/0164235 A1 | 7/2005 | Manoharan et al. |
| 2006/0148740 A1 | 7/2006 | Platenburg |
| 2006/0183886 A1 | 8/2006 | Tso et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203135 A1 | 8/2009 | Forst et al. |
| 2009/0239814 A1 | 9/2009 | Manoharan et al. |
| 2009/0286973 A1 | 11/2009 | Manoharan et al. |
| 2010/0240730 A1 | 9/2010 | Beigelman et al. |
| 2011/0077386 A1 | 3/2011 | Lee et al. |
| 2011/0097264 A1 | 4/2011 | Wang et al. |
| 2011/0123520 A1 | 5/2011 | Manoharan et al. |
| 2011/0201798 A1 | 8/2011 | Manoharan |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0183602 A1 | 7/2012 | Chen et al. |
| 2012/0225927 A1 | 9/2012 | Sah et al. |
| 2012/0230938 A1 | 9/2012 | Rozema et al. |
| 2013/0004427 A1 | 1/2013 | El-sayed et al. |
| 2013/0035366 A1 | 2/2013 | Swayze et al. |
| 2013/0121954 A1 | 5/2013 | Wakefield et al. |
| 2013/0178512 A1 | 9/2013 | Manoharan et al. |
| 2013/0236968 A1 | 9/2013 | Manoharan et al. |
| 2015/0018540 A1 | 1/2015 | Prakash et al. |
| 2015/0065558 A1 | 3/2015 | Forst et al. |
| 2015/0246133 A1 | 9/2015 | Tellers et al. |
| 2015/0361427 A1 | 12/2015 | Wooddell et al. |
| 2015/0368642 A1 | 12/2015 | Albaek et al. |
| 2016/0017323 A1 | 1/2016 | Prakash et al. |
| 2017/0035796 A1 | 2/2017 | Wooddell et al. |

FOREIGN PATENT DOCUMENTS

| | | |
|---|---|---|
| WO | 1999065925 A1 | 12/1999 |
| WO | 2002043771 A2 | 6/2002 |
| WO | 2002085908 A1 | 10/2002 |
| WO | 2002094185 A2 | 11/2002 |
| WO | 2004024757 A2 | 3/2004 |
| WO | 2004080406 A2 | 9/2004 |
| WO | 2004090108 A2 | 10/2004 |
| WO | 2004094595 A2 | 11/2004 |
| WO | 2004101619 A1 | 11/2004 |
| WO | 2006020768 A2 | 2/2006 |
| WO | 2006031461 A2 | 3/2006 |
| WO | 2008098788 A2 | 8/2008 |
| WO | 2009073809 A2 | 6/2009 |
| WO | 2009082606 A2 | 7/2009 |
| WO | 2009126933 A2 | 10/2009 |
| WO | 2009134487 A2 | 11/2009 |
| WO | 2010048585 A2 | 4/2010 |
| WO | 2011038356 A2 | 3/2011 |
| WO | 2012037254 A1 | 3/2012 |
| WO | 2012083046 A2 | 6/2012 |
| WO | 2012083185 A2 | 6/2012 |
| WO | 2012089352 A1 | 7/2012 |
| WO | 2012089602 A1 | 7/2012 |
| WO | 2013033230 A1 | 3/2013 |
| WO | 2013165816 A2 | 11/2013 |
| WO | 2013166121 A1 | 11/2013 |
| WO | 2014025805 A1 | 2/2014 |
| WO | 2014076195 A1 | 5/2014 |
| WO | 2014076196 A1 | 5/2014 |
| WO | 2014118267 A1 | 8/2014 |
| WO | 2014118272 A1 | 8/2014 |
| WO | 2014179620 A1 | 11/2014 |
| WO | 2014179627 A2 | 11/2014 |
| WO | 2014179629 A2 | 11/2014 |
| WO | 2015006740 A2 | 1/2015 |
| WO | 2015069587 A2 | 5/2015 |
| WO | 2015168618 A2 | 11/2015 |
| WO | 2015188194 A1 | 12/2015 |
| WO | 2016055601 A1 | 4/2016 |

OTHER PUBLICATIONS

Riedi et al., "Targeting the Eph System with Peptides and Peptide Conjugates" Current Drug Targets (2015) vol. 16 No. 10, pp. 10-31-1047 (Year: 2015).*

Ming et al., "Bioconjugates for Targeted Delivery of Therapeutic Oligonucleotides" Advanced Drug Delivey Review (2015) vol. 87 pp. 81-89 (Year: 2015).*

Zhu et al., "Aptamer-Drug Conjugates" Bioconjugate Chemistry (2015) vol. 26 No. 11 pp. 2186-2197 (Year: 2015).*

Vaino et al.; "synthesis of a D-Lactosyl Cluster-Nucleoside Conjugate"; Chem. Commun.; 19:1871-72; (1997).

Valentijn et al., "Solid-phase Synthesis of Lysine-based Cluster Galactosides with High Affinity for the Asialoglycoprotein Receptor" Tetrahedron; 53(2): 759-770; (1997).

Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal; 21: 227-241; (2004).

Wu et al., "A New N-Acetylgalactosamine Containing Peptide as a Targeting Vehicle for Mammalian Hepatocytes Via Asialoglycoprotein Receptor Endocytosis" Current Drug Delivery; 1: 119-127; (2004).

Zatsepin et al.; "Synthesis and Applications of Oligonucleotide-Carbohydrate Conjugates"; Chem. Biodivers; 1(10):1401-17; (2004).

Zhang, Xiao-Ru; Jia, Ji-Long; Zhang, Rong-Jun; Xu, Min-Hua; Zhang, Shu-Sheng; Design of multivalent galactoside ligands and their binding to hepatic asialoglycoprotein receptor; Chinese Journal of Chemistry; 24(8), 1058-1061; (2006).

Zheng et al.; "Distribution and Anti-HBV Effects of Antisense Oligodeoxynucleotides Conjugated to Galactosylated Poly-L-Lysine"; World J. Gastroentero 9(6):1251-55; (2003).

International Search Report and Written Opinion for corresponding International Application No. PCT/US17/21147 dated Jun. 1, 2017.

International Search Report and Written Opinion for corresponding International Application No. PCT/US17/21175 dated Jun. 1, 2017.

Akinc et al.; "Targeted Delivery of RNAi Therapeutics with Endogenous and Exogenous Ligand-Based Mechanisms"; Molecular Therapy; 18(7)1357-1364; (2010).

Alnylam; RNAi Roundtable: Advances in Delivery of RNAi Therapeutics with Enhanced Stabilization Chemistry (ESC)-GalNAc-siRNA Conjugates; (Jul. 22, 2014).

(56) References Cited

OTHER PUBLICATIONS

Andre et al.; "Determination of modulation of ligand properties of synthetic complex-type biantennary N-glycans by introduction of bisecting GlcNAc in silico, in vitro and in vivo"; Cur. J. Biochem.; 271:118-134; (2004).

Biessen et al. "Synthesis of Cluster Galactosides with High Affinity for the Hepatic Asialoglycoprotein Receptor" Journal of Medicinal Chemistry; 38(9): 1538-1546; (1995).

Biessen et al.; "The Cholesterol Derivative of a Triantennary Galactoside with High Affinity for Hepatic Asialoglycoprotein Receptor: A Potent Cholesterol Lowering Agent"; J. Med. Chem; 38(11):1846-52; (1995).

Chiu et al.; "RNAi in Human Cells: Basic Structural and Functional Features of Small Interfering RNA"; Mol. Cell; 10:549-61; (2002).

Coltart et al.; "Principles of Mucin Architecture: Structural Studies on Synthetic Glycopeptides Bearing Clustered Mono-, Di-, Tri-, and Hexasaccharide Glycodomains"; J. Am. Chem. Soc.; 124: 9833-9844; (2002).

Connolly et al.; "Binding and Endocytosis of Cluster Glycosides by Rabbit Hepatocytes"; J. Biol. Chem; 257 (2):939-45; (1982).

Crossman et al.; "Synthesis of Some Second-Generation Substrate Analogues of Early Intermediates in the Biosynthetic Pathway of Glycosylphatidylinositol Membrane Anchors"; Carbohyd. Res.; 321(1-2):42-51; (1999).

Dubber et al.; "Solid-Phase Synthesis of Multivalent Glycoconjugates on a DNA Synthesizer"; Bioconjugate Chem.; 14(1):239-46; (2003).

Elbashir et al.; Duplexes of 21-nucleotide RNAs mediate RNA interference in cultured mammalian cells; Nature; 411: 494-498; (2001).

Englisch et al., "Chemically Modified Oligonucleotides as Probes and Inhibitors" Agnew Chem. Int. Ed. Engl.; 30:613-629; (1991).

Guo et al.; "Construction of Folate-Conjugated pRNA Of Bateriophase phi29 DNA Packaging Motor for Delivery of Chimeric siRNA to Nasopharyngeal Carcinoma Cells"; Gene Ther.; 13(10):814-20; (2006).

Hamzavi et al.; "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers"; Bioconjugate Chem.; 14:941-54; (2003).

Ikeda et al.; "Ligand-Targeted Delivery of Therapeutic siRNA"; Pharm. Res.; 23(8):1631-40; (2006).

Iobst ST et al.; "Selective Sugar Binding to the Carbohydrate Recognition Domains of the Rat Hepatic and Macrophage Asialoglycoprotein Receptors." Journal of Biological Chemistry; 271(12), p. 6686-6693; (1996).

Jayaprakash et al., "Non-Nucleoside Building Blocks for Copper-Assisted and Copper-Free Click Chemistry for the Efficient Synthesis of RNA Conjugates" Organic Letters; 12(23): 5410-5413; (2010).

Kanasty et al., "Delivery Materials for siRNA Therapeutics" Nature Materials; 12: 967-977; (2013).

Karskela et al.; "Synthesis and Cellular Uptake of Fluorescently Labeled Multivalent Hyaluronan Disaccharide Conjugates of Oligonucleotide Phosphorothioates"; Bioconjugate Chem.; 19(12): 2549-58 (2008).

Katajisto et al.; "Solid-Phase Synthesis of Oligonucleotide Glycoconjugates Bearing Three Different Glycosyl Groups: Orthogonally Protected Bis (Hydroxymethyl)-N, N'-bis(3-Hydroxypropyl)malondiamide Phosphoramidite as Key Building Block"; J. Org. Chem; 69(22):7609-15; (2004).

Katajisto et al.; "Solid-Phase Synthesis of Multiantennary Oligonucleotide Glycoconjugates Utilizing On-Support Oximation"; Bioconjugate Chem.; 15(4):890-96; (2004).

Kato et al., "N-acetylgalactosamine incorporation into a peptide containing consecutive threonine residues by UDP-N-acetyl-D-galactosaminide:polypeptide N-acetylgalactosaminyltransferases" Glyobiology: 11: 821-829; (2001).

Khorev et al., "Trivalent, Gal/GalNAc-containing ligands designed for the asialoglycoprotein receptor" Bioorganic & Medicinal Chemistry; 16: 5216-5231; (2008).

Kornilova et al., "Development of a fluorescence polarization binding assay for asialoglycoprotein receptor" Analytical Biochemistry; 425: 43-46; (2012).

Lee et al., "Facile Synthesis of a High-Affinity Ligand for Mammalian Hepatic Lectin Containing Three Terminal N-Acetylgalactosamine Residues" Bioconjugate Chem.; 8: 762-765; (1997).

Lee et al., "New and more efficient multivalent glyco-ligands for asialoglycoprotein receptor of mammalian hepatocytes" Bioorganic & Medicinal Chemistry; 19:2494-2500; (2011).

Lee et al., "Preparation of Cluster Glycosides of N-acetylgalactosamine That Have Subnanomolar Binding Constants Towards the Mammalian Hepatic Gal/GalNAc-specific Receptor" Glycoconjugate J.; 4: 317-328; (1987).

Lee et al., "Synthesis of Peptide-Based Trivalent Scaffold for Preparation of Cluster Glycosides" Methods in Enzymology; 362: 38-43; (2003).

Lee et al., "New synthetic cluster ligands for galactose/N-acetylgalactosamine-specific lectin of mammalian liver" Biochem; 23: 4255-4261; (1984).

Lee et al., "Protein microarrays to study carbohydrate-recognition events" Bioorg Med Chem Lett; 16(19): 5132-5135; (2006).

Lee et al., "Synthesis of multivalent neoglyconjugates of MUC1 by the conjugation of carbohydratecentered, triazole-linked glycoclusters to MUC1 peptides using click chemistry." J Org Chem; 77:7564-7571; (2012).

Liang et al., "Hepatitis Be Antigen—The Dangerous Endgame of Hepatitis B" N Engl J Med.; 347: 208-210; (2002).

Liu et al.; "Targeted Drug Deligery to Chemoresistant Cells: Folic Acid Derivatization of FdUMP [10] Enhances Cytotoxicity Toward 5-FU-Resistant Human Colorector Tumor Cells"; J. Org. Chem.; 66(17):5655-63; (2001).

Maier et al.; "Synthesis of Antisense Oligonucleotides Conjugated to a Multivalent Carbohydrate Cluster for Celluarl Targeting"; Bioconjugate Chem.; 14:18-29; (2003).

Maierhofer et al., "Probing multivalent carbohydrate-lectin interactions by an enzyme-linked lectin assay employing covalently immobilized carbohydrates" Bioorganic & Medicinal Chemistry; 15: 7661-7676; (2007).

Manoharan et al., "Cholic Acid-Oligonucleotide Conjugates for Antisense Applications" Bioorg. Med. Chem. Lett.; 4:1053-1060; (1994).

Manoharan et al., "Introduction of a Lipophilic Tbioether Tether in the Minor Groove of Nucleic Acids for Antisense Applications" Bioorg. Med. Chem. Lett.; 3(12):2765-2770; (1993).

Manoharan et al., "Lipidic Nucleic Acids" Tetrahedron Lett.; 36(21):3651-3654; (1995).

Manoharan et al., "Oligonucleotide Conjugates: Alteration of the Pharmacokinetic Properties of Antisense Agents" Nucleosides & Nucleotides;14(3-5):969-973; (1995).

Manoharan, "Oligonucleotide Conjugates as Potential Antisense Drugs with Improved Uptake, Biodistribution, Targeted Delivery, and Mechanism of Action" Antisense & Nucleic Acid Drug Development; 12: 103-128; (2002).

Merwin et al., "Targeted delivery of DNA using YEE(GalNAcAH)3, a synthetic glycopeptide ligand for the asialoglycoprotein receptor" Bioconjug Chem; 5(6): 612-620; (1994).

Murata et al.; "Design of Quaternary Chitosan Conjugate Having Antennary Galactose Residues as a Gene Delivery Tool"; Carbohyd. Polym.; 32(2):105-9; (1997).

Park et al., "The asialoglycoprotein receptor clears glycoconjugates terminating with sialic acid α2,6GalNAc" PNAS; 102(47): 17125-17129; (2005).

Pujol et al., "A Sulfur Tripod Glycoconjugate that Releases a High-Affinity Copper Chelator in Hepatocytes" Angew. Chem. Int. Ed.; 51: 7445-7448; (2012).

Rajur et al., "Covalent Protein-Oligonucleotide Conjugates for Efficient Delivery of Antisense Molecules" Bioconjugate Chem.; 8: 935-940; (1997).

(56) References Cited

OTHER PUBLICATIONS

Rensen et al.; "Design and Synthesis of Novel N-Acetylgalactosamine-Terminated Glycolipids for Targeting of Lipoproteins to the Hepatic Asialoglycoprotein Receptor"; J. Med. Chem.; 47(23):5798-5808; (2004).
Rensen et al., "Determination of the Upper Size Limit for Uptake and Processing of Ligands by the Asialoglycoprotein Receptor on Hepatocytes in Vitro and in Vivo" J. Biol. Chem.; 276(40):37577-37584; (2001).
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vase Biol; 26: 169-175; (2006).
Sliedregt et al; "Design and Synthesis of Novel Amphiphilic Dendritic Galactosides for Selective Targeting of Liposomes to the Hepatic Asialoglycoprotein Receptor"; J. Med. Chem.; 42(4):609-18; (1999).
Tober et al., "Self-Metathesis of Polyol Allyl Ethers towards Carbohydrate-Based Oligohydroxy Derivatives" Eur. J. Org. Chem.; 3: 566-577; (2013).

\* cited by examiner

TARGETING LIGANDS

CROSS REFERENCE TO RELATED APPLICATIONS

This application claims priority from U.S. Provisional Patent Application Ser. No. 62/383,221, filed on Sep. 2, 2016, and U.S. Provisional Patent Application Ser. No. 62/456,339, filed on Feb. 8, 2017, the contents of each of which are incorporated herein by reference in their entirety.

BACKGROUND

Many compounds need to be delivered to a specific location (for example, to desired cell(s)) to have a therapeutic effect or to be useful for diagnostic purposes. This is frequently the case when attempting to deliver a therapeutic compound in vivo. Further, being able to efficiently deliver a compound to a specific location can limit or potentially eliminate unintended consequences (such as off-target effects) that may be caused by administration of the compound. One method to facilitate delivery of a compound, such as a therapeutic compound, to a desired location in vivo, is by linking or attaching the compound to a targeting ligand.

One class of therapeutic compounds that can be targeted using targeting ligands are oligomeric compounds. Oligomeric compounds that include nucleotide sequences at least partially complementary to a target nucleic acid have been shown to alter the function and activity of the target both in vitro and in vivo. When delivered to a cell containing a target nucleic acid (such as mRNA), oligomeric compounds have been shown to modulate the expression of the target resulting in altered transcription or translation of the target nucleic acid. In certain instances, the oligomeric compound can reduce the expression of the gene by inhibiting the nucleic acid target and/or triggering the degradation of the target nucleic acid.

If the target nucleic acid is mRNA, one mechanism by which an expression-inhibiting oligomeric compound can modulate the expression of the mRNA target is through RNA interference. RNA interference is a biological process by which RNA or RNA-like molecules (such as chemically modified RNA molecules) are able to silence gene expression through degradation. The process of post-transcriptional gene silencing is thought to be an evolutionarily-conserved cellular defense mechanism used to prevent the expression of foreign genes.

Synthetic RNA and RNA-like molecules have been shown to elicit RNA interference in vivo. For example, Elbashir et al. (*Nature* 2000, 411, 494-98) describes RNAi induced by introduction of duplexes of synthetic 21-nucleotide RNA molecules in cultured mammalian cells. The types of synthetic RNA or RNA-like molecules that can trigger the RNAi response mechanism may be comprised of modified nucleotides and/or one or more non-phosphodiester linkages.

Additionally, single-stranded RNA and RNA-like molecules, which can also include modified nucleotides and have one or more non-phosphodiester linkages, can also alter the expression of a target nucleic acid, such as a target mRNA.

SUMMARY

Disclosed herein are targeting ligands that can enhance the delivery of therapeutic compounds to a specific target site, e.g., a specific organ or tissue, within a subject such as a human patient or animal. In some embodiments, the targeting ligands described herein can enhance the targeted delivery of expression-inhibiting oligomeric compounds. In some embodiments, the targeting ligands can enhance the delivery of expression-inhibiting oligomeric compounds to the liver.

In some embodiments, the targeting ligands disclosed herein include, consist of, or consist essentially of one or more targeting moieties, one or more tethers, one or more branch point groups, and one or more linkers. Linkers suitable for use in the targeting ligands disclosed herein include a "rigid" linker, which can impart sufficient stability and rigidity to the overall targeting ligand to reduce potential interaction between one or more of the targeting moiety(ies) and the therapeutic compound to which it is or they are linked. Additionally, the "rigid" linkers suitable for use in the targeting ligands disclosed herein are useful in efficiently synthesizing the targeting ligands as phosphoramidite compounds (also referred to herein as "phosphoramidite-containing compounds").

In some embodiments, the targeting ligands disclosed herein include, consist of, or consist essentially of one or more targeting moieties, one or more tethers, and one or more branch point groups with a linker replacement moiety. The linker replacement moiety includes, consists of, or consists essentially of, one or more substituted or unsubstituted cycloalkyl, cycloalkenyl, aryl, heteroaryl, or heterocyclyl groups, or covalently linked combinations thereof, located within the branch point group. Having a linker replacement moiety within the branch point group confers properties similar to those of the "rigid" linkers disclosed herein, by providing sufficient stability and rigidity to the overall targeting ligand. Additionally, the branch point groups with linker replacement moieties suitable for use in the targeting ligands are useful in efficiently synthesizing the targeting ligands as phosphoramidite compounds.

Disclosed herein are targeting ligands comprising, consisting of, or consisting essentially of a structure of Formula I, as shown in FIG. 22, comprising a linker, a branch point group, one or more tethers, and one or more targeting moieties, wherein n is an integer from 1 to 4 (e.g., 1, 2, 3, or 4), and wherein the linker is a structure selected from the group consisting of:

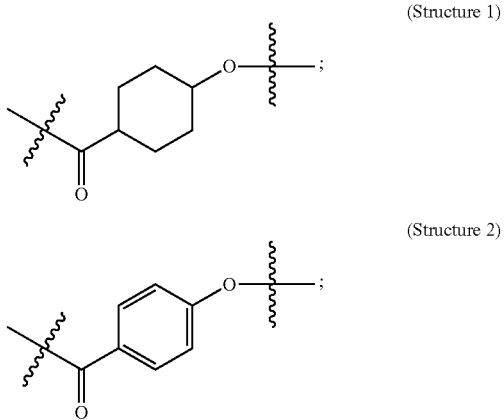

-continued (Structure 3) 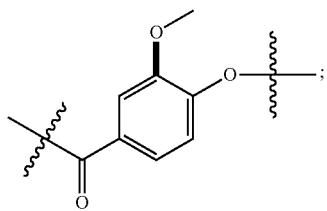

(Structure 4) 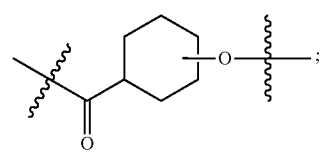

(Structure 5) 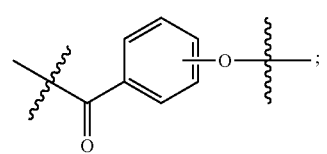

(Structure 6a) 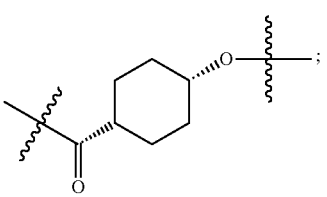

(Structure 6b) 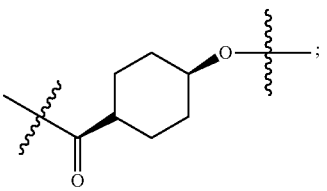

(Structure 6c) 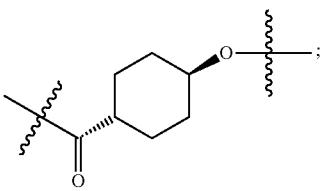

(Structure 6d) 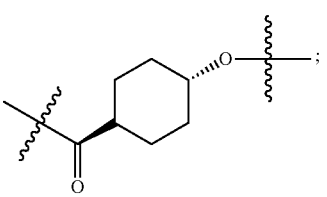

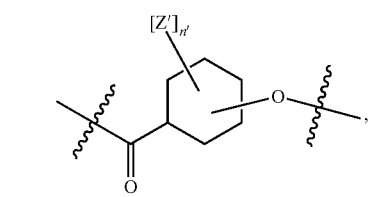

wherein n' is 0, 1, 2, 3, 4, 5, 6, 7, 8, 9, or 10, and when present, each Z' is independently selected from the group consisting of: C1-C6 alkyl, C2-C6 alkenyl, C2-C6 alkynyl, substituted or unsubstituted amino, carboxyl, C1-C6 alkoxy, substituted C1-C6 alkyl, C1-C6 aminoalkyl, substituted C2-C6 alkenyl, substituted C2-C6 alkynyl, substituted C1-C6 alkoxy, substituted C1-C6 aminoalkyl, halogen (e.g., F), hydroxyl, amido, substituted amide, cyano, substituted or unsubstituted keto, substituted or unsubstituted alkoxycarbonyl, substituted or unsubstituted aryloxycarbonyl, substituted or unsubstituted heteroaryloxycarbonyl, and sulfhydryl (Structure 7);

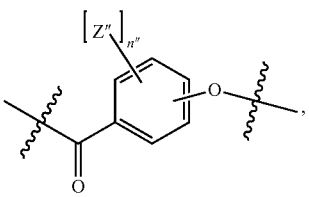

wherein n" is 0, 1, 2, 3, 4 (e.g., 1, 2, 3, or 4), and when present, each Z" is independently selected from the group consisting of: C1-C6 alkyl, C2-C6 alkenyl, C2-C6 alkynyl, C1-C6 alkoxy, substituted C1-C6 alkyl, C1-C6 aminoalkyl, substituted C2-C6 alkenyl, substituted C2-C6 alkynyl, substituted or un substituted amino, carboxyl, substituted C1-C6 alkoxy, substituted C1-C6 aminoalkyl, halogen (e.g., F), hydroxyl, amide, substituted amide, cyano, substituted or unsubstituted keto, substituted or unsubstituted alkoxycarbonyl, substituted or unsubstituted aryloxycarbonyl, substituted or unsubstituted heteroaryloxycarbonyl, and sulfhydryl (Structure 8); and

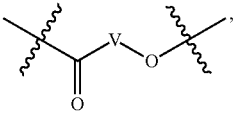

wherein V comprises one or more substituted or unsubstituted cycloalkyl (e.g., cyclohexyl, cyclopropyl, cyclobutyl, cyclopentyl, cycloheptyl, cycloocty, etc.), substituted or unsubstituted cycloalkenyl (e.g., cyclohexenyl, cyclobutenyl, cyclopentenyl, cycloheptenyl, cyclooctenyl, cyclohexadienyl, cyclopentadienyl, cycloheptadienyl, cyclooctadienyl, etc.), substituted or unsubstituted aryl (e.g., phenyl, naphthyl, binapthyl, anthracenyl, etc.), substituted or unsubstituted heteroaryl (e.g., pyridyl, pyrimidinyl, pyrrole, imidazole, furan, benzofuran, indole, etc.), or substituted or unsubstituted heterocyclyl (e.g., tetrahydrofuran, tetrahydropyran, piperidine, pyrrolidine, etc.), or any covalently linked combination thereof. (Structure 9).

In some embodiments, the targeting ligands include a branch point group with a linker replacement moiety.

Disclosed herein are targeting ligands comprising, consisting of, or consisting essentially of a structure of Formula II, as shown in FIG. 23, comprising a branch point group with linker replacement moiety, one or more tethers, and one or more targeting moieties, wherein n is an integer between 1 and 4 (e.g., 1, 2, 3, or 4), and wherein the linker replacement moiety includes one or more substituted or unsubstituted cycloalkyl (e.g., cyclohexyl, cyclopropyl, cyclobutyl, cyclopentyl, cycloheptyl, cycloocty, etc.), substituted or unsubstituted cycloalkenyl (e.g., cyclohexenyl, cyclobutenyl, cyclopentenyl, cycloheptenyl, cyclooctenyl, cyclohexadienyl, cyclopentadienyl, cycloheptadienyl, cyclooctadienyl, etc.), substituted or unsubstituted aryl (e.g., phenyl, naphthyl, binapthyl, anthracenyl, etc.), substituted or unsubstituted heteroaryl (e.g., pyridyl, pyrimidinyl, pyrrole, imidazole, furan, benzofuran, indole, etc.), or substituted or unsubstituted heterocyclyl (e.g., tetrahydrofuran, tetrahydropyran, piperidine, pyrrolidine, etc.), or any covalently linked combination thereof, is located within the branch point group.

The targeting ligands disclosed herein can be linked, directly or indirectly, to a compound, such as a therapeutic compound, e.g., an expression-inhibiting oligomeric compound, for example, to the 3' or 5' terminal end of the expression-inhibiting oligomeric compound. In some embodiments, the expression-inhibiting oligomeric compound includes one or more modified nucleotides. In some embodiments, the expression-inhibiting oligomeric compound is an RNAi agent, such as a double-stranded RNAi agent. In some embodiments, the targeting ligands disclosed herein are linked to the 5' terminal end of the sense strand of a double-stranded RNAi agent. In some embodiments, the targeting ligands disclosed herein are linked to the RNAi agent via a phosphate, phosphorothioate, or phosphonate group at the 5' terminal end of the sense strand of a double-stranded RNAi agent.

The targeting ligands disclosed herein include one or more targeting moieties. In some embodiments, the targeting ligands disclosed herein include N-acetyl-galactosamine as the targeting moiety.

In some embodiments, the targeting ligands disclosed herein have structures represented by the following:

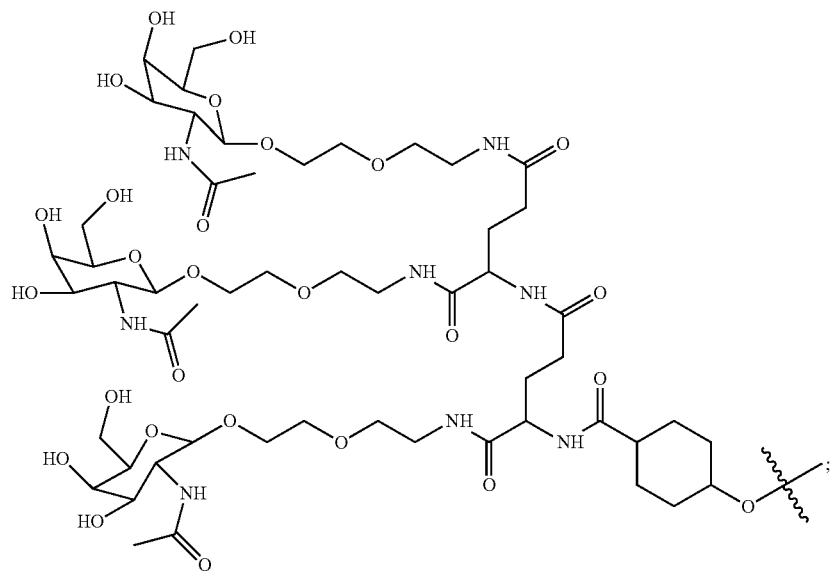

(Structure 1003)

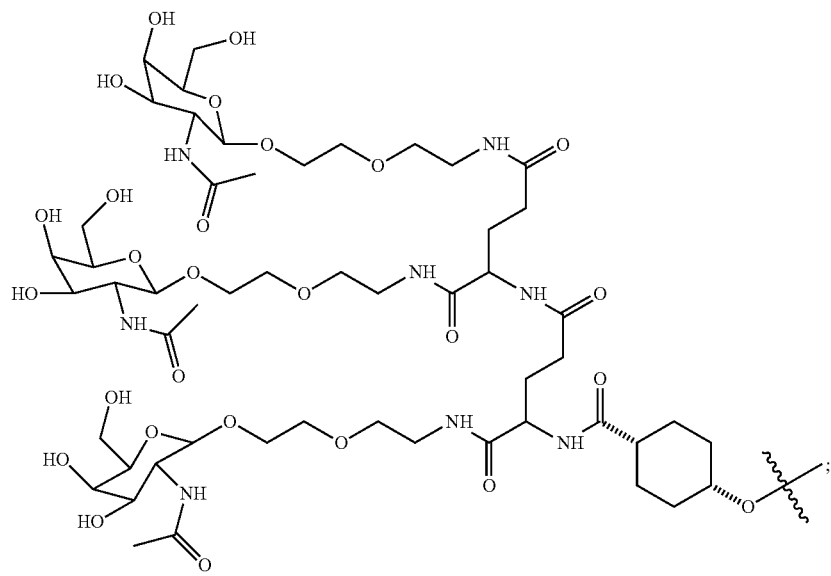

(Structure 1008)

-continued

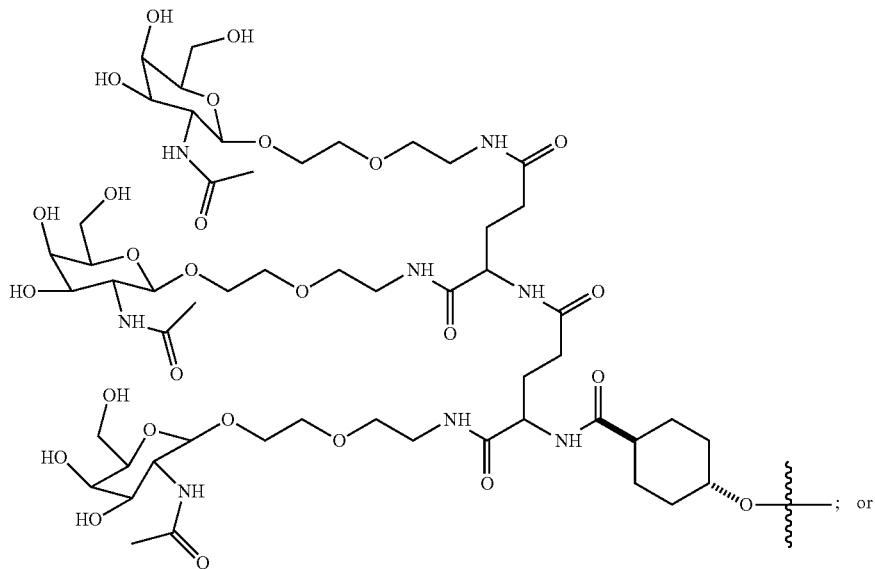

(Structure 1023)

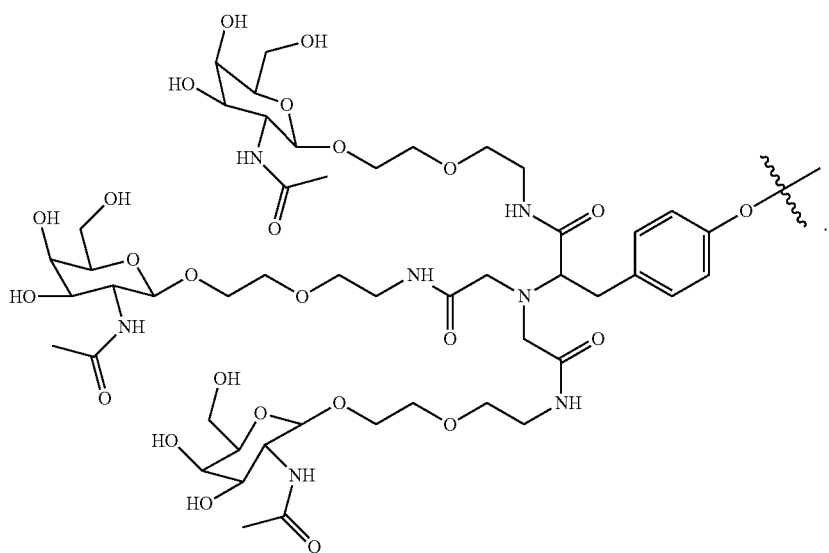

(Structure 1027)

Disclosed herein are compositions including, consisting of, or consisting essentially of, a targeting ligand and an expression-inhibiting oligomeric compound. Disclosed herein are compositions including a targeting ligand and an RNAi agent.

In some embodiments, the compositions disclosed herein including a targeting ligand and an RNAi agent have the structure represented by:

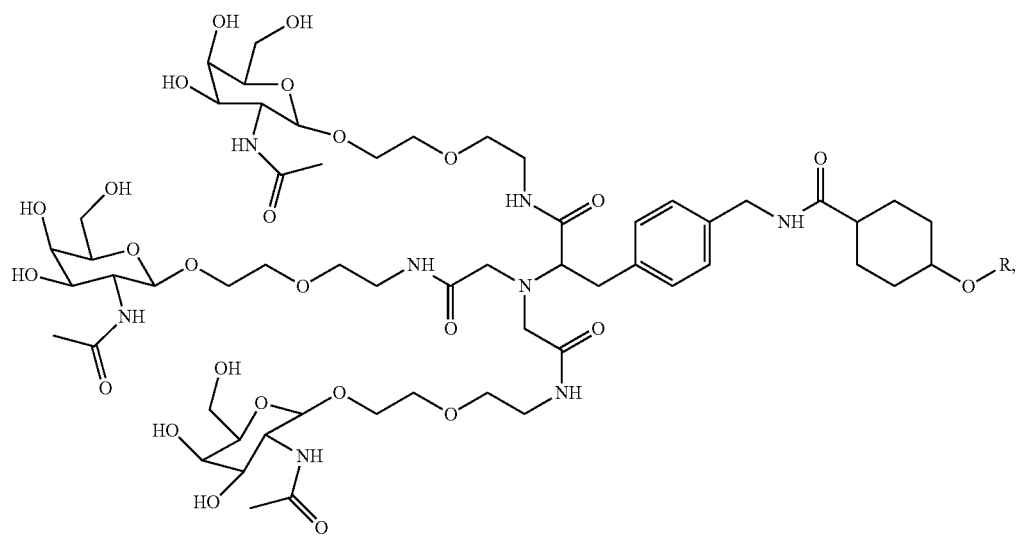
wherein R includes or consists of an expression-inhibiting oligomeric compound. (Structure 1002a);
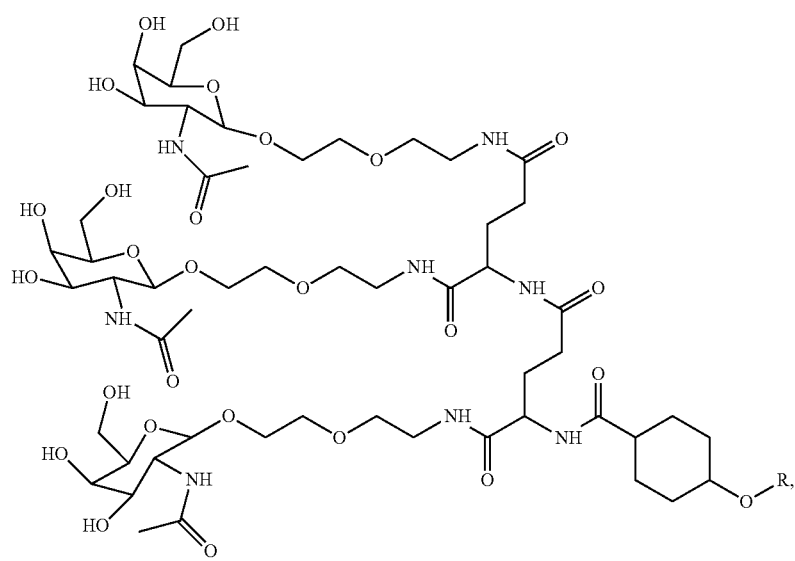
wherein R includes or consists of an expression-inhibiting oligomeric compound. (Structure 1003a);

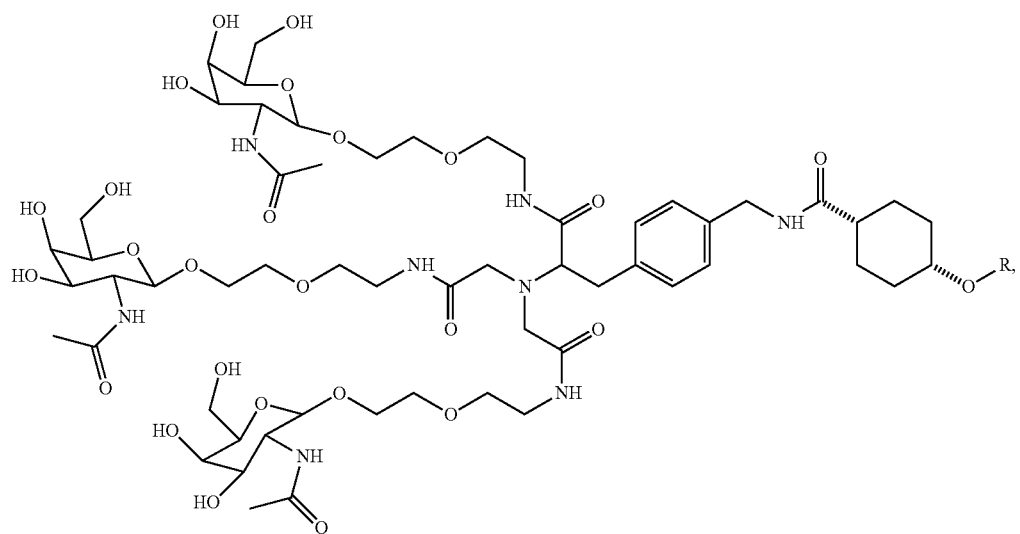
wherein R includes or consists of an expression-inhibiting oligomeric compound. (Structure 1005a);
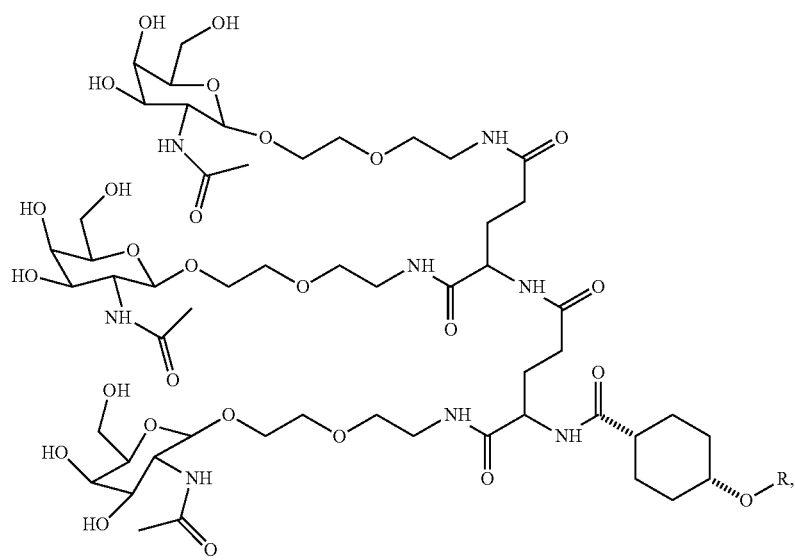
wherein R includes or consists of an expression-inhibiting oligomeric compound. (Structure 1008a);

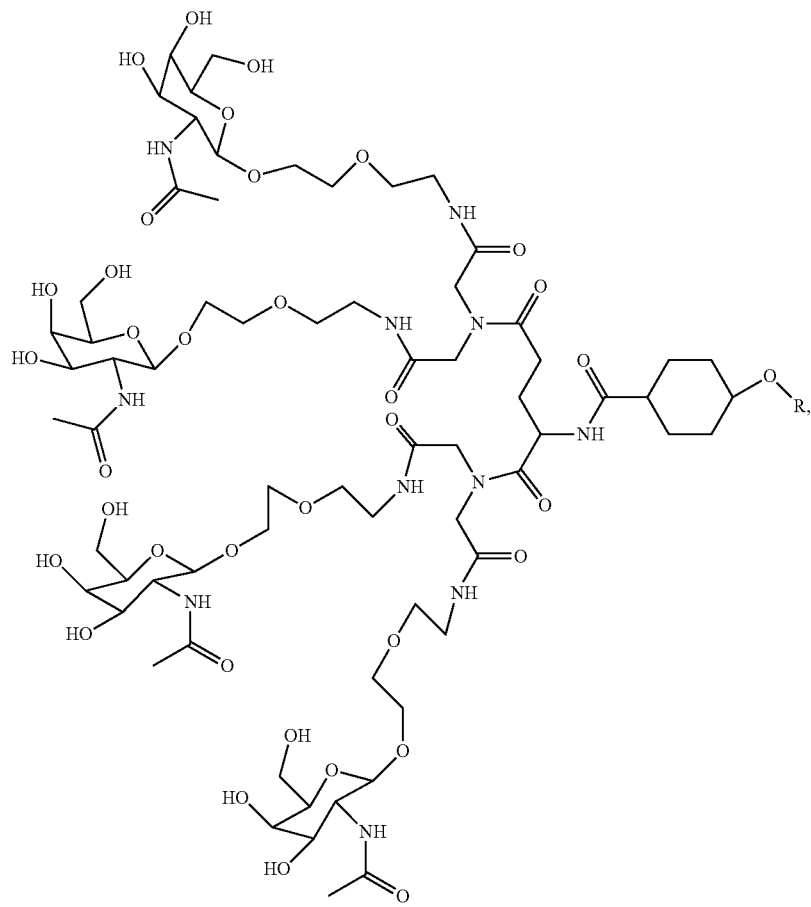
wherein R includes or consists of an expression-inhibiting oligomeric compound. (Structure 1012a); or
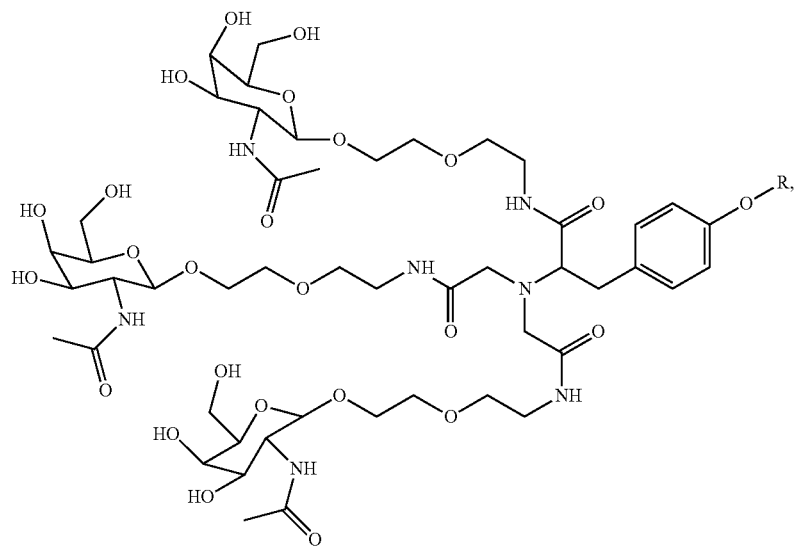
wherein R includes or consists of an expression-inhibiting oligomeric compound. (Structure 1027a).
Disclosed herein are phosphoramidite compounds including targeting ligands.

In some embodiments, the phosphoramidite compounds including targeting ligands disclosed herein have the structure represented by:
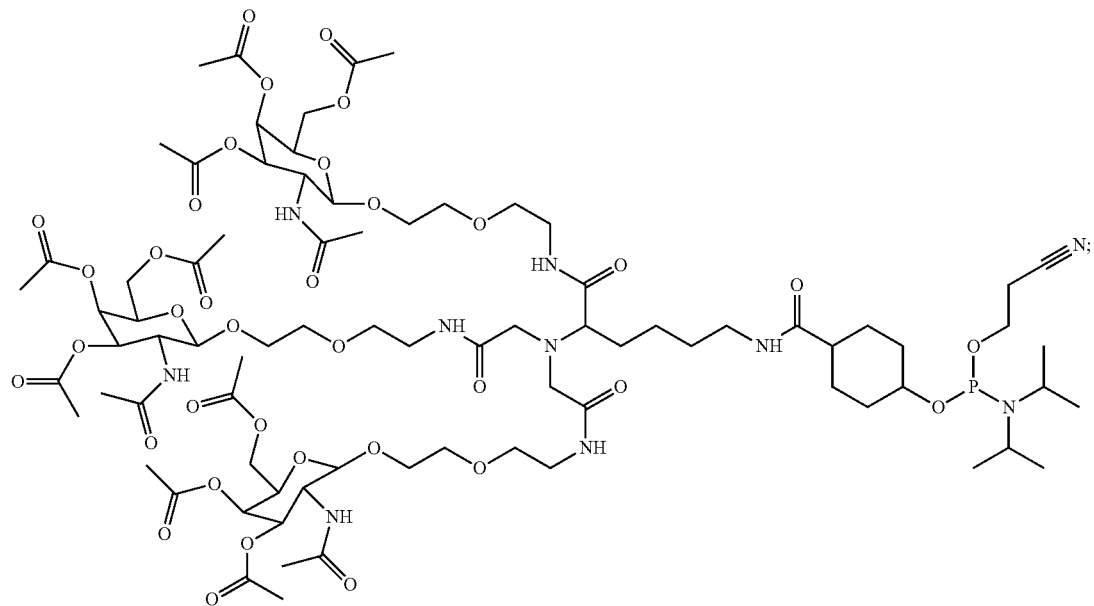
(Structure 1001b)
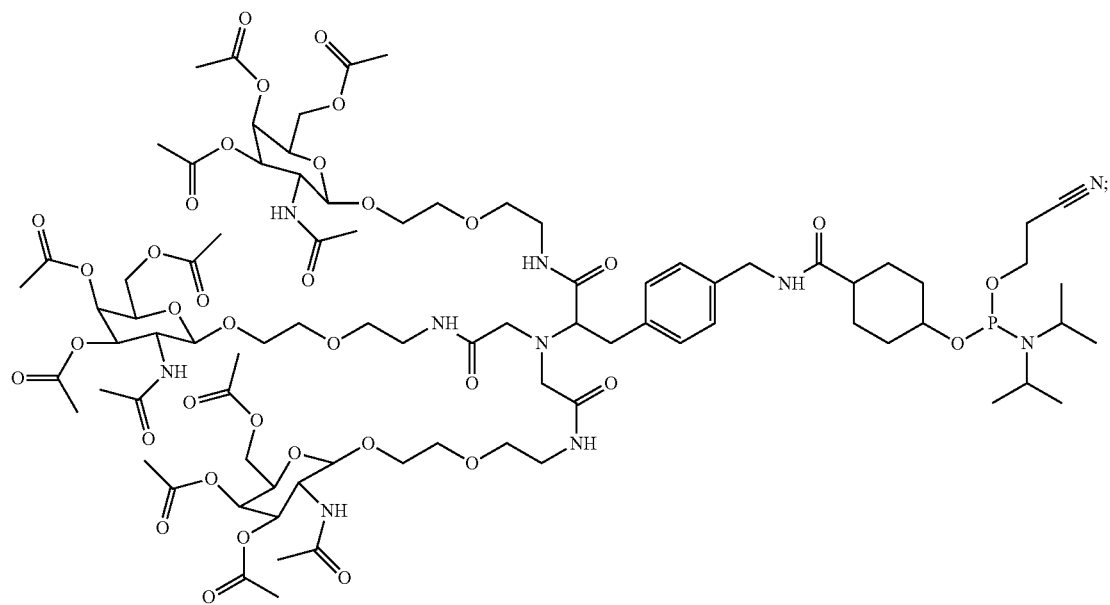
(Structure 1002b)

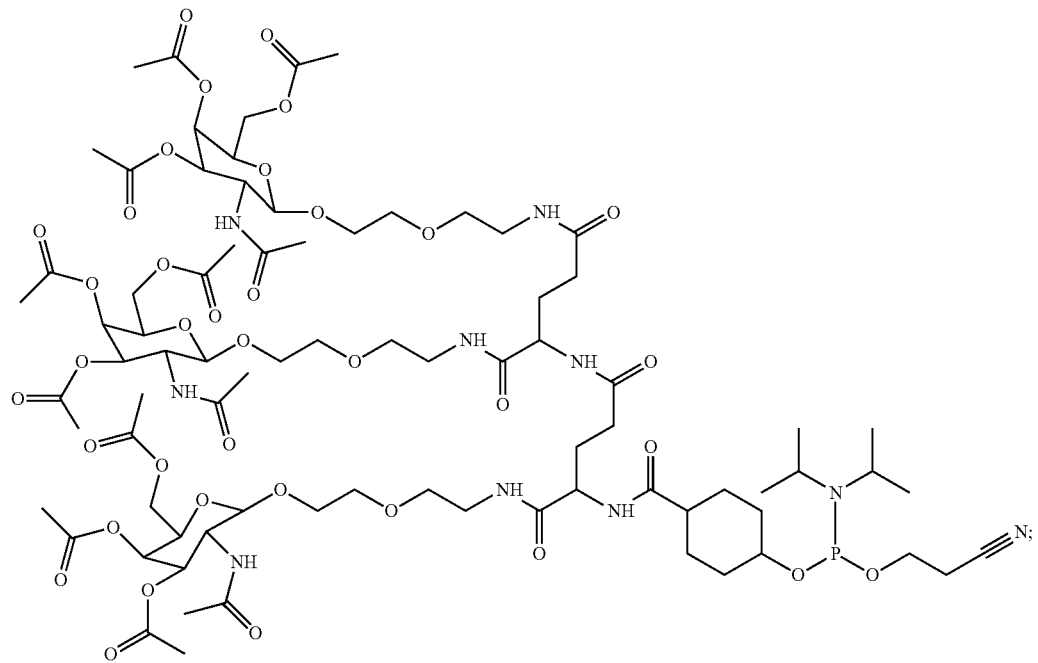
(Structure 1003b)
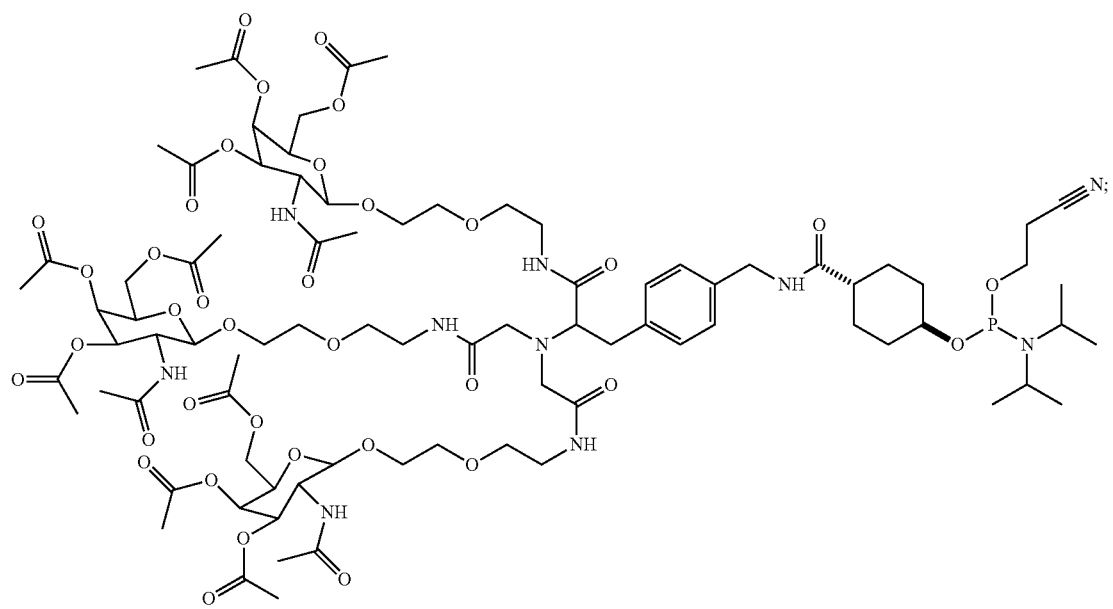
(Structure 1004b)

-continued
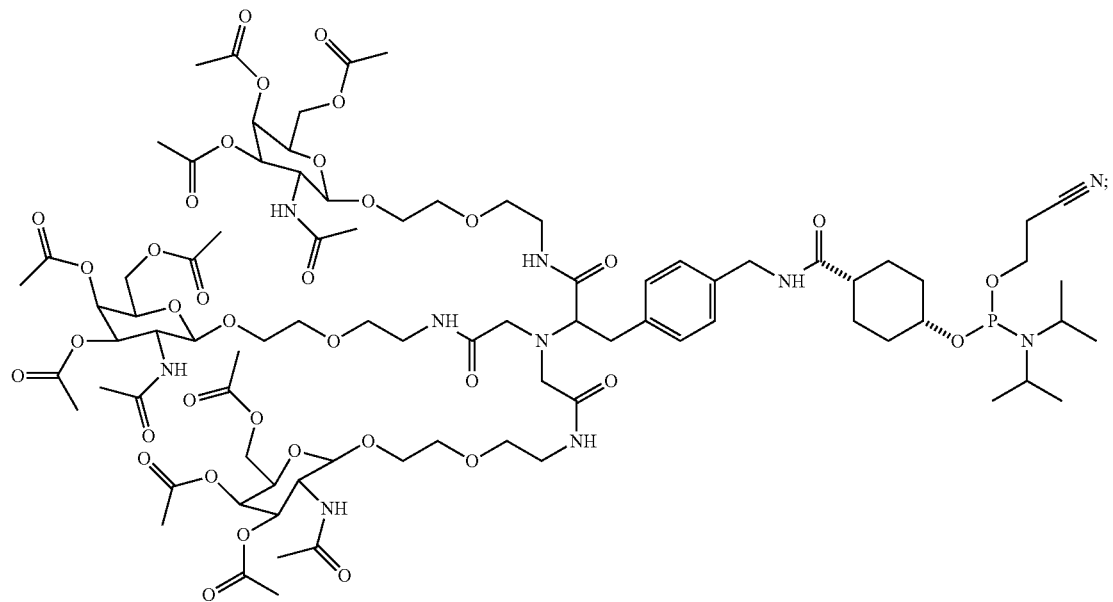
(Structure 1005b)
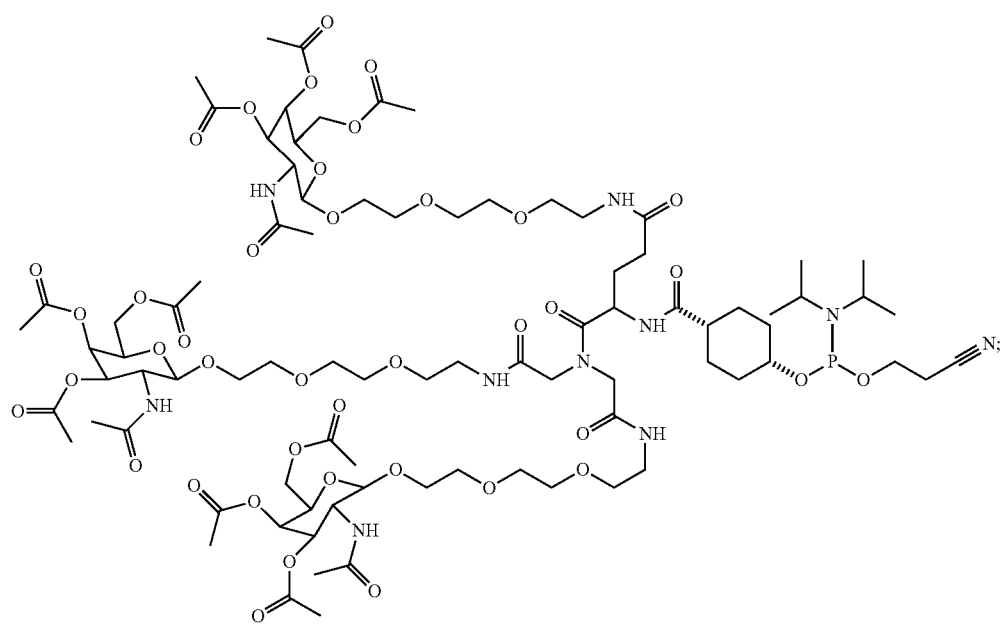
(Structure 1006b)

-continued
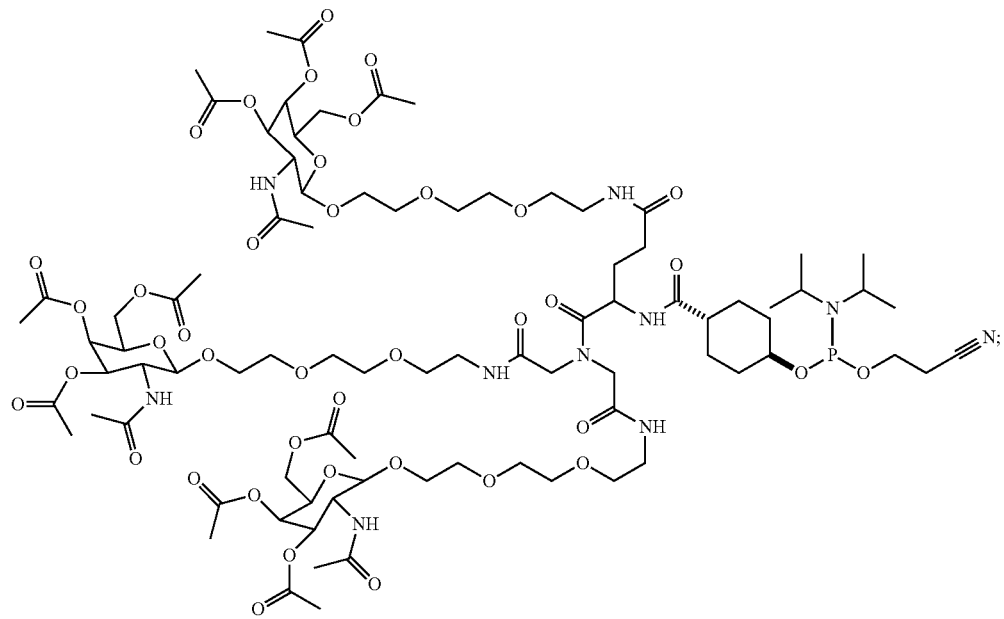
(Structure 1007b)
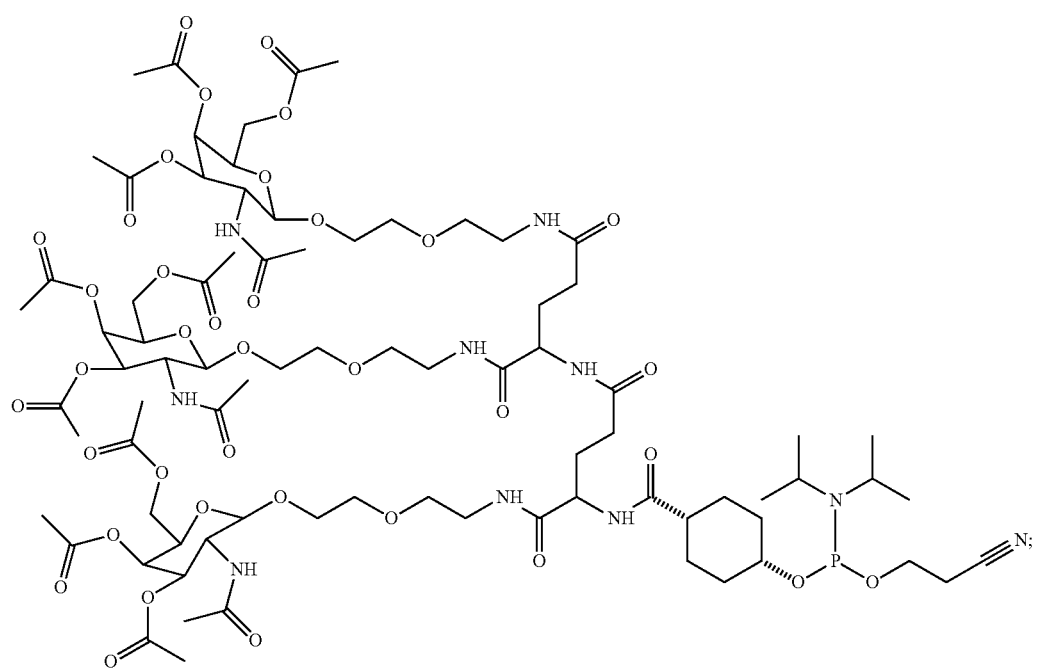
(Structure 1008b)

(Structure 1009b)
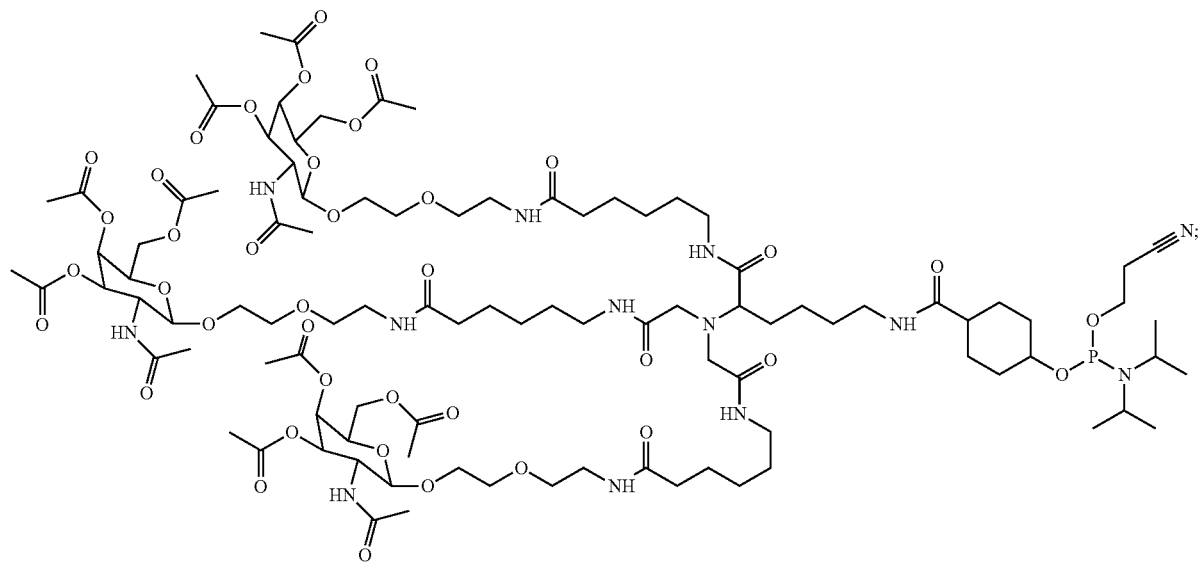
(Structure 1010b)
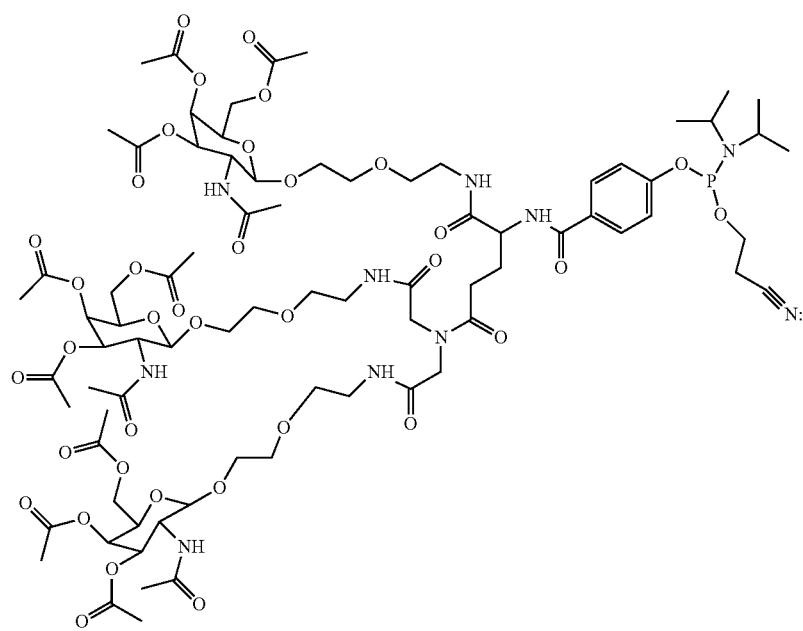

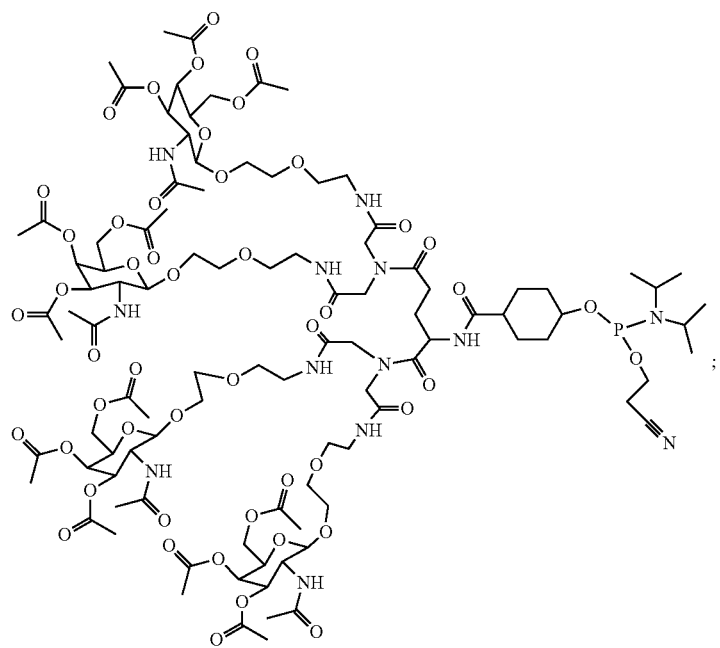
(Structure 1012b)
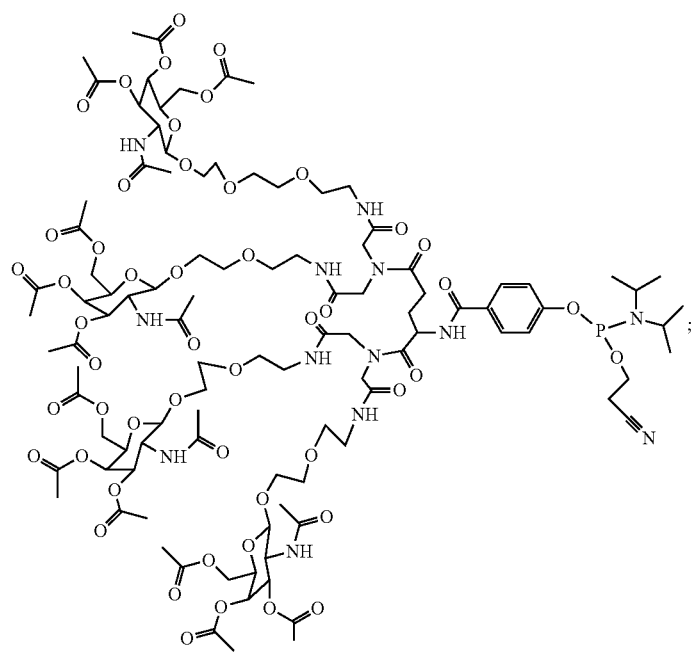
(Structure 1013b)

-continued
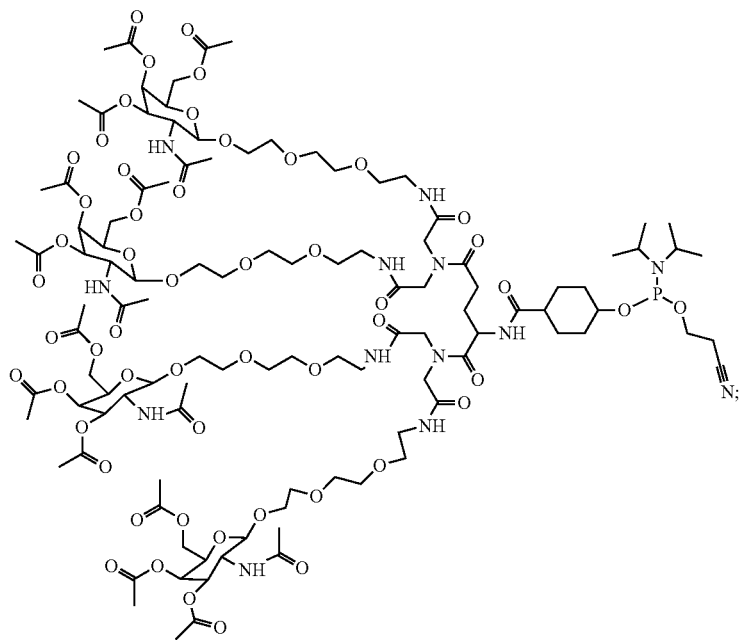
(Structure 1014b)
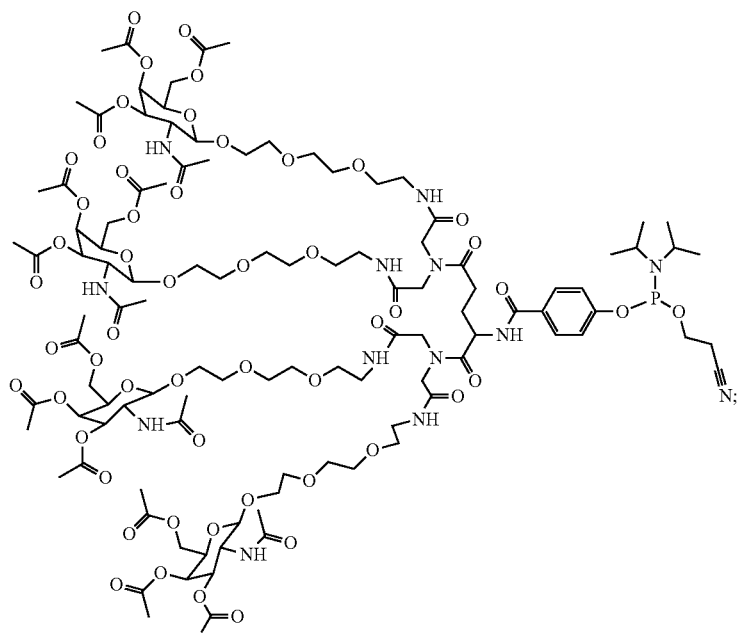
(Structure 1015b)

-continued
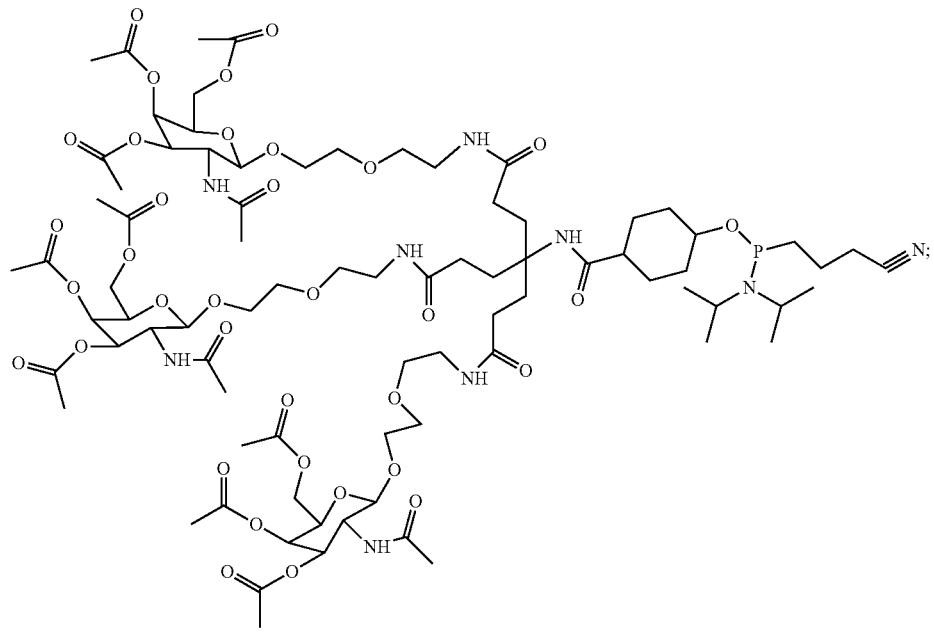
(Structure 1016b)
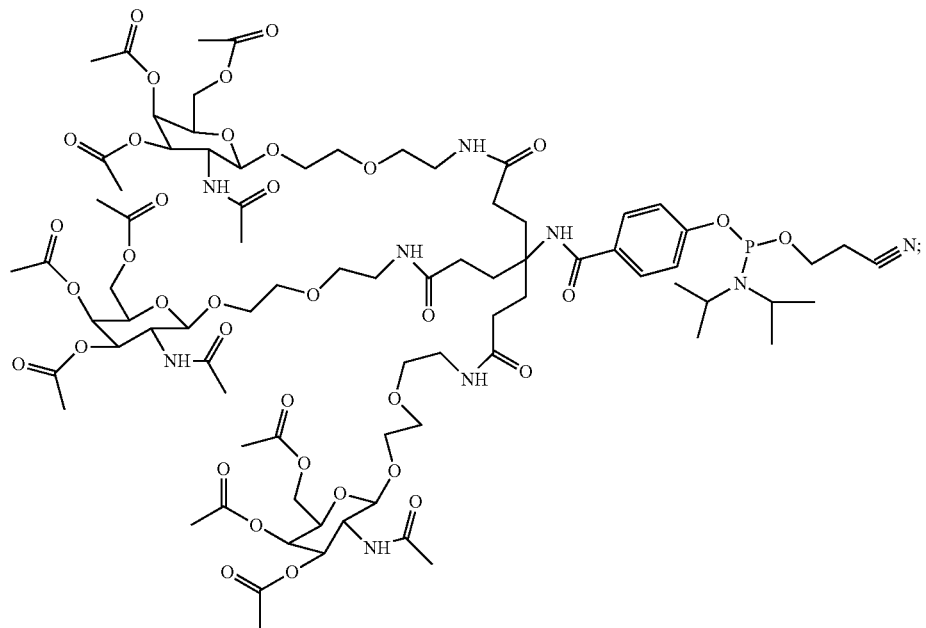
(Structure 1017b)

-continued
(Structure 1018b)
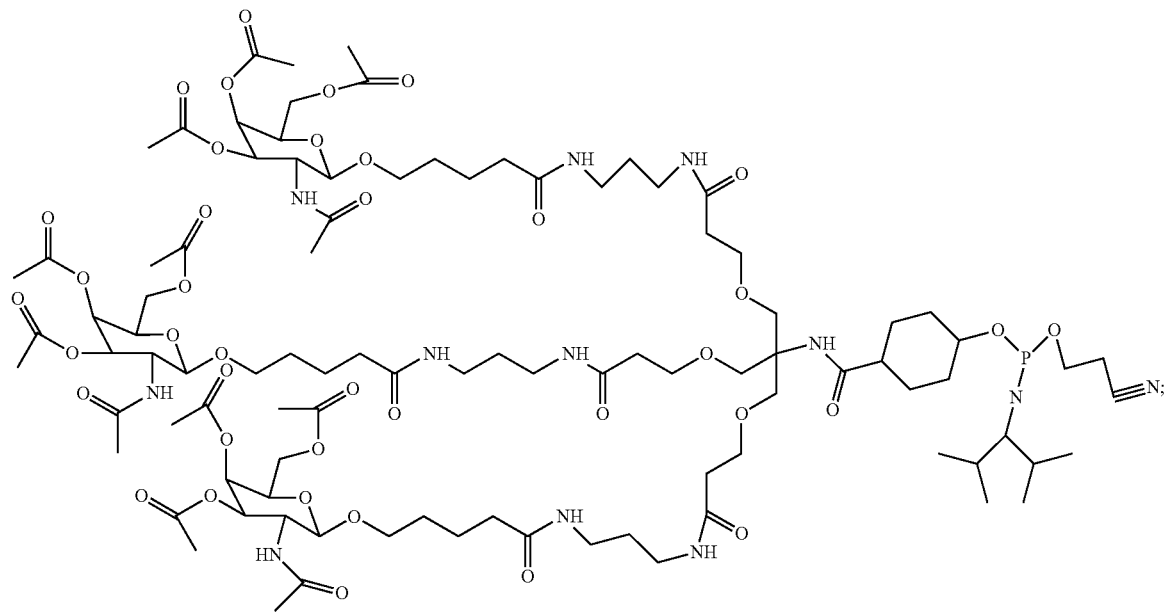
(Structure 1019b)
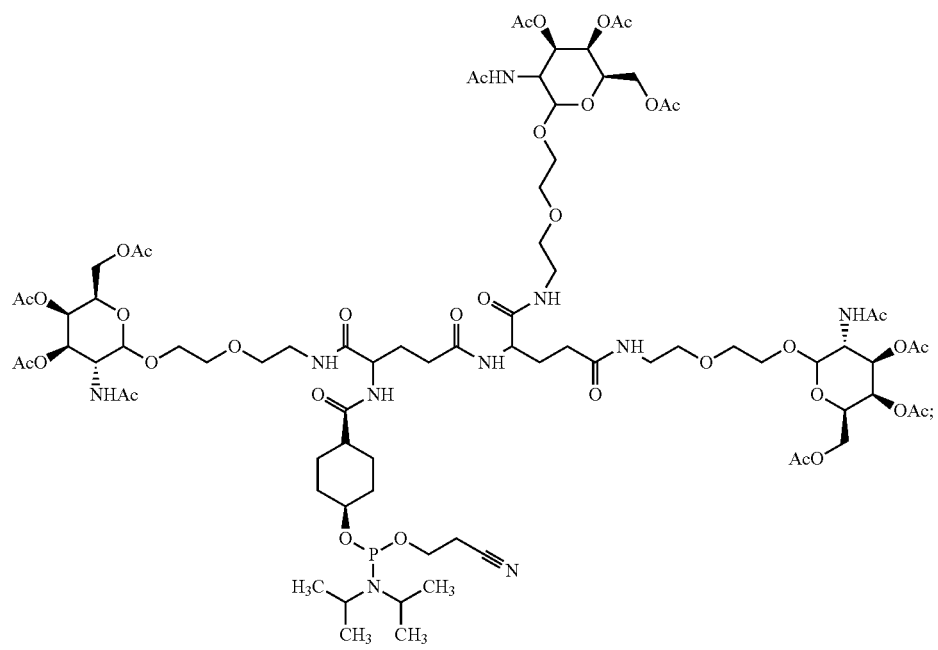

(Structure 1020b)
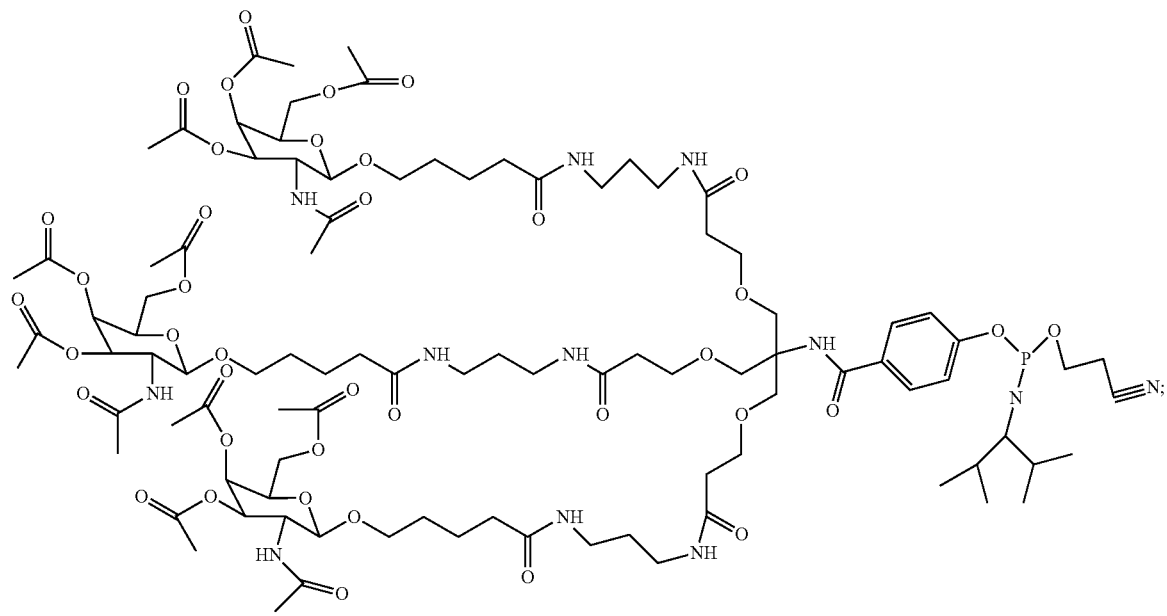
(Structure 1021b)
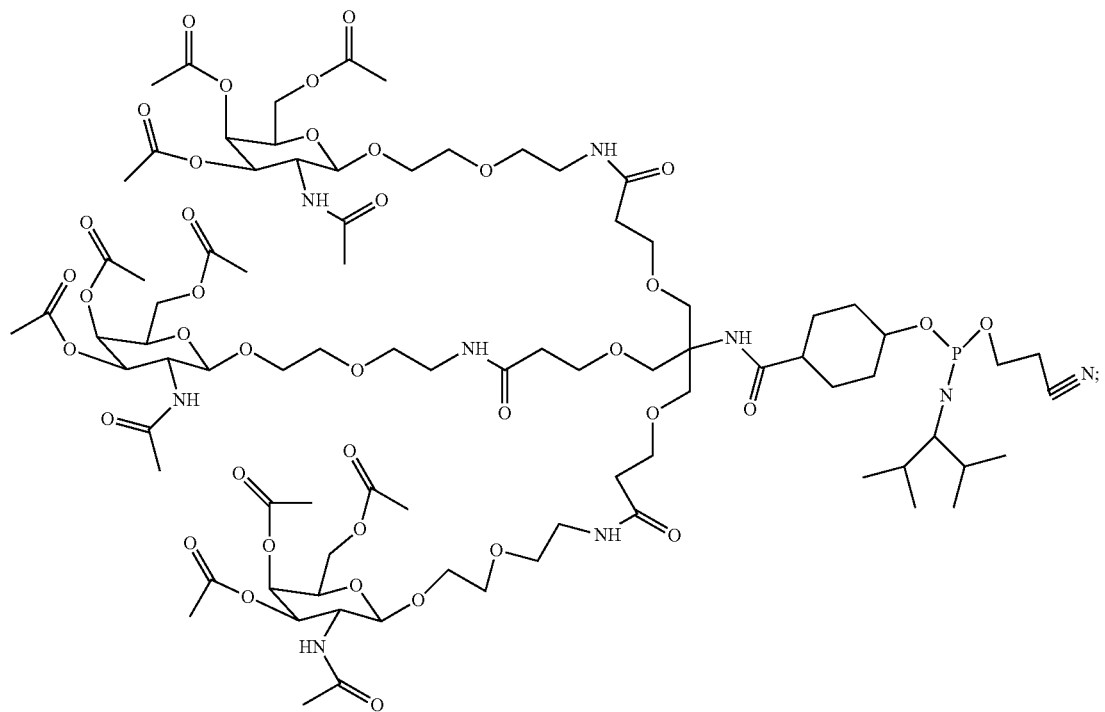

-continued
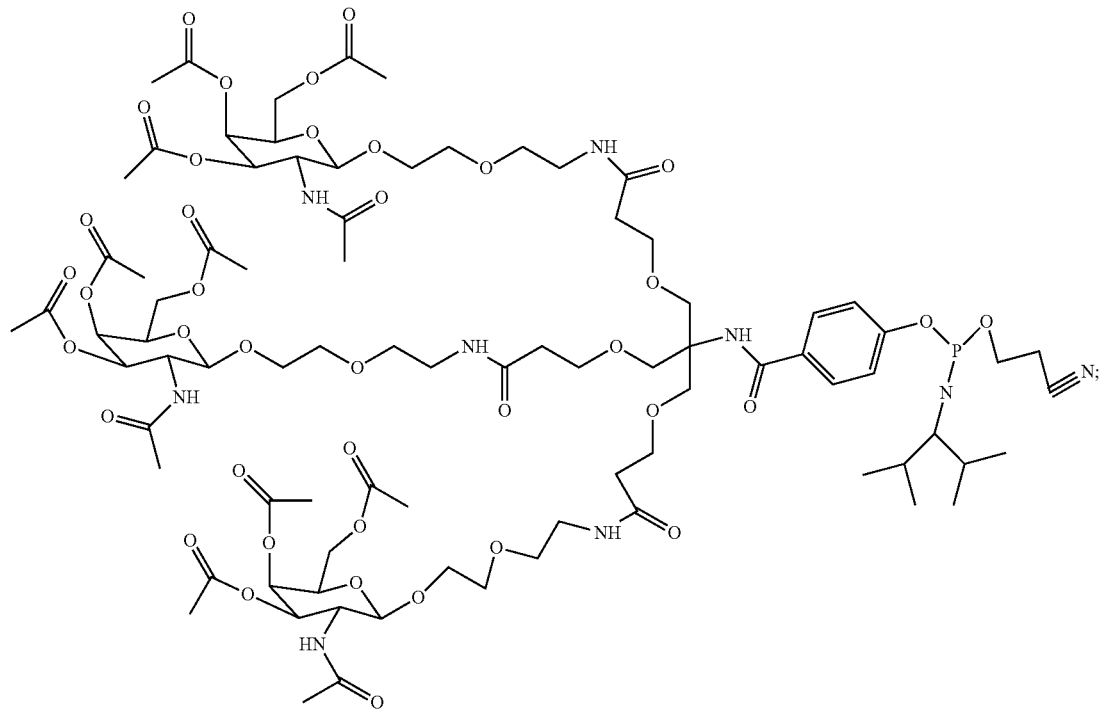
(Structure 1022b)
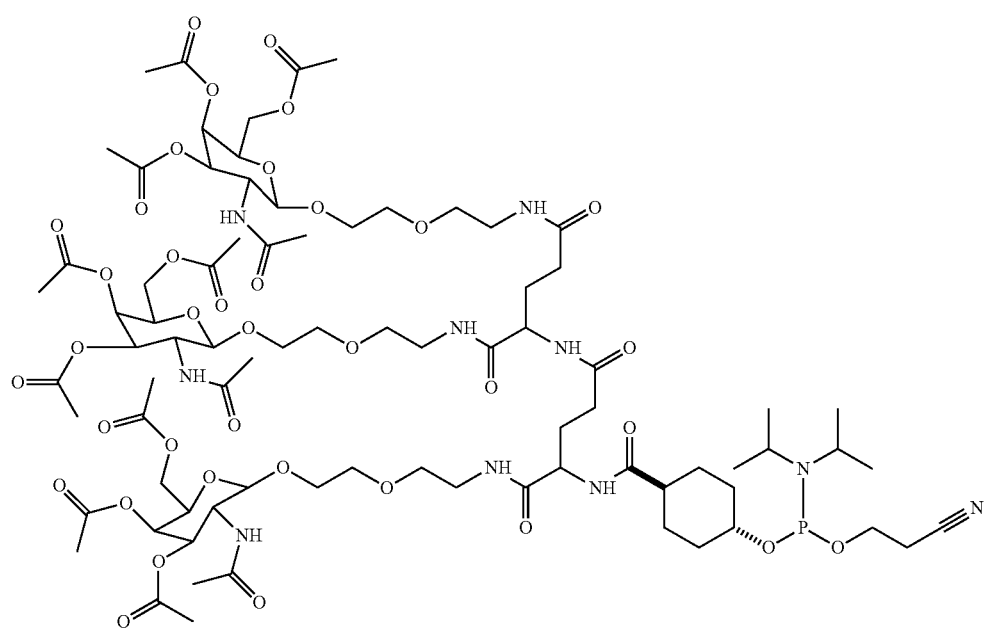
(Structure 1023b)

-continued
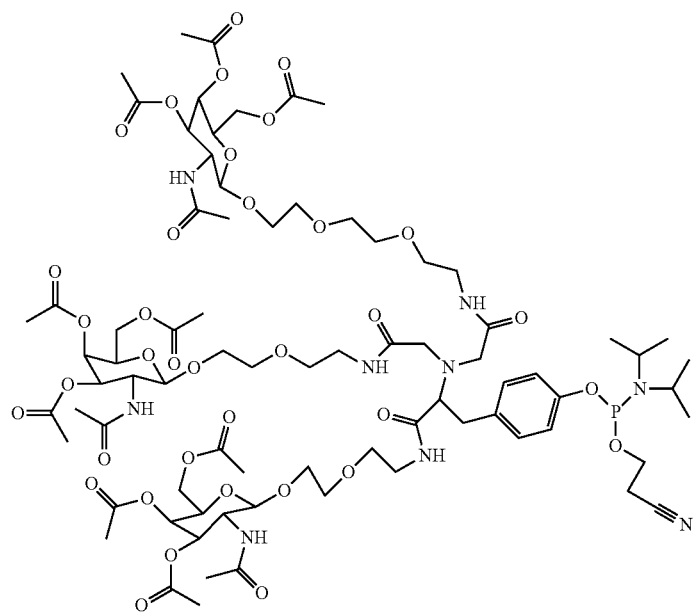
(Structure 1024b)
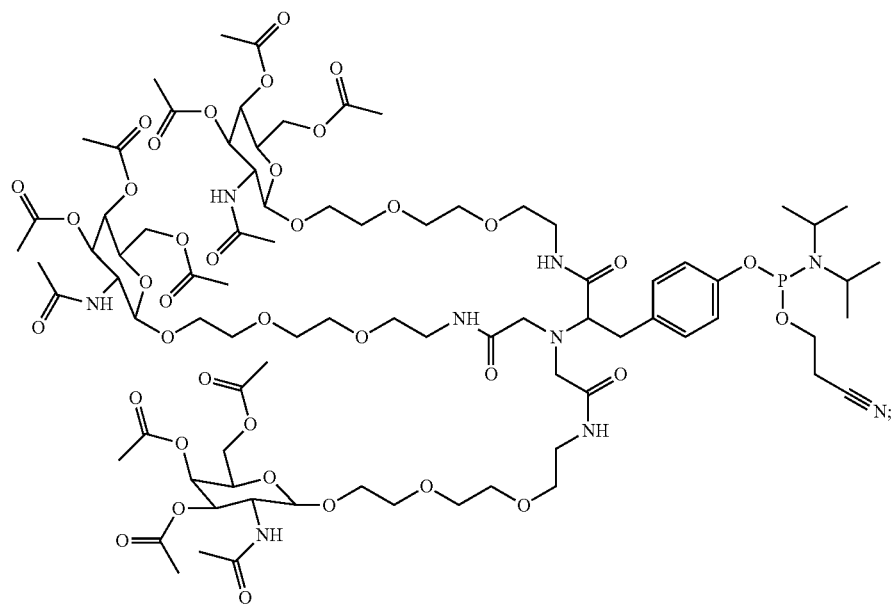
(Structure 1025b)

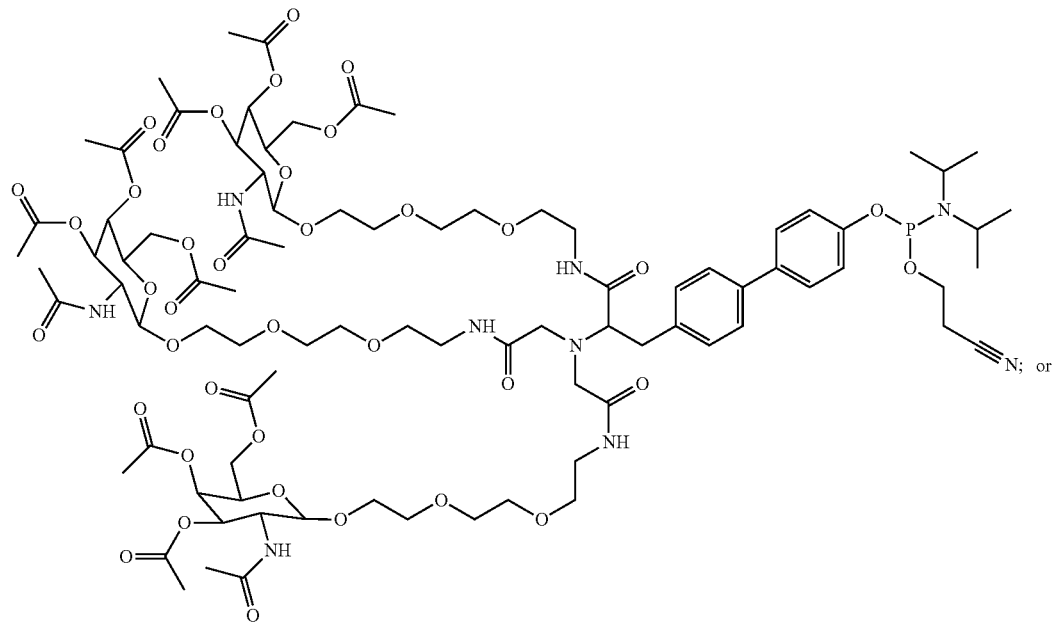

(Structure 1026b)

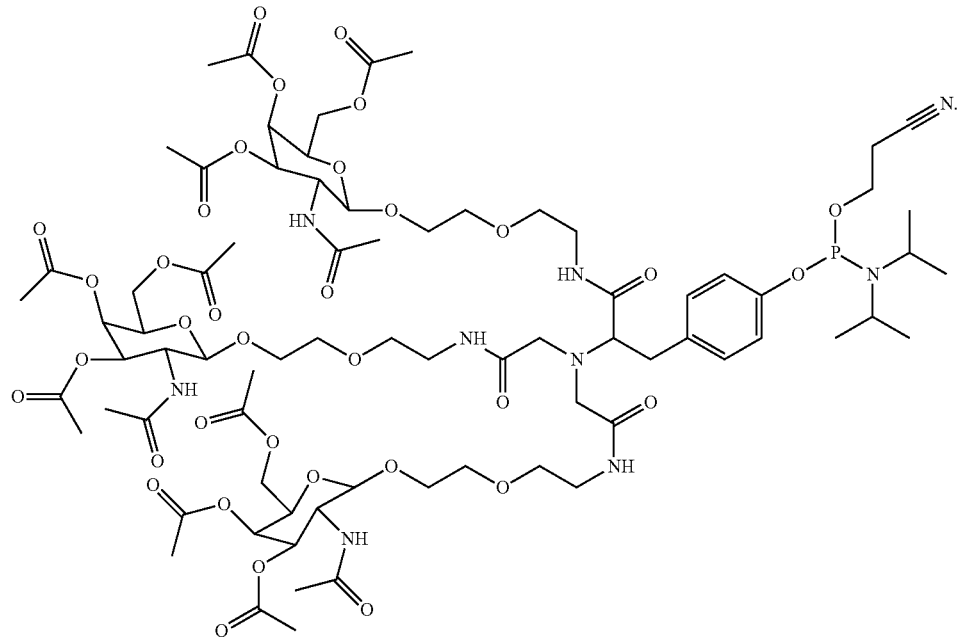

(Structure 1027b)

Also disclosed are pharmaceutical compositions that include the targeting ligands disclosed herein.

Disclosed are methods of treating a disease or disorder that would benefit from administration of a compound, the methods including administering to a subject a compound linked to a targeting ligand disclosed herein.

Disclosed herein are methods of inhibiting expression of a target nucleic acid in a subject, the methods including administering a therapeutic amount of an expression-inhibiting oligomeric compound linked to the targeting ligands disclosed herein.

Disclosed herein are methods of delivering an expression-inhibiting oligomeric compound to the liver in vivo, comprising administering an expression-inhibiting oligomeric compound linked to a targeting ligand disclosed herein to a subject.

Disclosed herein are processes or methods of manufacturing a phosphoramidite compound including a targeting ligand, the method comprising (i) covalently linking the linker to the branch point group, and (ii) linking the linker to a phosphorus atom of a phosphoramidite through a phosphytylation reaction with a phosphoramidite forming reagent, thereby forming a phosphoramidite compound.

As used herein, the term "linked" when referring to the connection between two molecules means that two molecules are joined by a covalent bond or that two molecules are associated via noncovalent bonds (e.g., hydrogen bonds or ionic bonds). In some examples, where the term "linked"

refers to the association between two molecules via noncovalent bonds, the association between the two different molecules has a $K_D$ of less than $1 \times 10^{-4}$ M (e.g., less than $1 \times 10^{-5}$ M, less than $1 \times 10^{-6}$ M, or less than $1 \times 10^{-7}$ M) in physiologically acceptable buffer (e.g., phosphate buffered saline).

As used herein, the term "directly linked" refers to a first compound or group being linked to a second compound or group without any intervening atoms or groups of atoms. As used herein, the term "indirectly linked" refers to a first compound being linked to a second compound or group through an intermediary group, compound, or molecule, such as, for example, a linking group. Unless otherwise stated, the term "linked" as used herein includes both "directly linked" and "indirectly linked" as those terms are defined herein.

As used herein, an "oligomeric compound" is a nucleotide sequence containing about 10-50 nucleotides or nucleotide base pairs. In some embodiments, an oligomeric compound has a nucleobase sequence that is at least partially complementary to a coding sequence in an expressed target nucleic acid or target gene within a cell. In some embodiments, the oligomeric compounds, upon delivery to a cell expressing a gene, are able to inhibit the expression of the underlying gene, and are referred to herein as "expression-inhibiting oligomeric compounds." The gene expression can be inhibited in vitro or in vivo. "Oligomeric compounds" include, but are not limited to: oligonucleotides, single-stranded oligonucleotides, single-stranded antisense oligonucleotides, short interfering RNAs (siRNAs), double-strand RNAs (dsRNA), micro RNAs (miRNAs), short hairpin RNAs (shRNA), ribozymes, interfering RNA molecules, and dicer substrates.

As used herein, the term "oligonucleotide" means a polymer of linked nucleosides each of which can be independently modified or unmodified.

As used herein, the term "single-stranded oligonucleotide" means a single-stranded oligomeric compound having a sequence at least partially complementary to a target mRNA, that is capable of hybridizing to a target mRNA through hydrogen bonding under mammalian physiological conditions (or comparable conditions in vitro). In some embodiments, a single-stranded oligonucleotide is a single stranded antisense oligonucleotide.

As used herein, an "RNAi agent" means an agent that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents include, but are not limited to: single-stranded oligonucleotides, single-stranded antisense oligonucleotides, short interfering RNAs (siRNAs), double-strand RNAs (dsRNA), micro RNAs (miRNAs), short hairpin RNAs (shRNA), and dicer substrates. The RNAi agents described herein are comprised of an oligonucleotide having a strand that is at least partially complementary to the mRNA being targeted. In some embodiments, the RNAi agents described herein are double-stranded, and are comprised of an antisense strand and a sense strand that is at least partially complementary to the antisense strand. RNAi agents may be comprised of modified nucleotides and/or one or more non-phosphodiester linkages. In some embodiments, the RNAi agents described herein are single-stranded.

As used herein, the terms "silence," "reduce," "inhibit," "down-regulate," or "knockdown" When referring to expression of a given gene, mean that the expression of the gene, as measured by the level of RNA transcribed from the gene or the level of polypeptide, protein or protein subunit translated from the mRNA in a cell, group of cells, tissue, organ, or subject in which the gene is transcribed, is reduced when the cell, group of cells, tissue, organ, or subject is treated with oligomeric compounds linked to the targeting ligands described herein as compared to a second cell, group of cells, tissue, organ, or subject that has not or have not been so treated.

As used herein, the term "sequence" or "nucleotide sequence" mean a succession or order of nucleobases or nucleotides, described with a succession of letters using the standard nucleotide nomenclature.

As used herein, and unless otherwise indicated, the term "complementary," when used to describe a first nucleotide sequence (e.g., RNAi agent sense strand or targeted mRNA) in relation to a second nucleotide sequence (e.g., single-stranded antisense oligonucleotide or a double-stranded RNAi agent antisense strand), means the ability of an oligonucleotide or polynucleotide including the first nucleotide sequence to hybridize (form base pair hydrogen bonds under mammalian physiological conditions (or comparable conditions in vitro)) and form a duplex or double helical structure under certain conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above requirements with respect to the ability to by are fulfilled.

As used herein, "perfectly complementary" or "fully complementary" means that all (100%) of the bases in a contiguous sequence of a first polynucleotide will hybridize with the same number of bases in a contiguous sequence of a second polynucleotide. The contiguous sequence may comprise all or a part of a first or second nucleotide sequence.

As used herein, "partially complementary" means that in a hybridized pair of nucleobase sequences, at least 70%, but not all, of the bases in a contiguous sequence of a first polynucleotide will hybridize with the same number of bases in a contiguous sequence of a second polynucleotide.

As used herein, "substantially complementary" means that in a hybridized pair of nucleobase sequences, at least 85%, but not all, of the bases in a contiguous sequence of a first polynucleotide will hybridize with the same number of bases in a contiguous sequence of a second polynucleotide. The terms "complementary," "fully complementaty," and "substantially complementary" herein may be used with respect to the base matching between the sense strand and the antisense strand of a double-stranded RNAi agent, between the antisense strand of a double-stranded RNAi agent and a sequence of a target mRNA, or between a single-stranded antisense oligonucleotide and a sequence of a target mRNA.

As used herein, the terms "treat," "treatment," and the like, mean the methods or steps taken to provide relief from or alleviation of the number, severity, and/or frequency of one or more symptoms of a disease in a subject.

As used herein, the phrase "introducing into a cell," when referring to an oligomeric compound, means functionally delivering the oligomeric compound into a cell. The phrase "functional delivery," means that delivering the oligomeric compound to the cell in a manner that enables the oligomeric compound to have the expected biological activity, e.g., sequence-specific inhibition of gene expression.

Unless stated otherwise, use of the symbol

as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

The term "substituted," as used herein, means that any one or more hydrogens on the designated atom, usually a carbon, oxygen, or nitrogen atom, is replaced with any group as defined herein, provided that the designated atom's normal valency is not exceeded, and that the substitution results in a stable compound. Non-limiting examples of substituents include C1-C6 alkyl, C2-C6 alkenyl, C2-C6 alkynyl, cyano, hydroxyl, oxo, carboxyl, cycloalkyl, cycloalkenyl, heterocyclyl, heteroaryl, aryl, keto, alkoxycarbonyl, aryloxycarbonyl, heteroaryloxycarbonyl, or halo (e.g., F, Cl, Br, I). When a substituent is keto or oxo (i.e., =O), then two (2) hydrogens on the atom are replaced. Ring double bonds, as used herein, are double bonds that are formed between two adjacent ring atoms (e.g., C=C, C=N, N=N, etc.).

Some compounds of the present disclosure can exist in a tautomeric form that is also intended to be encompassed within the scope of the present disclosure. "Tautomers" are compounds whose structures differ markedly in the arrangement of atoms, but which exist in easy and rapid equilibrium. It is to be understood that compounds of the present disclosure may be depicted as different tautomers. It should also be understood that when compounds have tautomeric forms, all tautomeric forms are intended to be within the scope of the disclosure, and the naming of the compounds does not exclude any tautomeric form.

The compounds and pharmaceutically acceptable salts of the present disclosure can exist in one or more tautomeric forms, including ketone-enol, amide-nitrile, lactam-lactim, amide-imidic acid tautomerism in heterocyclic rings (e.g., in the nucleobases guanine, thymine, and cytosine), amine-enamine and enamine-enamine and geometric isomers and mixtures thereof. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein. The concept of tautomers that are interconvertible by tautomerizations is called tautomerism. In tautomerism, a simultaneous shift of electrons and a hydrogen atom occurs.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

As used herein, the term "alkyl" refers to a saturated aliphatic hydrocarbon group, straight chain or branched, having from 1 to 10 carbon atoms unless otherwise specified. For example, "C1-C6 alkyl" includes alkyl groups having 1, 2, 3, 4, 5, or 6 carbons in a linear or branched arrangement. As used herein, the term "aminoalkyl" refers to an alkyl group as defined above, substituted at any position with one or more amino groups as permitted by normal valency. The amino groups may be unsubstituted, monosubstituted, or di-substituted.

As used herein, the term "cycloalkyl" means a saturated or unsaturated nonaromatic hydrocarbon ring group having from 3 to 14 carbon atoms, unless otherwise specified. Examples of cycloalkyl groups include, but are not limited to, cyclopropyl, methyl-cyclopropyl, 2,2-dimethyl-cyclobutyl, 2-ethyl-cyclopentyl, cyclohexyl, etc. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight or branched, containing at least one carbon-carbon double bond, and having from 2 to 10 carbon atoms unless otherwise specified. Up to five carbon-carbon double bonds may be present in such groups. For example, "C2-C6" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "C2-C6 alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may contain triple bonds as permitted by normal valency, and may be optionally mono-, di-, tri-, tetra-, or penta-substituted on any position as permitted by normal valency.

As used herein, "alkoxyl" or "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, hexanoyl), alkenoyl (e.g., acryloyl) alkynoyl (e.g., ethynoyl, propynoyl, butynoyl, pentynoyl, hexynoyl), aryloyl (e.g., benzoyl), heteroaryloyl (e.g., pyrroloyl, imidazoloyl, quinolinoyl, pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

As used herein, "aryl" or "aromatic" means any stable monocyclic or polycyclic carbon ring of up to 7 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N and S. Examples of heteroaryl groups include, but are not limited to, acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
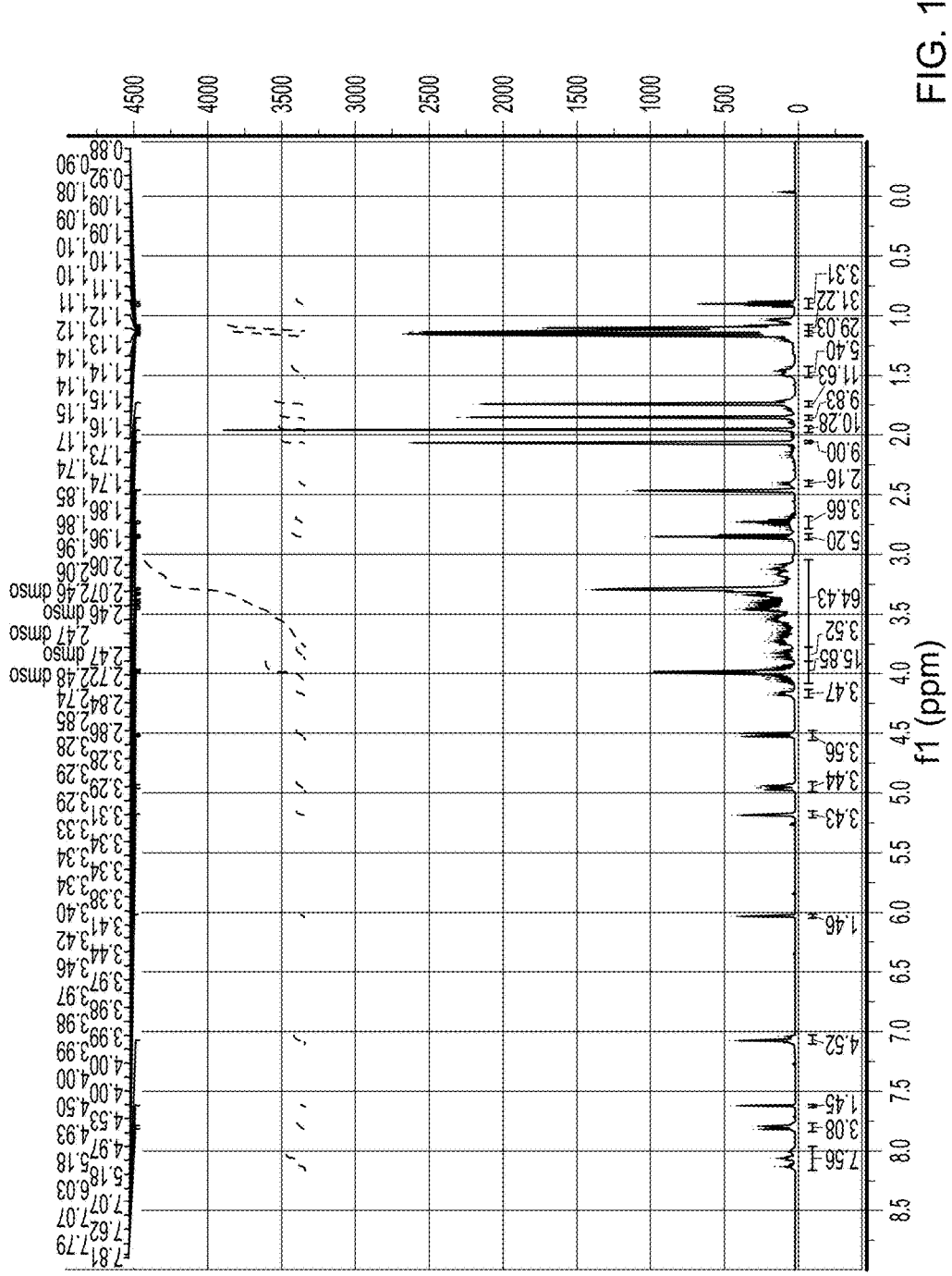
FIG. 1 is a $^1$H NMR spectra of compound 11 (which is described below in Example 1 and has the chemical structure of Structure 1005b herein).

Described herein are targeting ligands that are linked to compounds, such as therapeutic or diagnostic compounds. In some embodiments, the compounds that are linked to the targeting ligands described herein include or consist of therapeutic compounds such as expression-inhibiting oligomeric compounds. The targeting ligands can be used to target therapeutic compounds to a desired location of a target nucleic acid or target gene. Also described herein are compositions including targeting ligands and therapeutic compounds, such as compositions including or consisting of targeting ligands and expression-inhibiting oligomeric compounds.

The new targeting ligands described herein provide advantages over previously known targeting ligands to facilitate the delivery of therapeutic compounds. These advantages include, for example, improvements to the ease and efficiency of manufacture, while also providing efficient targeting or bio-distribution, sufficient stability in vivo and/or in vitro, and/or other improvements desirable for oligonucleotide therapeutic product delivery. The new targeting ligands are also particularly suitable for synthesis as phosphoramidite compounds, which reduces the cost and burden of manufacture, and facilitates the convenient attachment of the targeting ligand to compounds, especially expression-inhibiting oligomeric compounds (such as RNAi agents), while providing similar, or in some cases improved, delivery and/or efficacy of the therapeutic compound.

Targeting Ligands

Targeting ligands are comprised of one or more targeting group(s) or targeting moiety(ies), which can serve to enhance the pharmacokinetic or bio-distribution properties of the compound to which they are linked, and improve cell- or tissue-specific distribution and cell-specific uptake of the conjugated composition. In general, a targeting ligand aids in directing the delivery of the therapeutic compound to which it is linked to the desired target site. In some instances, the targeting moiety may bind to a cell or cell receptor, and initiate endocytosis to facilitate entry of the therapeutic compound into the cell. Targeting moieties can include compounds with affinity to cell receptors or cell surface molecules or antibodies. A variety of targeting ligands that contain targeting moieties can be linked to therapeutic agents and other compounds to target the agents to cells and specific cellular receptors. Types of targeting moieties include carbohydrates, cholesterol and cholesteryl groups, and steroids. Targeting moieties that can bind to cell receptors include saccharides, such as galactose, galactose derivatives (such as N-acetyl-galactosamine), mannose, and mannose derivatives; other carbohydrates; glycans; haptens;

vitamins; folate; biotin; aptamers; and peptides, such as RGD-containing peptides, insulin, EGF, and transferrin.

Targeting moieties that are known to bind to the asialoglycoprotein receptor (ASGPR) are particularly useful in directing the delivery of oligomeric compounds to the liver. Asialoglycoprotein receptors are abundantly expressed on liver cells, including hepatocytes. Cell receptor targeting moieties that target ASGPR include galactose and galactose derivatives. In particular, clusters of galactose derivatives, including clusters comprised of two, three, or four N-acetyl-galactosamines (GalNAc or NAG), can facilitate uptake of certain compounds in liver cells. GalNAc clusters conjugated to oligomeric compounds serve to direct the composition to the liver, where the N-acetyl-galactosamine sugars are able to bind to the asialoglycoprotein receptors on the surface of the liver cell. The binding to an asialoglycoprotein receptor is believed to initiate receptor-mediated endocytosis, thereby facilitating entry of the compound into the interior of the cell.

The targeting ligands disclosed herein may include one, two, three, four, or more than four targeting moieties. In some embodiments, the targeting ligands disclosed herein can include one, two, three, four, or more than four targeting moieties linked to a branch point group. In some embodiments, the targeting ligands disclosed herein can include one, two, three, four, or more than four targeting moieties linked to a branch point group wherein each targeting moiety is linked to the branch point group via a tether.

In some embodiments, the targeting ligands disclosed herein can include one, two, three, four, or more than four asialoglycoprotein receptor (ASGPR) targeting moieties linked to a branch point group. In some embodiments, the targeting ligands disclosed herein can include one, two, three, four, or more than four ASGPR targeting moieties linked to a branch point group wherein each ASGPR targeting moiety is linked to the branch point group via a tether.

In some embodiments, the branch point group is linked to a linker. In some embodiments, the branch point group includes a linker replacement moiety, and the branch point group is linked to a therapeutic compound. In some embodiments, the branch point group is linked to an oligomeric compound. In some embodiments, the branch point group is linked to an expression-inhibiting oligomeric compound.

Figure 22:
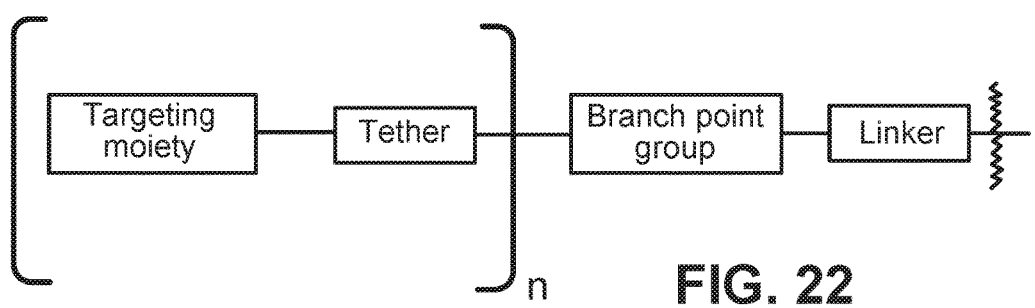
FIG. 22 is a structure showing Formula I.

In some embodiments, the targeting ligand is represented by the following Formula I, as shown in FIG. 22, wherein n is an integer from 1 to 4 (e.g., 1, 2, 3 or 4) (Formula I). In some embodiments, n in Formula I is an integer from 1-3, 1-2, 2-4, 2-3, or 3-4.

The linker of Formula I is a group that includes one or more substituted or unsubstituted moieties selected from cycloalkyl, cycloalkenyl, aryl, heteroaryl, or heterocyclyl group(s), or covalently linked combination(s) thereof, that connects a branch point group on one end of the linker to a therapeutic compound (or to the phosphorous atom of a phosphoramidite when the targeting ligand is synthesized as a phosphoramidite compound) on the other end of the linker. In some embodiments, one or more additional groups, such as cleavable moieties (such as phosphate group or a group containing a disulfide bond) or groups forming phosphorothioate or phosphonate linkage(s), are inserted between the therapeutic compound and the linker. The linkers are "rigid" in that they impart sufficient stability and rigidity to the overall targeting ligand to reduce interaction between the targeting moiety(ies) of Formula I and the therapeutic compound to which it is linked. This, in turn, can improve the interaction of the targeting moiety with the target site. Additionally, the linkers for use in the targeting ligands disclosed herein are specifically designed for synthesizing the targeting ligand(s) as phosphoramidite compounds, which enables the efficient linkage of the targeting ligand to the 5' terminal end of an oligomeric compound.

The branch point group of Formula I is any group that enables attachment of one or more targeting moieties (via one or more tethers) to the linker.

Figure 23:
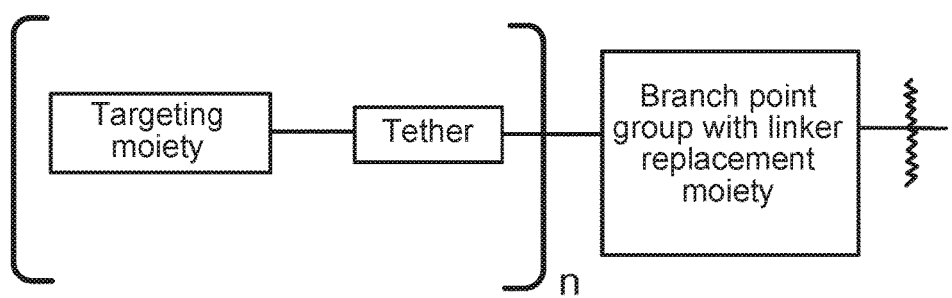
FIG. 23 is a structure showing Formula II.

In some embodiments, the targeting ligand is represented by the following Formula II, as shown in FIG. 23, wherein n is an integer from 1 to 4 (e.g., 1, 2, 3 or 4). In some embodiments, n in Formula II is an integer from 1-3, 1-2, 2-4, 2-3, or 3-4.

In Formula II, the branch point group is any group that enables attachment of one or more targeting moieties (via one or more tethers) to a therapeutic compound (or to the phosphorous atom of a phosphoramidite when the targeting ligand is synthesized as a phosphoramidite compound) via a linker replacement moiety. As used herein, a branch point group includes a linker replacement moiety when the branch point group includes one or more substituted or unsubstituted cycloalkyl, cycloalkenyl, aryl, heteroaryl, or heterocyclyl group(s), or combination(s) thereof (including fused, within the branch point group, which serves the same function as the rigid linkers of Formula I as disclosed herein.

The one or more tethers of Formula I and II are groups that serve as a spacer that may further add flexibility and/or length to the linkage between the targeting moiety and the branch point group. The tether provides an efficient way to link a targeting moiety to the branch point group. For the targeting ligands disclosed herein, there is at least one tether for each targeting moiety. In some embodiments, there are multiple (i.e., two or more) tethers between the branch point group and the targeting moiety.

The targeting moieties of Formulas I and II are groups that serve to enhance the pharmacokinetic or bio-distribution properties of the therapeutic compound to which they are linked, and improve cell- or tissue-specific distribution and cell-specific uptake of the conjugated composition. Targeting moieties can include compounds with affinity to cell receptors or cell surface molecules or antibodies. Types of targeting moieties include carbohydrates, cholesterol and cholesteryl groups, and steroids. Targeting moieties that can bind to cell receptors include saccharides, such as galactose, galactose derivatives (such as N-acetyl-galactosamine), mannose, and mannose derivatives; other carbohydrates; glycans; haptens; vitamins; folate; biotin; aptamers; and peptides, such as RGD-containing peptides, insulin, EGF, and transferrin.

The targeting ligands disclosed herein can be linked to therapeutic compounds. In some embodiments, the targeting ligand is linked to the therapeutic compound via an additional linker and/or a cleavable moiety, which is then linked to the therapeutic compound. In some embodiments, targeting ligands are ligated to the therapeutic compound itself.

In some embodiments, the therapeutic compound is an oligomeric compound. In some embodiments, the therapeutic compound is an expression-inhibiting oligomeric compound. In some embodiments, the expression-inhibiting oligomeric compound is an RNAi agent. In some embodiments, the expression-inhibiting oligomeric compound is a double-stranded RNAi agent.

In some embodiments, a targeting ligand is linked directly or indirectly to the 5' end of the sense strand of a double-stranded RNAi agent. In some embodiments, the targeting ligand is linked directly or indirectly to the 3' end of the sense strand of a double-stranded RNAi agent. In some embodiments, the targeting ligand is linked directly or indirectly to the 5' end or the 3' end of the antisense strand of a double-stranded RNAi agent. In some embodiments, the targeting ligand is linked directly or indirectly to the 5' end or the 3' end of a single-stranded RNAi agent.

In some embodiments, a targeting ligand is linked to a double-stranded RNAi agent via a phosphate, phosphonate, phosphorothioate, or other internucleoside linking group, at the 5' end of the terminal nucleoside of the sense strand of the double-stranded RNAi agent.

In some embodiments, a targeting ligand disclosed herein includes a cleavable moiety. In some embodiments, a cleavable moiety includes or consists of a phosphate or other internucleoside linking group that may be cleaved. In some embodiments, the targeting ligand is linked to a therapeutic compound via a cleavable moiety.

In some embodiments, a targeting ligand disclosed herein is linked to an additional group or groups that includes a cleavable moiety. In some embodiments, the targeting ligand is linked to a cleavable moiety, which is then linked to an expression-inhibiting oligomeric compound.

In some embodiments, the targeting ligand is a phosphoramidite-containing compound. A phosphoramidite compound including a targeting ligand described herein may be useful to readily attach the targeting ligand to the therapeutic compound or to other groups, using methods generally known in the art for phosphoramidite synthesis. In some embodiments, the phosphoramidite compound including the targeting ligand is linked to an expression-inhibiting oligomeric compound using methods generally known in the art. In some embodiments, the targeting ligand-containing phosphoramidite is linked to the 5' end of the sense strand of a double-stranded RNAi agent.

In some embodiments, an expression-inhibiting oligomeric compound linked to a targeting ligand includes a single-stranded oligonucleotide. In some embodiments, the single-stranded oligonucleotide is a single-stranded antisense oligonucleotide. In some embodiments, the targeting ligand is linked directly to a single-stranded antisense oligonucleotide. In some embodiments, additional groups are inserted between a targeting ligand and a single-stranded oligonucleotide.

In some embodiments, the targeting ligand linked to an RNAi agent includes one or more N-acetyl-galactosamine sugars as a targeting moiety or targeting moieties.

In some embodiments, the targeting ligand linked to an expression-inhibiting oligomeric compound includes a tether that includes polyethylene glycol (PEG). In some embodiments, a tether consists of PEG. In some embodiments a tether includes a PEG having 1 to 10 ethylene glycol units. In some embodiments a tether includes a PEG having 1, 2, 3, 4, 5, 6, 7, 8, 9, or 10 ethylene glycol units.

In some embodiments, an expression-inhibiting oligomeric compound linked to any of the targeting ligands disclosed herein includes an RNAi agent. In some embodiments, a targeting ligand disclosed herein is linked, either directly or indirectly, to an RNAi agent.

In some embodiments, a targeting ligand disclosed herein is linked directly to an RNAi agent. In some embodiments, a targeting ligand disclosed herein is linked indirectly to an RNAi agent, as additional group(s) are inserted between the RNAi agent and the linker of the targeting ligand. In some embodiments, a second linker is included between the linker and the therapeutic compound.

Linkers

The targeting ligands disclosed herein comprise a linker, as shown in Formula I, or alternatively the branch point group includes a linker replacement moiety, as shown in Formula II.

The linker is a group of atoms linked to a branch point group on one end, and linked to a therapeutic compound (or to the phosphorous atom of a phosphoramidite when the targeting ligand is synthesized as a phosphoramidite compound) on the other end. In some embodiments, the linker is linked to a branch point group on one end, and is ligated on the other end to a group or groups that are then ligated to an expression-inhibiting oligomeric compound. In some embodiments, the linker is directly linked to an oligomeric compound. In some embodiments, the linker is linked to a cleavable moiety, which is then linked to an oligomeric compound. Examples of cleavable moieties include, for example, phosphate groups, groups including a disulfide moiety, and/or other internucleoside linkages that may be cleaved. In some embodiments, the linker is not linked to a cleavable moiety. In some embodiments, the linker is linked to a phosphorothioate or phosphonate group.

For the targeting ligands disclosed herein according to Formula I, the linker is a "rigid" linker. A rigid linker is a linking group that includes one or more substituted or unsubstituted cycloalkyl, cycloalkenyl, aryl, heteroaryl, or heterocyclyl group(s), or covalently linked combination(s) thereof.

In some embodiments, the targeting ligand of Formula I includes or consists of a linker having the following structure:

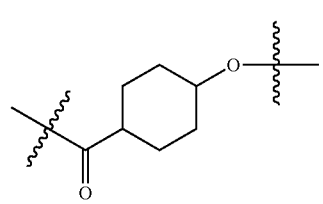

(Structure 1)

In some embodiments, the targeting ligand of Formula I includes or consists of a linker having the following structure:

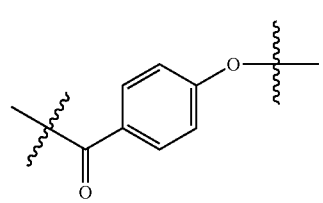

(Structure 2)

In some embodiments, the targeting ligand of Formula I includes or consists of a linker having the following structure:

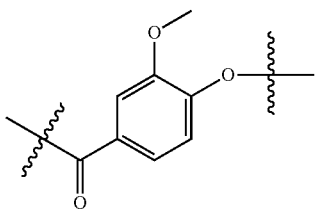
(Structure 3)

In some embodiments, the targeting ligand of Formula I includes or consists of a linker having the following structure:

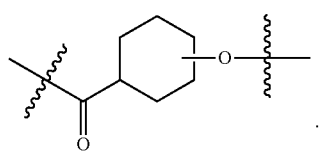
(Structure 4)

In some embodiments, the targeting ligand of Formula I includes or consists of a linker having the following structure:

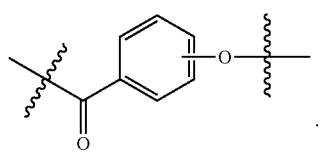
(Structure 5)

In some embodiments, the targeting ligand of Formula I includes or consists of a linker having the following structure:

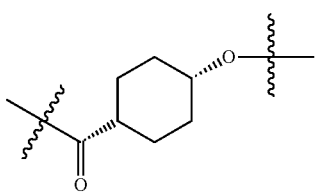
(Structure 6a)

In some embodiments, the targeting ligand of Formula I includes or consists of a linker having the following structure:

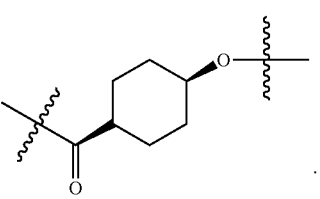
(Structure 6b)

In some embodiments, the targeting ligand of Formula I includes or consists of a linker having the following structure:

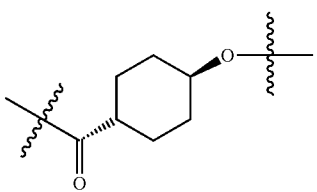
(Structure 6c)

In some embodiments, the targeting ligand of Formula I includes or consists of a linker having the following structure:

(Structure 6d)

In some embodiments, the targeting ligand of Formula I includes or consists of a linker having the following structure:

wherein n' is an integer from 0 to 10 (e.g., 0, 1, 2, 3, 4, 5, 6, 7, 8, 9, or 10), and for each Z' present, Z' is independently selected, and Z' is independently selected from the group consisting of: C1-C6 alkyl, C2-C6 alkenyl, C2-C6 alkynyl, substituted or unsubstituted amino, carboxyl, C1-C6 alkoxy, substituted C1-C6 alkyl, C1-C6 aminoalkyl, substituted C2-C6 alkenyl, substituted C2-C6 alkynyl, substituted C1-C6 alkoxy, substituted C1-C6 aminoalkyl, halogen (e.g., F), hydroxyl, amido, substituted amide, cyano, substituted or unsubstituted keto, substituted or unsubstituted alkoxycarbonyl, substituted or unsubstituted aryloxycarbonyl, substituted or unsubstituted heteroaryloxycarbonyl, and sulfhydryl (Structure 7).

In some embodiments, the targeting ligand of Formula I includes or consists of a linker having the following structure:

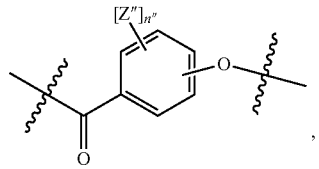

wherein n" is an integer from 0 to 4 (e.g., 1, 2, 3 or 4), and for each Z" present, Z" is independently selected, and Z" is independently selected from the group consisting of: C1-C6 alkyl, C2-C6 alkenyl, C2-C6 alkynyl, C1-C6 alkoxy, substituted C1-C6 alkyl, C1-C6 aminoalkyl, substituted C2-C6 alkenyl, substituted C2-C6 alkynyl, substituted or unsubstituted amino, carboxyl, substituted C1-C6 alkoxy, substituted C1-C6 aminoalkyl, halogen (e.g., F), hydroxyl, amido, substituted amide, cyano, substituted or unsubstituted keto, substituted or unsubstituted alkoxycarbonyl, substituted or unsubstituted aryloxycarbonyl, substituted or unsubstituted heteroaryloxycarbonyl, and sulfhydryl (Structure 8).

In some embodiments, the targeting ligand of Formula I includes or consists of a linker having the following structure:

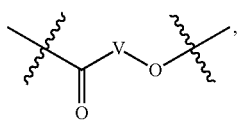

wherein V includes or consists of one or more substituted or unsubstituted cycloalkyl (e.g., cyclohexyl, cyclopropyl, cyclobutyl, cyclopentyl, cycloheptyl, cycloocty, etc.), cycloalkenyl (e.g., cyclohexenyl, cyclobutenyl, cyclopentenyl, cycloheptenyl, cyclooctenyl, cyclohexadienyl, cyclopentadienyl, cycloheptadienyl, cyclooctadienyl, etc.), aryl (e.g., phenyl, naphthyl, binapthyl, anthracenyl, etc.), heteroaryl (e.g., pyridyl, pyrimidinyl, pyrrole, imidazole, furan, benzofuran, indole, etc.), or heterocyclyl (e.g., tetrahydrofuran, tetrahydropyran, piperidine, pyrrolidine, etc.), or any covalently linked combination thereof. (Structure 9).

In some embodiments, the linkers suitable for use in the targeting ligands disclosed herein are generated from a compound that includes a rigid structure with a terminal carboxylic acid moiety (or activated ester thereof) on one end, and a terminal alcohol moiety on the other end. In some embodiments, the alcohol moiety is a secondary alcohol. In some embodiments, the alcohol moiety is a tertiary alcohol. In some embodiments, the alcohol moiety is a primary alcohol. The carboxylic acid moiety (or activated ester thereof) is suitable for attachment to the branch point group, while the alcohol moiety is suitable for attachment to the phosphorus atom of a phosphoramidite through a phosphitylation reaction with a phosphoramidite forming reagent. Example phosphitylation reactions using phosphoramidite forming reagents are described in the Examples herein. The linker structures disclosed herein are suitable for preparation of the targeting ligand as a phosphoramidite compound.

In some embodiments, the linker is linked to an expression-inhibiting oligomeric compound that is a double-stranded RNAi agent. In some embodiments, the linker is linked to the 5' end of the sense strand of a double-stranded RNAi agent. In some embodiments, the linker is linked to the 3' end of the sense strand of a double-stranded RNAi agent. In some embodiments the linker is linked to the 3' end of the antisense strand of a double-stranded RNAi agent. In some embodiments, the linker is linked to the 5' end of the antisense strand of a double-stranded RNAi agent.

In some embodiments, the linker is linked to a cleavable moiety. In some embodiments, a terminal phosphate group of an expression-inhibiting oligomeric compound can serve as a cleavable moiety. In some embodiments, an independently selected cleavable moiety is linked to a linker. As used herein, a cleavable moiety is a group that is stable outside of the cell, but upon entry into the target cell is cleaved. Cleavable moieties are susceptible to cleavage under certain conditions, such as pH, or certain cleavage agents, such as molecules that promote degradation or redox agents.

In some embodiments, the cleavable moiety may be susceptible to pH. For example, endosomes and lysosomes are known to generally have a more acidic pH (pH of approximately 4.5 to 6.5) than human blood (pH of approximately 7.35 to 7.45), and as such may promote the cleavage of a cleavable moiety.

In some embodiments, a cleavable moiety is a phosphate group. Phosphate groups may be cleaved by agents that are known to degrade or hydrolyze phosphate groups.

In some embodiments, the targeting ligands disclosed herein comprise a branch point group that includes a linker replacement group, instead of a linker, as shown in Formula II. When the linker is replaced with a linker replacement moiety, the linker replacement moiety is a part of the branch point group.

In some embodiments, the linkers and linker replacement moieties disclosed herein permits the incorporation of only a single isomer of a targeting ligand, which can provide additional advantages for oligonucleotide therapeutic products.

Branch Point Groups

The targeting ligands disclosed herein comprise at least one branch point group. In some embodiments, the branch point group of the targeting ligands disclosed herein is linked to a linker. In some embodiments, the branch point group is linked to a linker on one end, and the branch point group is linked to one or more tethers on the other end(s). In some embodiments, the branch point group is linked to an expression-inhibiting oligomeric compound via an additional group or groups. In some embodiments, the branch point group includes a linker replacement moiety and is linked to an expression-inhibiting oligomeric compound.

The branch point groups disclosed herein can be of any group which permits attachment of one or more targeting moieties and further permits attachment to a linker disclosed herein, or, alternatively, if the branch point group comprises a linker replacement moiety, the branch point group can be any group that includes a linker replacement moiety that permits attachment to a therapeutic compound, such as an expression-inhibiting oligomeric compound.

For the branch point groups of Formula I, disclosed herein, prior to conjugation to a linker, the branch point group compound that serves to generate the branch point group has one terminal amine for each desired linkage to a linker, and one terminal carboxylic acid moiety (or activated ester thereof) for each desired linkage to a tether.

In some embodiments, the targeting ligand includes a branch point having a structure selected from the following:

(Structure 201)

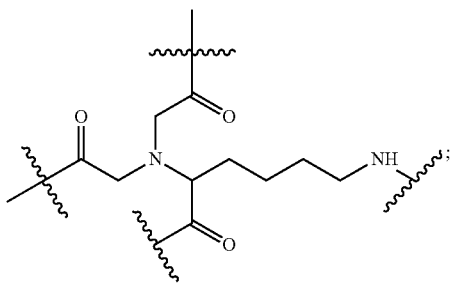

(Structure 202)
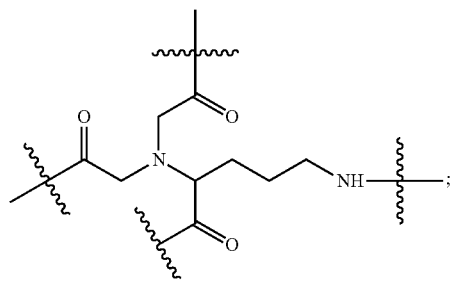
(Structure 203)
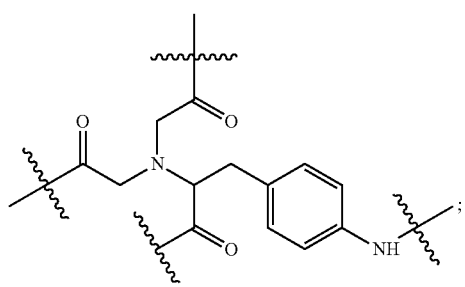
(Structure 204)
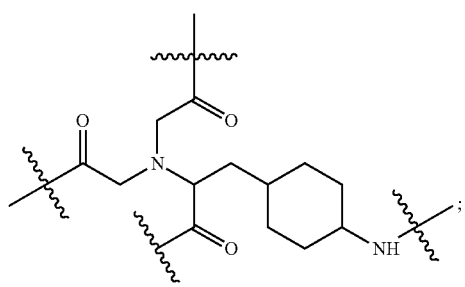
(Structure 205)
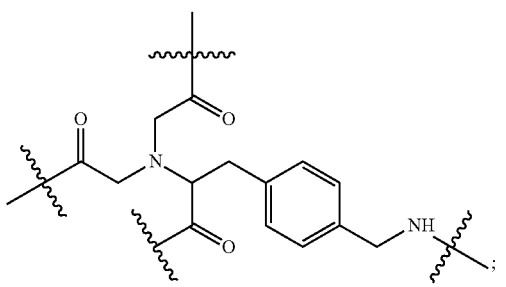
(Structure 206)
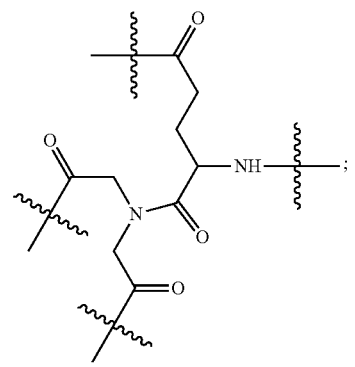
(Structure 207)
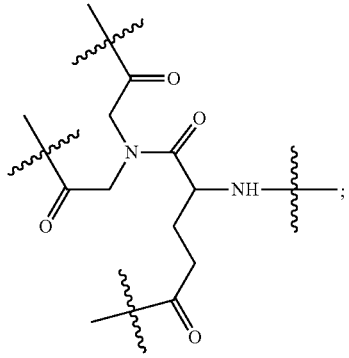
(Structure 208)
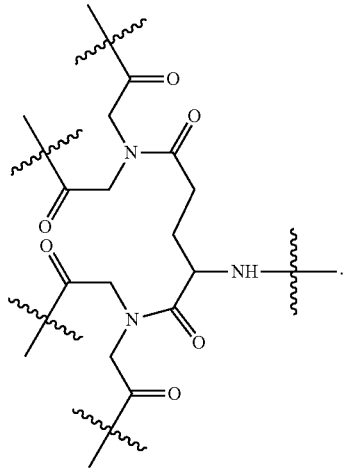
In some embodiments, the targeting ligand includes a branch point having the following structure:
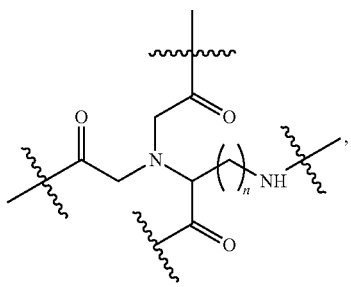
wherein n is an integer from 1 to 20 (Structure 209).
In some embodiments, the targeting ligand includes a branch point having the following structure:
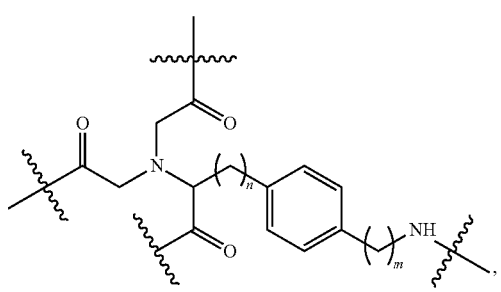

wherein m is an integer from 0 to 20 (e.g., 0, 1, 2, 3, 4, 5, 6, 7, 8, 9, 10, 11, 12, 13, 14, 15, 16, 17, 18, 19 or 20), and n is an integer from 0 to 20 (e.g., 0, 1, 2, 3, 4, 5, 6, 7, 8, 9, 10, 11, 12, 13, 14, 15, 16, 17, 18, 19 or 20) (Structure 210).

In some embodiments, the targeting ligand includes a branch point having the structure represented by the following:

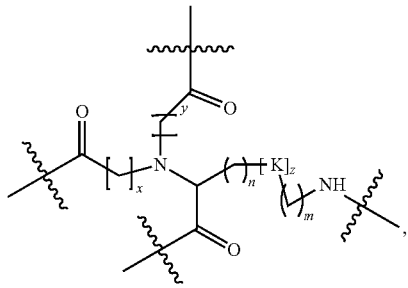

wherein m is an integer from 0 to 20 (e.g., 0, 1, 2, 3, 4, 5, 6, 7, 8, 9, 10, 11, 12, 13, 14, 15, 16, 17, 18, 19 or 20); n is an integer from 0 to 20 (e.g., 0, 1, 2, 3, 4, 5, 6, 7, 8, 9, 10, 11, 12, 13, 14, 15, 16, 17, 18, 19 or 20); x is an integer from to 1 to 10 (e.g., 1, 2, 3, 4, 5, 6, 7, 8, 9, or 10); y is an integer from 1 to 10 (e.g., 1, 2, 3, 4, 5, 6, 7, 8, 9, 10, 11, 12, 13, 14, 15, 16, 17, 18, 19 or 20); z is an integer from 1 to 4 (e.g., 1, 2, 3, or 4); and K is selected from the group consisting of substituted or unsubstituted cycloalkyl (e.g., cyclohexyl, cyclopropyl, cyclobutyl, cyclopentyl, cycloheptyl, cycloocty, etc.), substituted or unsubstituted cycloalkenyl (e.g., cyclohexenyl, cyclobutenyl, cyclopentenyl, cycloheptenyl, cyclooctenyl, cyclohexadienyl, cyclopentadienyl, cycloheptadienyl, cyclooctadienyl, etc.), substituted or unsubstituted aryl (e.g., phenyl, naphthyl, binapthyl, anthracenyl, etc.), substituted or unsubstituted heteroaryl (e.g., pyridyl, pyrimidinyl, pyrrole, imidazole, furan, benzofuran, indole, etc.), and substituted or unsubstituted heterocyclyl (e.g., tetrahydrofuran, tetrahydropyran, piperidine, pyrrolidine, etc.), or covalently linked combinations thereof (Structure 211).

In some embodiments, the targeting ligand includes a branch point having the following structure:

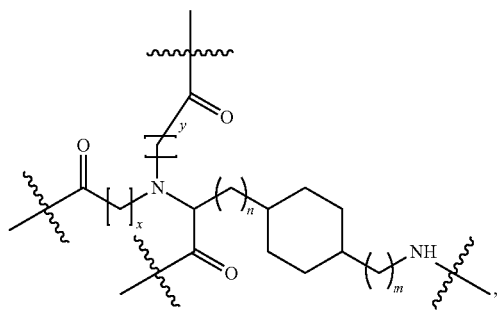

wherein m is an integer from 0 to 20 (e.g., 0, 1, 2, 3, 4, 5, 6, 7, 8, 9, 10, 11, 12, 13, 14, 15, 16, 17, 18, 19 or 20); n is an integer from 0 to 20 (e.g., 0, 1, 2, 3, 4, 5, 6, 7, 8, 9, 10, 11, 12, 13, 14, 15, 16, 17, 18, 19 or 20); x is an integer from to 1 to 10 (e.g., 1, 2, 3, 4, 5, 6, 7, 8, 9, or 10); and y is an integer from 1 to 10 (e.g., 1, 2, 3, 4, 5, 6, 7, 8, 9, or 10) (Structure 212).

In some embodiments, the targeting ligand includes a branch point having the following structure:

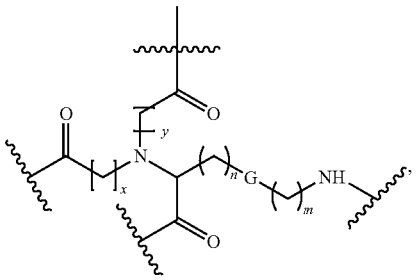

wherein m is an integer from 0 to 20 (e.g., 0, 1, 2, 3, 4, 5, 6, 7, 8, 9, 10, 11, 12, 13, 14, 15, 16, 17, 18, 19 or 20); n is an integer from 0 to 20 (e.g., 0, 1, 2, 3, 4, 5, 6, 7, 8, 9, 10, 11, 12, 13, 14, 15, 16, 17, 18, 19 or 20); x is an integer from to 1 to 10 (e.g., 1, 2, 3, 4, 5, 6, 7, 8, 9, or 10); y is an integer from 1 to 10 (e.g., 1, 2, 3, 4, 5, 6, 7, 8, 9, or 10); and G is selected from the group consisting of

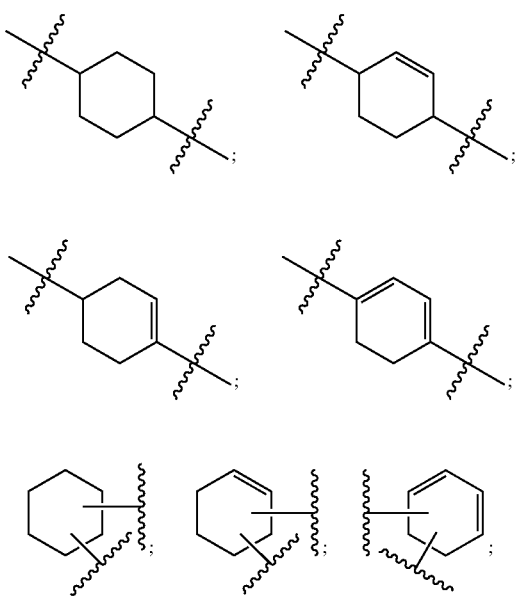

or any substituted or unsubstituted cyclic or heterocyclic structure having a ring size of 5, 6, 7, 8, or 9 atoms, for example, substituted or unsubstituted cycloalkyl (e.g., cyclohexyl, cyclopropyl, cyclobutyl, cyclopentyl, cycloheptyl, cycloocty, etc.), substituted or unsubstituted cycloalkenyl (e.g., cyclohexenyl, cyclobutenyl, cyclopentenyl, cycloheptenyl, cyclooctenyl, cyclohexadienyl, cyclopentadienyl, cycloheptadienyl, cyclooctadienyl, etc.), substituted or unsubstituted aryl (e.g., phenyl, naphthyl, binapthyl, anthracenyl, etc.), substituted or unsubstituted heteroaryl (e.g., pyridyl, pyrimidinyl, pyrrole, imidazole, furan, benzofuran, indole, etc.), or substituted or unsubstituted heterocyclyl (e.g., tetrahydrofuran, tetrahydropyran, piperidine, pyrrolidine, etc.) (Structure 213).

In some embodiments, the targeting ligand includes a branch point group having the following structure:

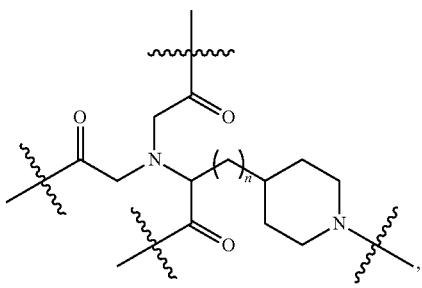

wherein n is an integer from 0 to 20 (e.g., 0, 1, 2, 3, 4, 5, 6, 7, 8, 9, 10, 11, 12, 13, 14, 15, 16, 17, 18, 19 or 20) (Structure 214).

In some embodiments, the targeting ligand includes a branch point group having the following structure:

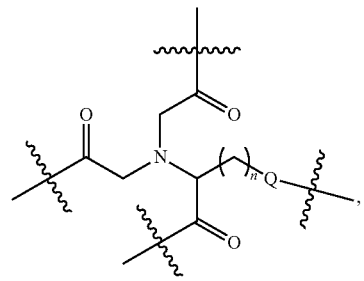

wherein n is an integer from 0 to 20 (e.g., 0, 1, 2, 3, 4, 5, 6, 7, 8, 9, 10, 11, 12, 13, 14, 15, 16, 17, 18, 19 or 20), and Q is selected from the group consisting of:

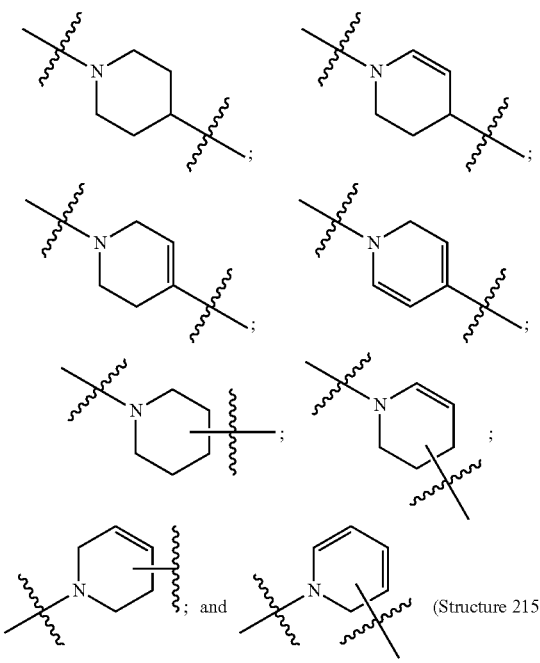

(Structure 215).

In some embodiments, the targeting ligand includes a branch point group having the following structure:

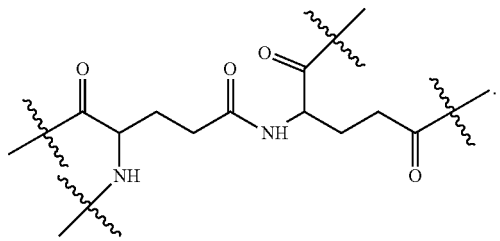

(Structure 216)

In some embodiments, the targeting ligand includes a branch point group having the following structure:

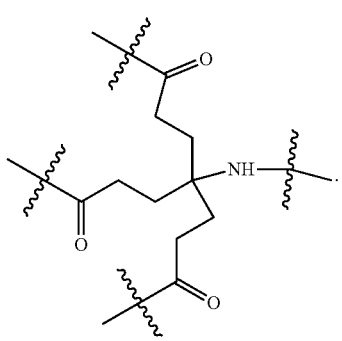

(Structure 217)

In some embodiments, the targeting ligand includes a branch point group having the following structure:

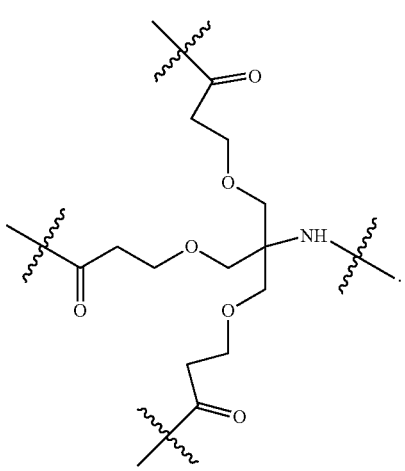

(Structure 218)

In some embodiments, the targeting ligand includes a branch point group having the following structure:

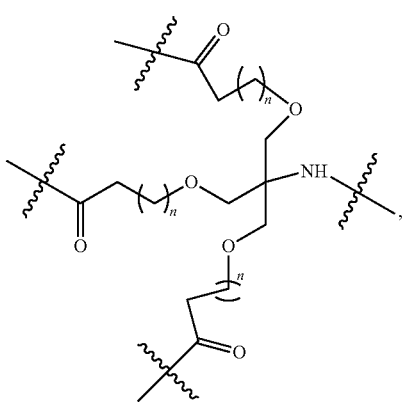

wherein n is an integer selected from 1 to 7 (e.g., 1, 2, 3, 4, 5, 6, or 7) (Structure 219). In some embodiments, n in Structure 219 is 1. In some embodiments, n in Structure 219 is 2. In some embodiments, n in Structure 219 is 3. In some embodiments, n in Structure 219 is 4. In some embodiments, n in Structure 219 is 5. In some embodiments, n in Structure 219 is 6. In some embodiments, n in Structure 219 is 7.

In some embodiments, the targeting ligand includes a branch point group that includes a linker replacement group.

In some embodiments, the targeting ligand includes a branch point group that includes a linker replacement moiety having the structure represented by the following:

(Structure 220)

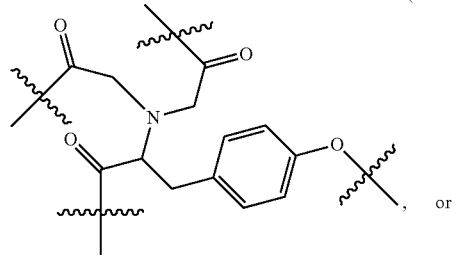, or (Structure 221)

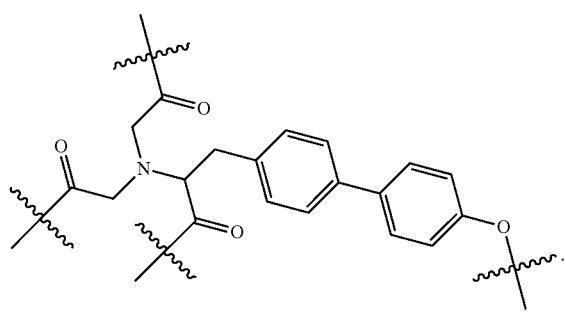.

Tethers

The targeting ligands disclosed herein comprise one or more tethers. A tether is linked between the branch point group and each targeting moiety. In some embodiments, the tether is linked directly to the targeting ligand on one end and directly to the branch point group on the other end. In some embodiments, the tether is linked directly to the targeting ligand on one end, and indirectly to the branch point group on the other end. In some embodiments, the tether is linked indirectly to the targeting ligand on one end and indirectly to the branch point group on the other end. In some embodiments, a targeting ligand described herein includes three tethers and three targeting moieties. In some embodiments, a targeting ligand described herein includes four tethers and four targeting moieties. In some embodiments, a targeting ligand described herein includes one tether and one targeting moiety. In some embodiments, a targeting ligand described herein includes multiple tethers and multiple targeting moieties.

In some embodiments, additional tethers or other groups are inserted between the tether and the targeting moiety of Formula I or Formula II. In some embodiments, a second tether is inserted between a tether and a targeting moiety of Formula I or Formula II. In some embodiments, a second tether and a third tether is inserted between a tether and a targeting moiety of Formula I or Formula II. In some embodiments, a second, third, and fourth tether is inserted between a tether and a targeting moiety of Formula I or Formula II. As disclosed herein, there is at least one tether present for every targeting moiety. In some embodiments, there is more than one tether present for each targeting moiety. The targeting ligands disclosed herein are intended to cover such compositions.

In some embodiments, additional groups can be inserted between the tether and the branch point group of Formula I or Formula II.

As disclosed herein, the tether serves as a spacer that may further add flexibility and/or length to the linkage between the targeting moiety and the branch point group, linker, and therapeutic compound. In some embodiments, the tether includes alkyl groups (including cycloalkyl groups), alkenyl groups (including cycloalkenyl groups), alkynyl groups, aryl groups, aralkyl groups, aralkenyl groups, or aralkynyl groups. In some embodiments, the tether includes one or more heteroatoms, heterocycles, heteroaryls, amino acids, nucleotides, or saccharides.

In some embodiments, the targeting ligand includes a tether having the following structure:

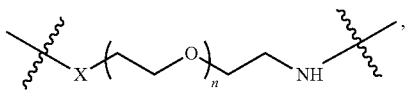, wherein n is an integer from 1 to 20 (e.g., 1, 2, 3, 4, 5, 6, 7, 8, 9, 10, 11, 12, 13, 14, 15, 16, 17, 18, 19 or 20), and X is O, S, or NH (Structure 301).

In some embodiments, the targeting ligand includes a tether having the following structure:

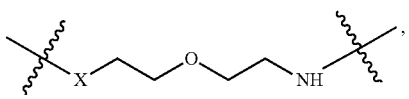, wherein X is O, S, or NH (Structure 302).

In some embodiments, the targeting ligand includes a tether having the following structure:

(Structure 302a)

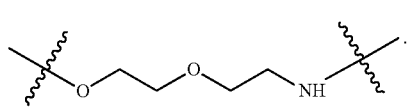.

In some embodiments, the targeting ligand includes a tether having the following structure:

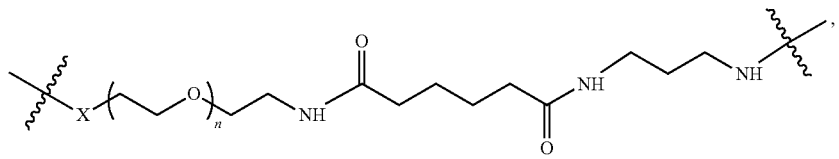

wherein n is an integer from 1 to 20 (e.g., 1, 2, 3, 4, 5, 6, 7, 8, 9, 10, 11, 12, 13, 14, 15, 16, 17, 18, 19 or 20), and X is O, S, or NH. (Structure 303).

In some embodiments, the targeting ligand includes a tether having the following structure:

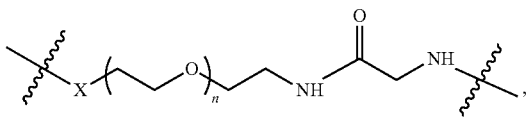

wherein n is an integer from 1 to 20 (e.g., 1, 2, 3, 4, 5, 6, 7, 8, 9, 10, 11, 12, 13, 14, 15, 16, 17, 18, 19 or 20), and X is O, S, or NH. (Structure 304).

In some embodiments, the targeting ligand includes a tether having the following structure:

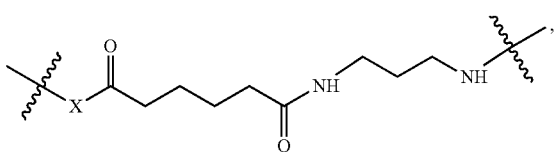

wherein X is O, S, or NH (Structure 305).

In some embodiments, the targeting ligand includes a tether having the following structure:

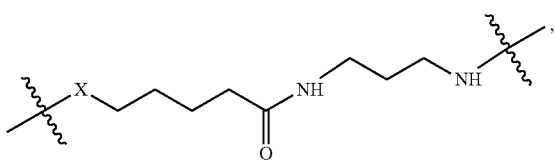

wherein X is O, S, or NH (Structure 306).

In some embodiments, the targeting ligand includes more than one type of tether. In some embodiments, the tether acts as a flexible hydrophilic spacer (See, for example, U.S. Pat. No. 5,885,968; and Biessen et al. J. Med. Chem. 1995, 39, 1538-1546, both of which are incorporated herein by reference in their entirety), and includes a PEG spacer. In other embodiments, the PEG spacer has 1 to 20 ethylene units (PEG$_1$ to PEG$_{20}$). For example, the PEG spacer has 1, 2, 3, 4, 5, 6, 7, 8, 9, 10, 11, 12, 13, 14, 15, 16, 17, 18, 19, or 20 ethylene units.

Targeting Moieties

The targeting ligands disclosed herein can include one to four, or more than four, targeting moieties.

In some embodiments, the targeting ligands may be a galactose cluster. As used herein, a galactose cluster includes a targeting ligand having two to four terminal galactose derivatives.

As used herein, the term galactose derivative includes both galactose and derivatives of galactose having affinity for the asialoglycoprotein receptor equal to or greater than that of galactose. A galactose derivative is a saccharide sugar that is a type of targeting moiety. A terminal galactose derivative is linked to a tether through the C-1 carbon of the saccharide.

In some embodiments, the targeting ligand is comprised of three terminal galactosamines or galactosamine derivatives (such as N-acetyl-galactosamine) each having affinity for the asialoglycoprotein receptor. In some embodiments, the targeting ligand includes three terminal N-acetyl-galactosamines (GalNAc or NAG) as the targeting moieties. For example, each of Structures 1001, 1002, 1004 and 1008 are targeting ligands having three terminal N-acetyl-galactosamines as the targeting moieties.

In some embodiments, each targeting moiety includes a galactosamine derivative that is N-acetyl-galactosamine. Other saccharides having affinity for the asialoglycoprotein receptor that may be used as targeting moieties may be selected from the list including: galactose, galactosamine, N-formyl-galactosamine, N-propionyl-galactosamine, N-n-butanoylgalactosamine, and N-iso-butanoylgalactosamine. The affinities of numerous galactose derivatives for the asialoglycoprotein receptor have been studied (see, for example, Iobst, S. T. and Drickamer, K. J.B.C. 1996, 271, 6686, which is incorporated by reference herein in its entirety) or are readily determined using methods well known and commonly used in the art.

In some embodiments, the targeting moiety is a cell-targeting moiety.

In some embodiments, the targeting moiety includes an N-acetyl-galactosamine:

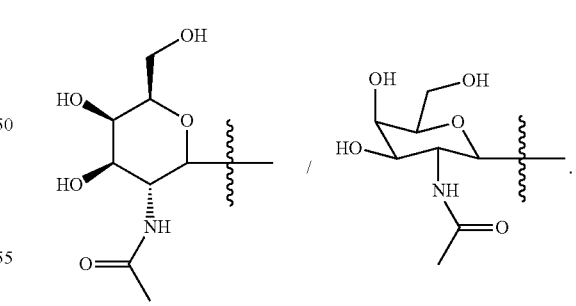

In some embodiments, the targeting ligand includes three targeting moieties. In some embodiments, the targeting ligand includes four targeting moieties. In some embodiments, the targeting ligand includes one targeting moiety. In some embodiments, the targeting ligand includes two targeting moieties. In some embodiments, the targeting ligand includes four or more targeting moieties.

In some embodiments, the targeting moiety includes one or more of galactose, galactosamine, N-formyl-galactosamine, N-acetyl-galactosamine, N-propionyl-galactosamine, N-n-butanoylgalactosamine, or N-iso-butanoylgalactosamine.

For example, in some embodiments, the N-acetyl-galactosamine targeting moieties in any of Structures 1001 through 1027 can be replaced with alternative targeting moieties. Such alternative targeting moieties include, for example, galactose, galactosamine, N-formyl-galactosamine, N-acetyl-galactosamine, N-propionyl-galactosamine, N-n-butanoylgalactosamine, or N-iso-butanoylgalactosamine.

Additionally, in some embodiments, the targeting moieties of Structures 1001 through 1027 may be replaced with, for example, other carbohydrates; glycans; haptens; vitamins; folate; biotin; aptamers; and/or peptides, such as RGD-containing peptides, insulin, EGF, and/or transferrin.

In some embodiments, the targeting ligand is in the form of an N-acetyl-galactosamine trimer. In some embodiments, the targeting ligand is in the form of an N-acetyl-galactosamine tetramer.

Representative Targeting Ligand Structures, and Phosphoramidite Compounds Including Targeting Ligands The targeting ligands disclosed herein may be comprised of one or more targeting moieties, tethers, branch point groups, and linkers. The targeting ligands disclosed herein may be comprised of one, two, three, four, or more than four targeting moieties.

chemical synthesis of RNA and DNA. In some embodiments, the phosphoramidite-containing targeting ligands disclosed herein are added to the 5' end of the sense strand of a double-stranded RNAi agent. It can be especially advantageous to prepare the targeting ligand as a phosphoramidite when the targeting ligand is to be linked to the 5' terminal end of an expression-inhibiting oligomeric compound. Not wishing to be bound by theory, it is understood that preparing the targeting ligand as a phosphoramidite when the targeting ligand is linked to the 5' terminal end of an expression-inhibiting oligomeric compound allows for the linkage of the targeting ligand as the last component (thus reducing manufacturing costs), as well as potentially permits the targeting ligand to block the loading of the sense strand into RISC when the targeting ligand is attached to the 5' terminal end of the sense strand of a double-stranded RNAi agent. When an expression-inhibiting oligomeric compound is a double-stranded RNAi agent, the targeting ligand can be prepared as a phosphoramidite compound when the targeting ligand is to be linked to the 5' terminal end of the sense strand of the RNAi agent.

In some embodiments, the targeting ligand has the structure represented by the following:

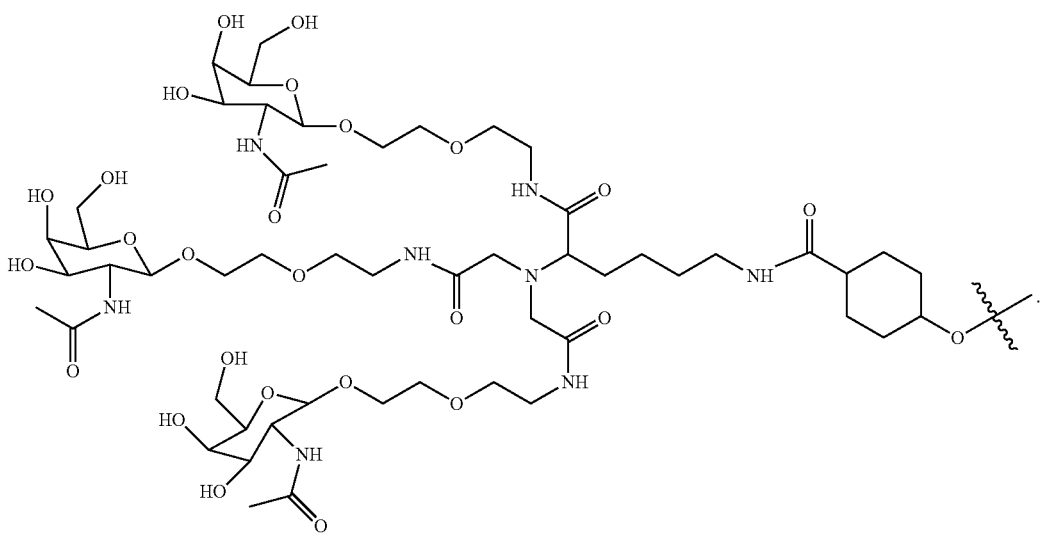

(Structure 1001)

In some embodiments, the targeting ligands disclosed herein are synthesized to be in the form of a phosphoramidite compound. Phosphoramidites are widely used in the In some embodiments, an expression-inhibiting oligomeric compound is linked to the targeting ligand and has the structure represented by the following:

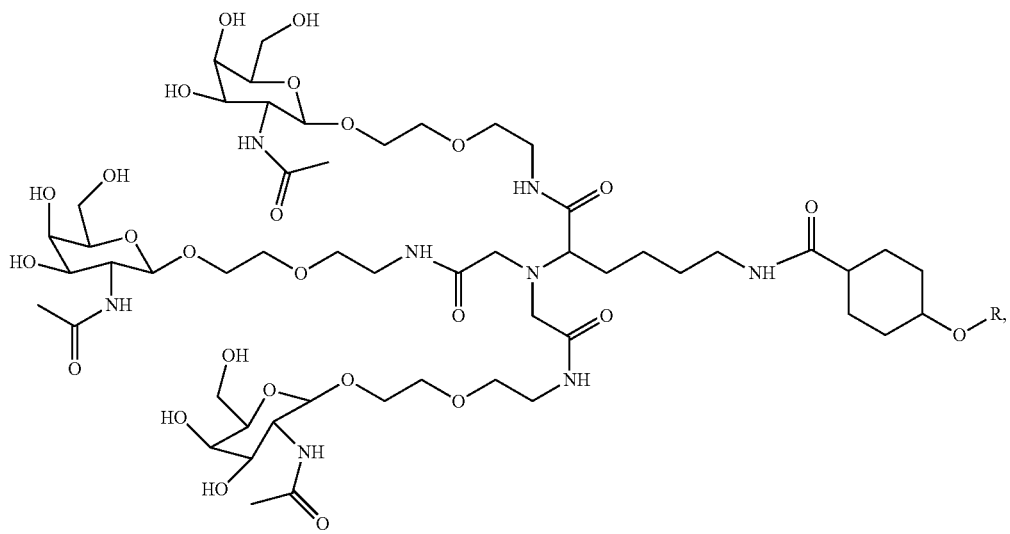

wherein R includes or consists of an expression-inhibiting oligomeric compound. (Structure 1001a).

In some embodiments, an expression-inhibiting oligomeric compound is linked to the targeting ligand and has the structure represented by the following:

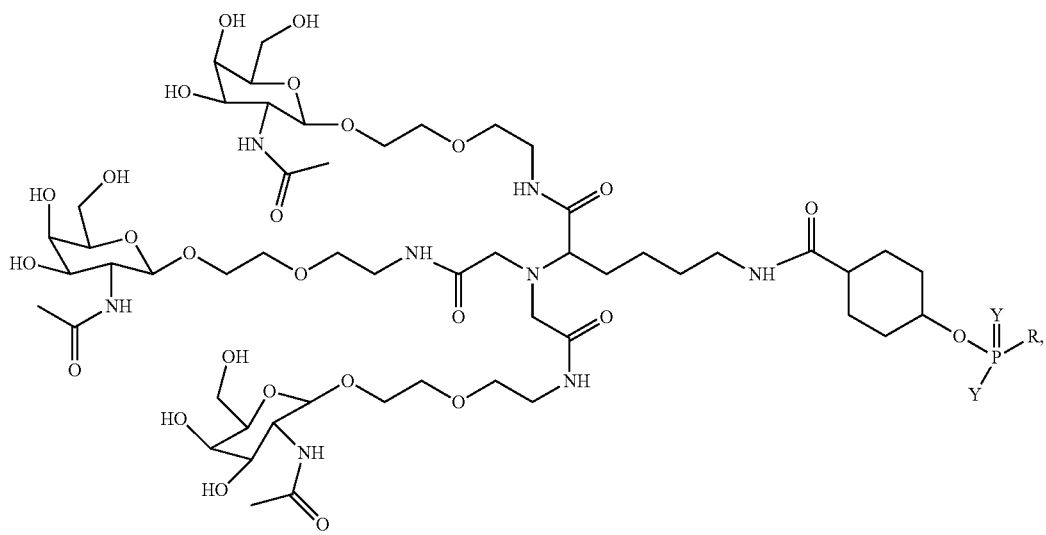

wherein R consists of or includes an expression-inhibiting oligomeric compound; Y is O or S; and Y' is O⁻, S⁻, or NH⁻. (Structure 1001a(i)).

In some embodiments, the targeting ligand is a phosphoramidite-containing compound having the structure represented by the following:

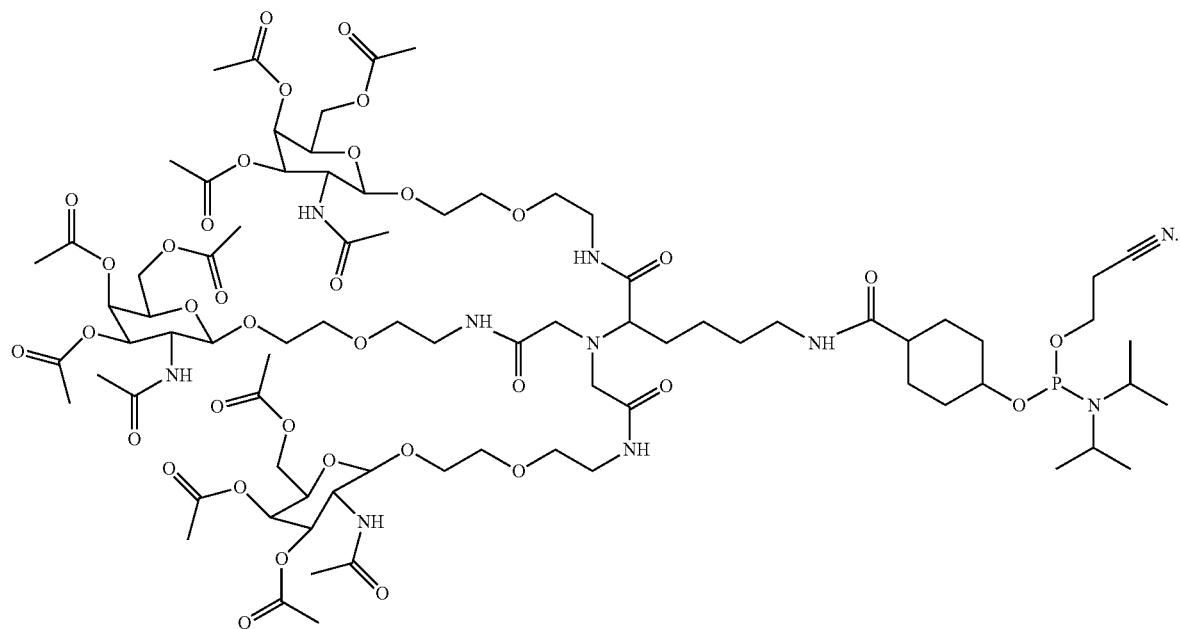
(Structure 1001b)
In some embodiments, the targeting ligand has the structure represented by the following:
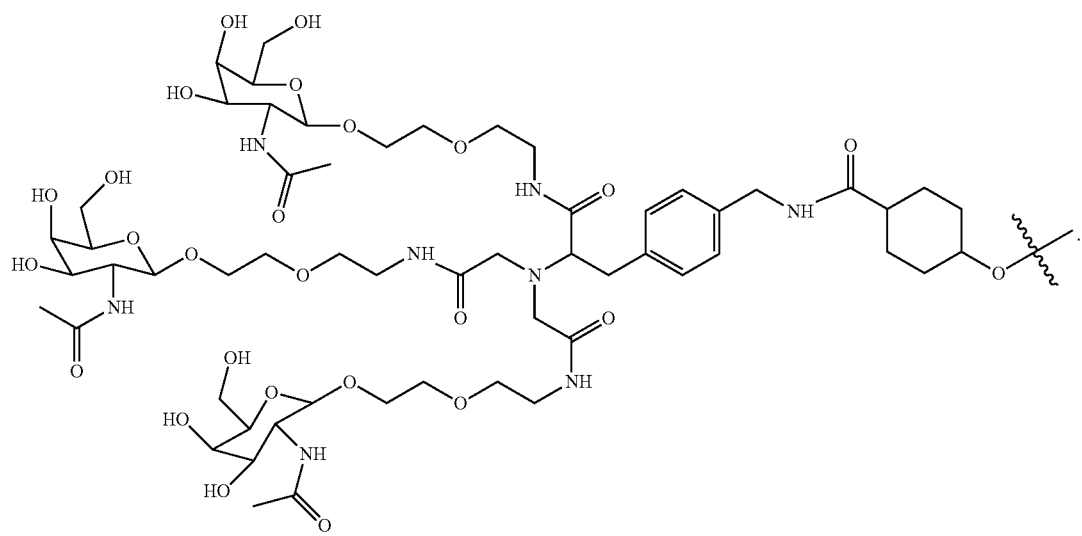
(Structure 1002)
In some embodiments, an expression-inhibiting oligomeric compound is linked to the targeting ligand and has the structure represented by the following:

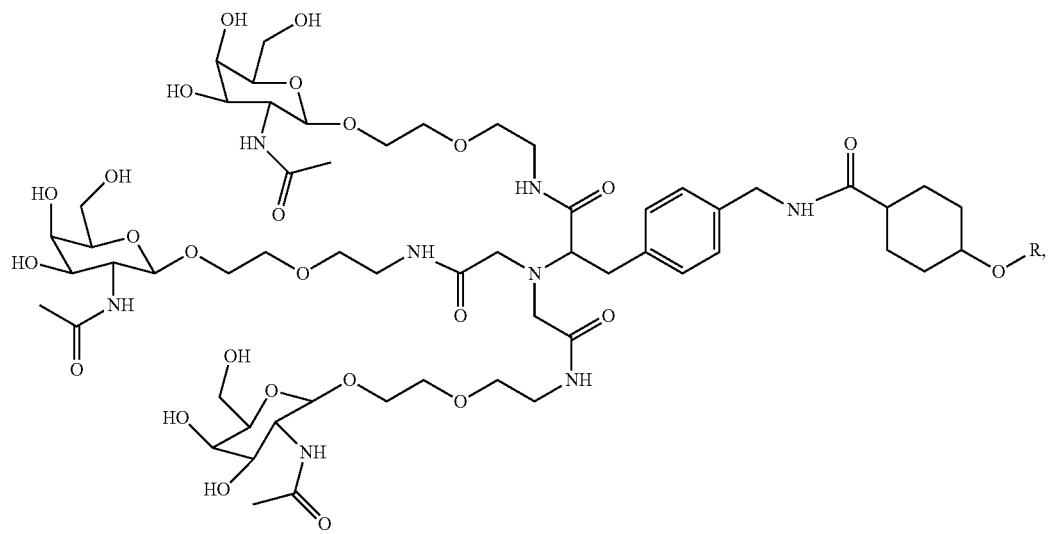

wherein R includes or consists of an expression-inhibiting oligomeric compound. (Structure 1002a).

In some embodiments, an expression-inhibiting oligomeric compound is linked to the targeting ligand and has the structure represented by the following:

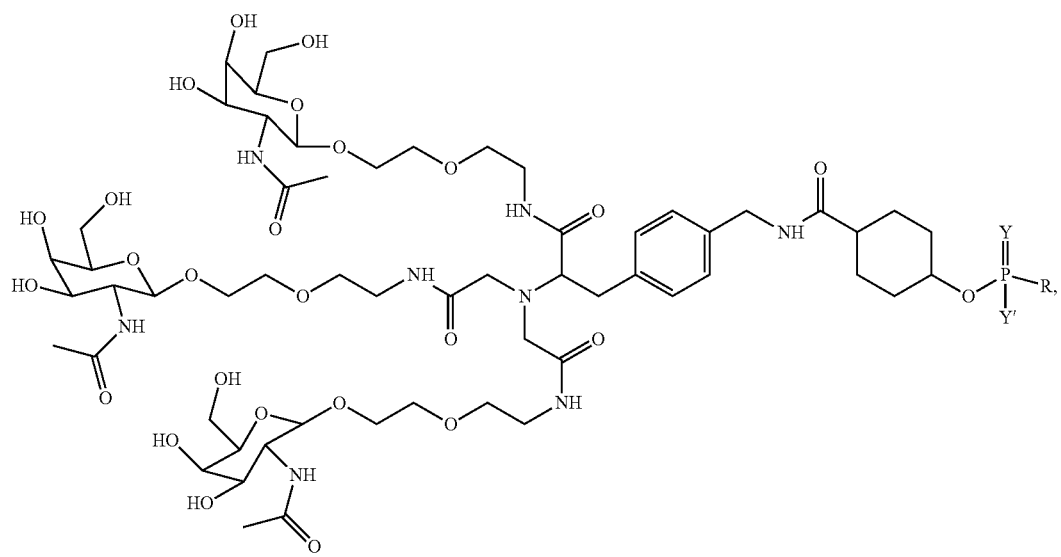

wherein R consists of or includes an expression-inhibiting oligomeric compound; Y is O or S; and Y' is O⁻, S⁻, or NH⁻. (Structure 1002a(i)).

In some embodiments, the targeting ligand is a phosphoramidite-containing compound having the structure represented by the following:

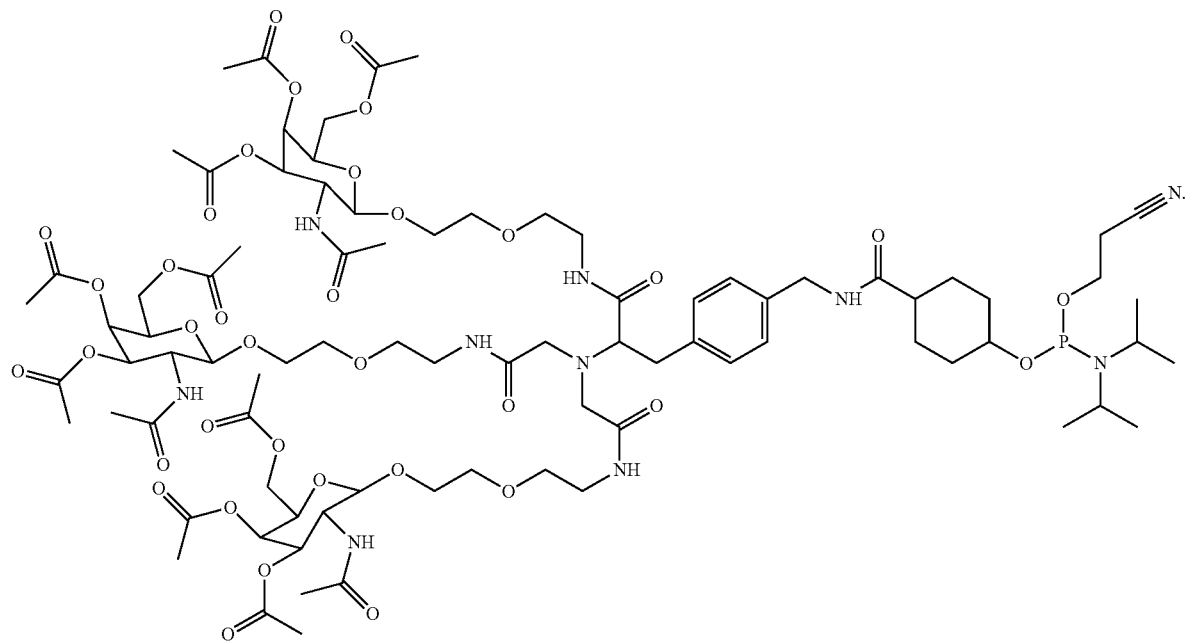
(Structure 1002b)
In some embodiments, the targeting ligand has the structure represented by the following:
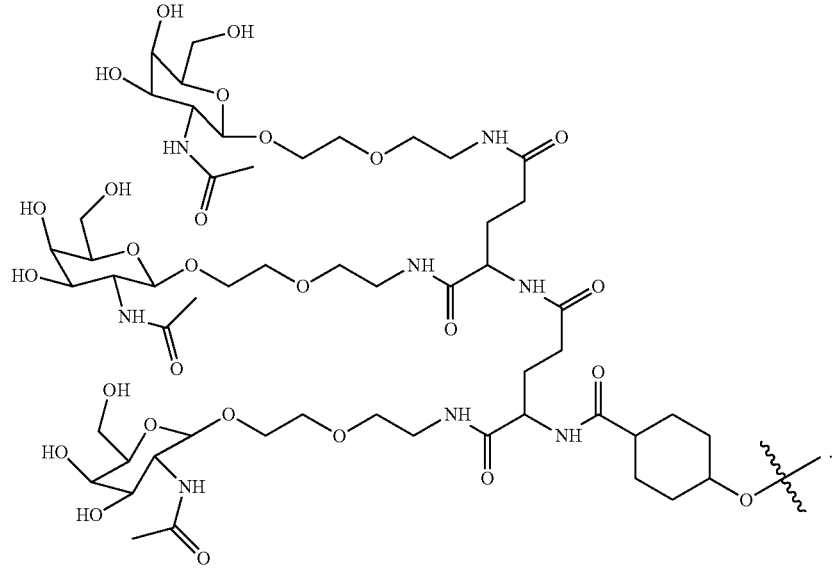
(Structure 1003)
In some embodiments, an expression-inhibiting oligomeric compound is linked to the targeting ligand and has the structure represented by the following:

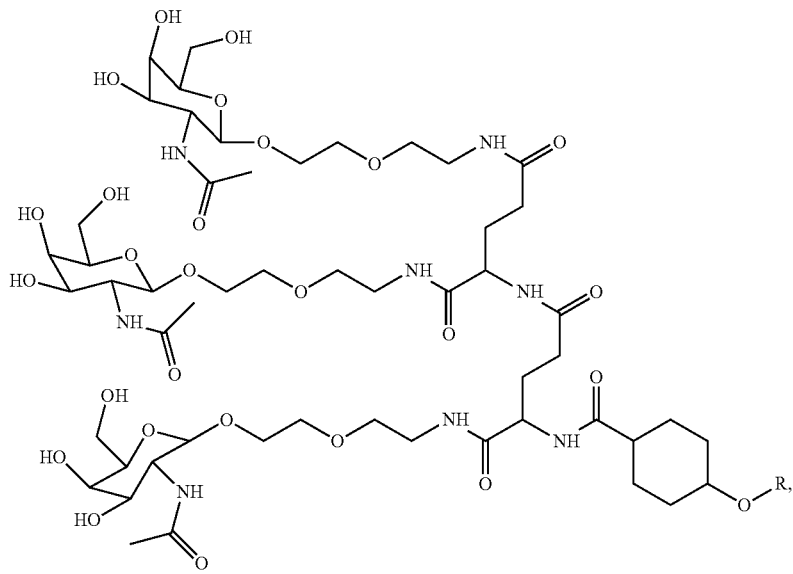

wherein R includes or consists of an expression-inhibiting oligomeric compound. (Structure 1003a).

In some embodiments, an expression-inhibiting oligomeric compound is linked to the targeting ligand and has the structure represented by the following:

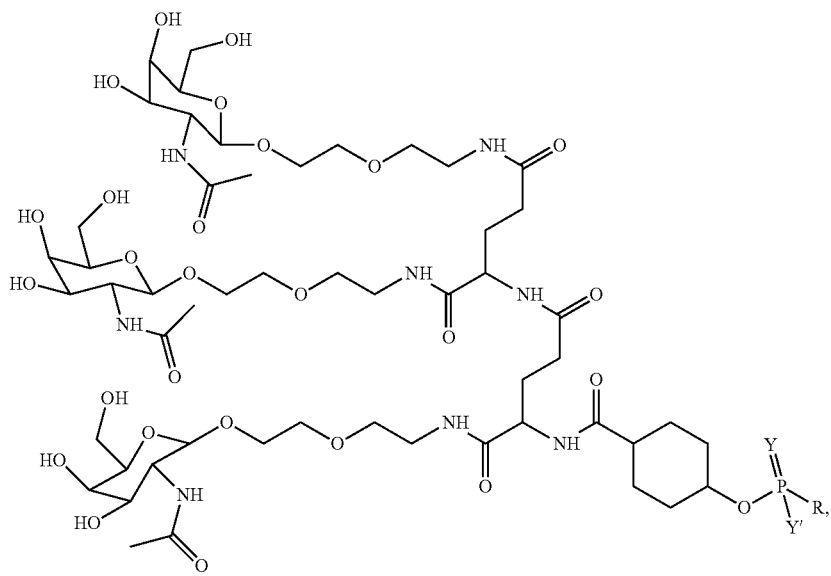

wherein R consists of or includes an expression-inhibiting oligomeric compound; Y is O or S; and Y' is O$^-$, S$^-$, or NH$^-$. (Structure 1003a(i)).

In some embodiments, the targeting ligand is a phosphoramidite-containing compound having the structure represented by the following:

(Structure 1003b)
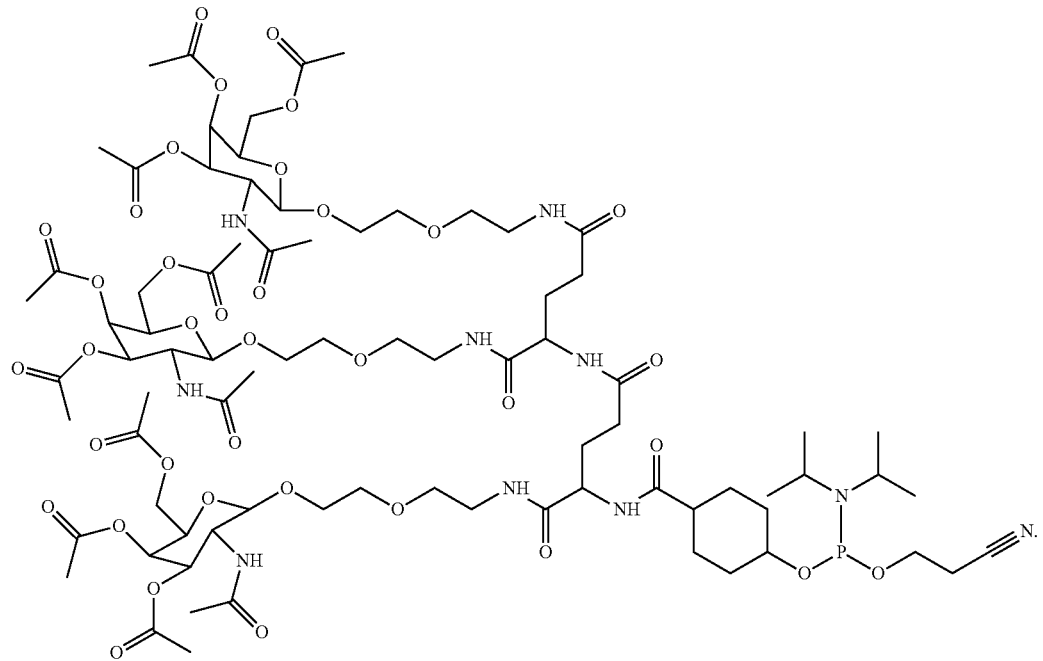
In some embodiments, the targeting ligand has the structure represented by the following:
(Structure 1004)
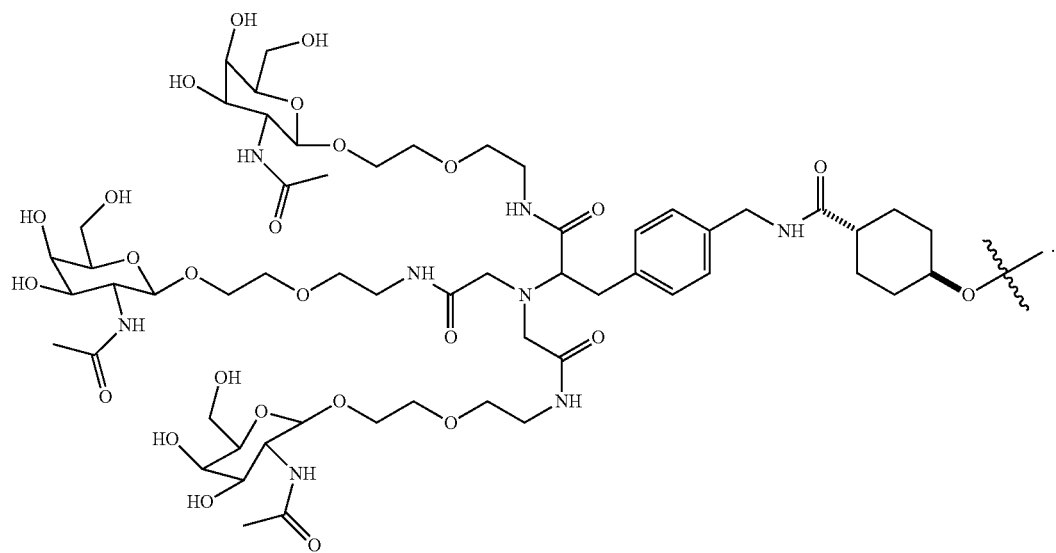
In some embodiments, an expression-inhibiting oligomeric compound is linked to the targeting ligand and has the structure represented by the following:

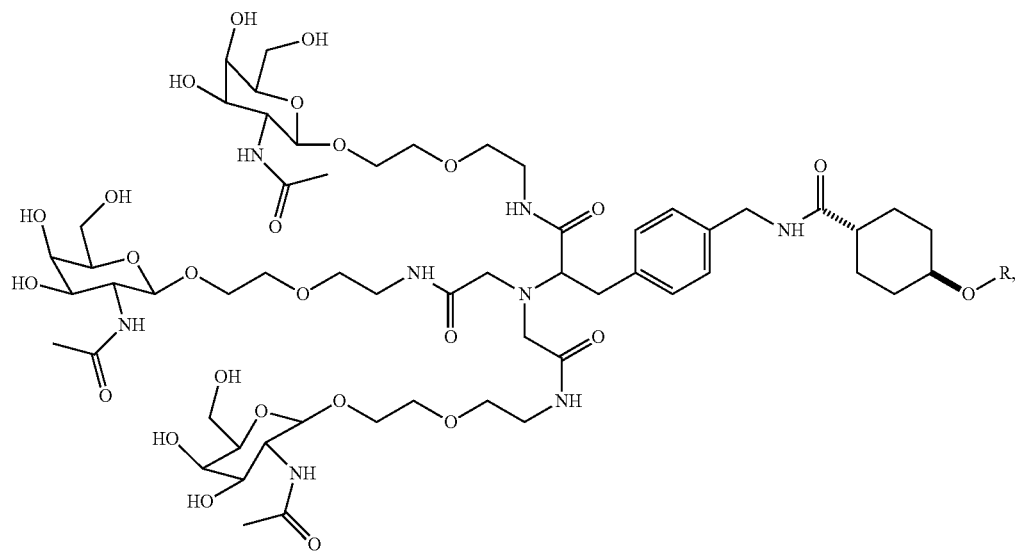

wherein R includes or consists of an expression-inhibiting oligomeric compound. (Structure 1004a).

In some embodiments, an expression-inhibiting oligomeric compound is linked to the targeting ligand and has the structure represented by the following:

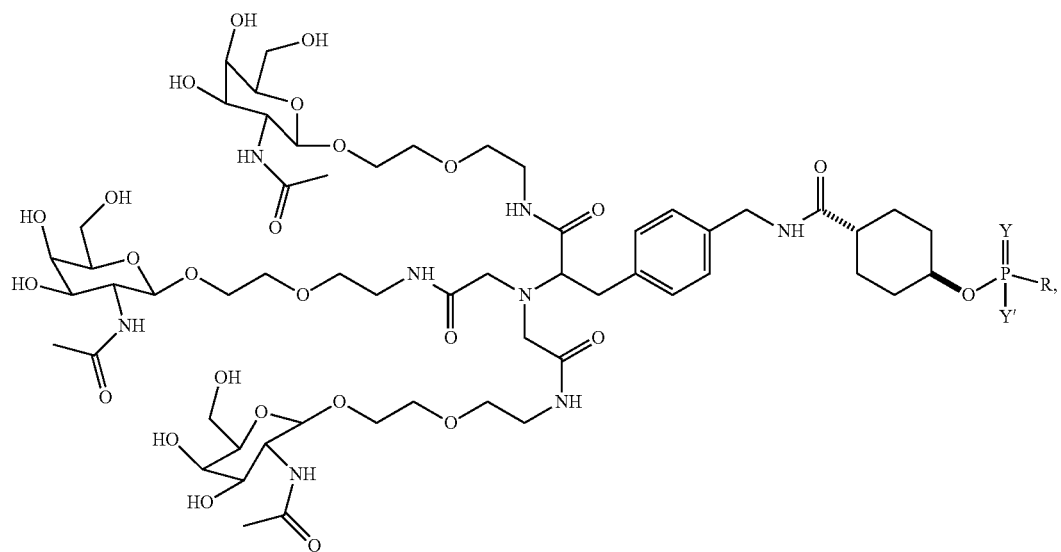

wherein R consists of or includes an expression-inhibiting oligomeric compound; Y is O or S; and Y' is O⁻, S⁻, or NH⁻. (Structure 1004a(i)).

In some embodiments, the targeting ligand is a phosphoramidite-containing compound having the structure represented by the following:

(Structure 1004b)
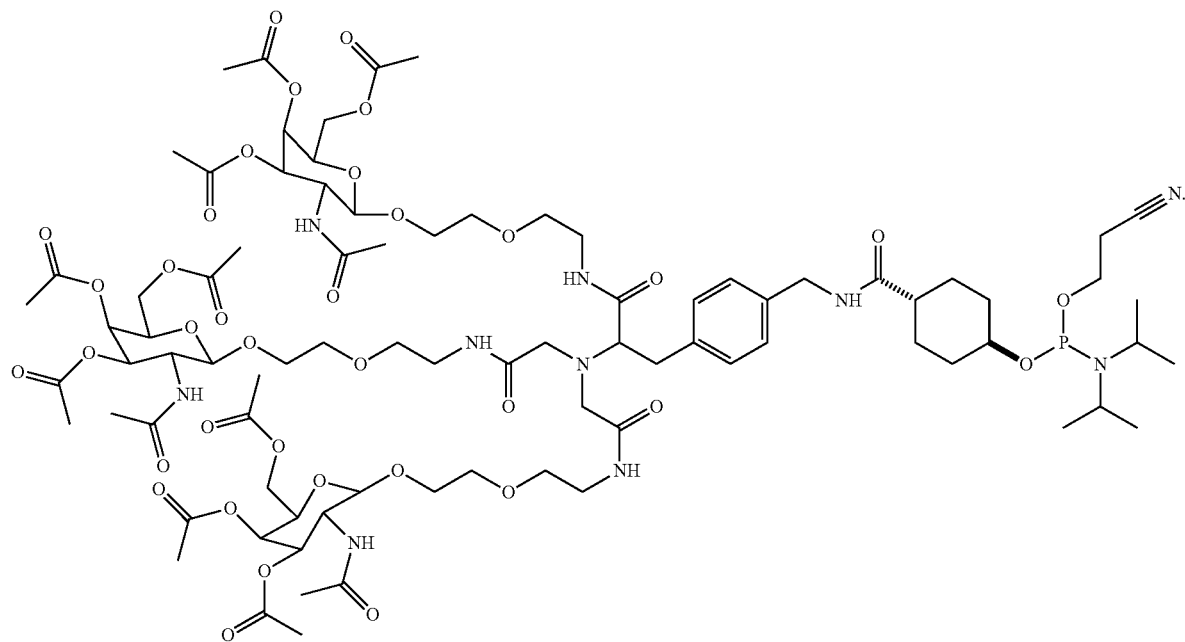
In some embodiments, the targeting ligand has the structure represented by the following:
(Structure 1005)
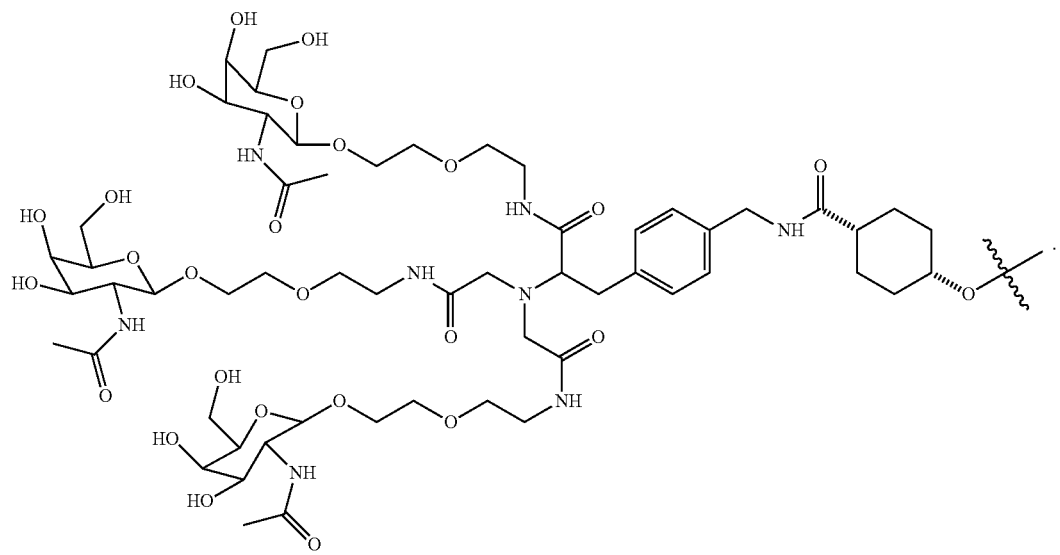
In some embodiments, an expression-inhibiting oligomeric compound is linked to the targeting ligand and has the structure represented by the following:

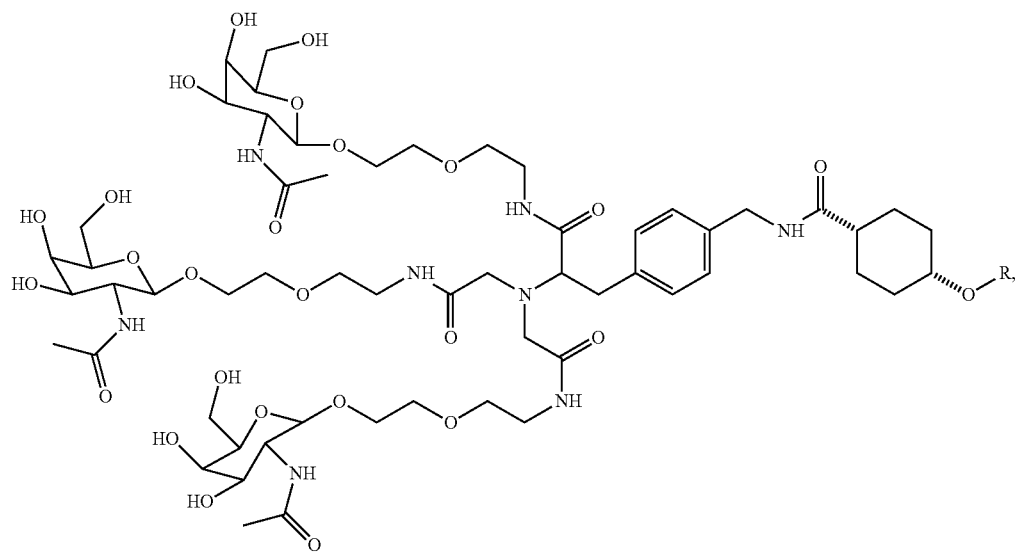

wherein R includes or consists of an expression-inhibiting oligomeric compound. (Structure 1005a).

In some embodiments, an expression-inhibiting oligomeric compound is linked to the targeting ligand and has the structure represented by the following:

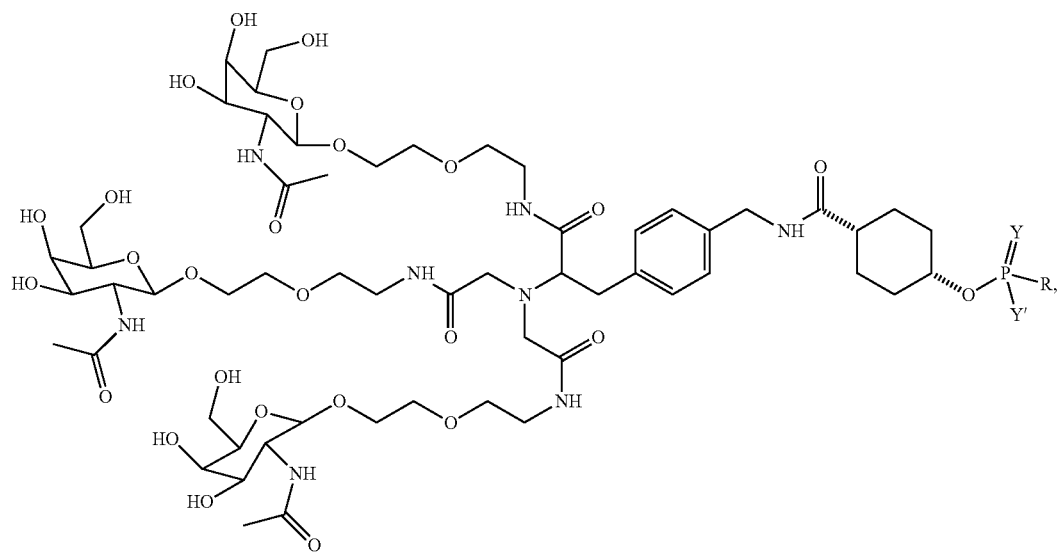

wherein R consists of or includes an expression-inhibiting oligomeric compound; Y is O or S; and Y' is O⁻, S⁻, or NH⁻. (Structure 1005a(i)).

In some embodiments, the targeting ligand is a phosphoramidite-containing compound having the structure represented by the following:

(Structure 1005b)
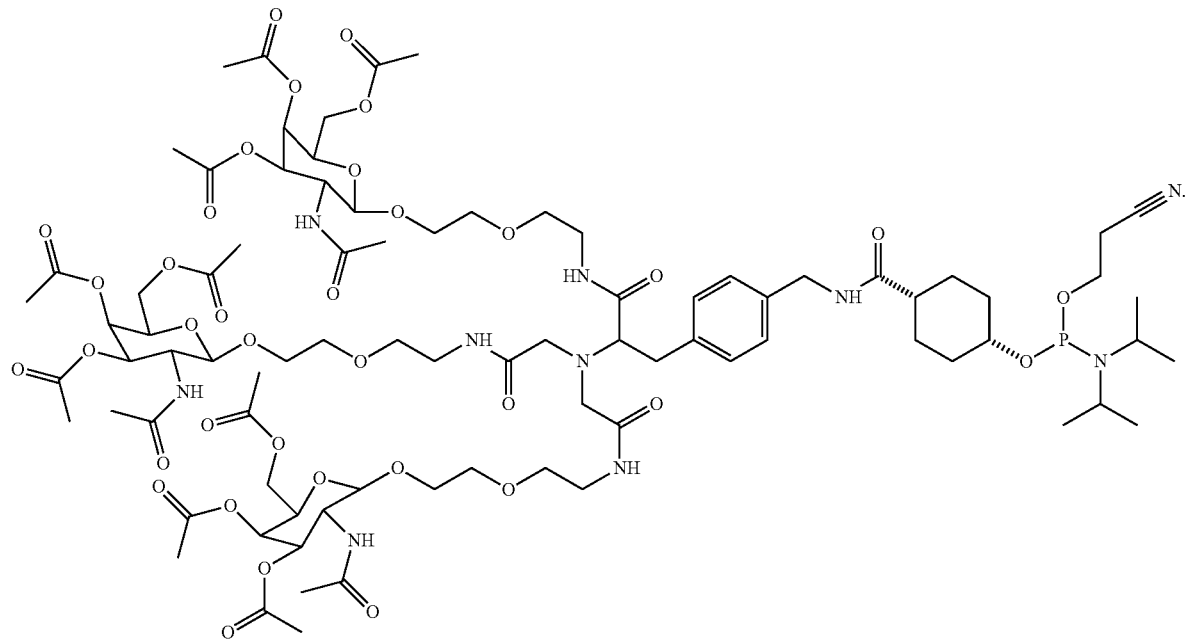
In some embodiments, the targeting ligand has the structure represented by the following:
(Structure 1006)
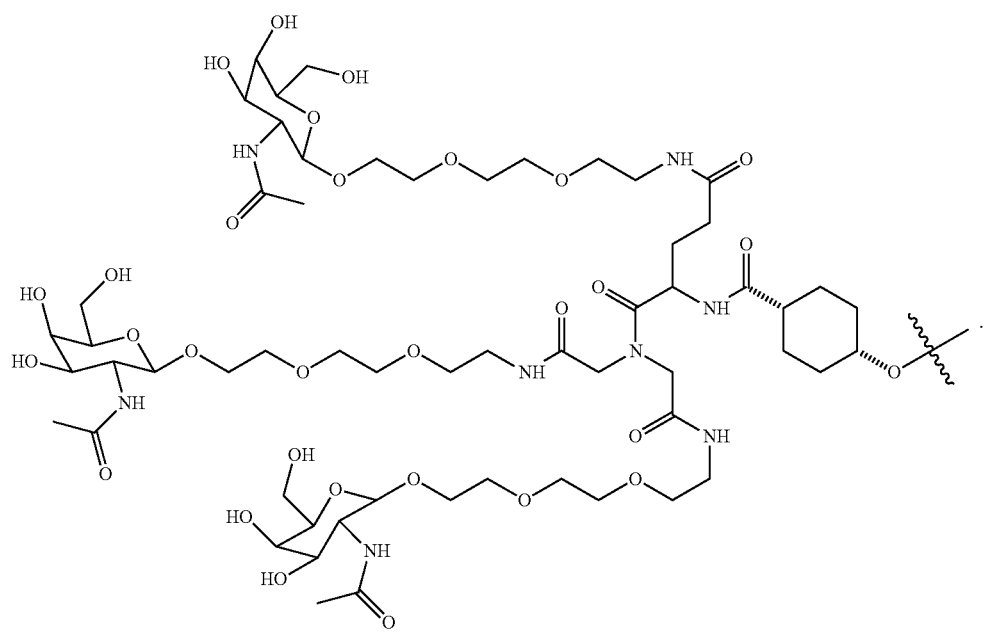
In some embodiments, an expression-inhibiting oligomeric compound is linked to the targeting ligand and has the structure represented by the following:

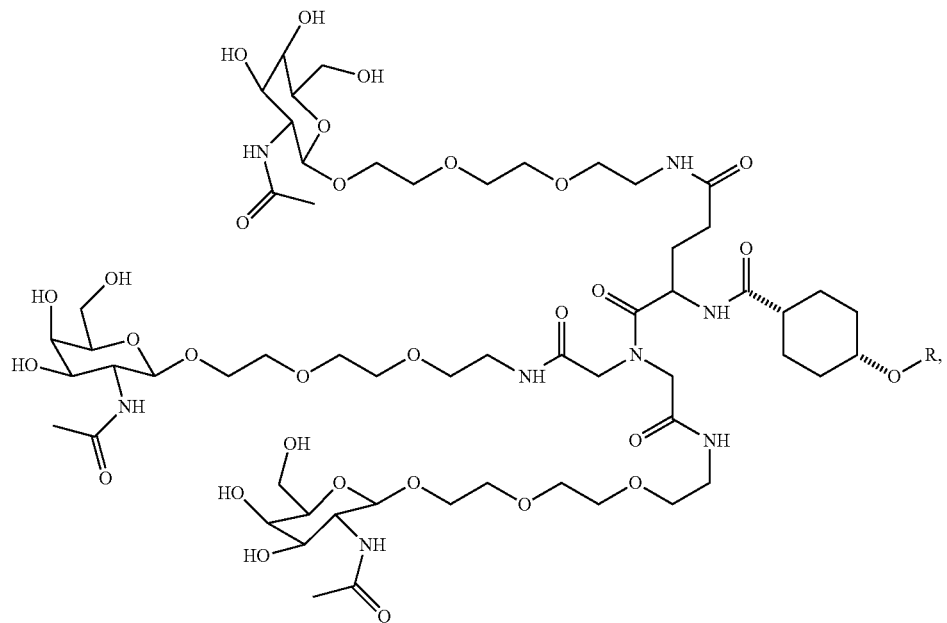

wherein R includes or consists of an expression-inhibiting oligomeric compound. (Structure 1006a).

In some embodiments, an expression-inhibiting oligomeric compound is linked to the targeting ligand and has the structure represented by the following:

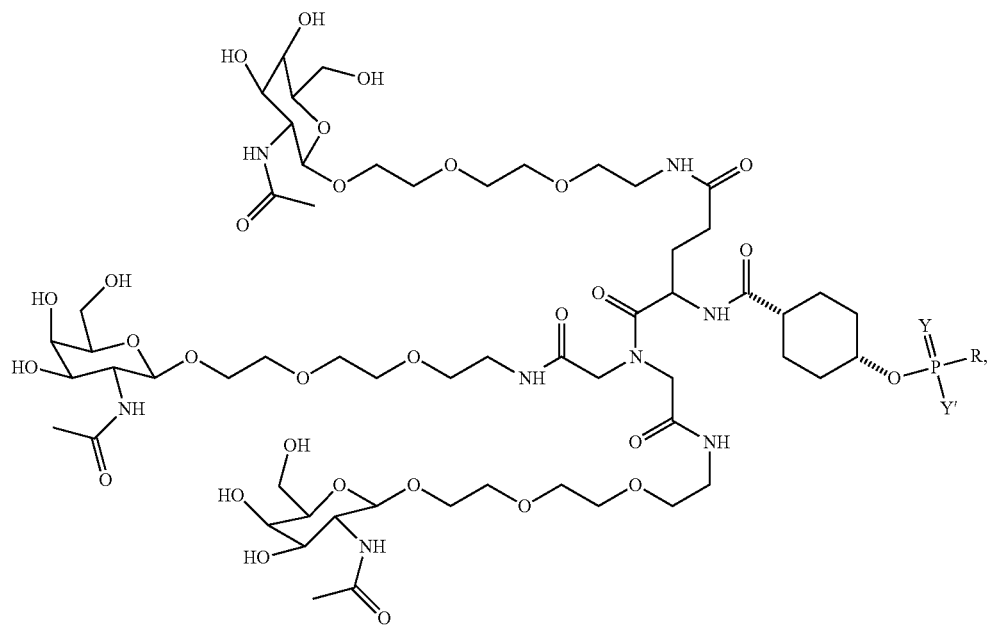

wherein R consists of or includes an expression-inhibiting oligomeric compound; Y is O or S; and Y' is O⁻, S⁻, or NH⁻. (Structure 1006a(i)).

In some embodiments, the targeting ligand is a phosphoramidite-containing compound having the structure represented by the following:

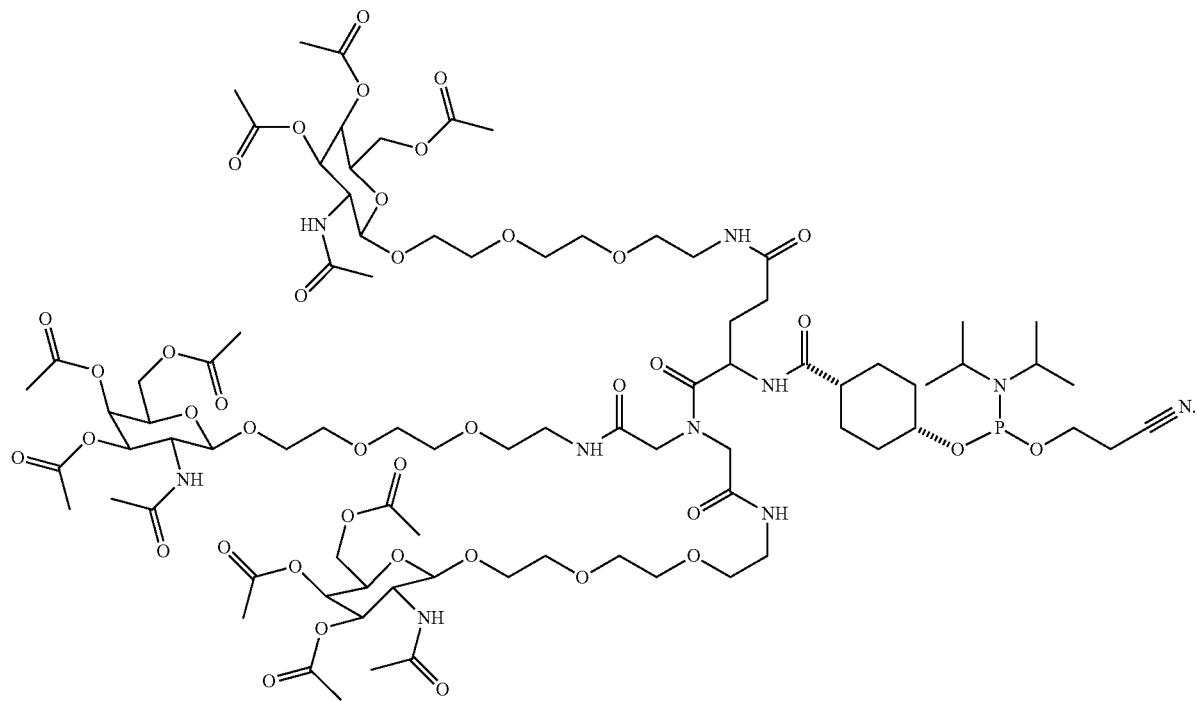
(Structure 1006b)
In some embodiments, the targeting ligand has the structure represented by the following:
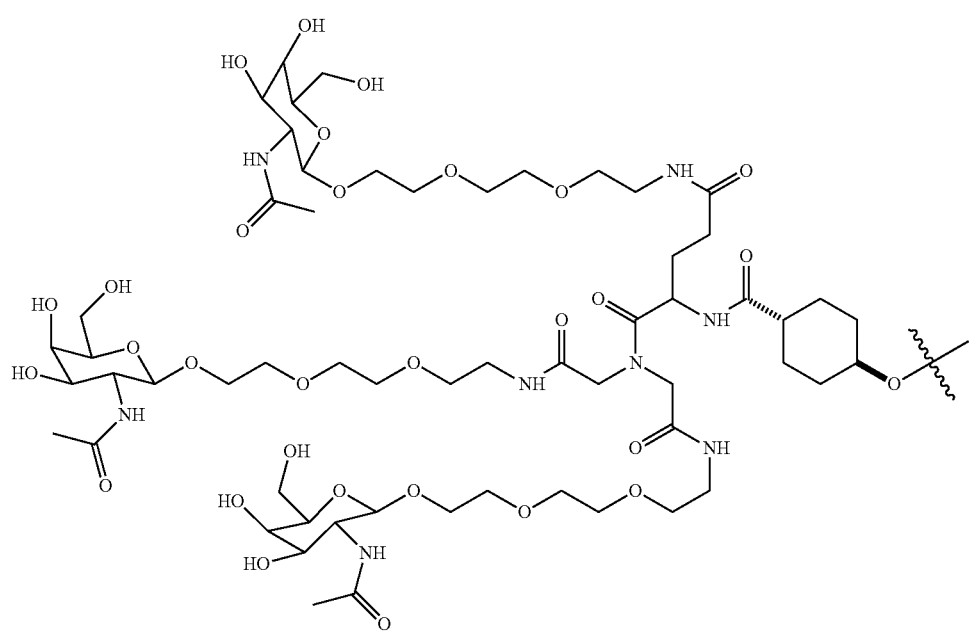
(Structure 1007)
In some embodiments, an expression-inhibiting oligomeric compound is linked to the targeting ligand and has the structure represented by the following:

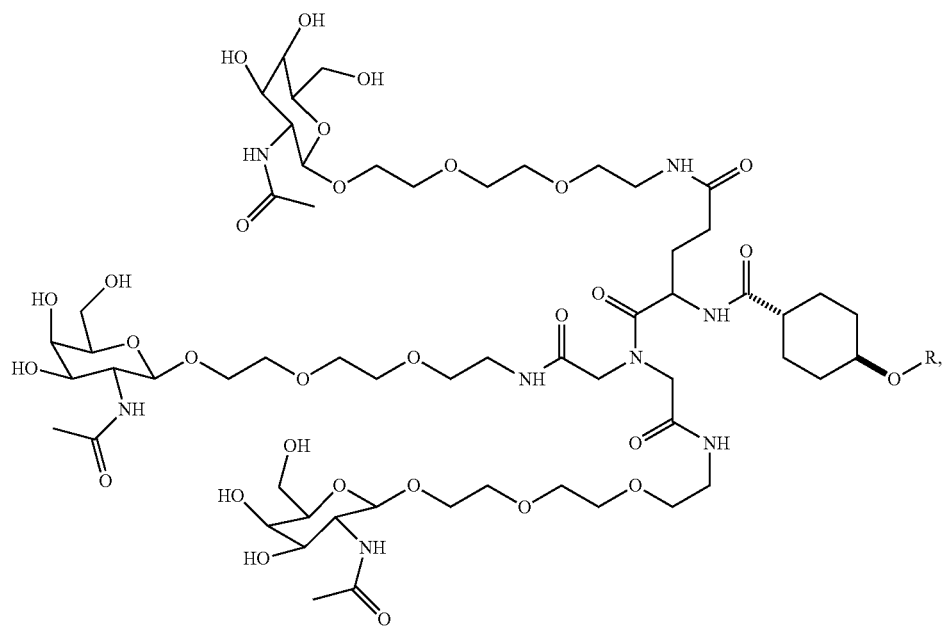

wherein R includes or consists of an expression-inhibiting oligomeric compound. (Structure 1007a).

In some embodiments, an expression-inhibiting oligomeric compound is linked to the targeting ligand and has the structure represented by the following:

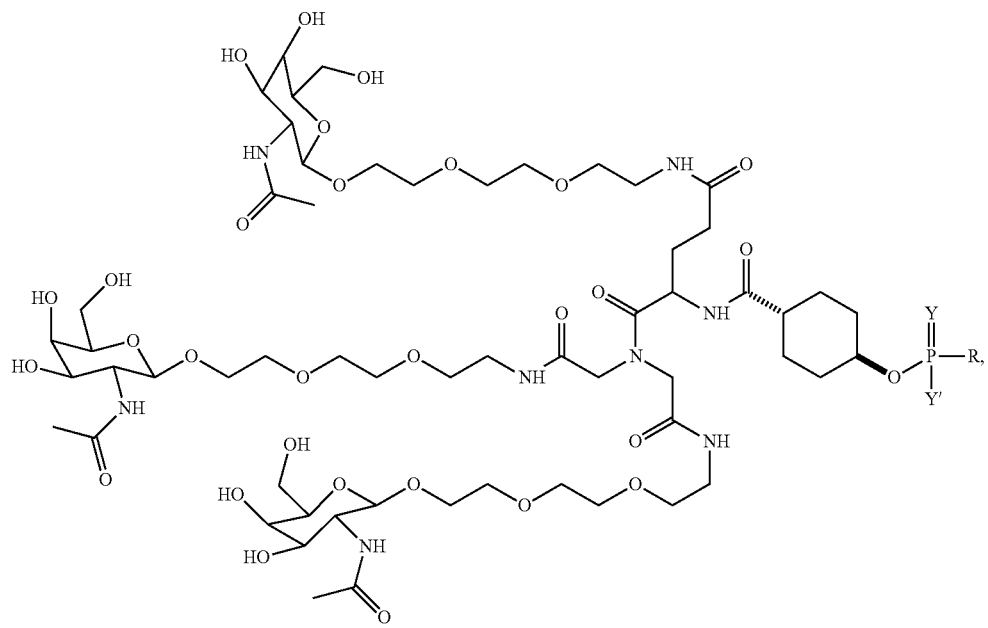

wherein R consists of or includes an expression-inhibiting oligomeric compound; Y is O or S; and Y' is O⁻, S⁻, or NH⁻. (Structure 1007a(i)).

In some embodiments, the targeting ligand is a phosphoramidite-containing compound having the structure represented by the following:

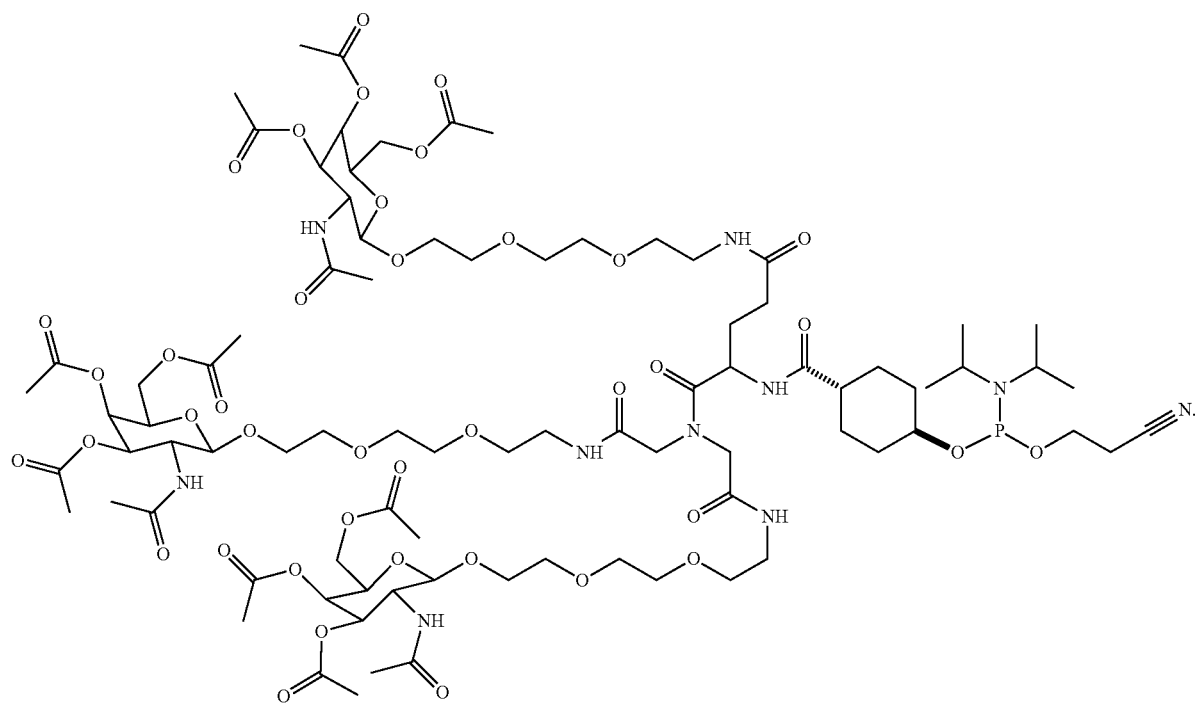
(Structure 1007b)
In some embodiments, the targeting ligand has the structure represented by the following:
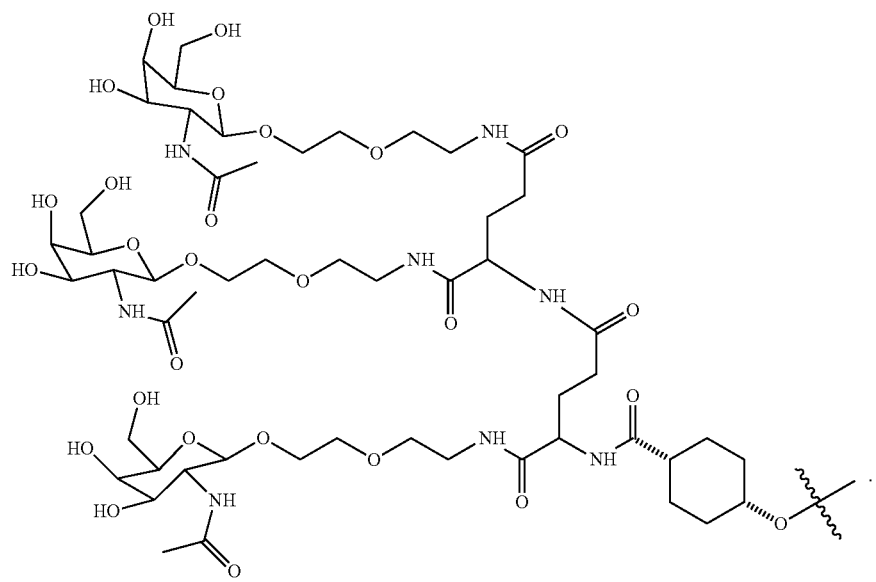
(Structure 1008)
In some embodiments, an expression-inhibiting oligomeric compound is linked to the targeting ligand and has the structure represented by the following:

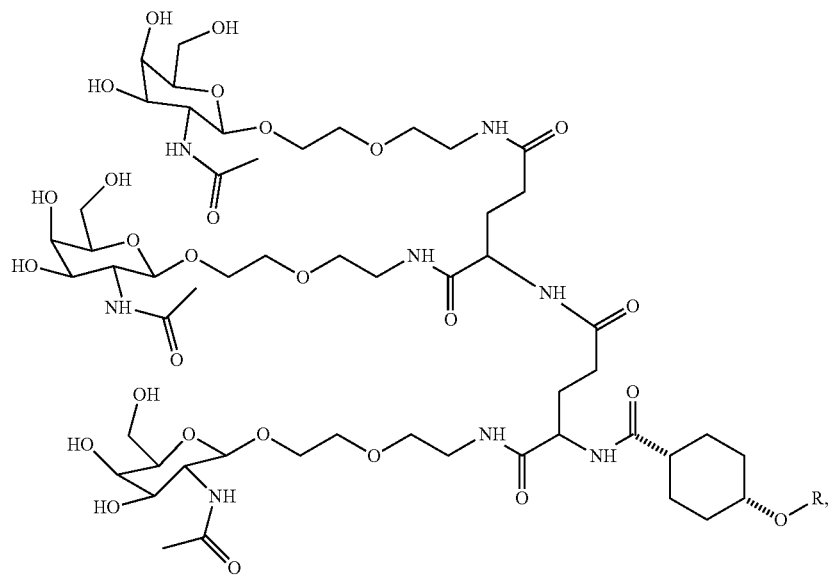

wherein R includes or consists of an expression-inhibiting oligomeric compound. (Structure 1008a).

In some embodiments, an expression-inhibiting oligomeric compound is linked to the targeting ligand and has the structure represented by the following:

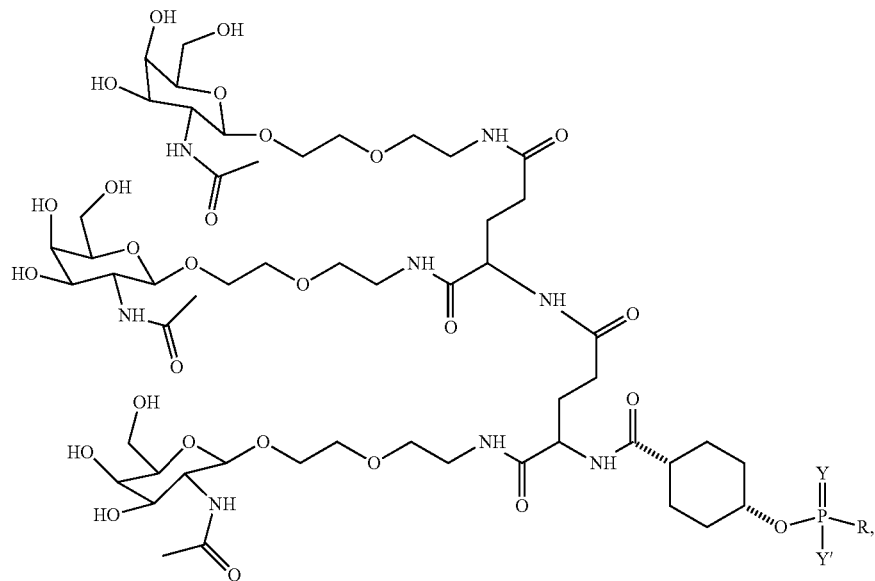

wherein R consists of or includes an expression-inhibiting oligomeric compound; Y is O or S; and Y' is O⁻, S⁻, or NH⁻. (Structure 1008a(i)).

In some embodiments, the targeting ligand is a phosphoramidite-containing compound having the structure represented by the following:

(Structure 1008b)
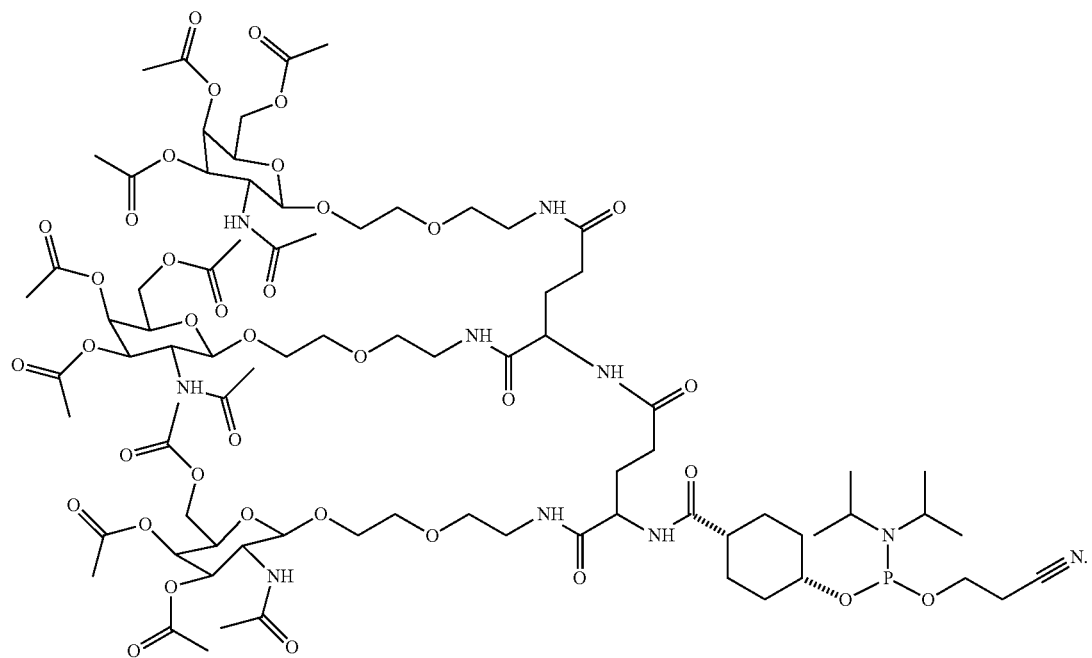
In some embodiments, the targeting ligand has the structure represented by the following:
(Structure 1009)
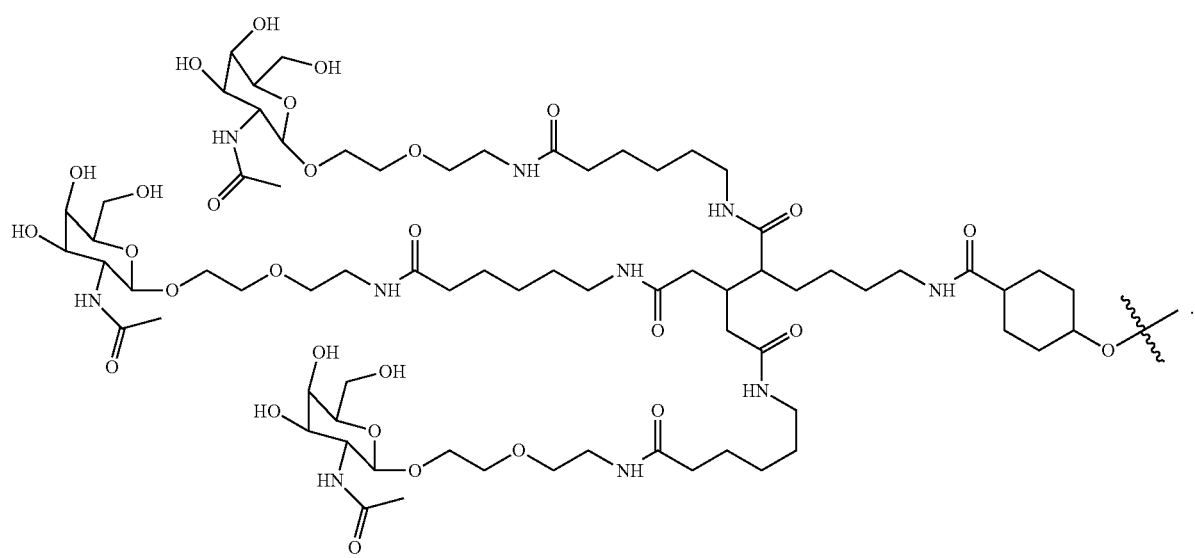
In some embodiments, an expression-inhibiting oligomeric compound is linked to the targeting ligand and has the structure represented by the following:

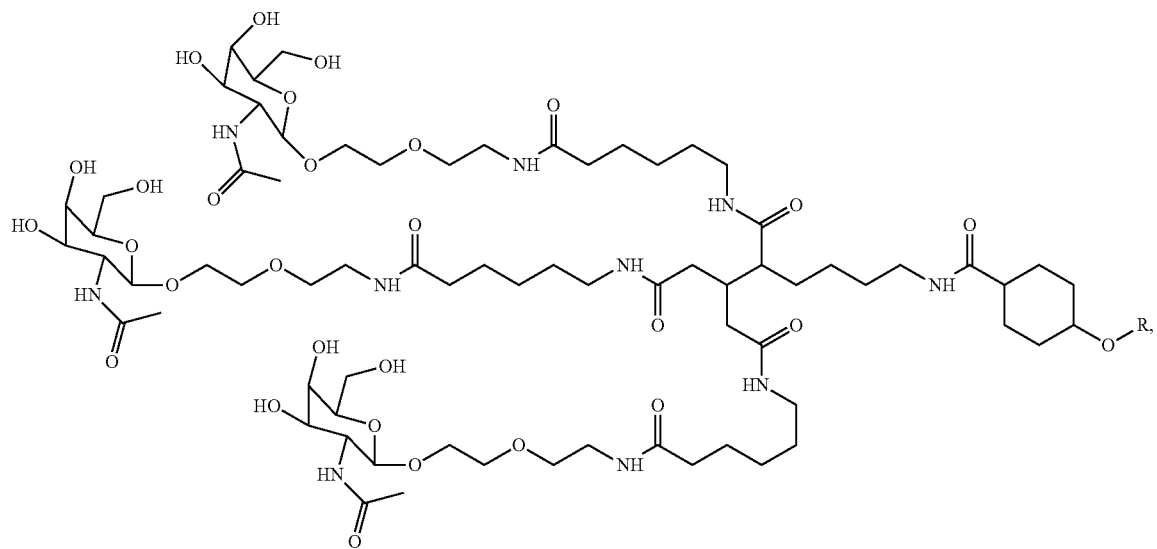

wherein R includes or consists of an expression-inhibiting oligomeric compound. (Structure 1009a).

In some embodiments, an expression-inhibiting oligomeric compound is linked to the targeting ligand and has the structure represented by the following:

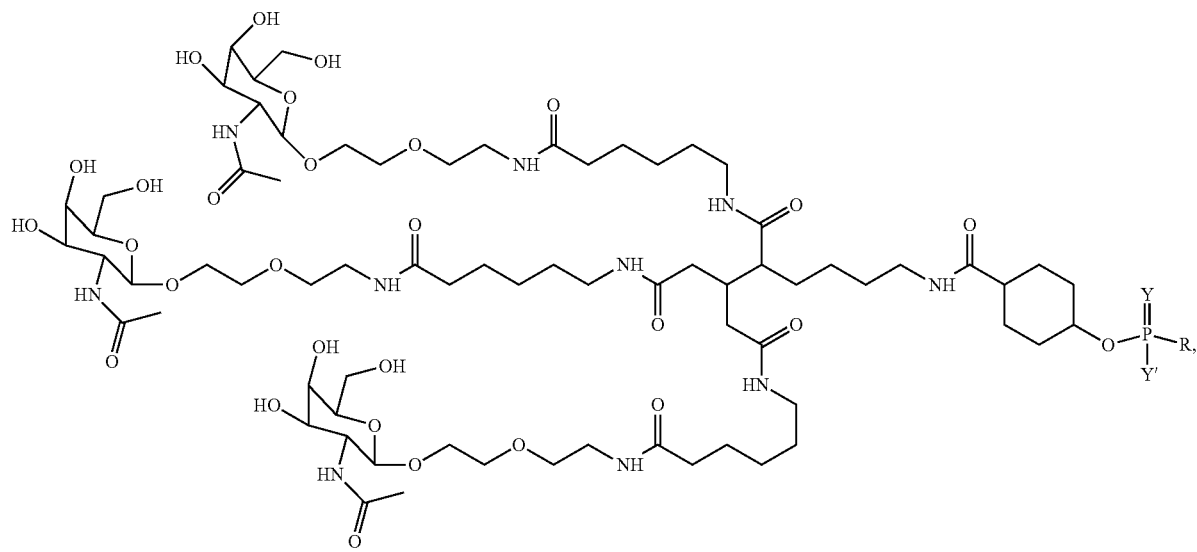

wherein R consists of or includes an expression-inhibiting oligomeric compound; Y is O or S; and Y' is O⁻, S⁻, or NH⁻. (Structure 1009a(i)).

In some embodiments, the targeting ligand is a phosphoramidite-containing compound having the structure represented by the following:

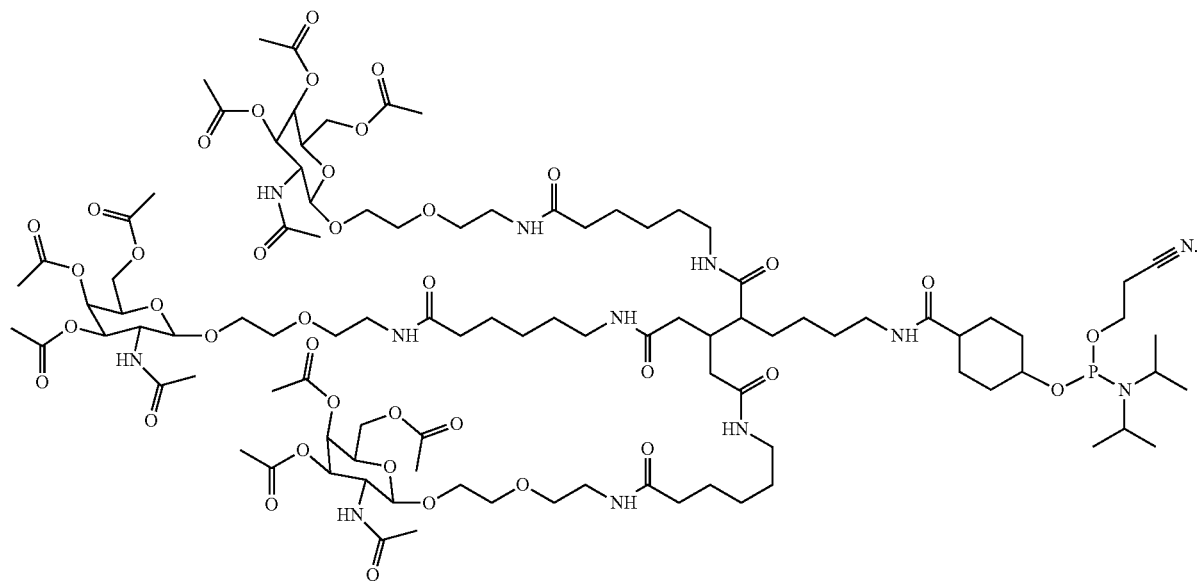

(Structure 1009b)

In some embodiments, the targeting ligand has the structure represented by the following:

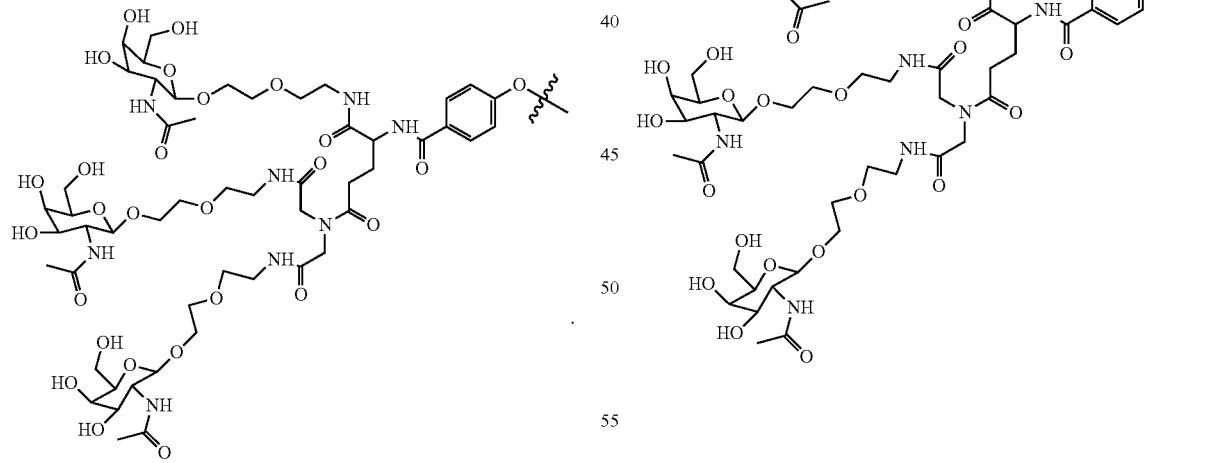

(Structure 1010)

wherein R includes or consists of an expression-inhibiting oligomeric compound. (Structure 1010a).

In some embodiments, an expression-inhibiting oligomeric compound is linked to the targeting ligand and has the structure represented by the following:

In some embodiments, an expression-inhibiting oligomeric compound is linked to the targeting ligand and has the structure represented by the following:

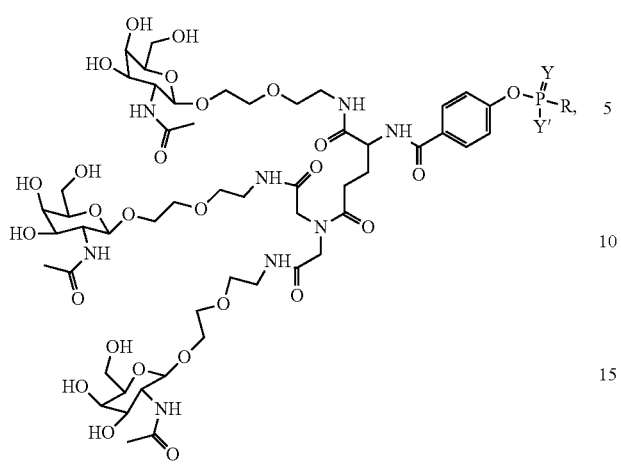

wherein R consists of or includes an expression-inhibiting oligomeric compound; Y is O or S; and Y' is O⁻, S⁻, or NH⁻. (Structure 1010a(i)).

In some embodiments, the targeting ligand is a phosphoramidite-containing compound having the structure represented by the following:

In some embodiments, an expression-inhibiting oligomeric compound is linked to the targeting ligand and includes the structure represented by the following:

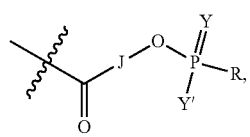

wherein J includes or consists of one or more substituted or unsubstituted cycloalkyl, cycloalkenyl, aryl, heteroaryl, or heterocyclyl groups, or covalently linked combinations thereof; Y is O or S; R consists of or includes an expression-inhibiting oligomeric compound; and Y' is O⁻, S⁻, or NH⁻ (Structure 1011).

In some embodiments, the targeting ligand has the structure represented by the following:

(Structure 1010b)

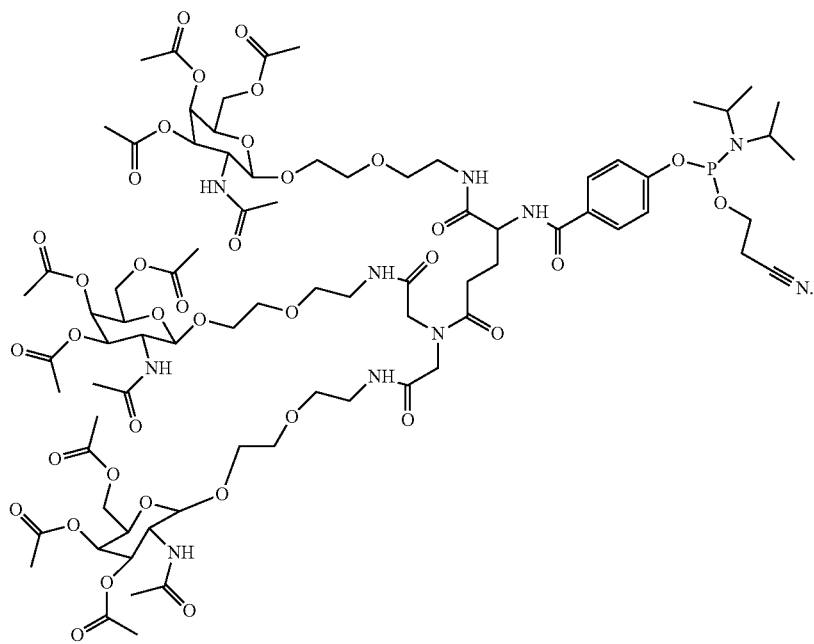

(Structure 1012)

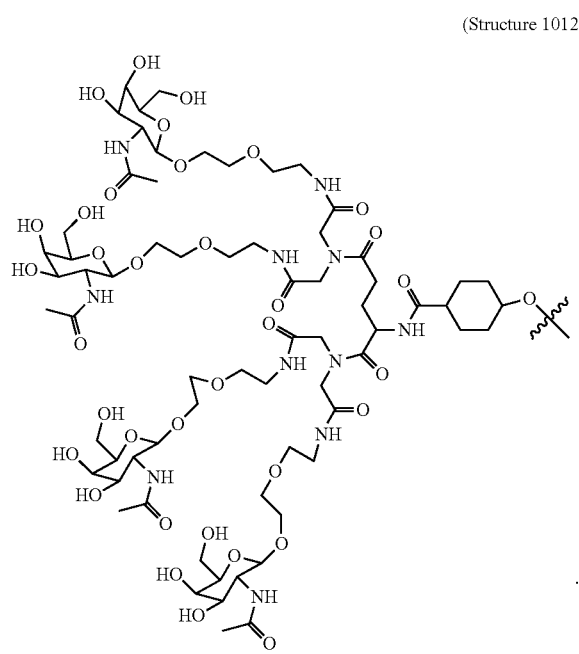 [SMILES: *OC1CCC(C(=O)NC(CCC(=O)N(CC(=O)NCCOCCOC2OC(CO)C(O)C(O)C2NC(C)=O)CC(=O)NCCOCCOC2OC(CO)C(O)C(O)C2NC(C)=O)C(=O)N(CC(=O)NCCOCCOC2OC(CO)C(O)C(O)C2NC(C)=O)CC(=O)NCCOCCOC2OC(CO)C(O)C(O)C2NC(C)=O)CC1]

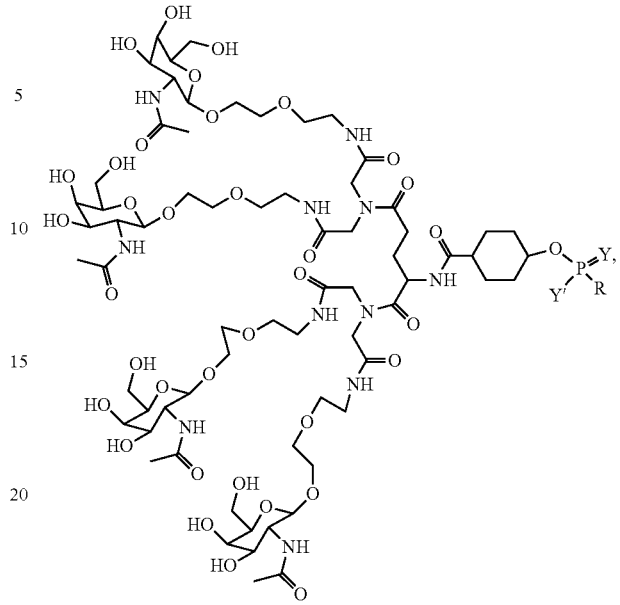

wherein R consists of or includes an expression-inhibiting oligomeric compound; Y is O or S; and Y' is O⁻, S⁻, or NH⁻. (Structure 1012a(i)).

In some embodiments, an expression-inhibiting oligomeric compound is linked to the targeting ligand and has the structure represented by the following:

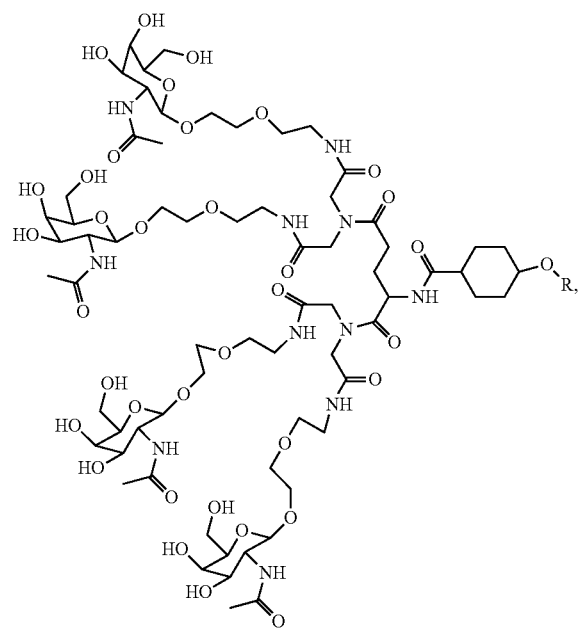

wherein R includes or consists of an expression-inhibiting oligomeric compound. (Structure 1012a).

In some embodiments, an expression-inhibiting oligomeric compound is linked to the targeting ligand and has the structure represented by the following:

In some embodiments, the targeting ligand is a phosphoramidite-containing compound having the structure represented by the following:

(Structure 1012b)

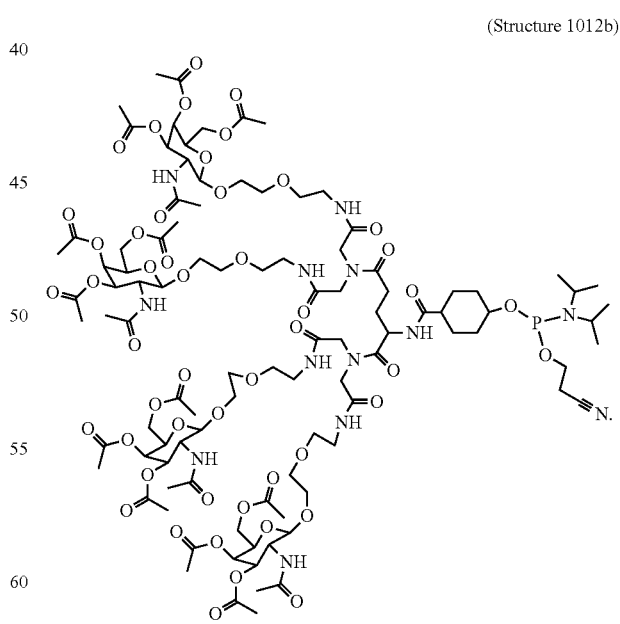

In some embodiments, the targeting ligand has the structure represented by the following:

(Structure 1013)

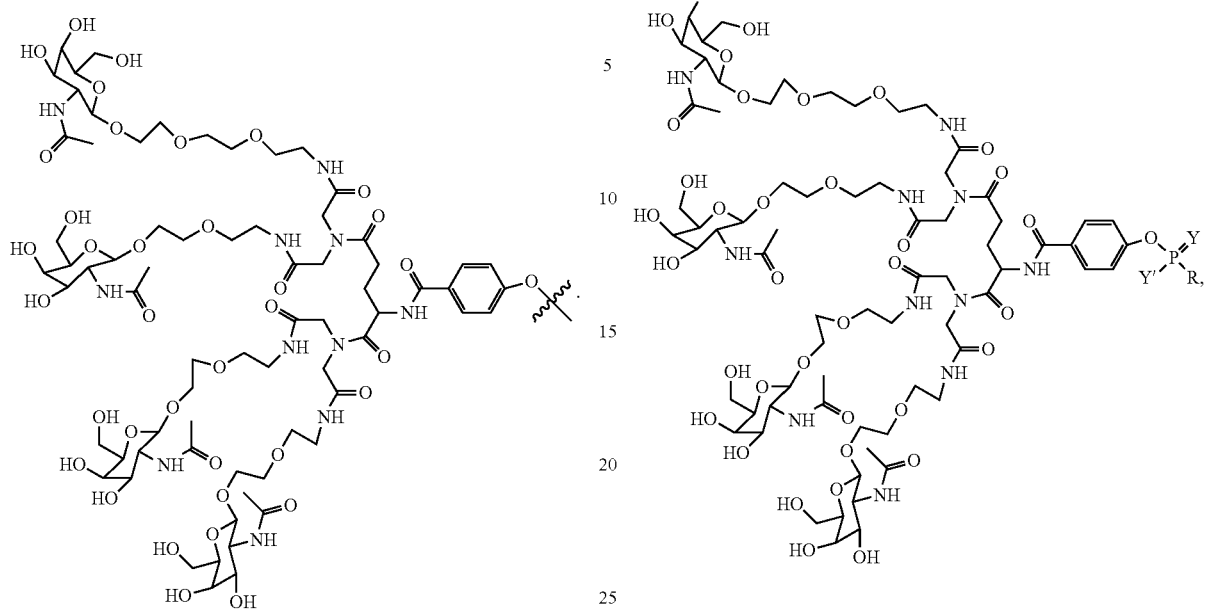

wherein R consists of or includes an expression-inhibiting oligomeric compound; Y is O or S; and Y' is O⁻, S⁻, or NH⁻. (Structure 1013a(i)).

In some embodiments, the targeting ligand is a phosphoramidite-containing compound having the structure represented by the following:

(Structure 1013b)

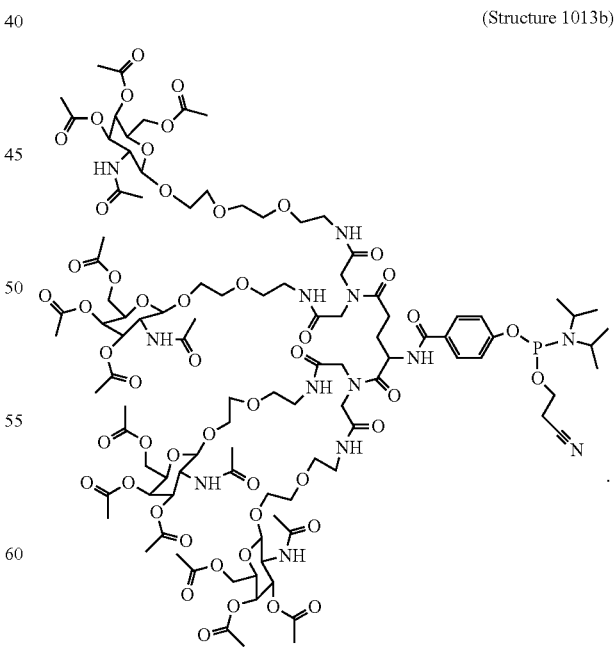

In some embodiments, an expression-inhibiting oligomeric compound is linked to the targeting ligand and has the structure represented by the following:

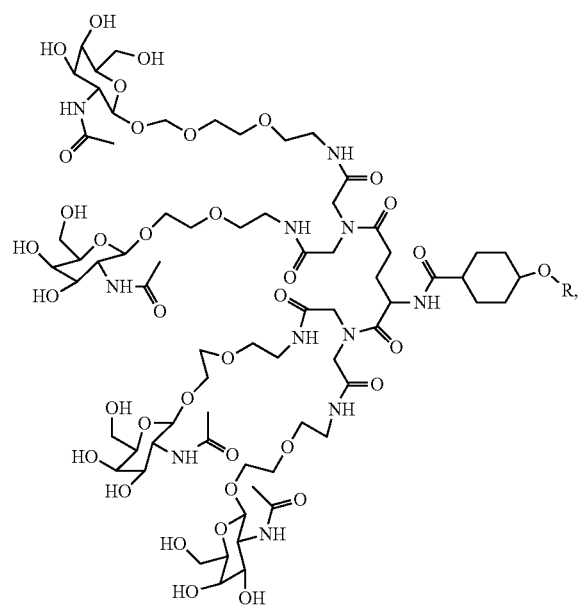

wherein R includes or consists of an expression-inhibiting oligomeric compound. (Structure 1013a).

In some embodiments, an expression-inhibiting oligomeric compound is linked to the targeting ligand and has the structure represented by the following:

In some embodiments, the targeting ligand has the structure represented by the following:

111

(Structure 1014)

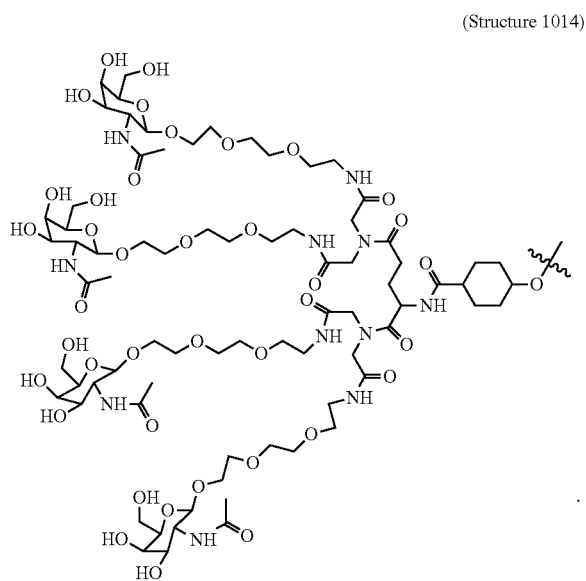 [SMILES: *OC1CCC(C(=O)NC(CCC(=O)N(CC(=O)NCCOCCOCCOC2OC(CO)C(O)C(O)C2NC(C)=O)CC(=O)NCCOCCOCCOC2OC(CO)C(O)C(O)C2NC(C)=O)C(=O)N(CC(=O)NCCOCCOCCOC2OC(CO)C(O)C(O)C2NC(C)=O)CC(=O)NCCOCCOCCOC2OC(CO)C(O)C(O)C2NC(C)=O)CC1]

In some embodiments, an expression-inhibiting oligomeric compound is linked to the targeting ligand and has the structure represented by the following:

112 wherein R includes or consists of an expression-inhibiting oligomeric compound. (Structure 1014a).

In some embodiments, an expression-inhibiting oligomeric compound is linked to the targeting ligand and has the structure represented by the following:

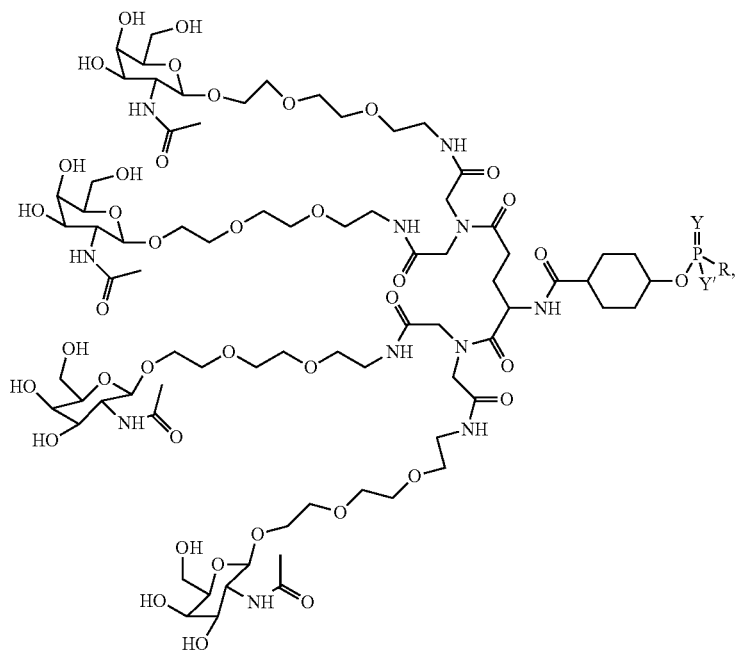

wherein R consists of or includes an expression-inhibiting oligomeric compound; Y is O or S; and Y' is O⁻, S⁻, or NH⁻. (Structure 1014a(i)).

In some embodiments, the targeting ligand is a phosphoramidite-containing compound having the structure represented by the following:

(Structure 1014b)

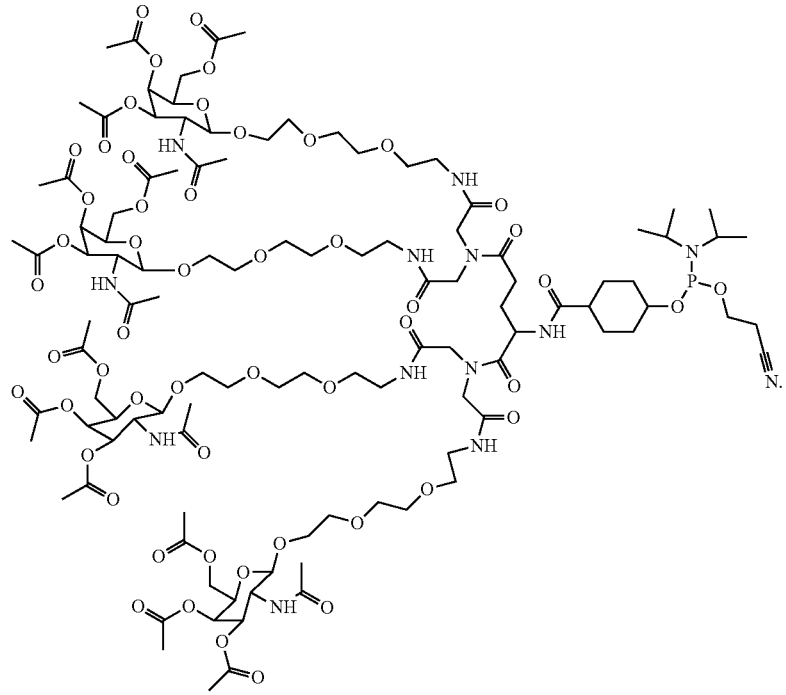

In some embodiments, the targeting ligand has the structure represented by the following:

(Structure 1015)

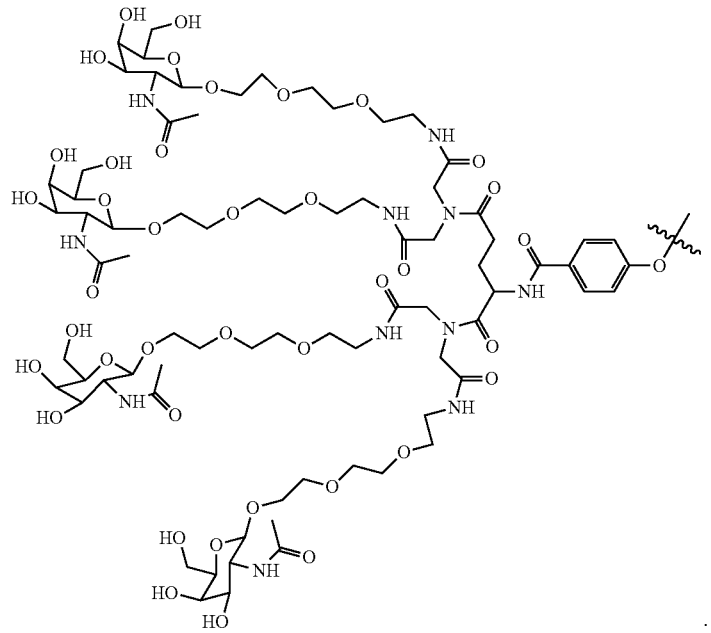

In some embodiments, an expression-inhibiting oligomeric compound is linked to the targeting ligand and has the structure represented by the following:

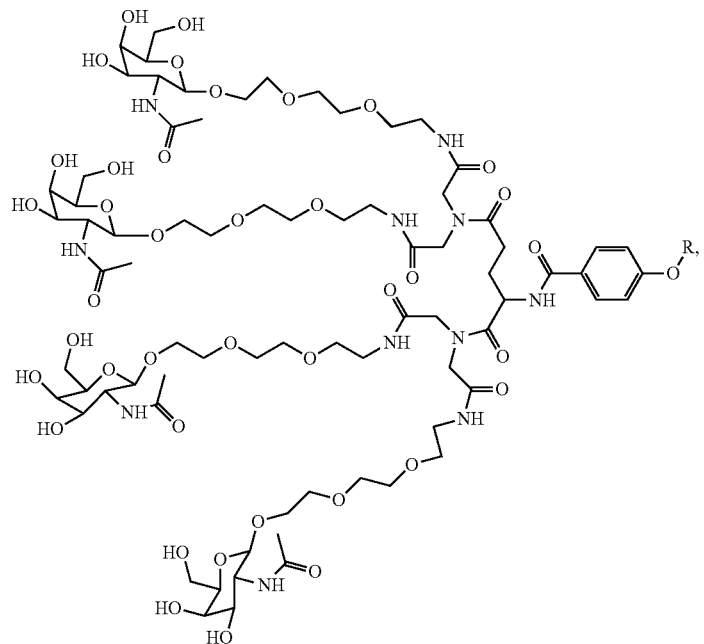

wherein R includes or consists of an expression-inhibiting oligomeric compound. (Structure 1015a).

In some embodiments, an expression-inhibiting oligomeric compound is linked to the targeting ligand and has the structure represented by the following:

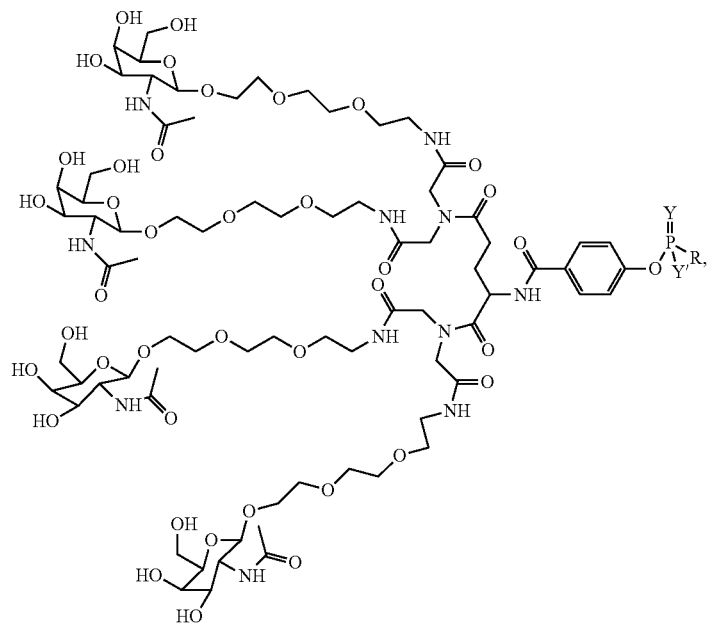

wherein R consists of or includes an expression-inhibiting oligomeric compound; Y is O or S; and Y' is O⁻, S⁻, or NH⁻. (Structure 1015a(i)).

In some embodiments, the targeting ligand is a phosphoramidite-containing compound having the structure represented by the following:

(Structure 1015b)
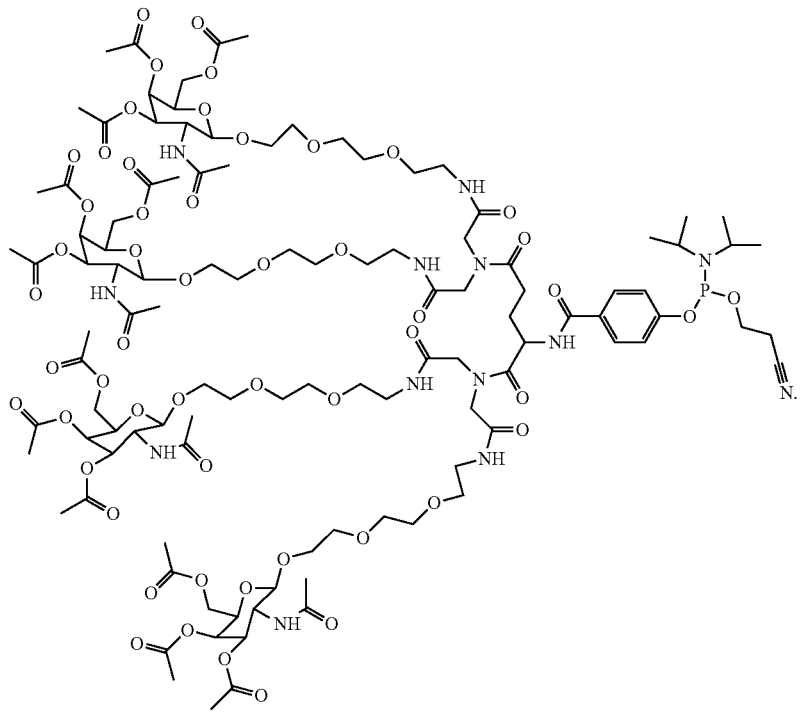
In some embodiments, the targeting ligand has the structure represented by the following:
(Structure 1016)
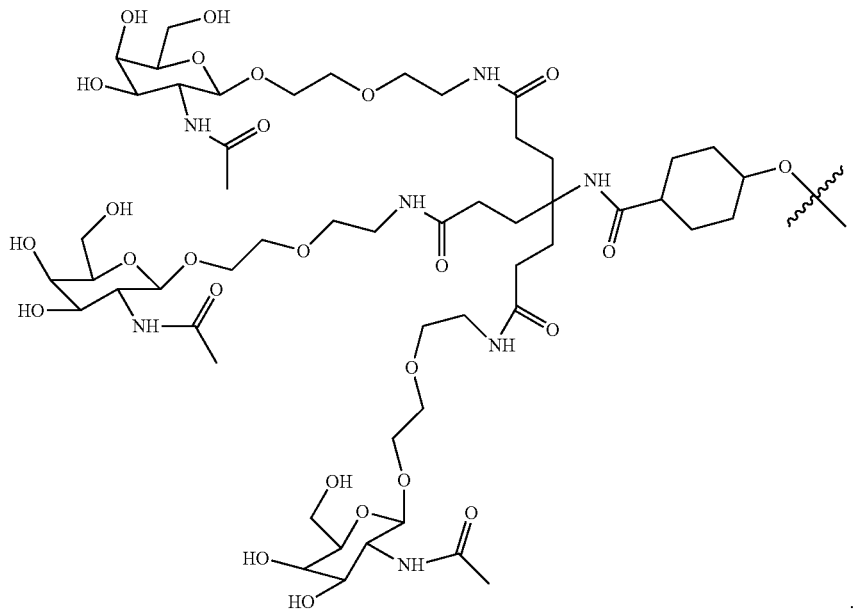
In some embodiments, an expression-inhibiting oligomeric compound is linked to the targeting ligand and has the structure represented by the following:

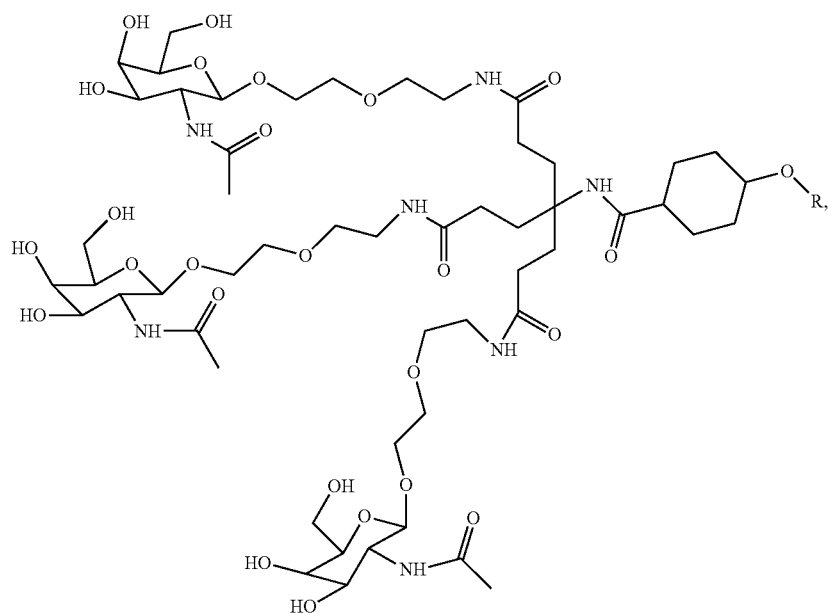

wherein R includes or consists of an expression-inhibiting oligomeric compound. (Structure 1016a).

In some embodiments, an expression-inhibiting oligomeric compound is linked to the targeting ligand and has the structure represented by the following:

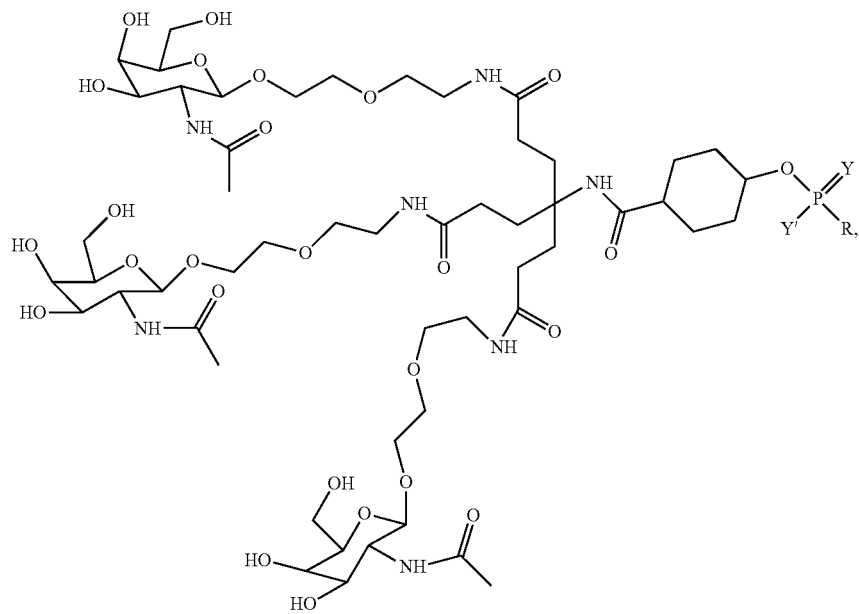

wherein R consists of or includes an expression-inhibiting oligomeric compound; Y is O or S; and Y' is O⁻, S⁻, or NH⁻. (Structure 1016a(i)).

In some embodiments, the targeting ligand is a phosphoramidite-containing compound having the structure represented by the following:

(Structure 1016b)
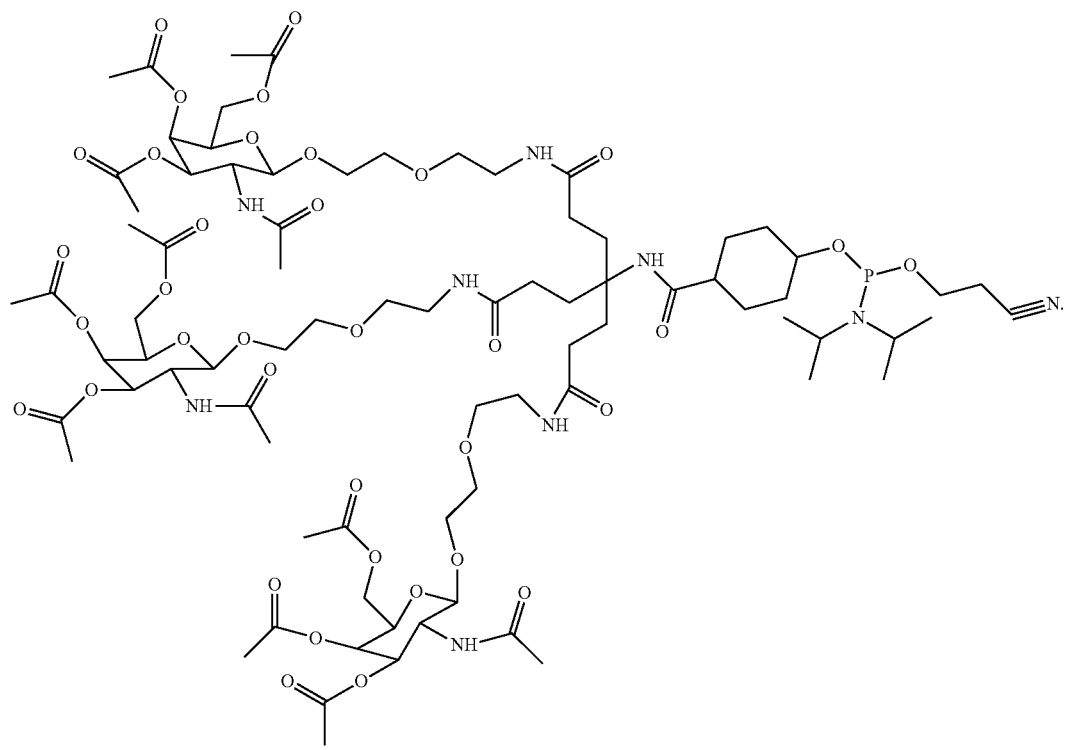
In some embodiments, the targeting ligand has the structure represented by the following:
(Structure 1017)
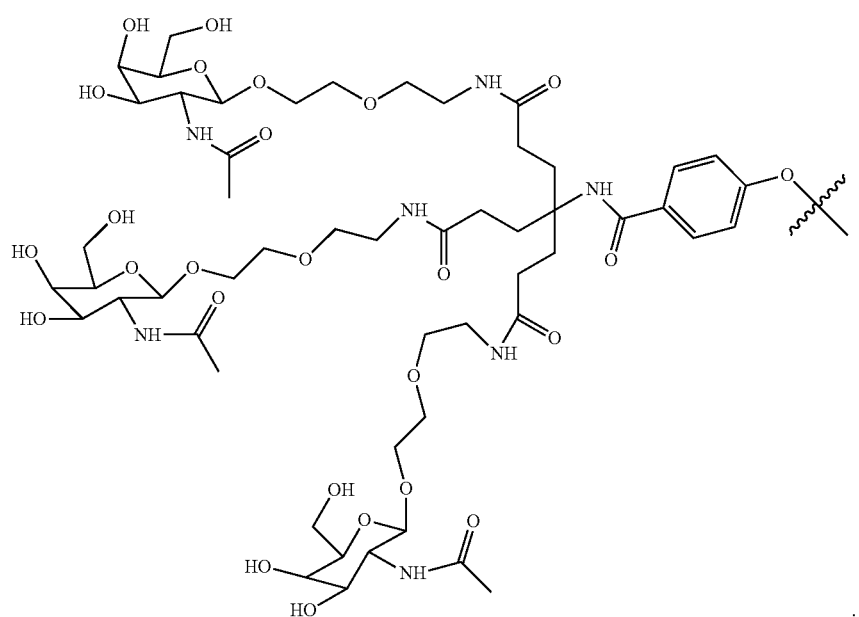
In some embodiments, an expression-inhibiting oligomeric compound is linked to the targeting ligand and has the structure represented by the following:

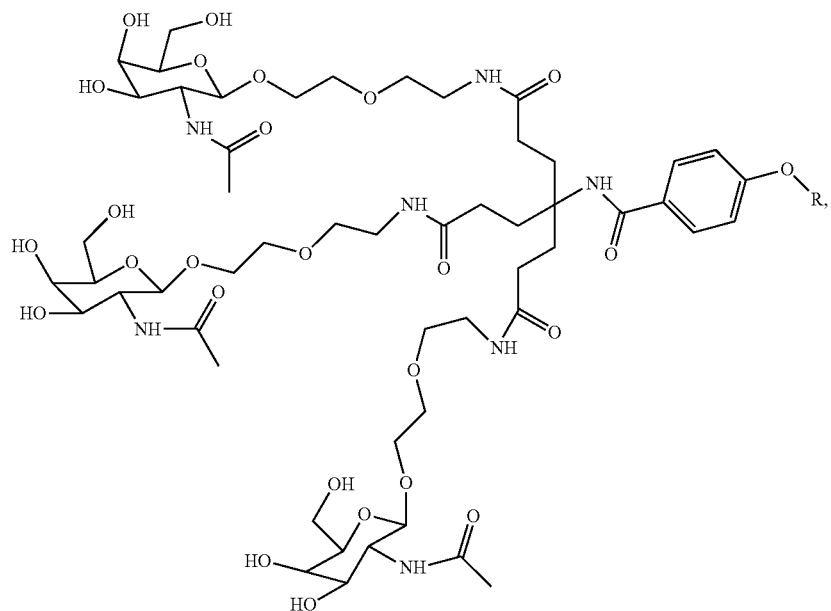

wherein R includes or consists of an expression-inhibiting oligomeric compound. (Structure 1017a).

In some embodiments, an expression-inhibiting oligomeric compound is linked to the targeting ligand and has the structure represented by the following:

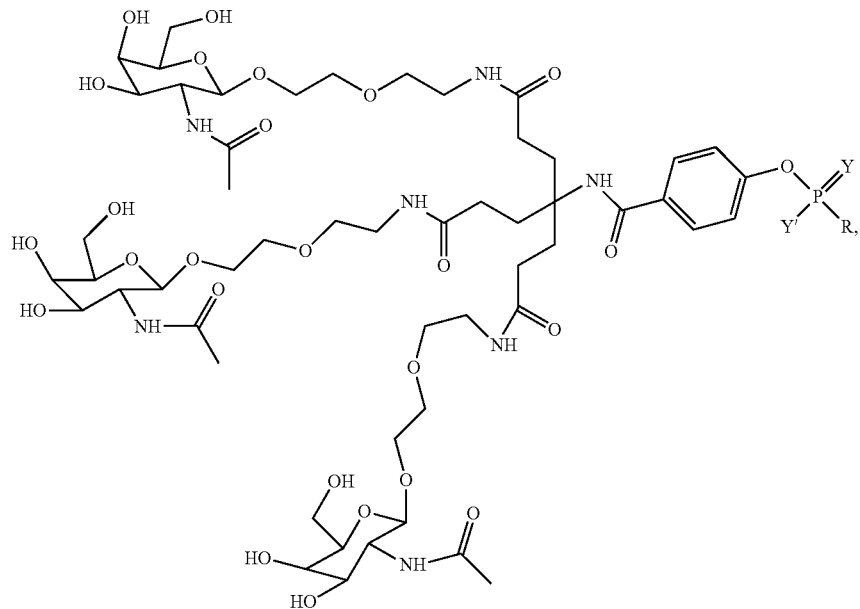

wherein R consists of or includes an expression-inhibiting oligomeric compound; Y is O or S; and Y' is O⁻, S⁻, or NH⁻. (Structure 1017a(i)).

In some embodiments, the targeting ligand is a phosphoramidite-containing compound having the structure represented by the following:

(Structure 1017b)
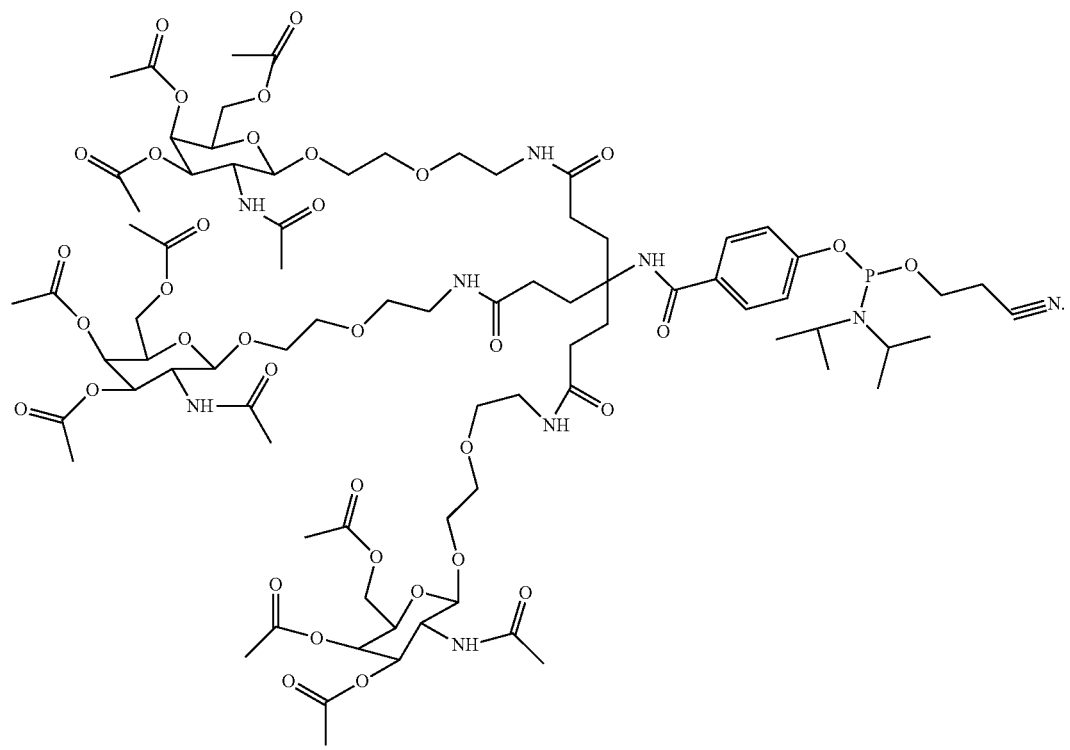
In some embodiments, the targeting ligand has the structure represented by the following:
(Structure 1018)
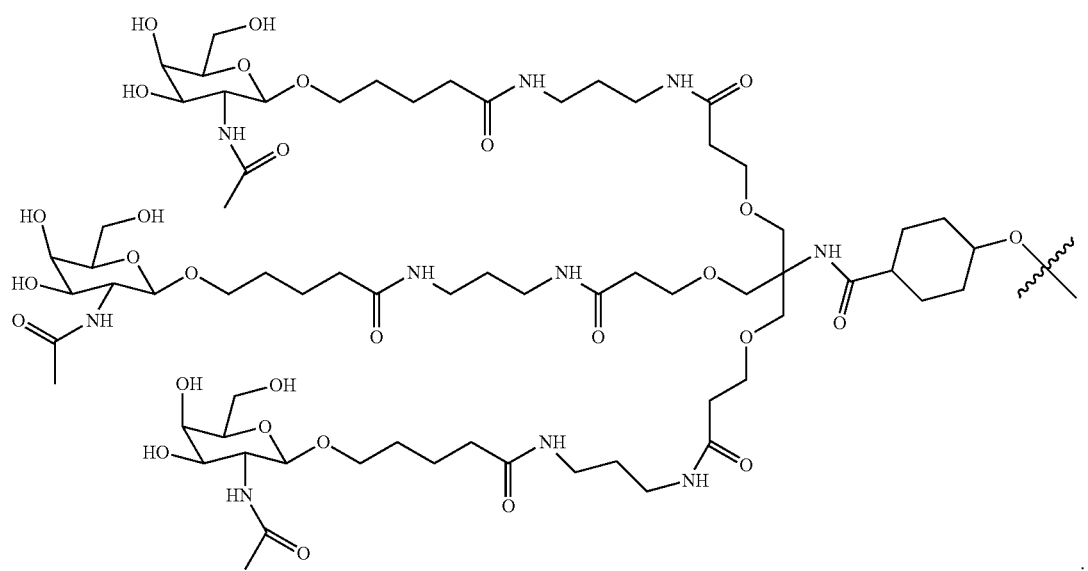
In some embodiments, an expression-inhibiting oligomeric compound is linked to the targeting ligand and has the structure represented by the following:

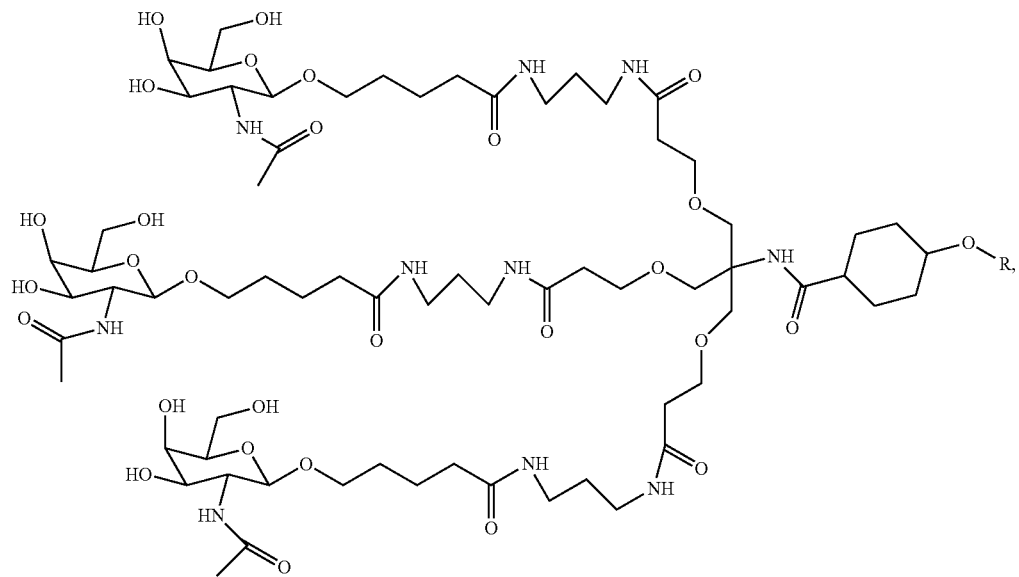

wherein R includes or consists of an expression-inhibiting oligomeric compound. (Structure 1018a).

In some embodiments, an expression-inhibiting oligomeric compound is linked to the targeting ligand and has the structure represented by the following:

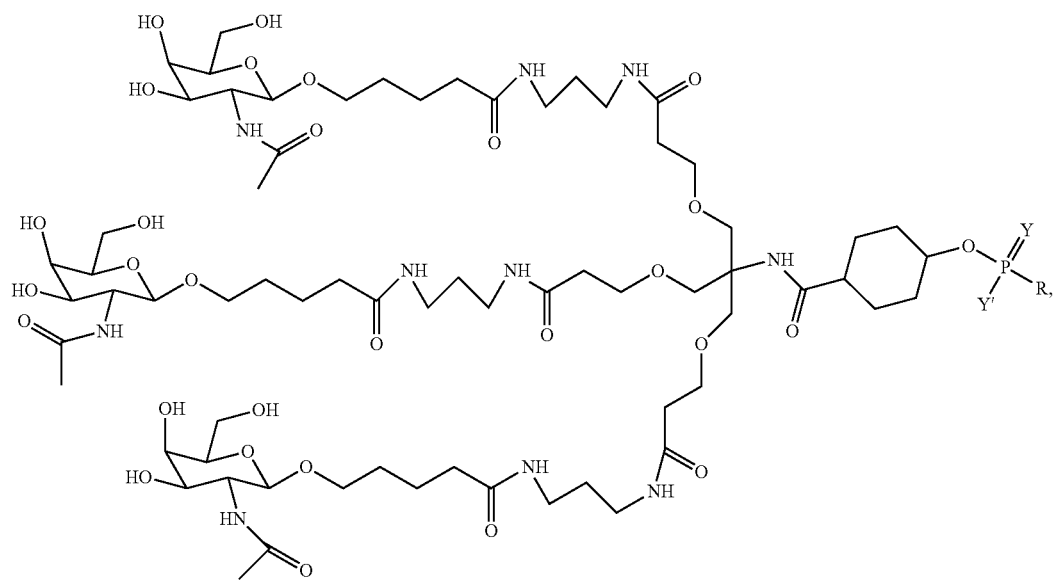

wherein R consists of or includes an expression-inhibiting oligomeric compound; Y is O or S; and Y' is O⁻, S⁻, or NH⁻. (Structure 1018a(i)).

In some embodiments, the targeting ligand is a phosphoramidite-containing compound having the structure represented by the following:

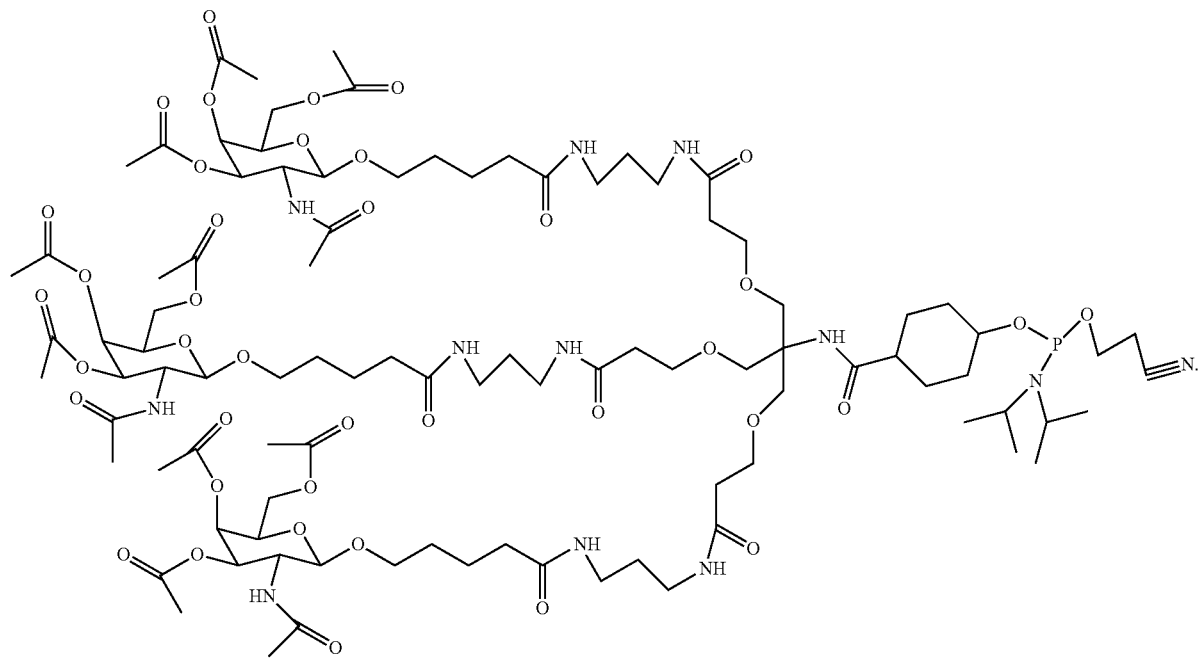
(Structure 1018b)
In some embodiments, the targeting ligand has the structure represented by the following:
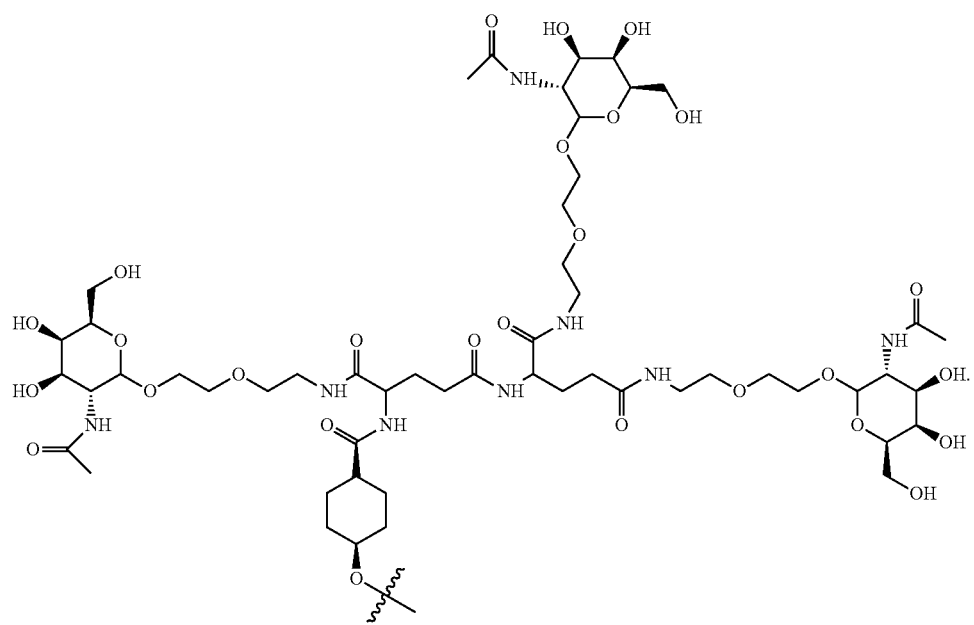
(Structure 1019)

In some embodiments, an expression-inhibiting oligomeric compound is linked to the targeting ligand and has the structure represented by the following:

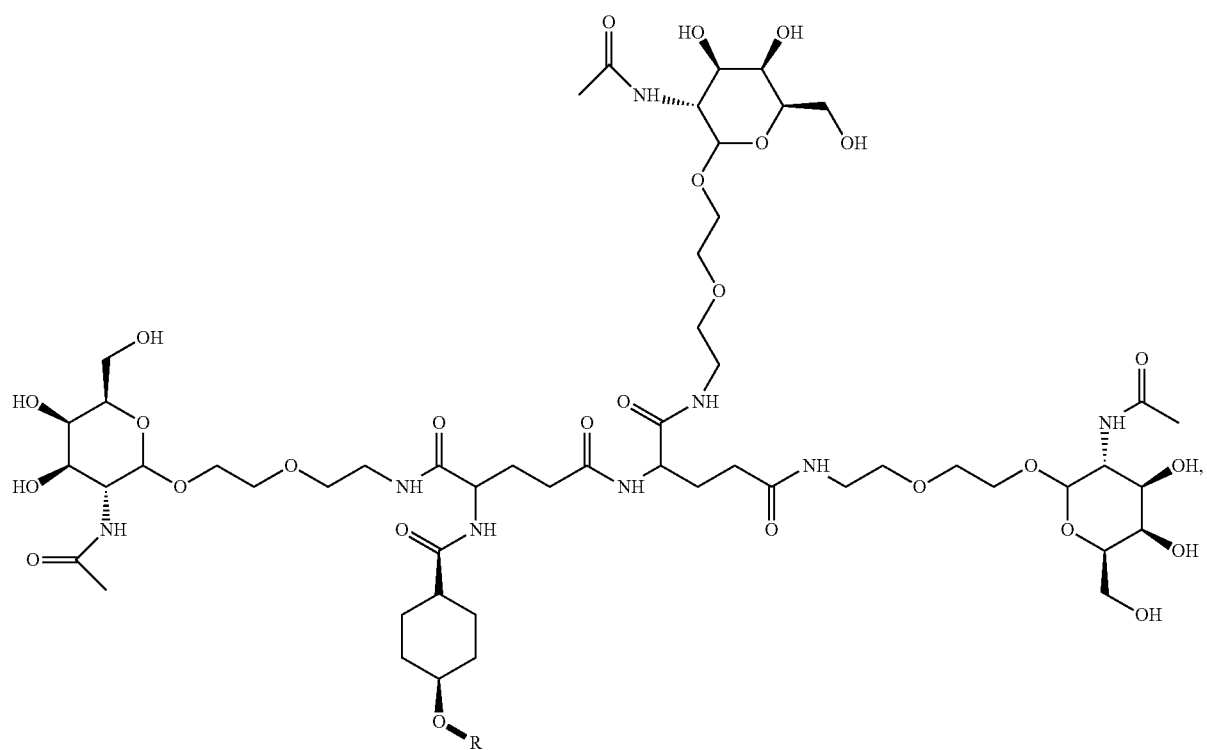

wherein R includes or consists of an expression-inhibiting oligomeric compound. (Structure 1019a).

In some embodiments, an expression-inhibiting oligomeric compound is linked to the targeting ligand and has the structure represented by the following:

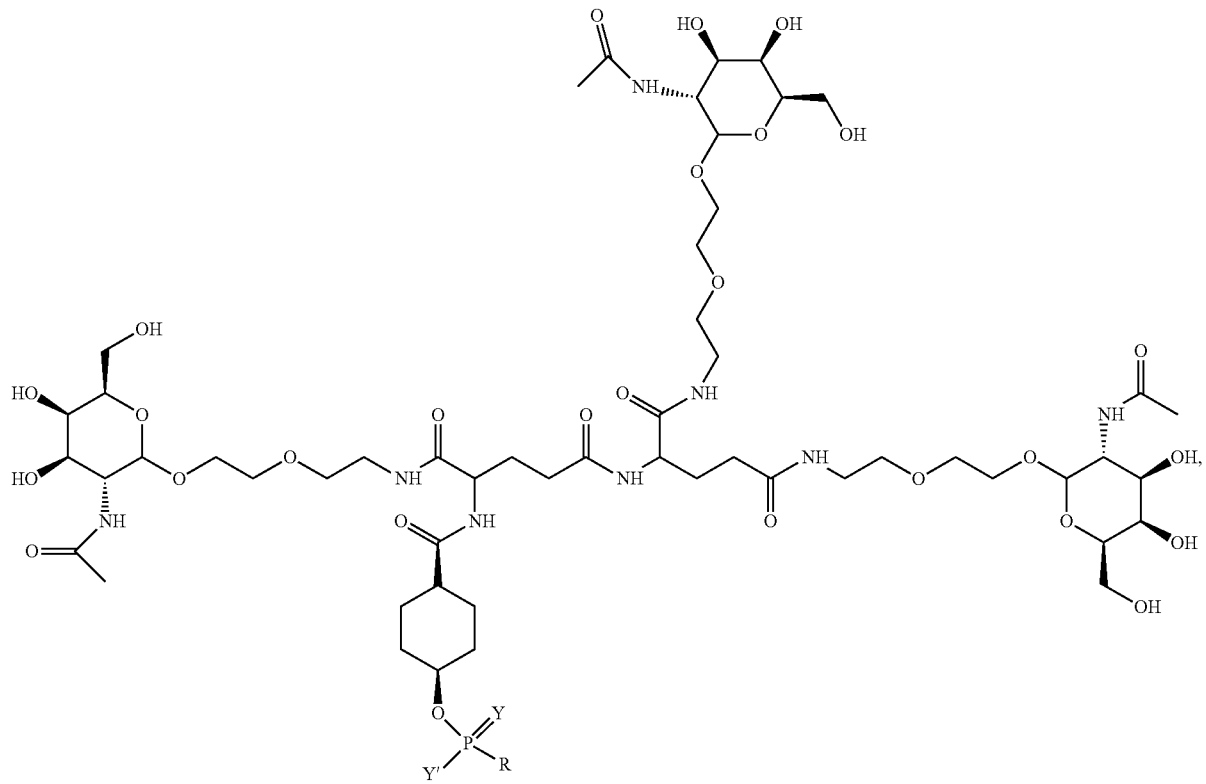
wherein R consists of or includes an expression-inhibiting oligomeric compound; Y is O or S; and Y' is O⁻, S⁻, or NH⁻. (Structure 1019a(i)).
In some embodiments, the targeting ligand is a phosphoramidite-containing compound having the structure represented by the following:
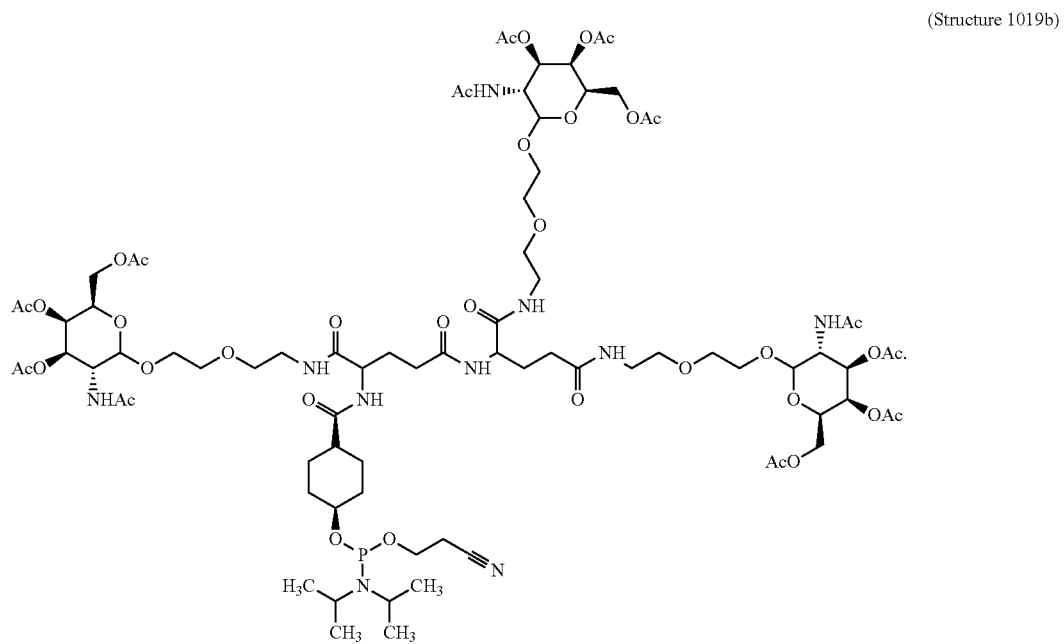
(Structure 1019b)

In some embodiments, the targeting ligand has the structure represented by the following:

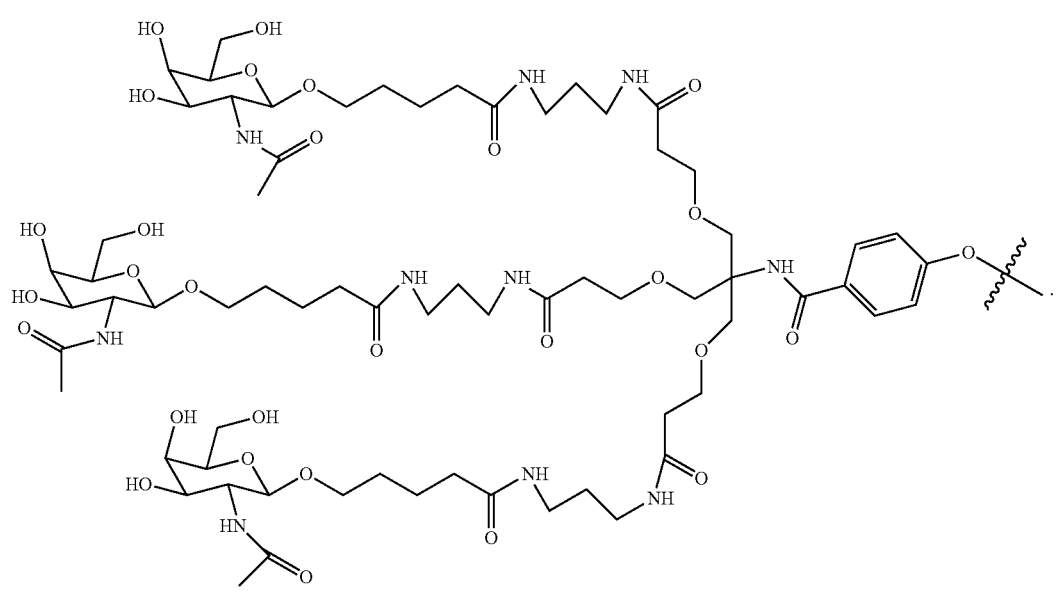

(Structure 1020)

In some embodiments, an expression-inhibiting oligomeric compound is linked to the targeting ligand and has the structure represented by the following:

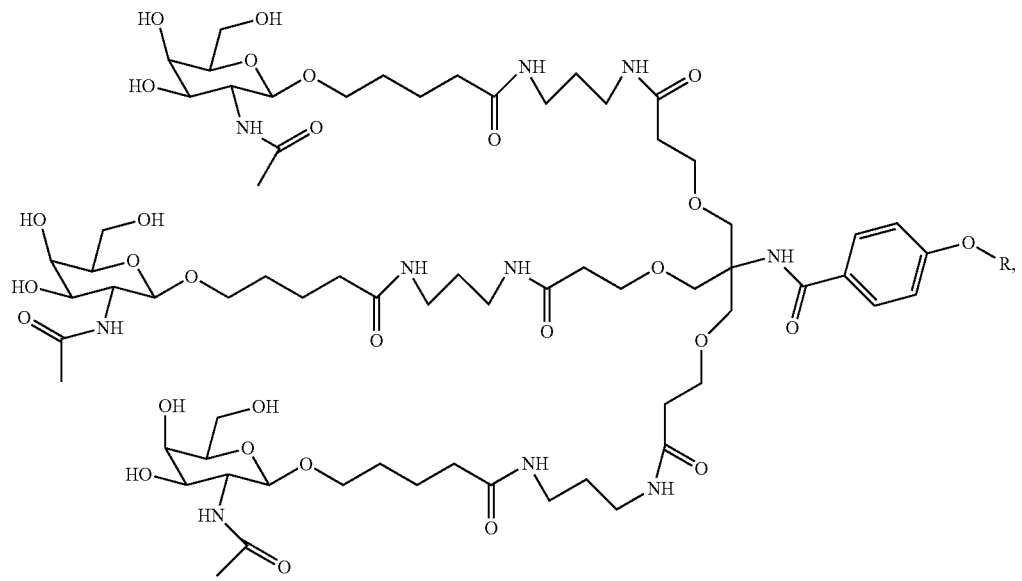

wherein R includes or consists of an expression-inhibiting oligomeric compound. (Structure 1020a).

In some embodiments, an expression-inhibiting oligomeric compound is linked to the targeting ligand and has the structure represented by the following:

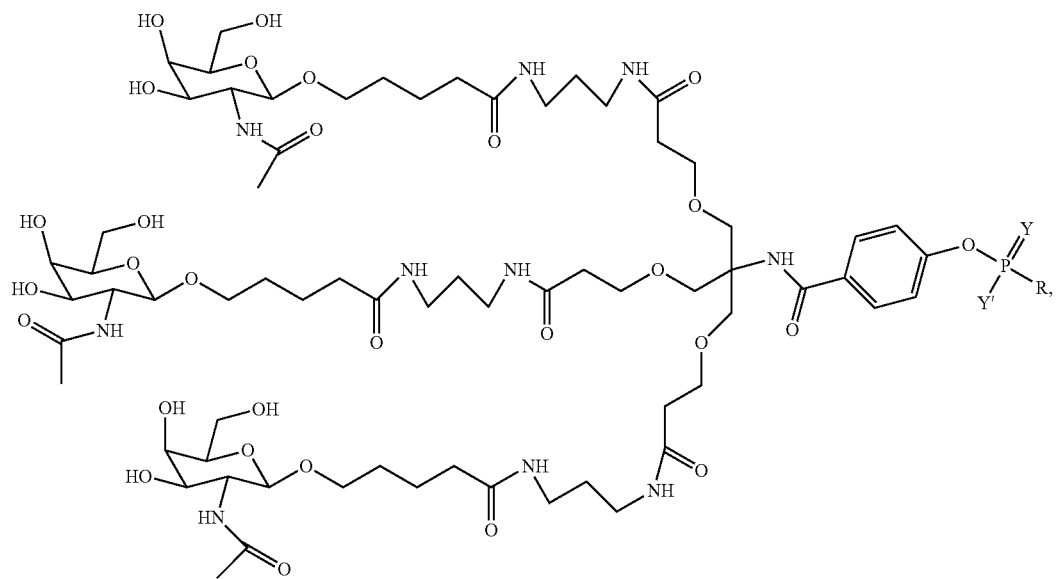

wherein R consists of or includes an expression-inhibiting oligomeric compound; Y is O or S; and Y' is O⁻, S⁻, or NH⁻. (Structure 1020a(i)).

In some embodiments, the targeting ligand is a phosphoramidite-containing compound having the structure represented by the following:

(Structure 1020b)

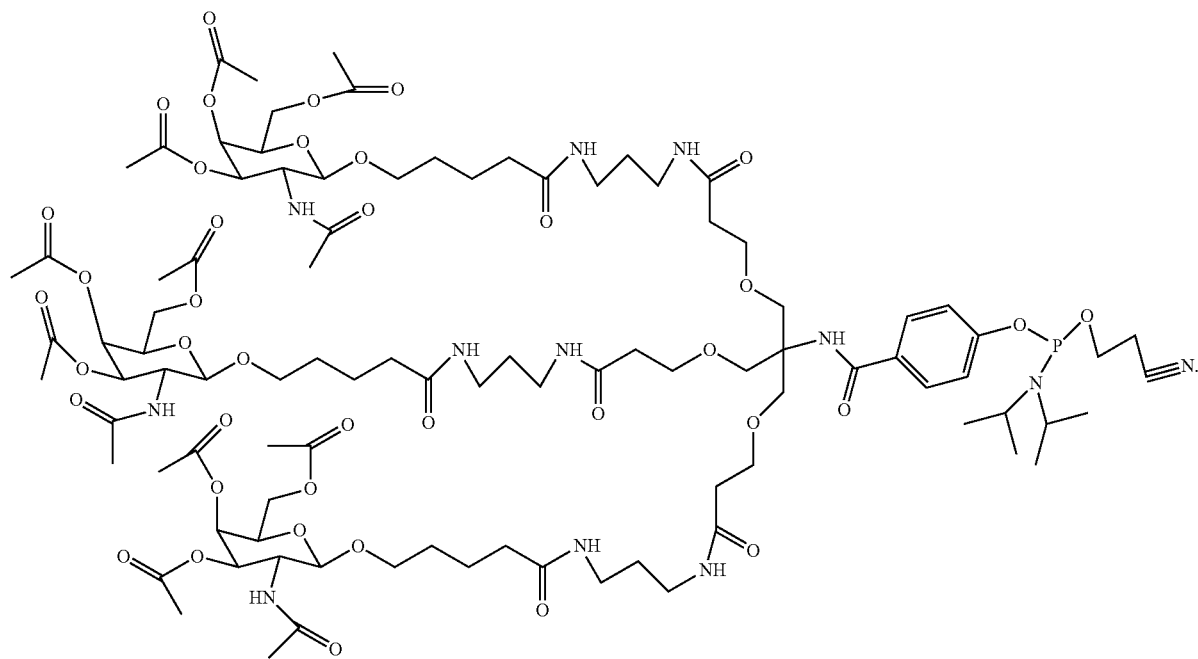

In some embodiments, the targeting ligand has the structure represented by the following:

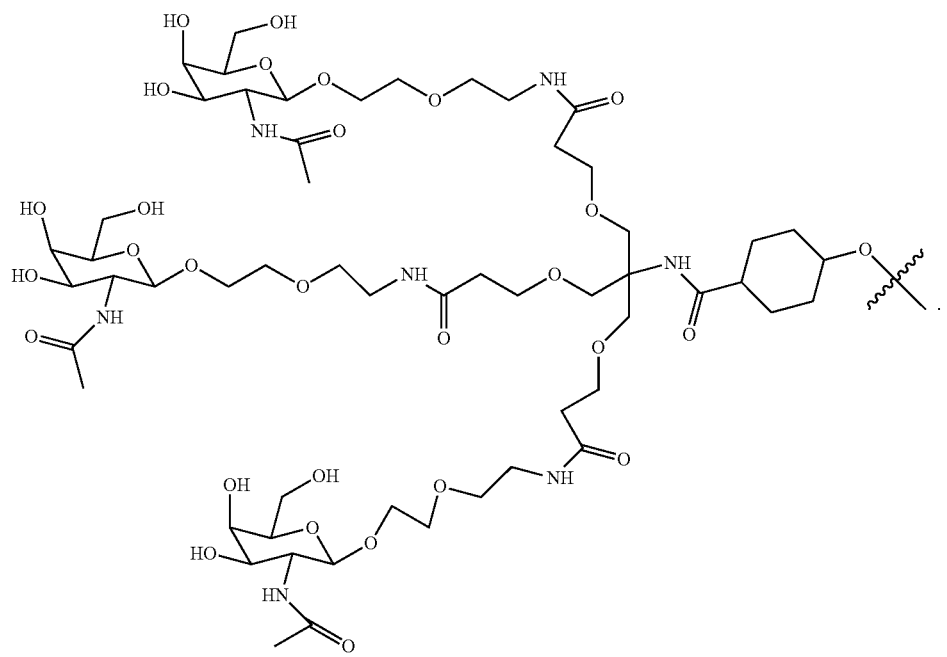

(Structure 1021)

In some embodiments, an expression-inhibiting oligomeric compound is linked to the targeting ligand and has the structure represented by the following:

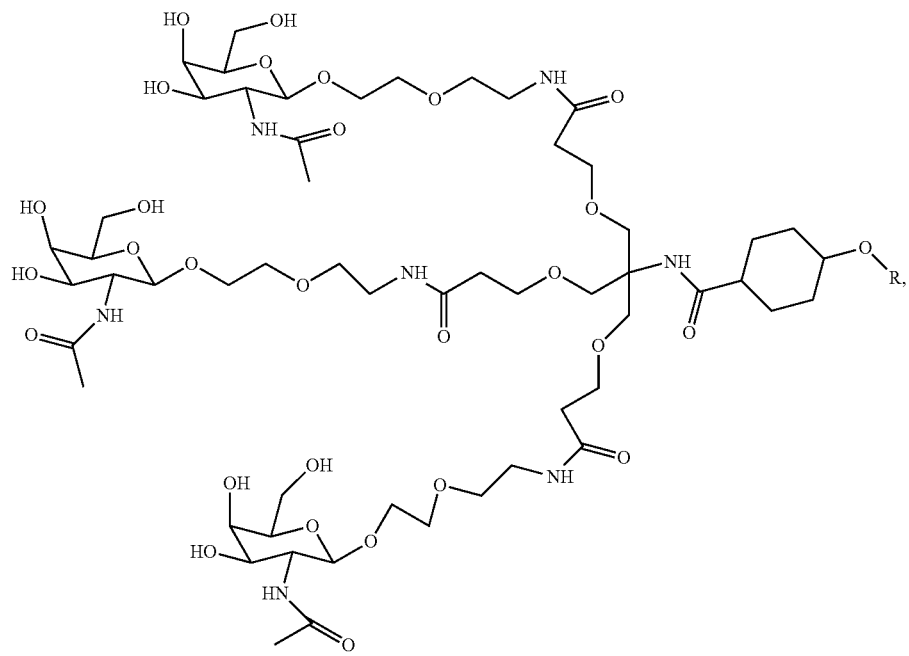

wherein R includes or consists of an expression-inhibiting oligomeric compound. (Structure 1021a).

In some embodiments, an expression-inhibiting oligomeric compound is linked to the targeting ligand and has the structure represented by the following:

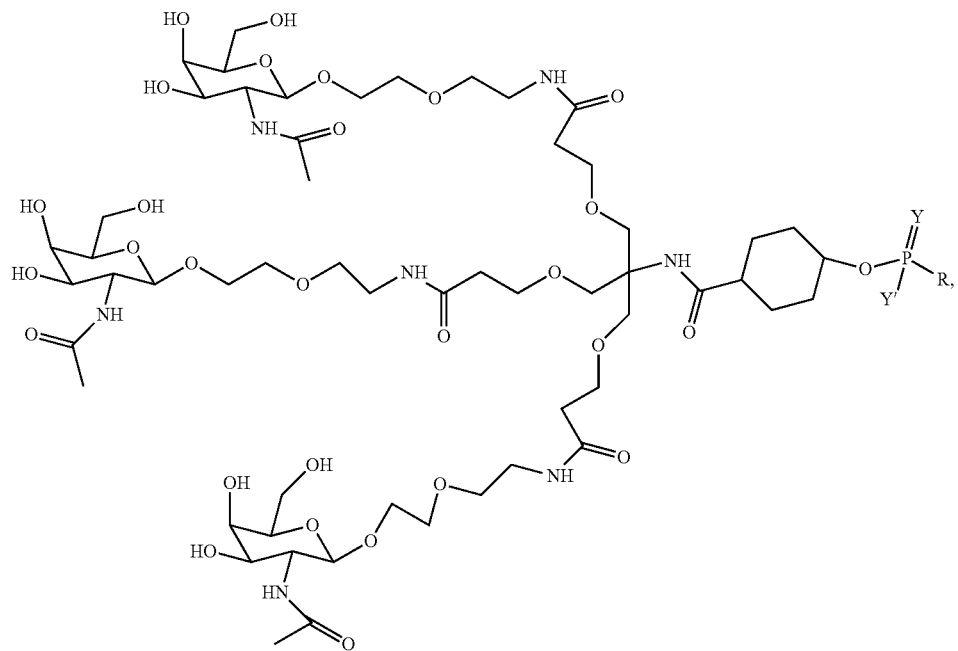
wherein R consists of or includes an expression-inhibiting oligomeric compound; Y is O or S; and Y' is O⁻, S⁻, or NH⁻. (Structure 1021a(i)).
In some embodiments, the targeting ligand is a phosphoramidite-containing compound having the structure represented by the following:
(Structure 1021b)
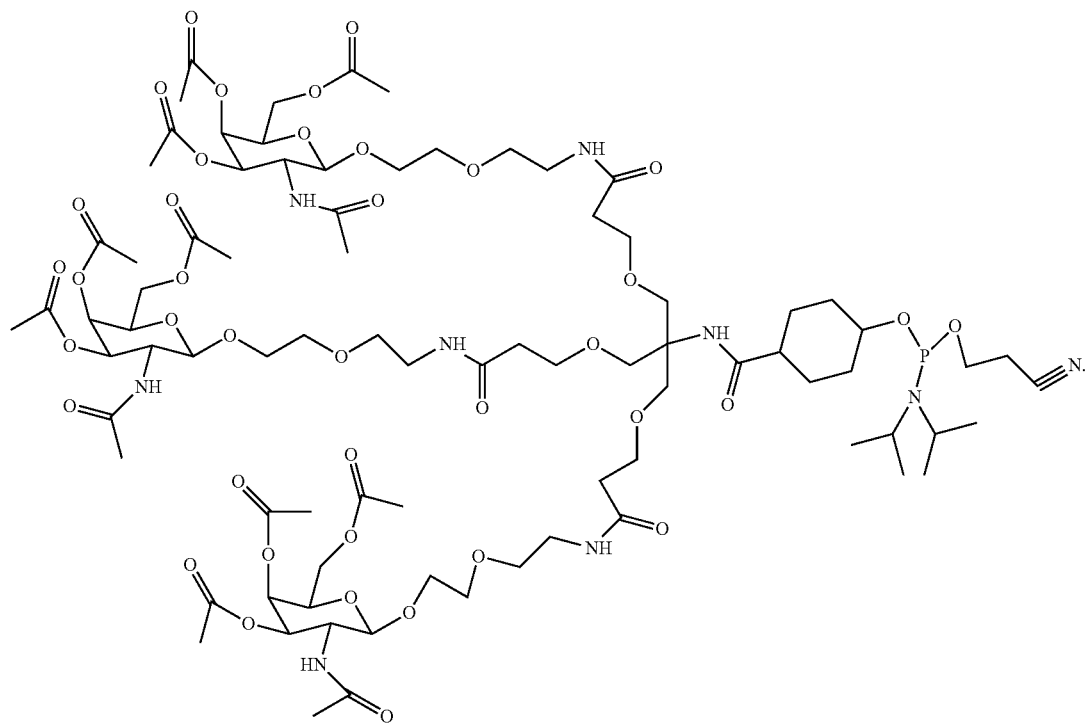

In some embodiments, the targeting ligand has the structure represented by the following:

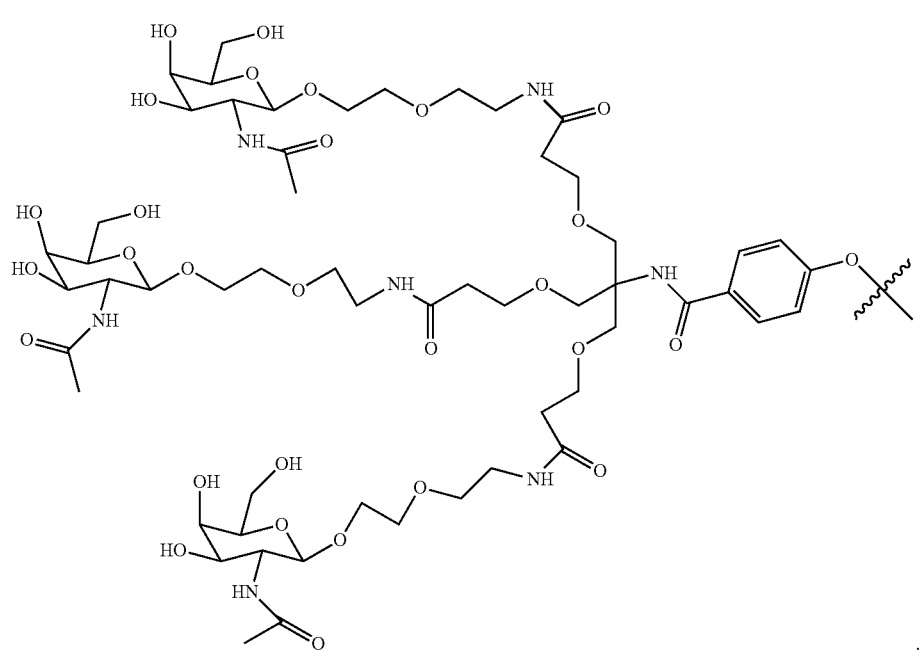

(Structure 1022)

In some embodiments, an expression-inhibiting oligomeric compound is linked to the targeting ligand and has the structure represented by the following:

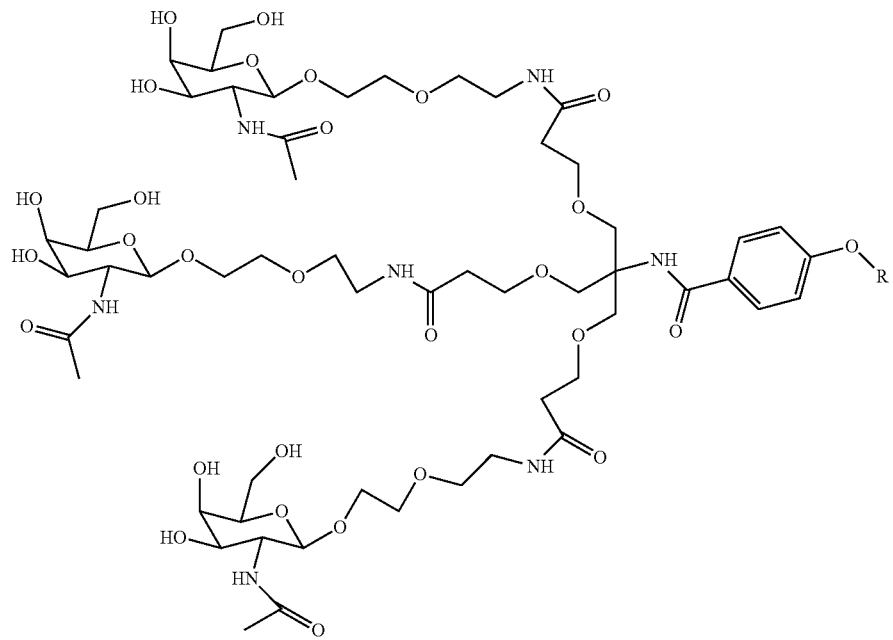

wherein R includes or consists of an expression-inhibiting oligomeric compound. (Structure 1022a).

In some embodiments, an expression-inhibiting oligomeric compound is linked to the targeting ligand and has the structure represented by the following:

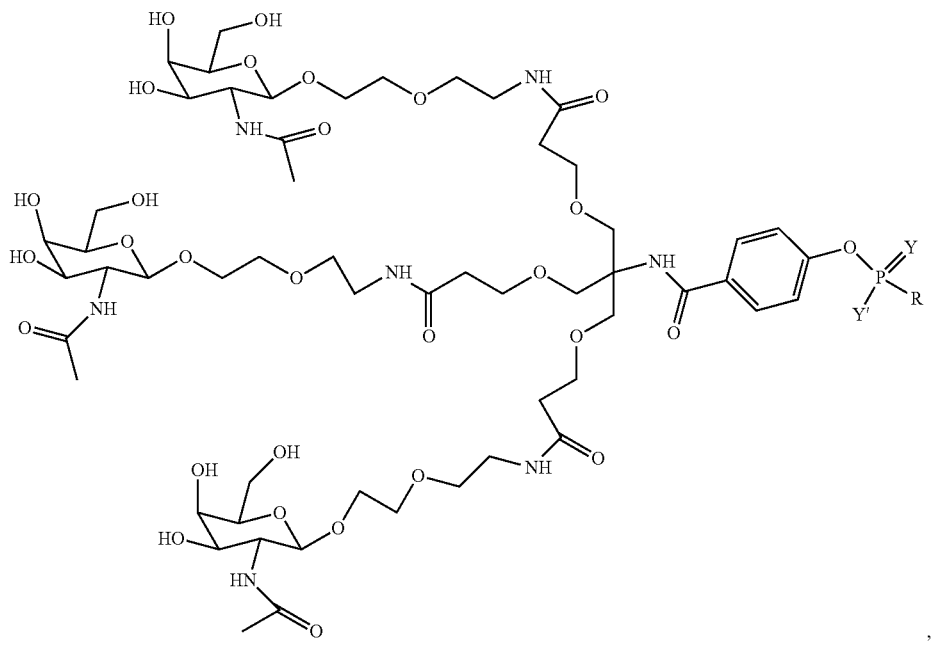

wherein R consists of or includes an expression-inhibiting oligomeric compound; Y is O or S; and Y' is O⁻, S⁻, or NH⁻. (Structure 1022a(i)).

In some embodiments, the targeting ligand is a phosphoramidite-containing compound having the structure represented by the following:

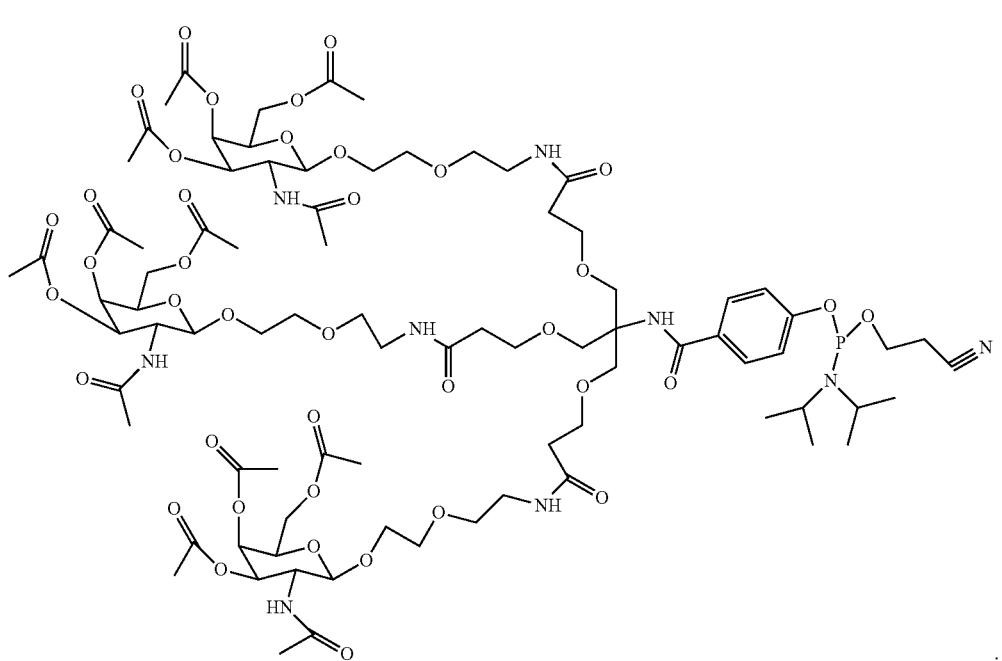

(Structure 1022b)

In some embodiments, the targeting ligand has the structure represented by the following:

(Structure 1023)

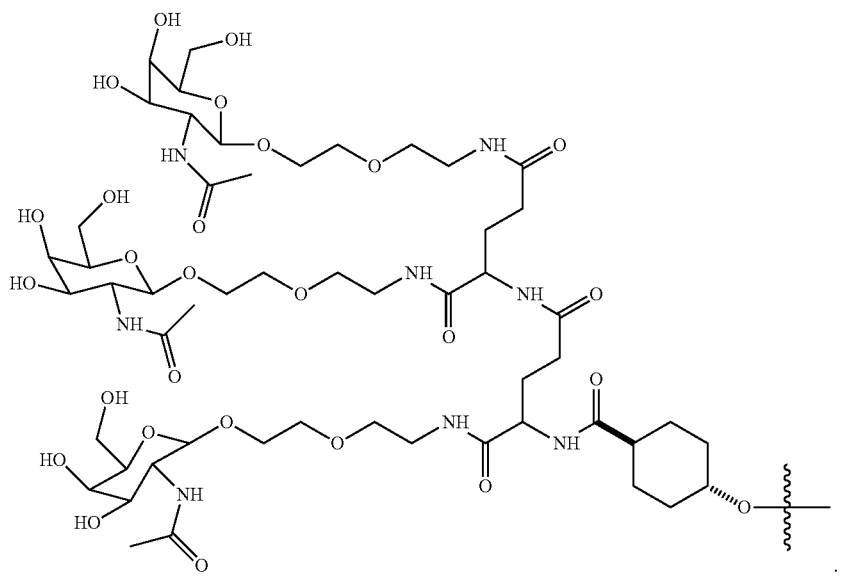

In some embodiments, an expression-inhibiting oligomeric compound is linked to the targeting ligand and has the structure represented by the following:

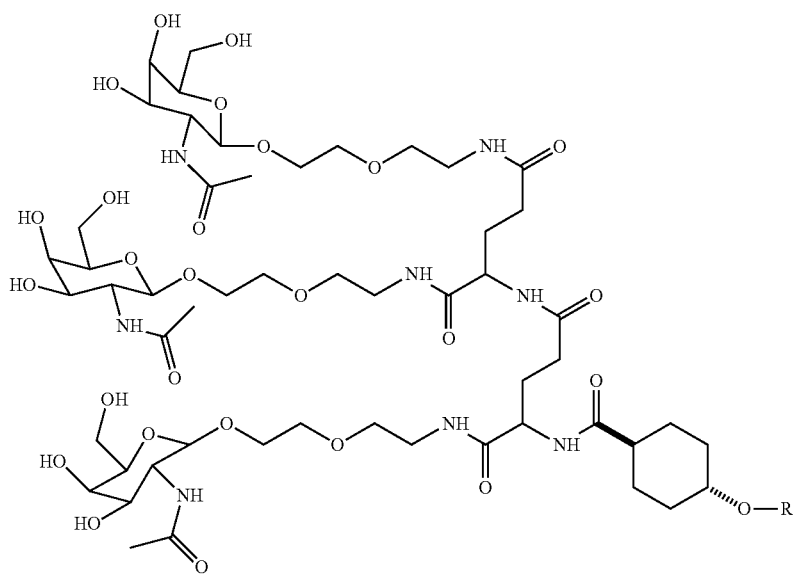

wherein R includes or consists of an expression-inhibiting oligomeric compound. (Structure 1023a).

In some embodiments, an expression-inhibiting oligomeric compound is linked to the targeting ligand and has the structure represented by the following:

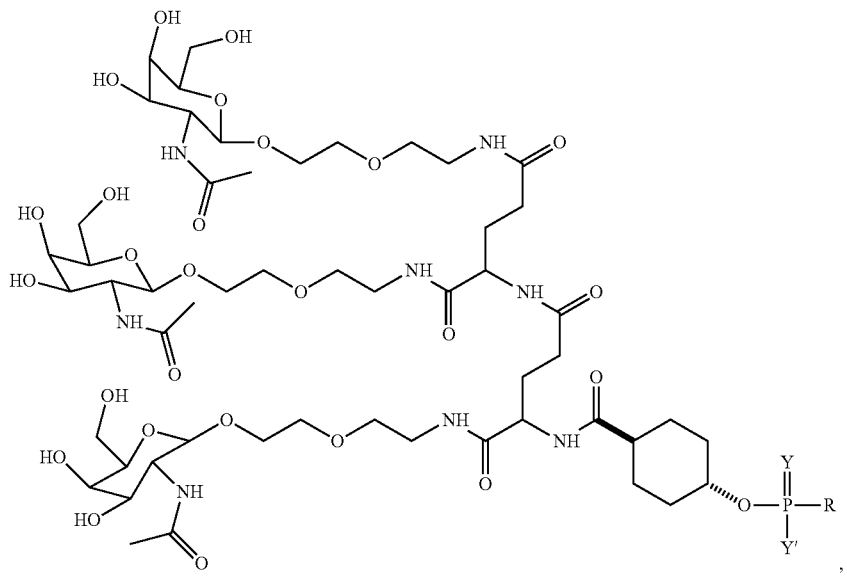

wherein R consists of or includes an expression-inhibiting oligomeric compound; Y is O or S; and Y' is O⁻, S⁻, or NH⁻. (Structure 1023a(i)).

In some embodiments, the targeting ligand is a phosphoramidite-containing compound having the structure represented by the following:

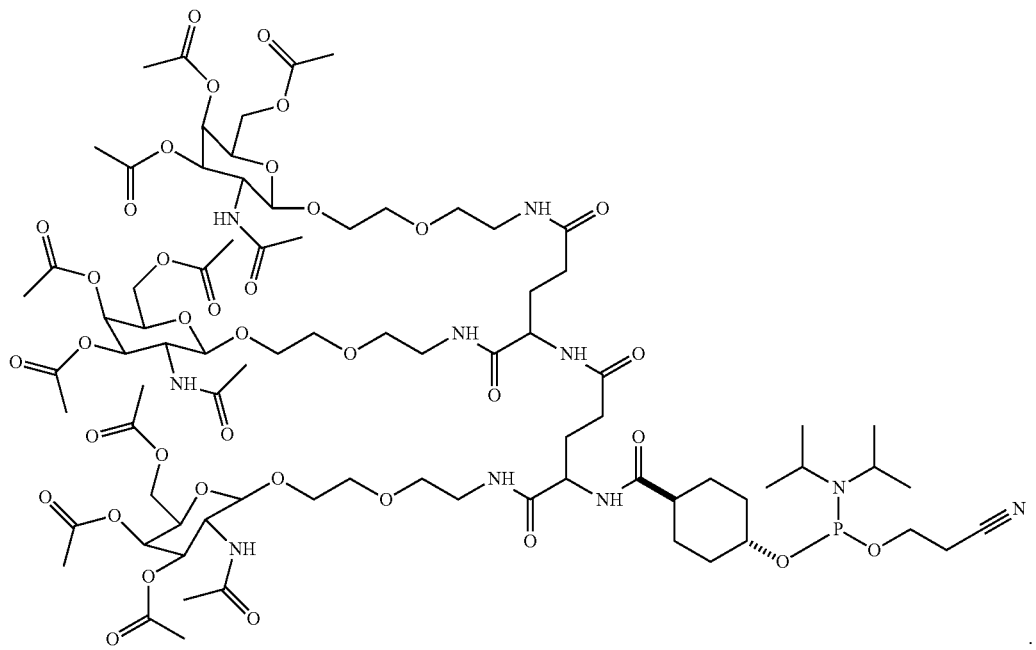

(Structure 1023b)

In some embodiments, as disclosed herein, the linker of the targeting ligand may be absent, so long as the branch point group includes at least one aryl, cycloalkyl, and/or heterocyclic group. Having one or more aryl, cycloalkyl, and/or heterocyclic groups located within the branch point group serves as a linker replacement group. In some embodiments, the one or more aryl, cycloalkyl, and/or heterocyclic groups within the branch point group are positioned between the central connection point(s) of the branch point group and the expression-inhibiting oligomeric compound.

In some embodiments, the targeting ligand has the structure represented by the following:

(Structure 1024)

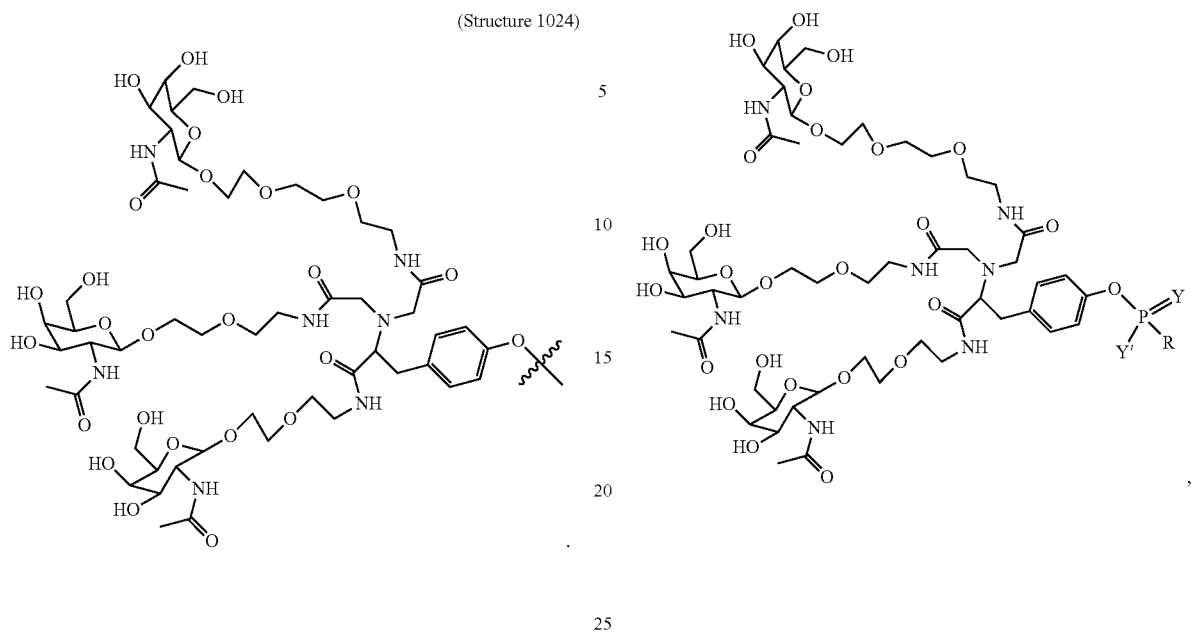

In some embodiments, an expression-inhibiting oligomeric compound is linked to the targeting ligand and has the structure represented by the following:

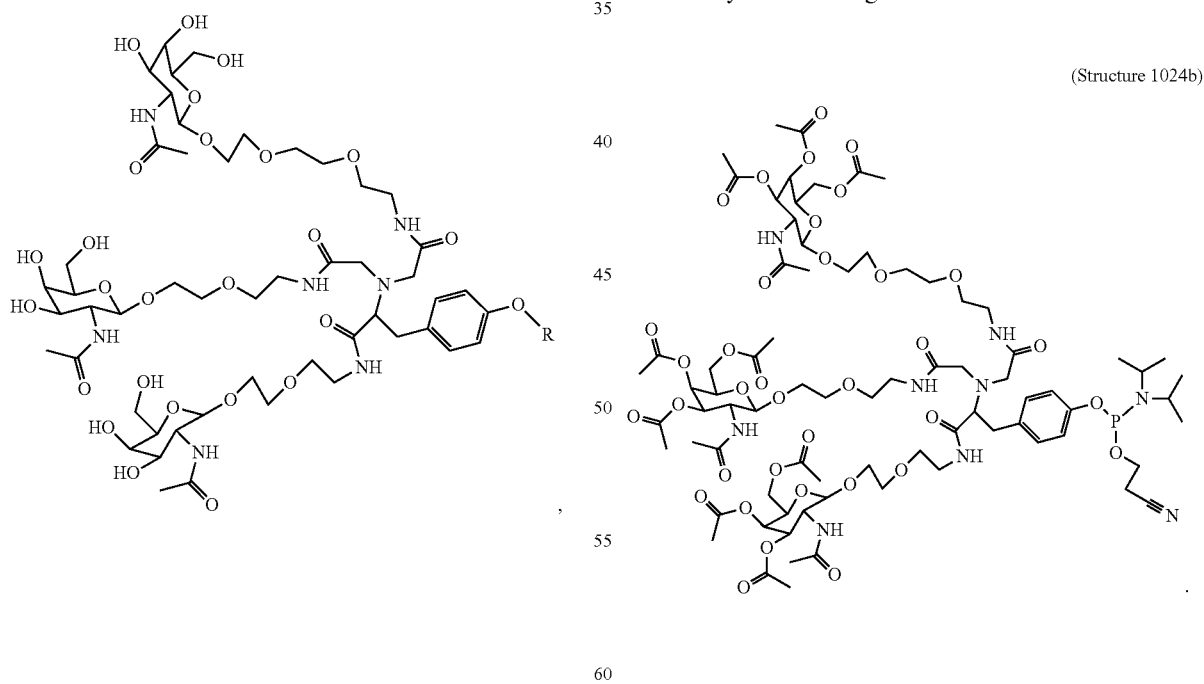

wherein R includes or consists of an expression-inhibiting oligomeric compound. (Structure 1024a).

In some embodiments, an expression-inhibiting oligomeric compound is linked to the targeting ligand and has the structure represented by the following:

wherein R consists of or includes an expression-inhibiting oligomeric compound; Y is O or S; and Y' is O⁻, S⁻, or NH⁻. (Structure 1024a(i)).

In some embodiments, the targeting ligand is a phosphoramidite-containing compound having the structure represented by the following:

(Structure 1024b)

In some embodiments, the targeting ligand has the structure represented by the following:

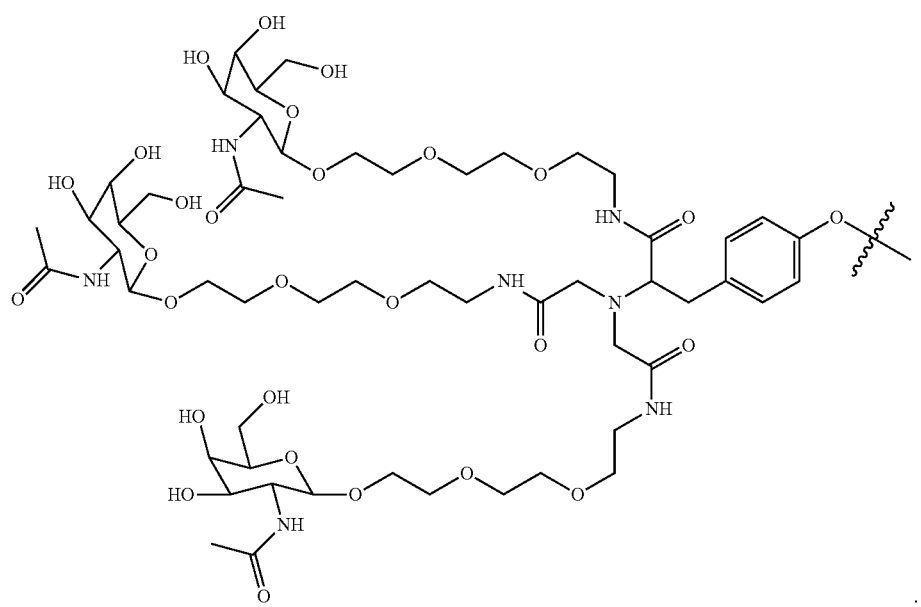

(Structure 1025)

In some embodiments, an expression-inhibiting oligomeric compound is linked to the targeting ligand and has the structure represented by the following:

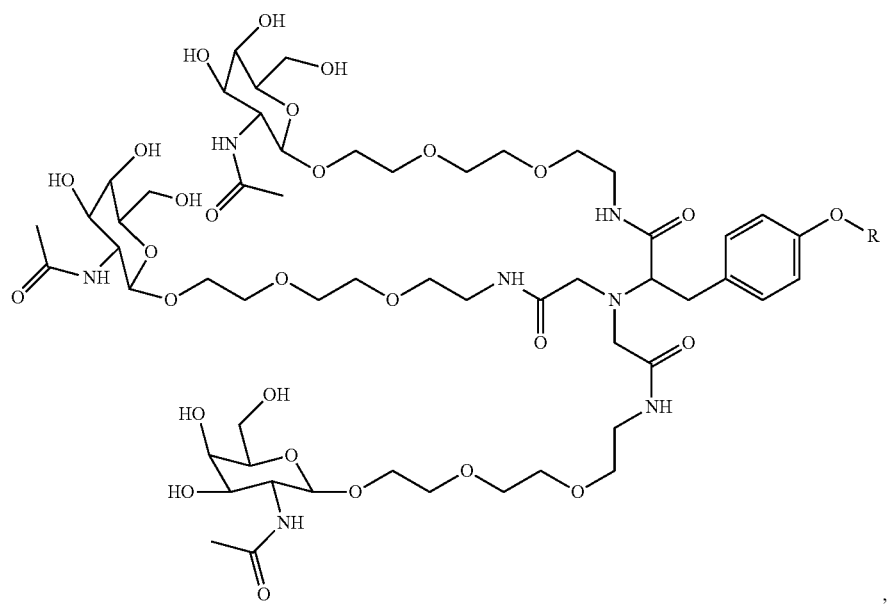

wherein R includes or consists of an expression-inhibiting oligomeric compound. (Structure 1025a).

In some embodiments, an expression-inhibiting oligomeric compound is linked to the targeting ligand and has the structure represented by the following:

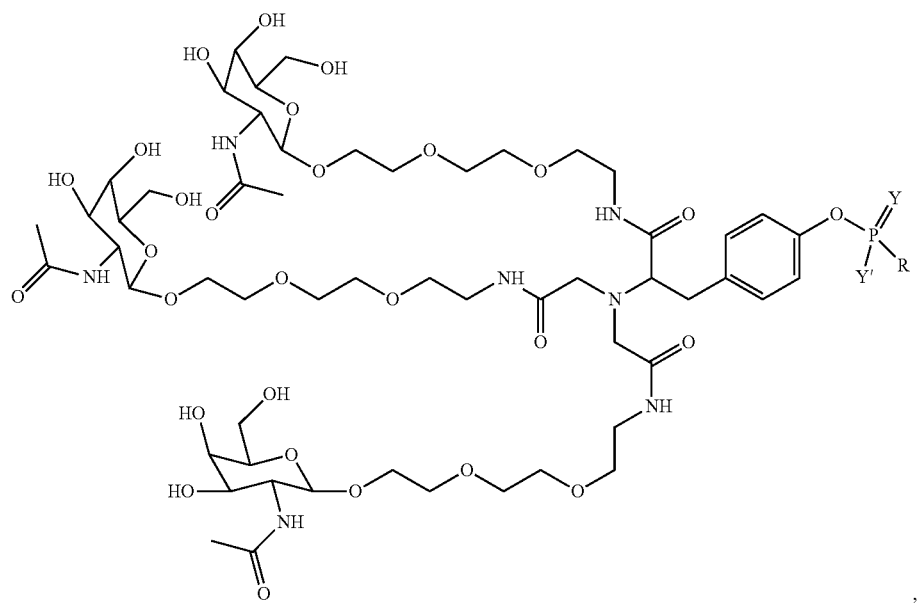

(Structure 1025a(i)).

wherein R consists of or includes an expression-inhibiting oligomeric compound; Y is O or S; and Y' is O⁻, S⁻, or NH⁻. (Structure 1025a(i)).

In some embodiments, the targeting ligand is a phosphoramidite-containing compound having the structure represented by the following:

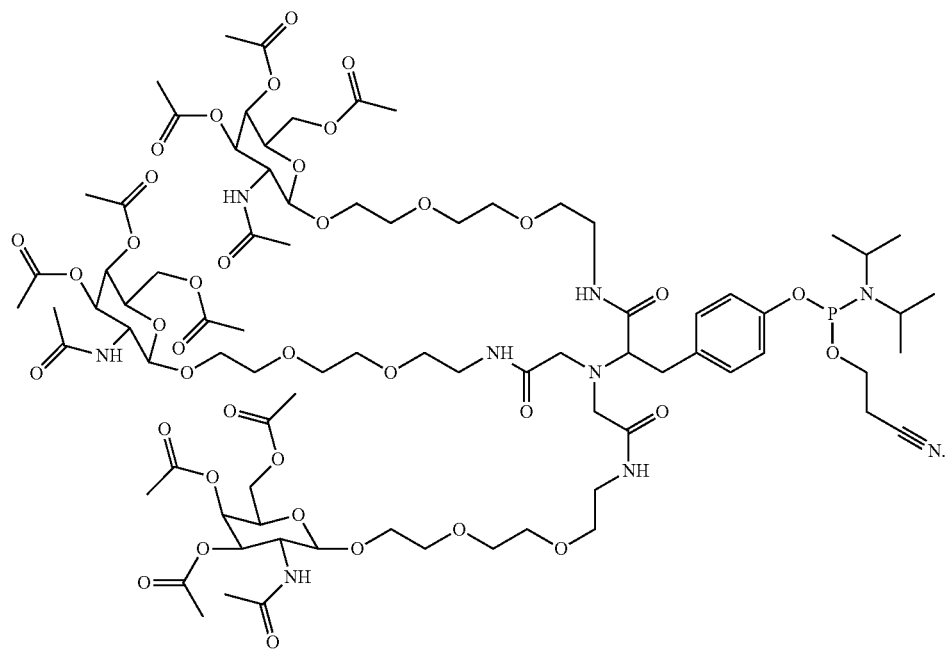

(Structure 1025b)

In some embodiments, the targeting ligand has the structure represented by the following:

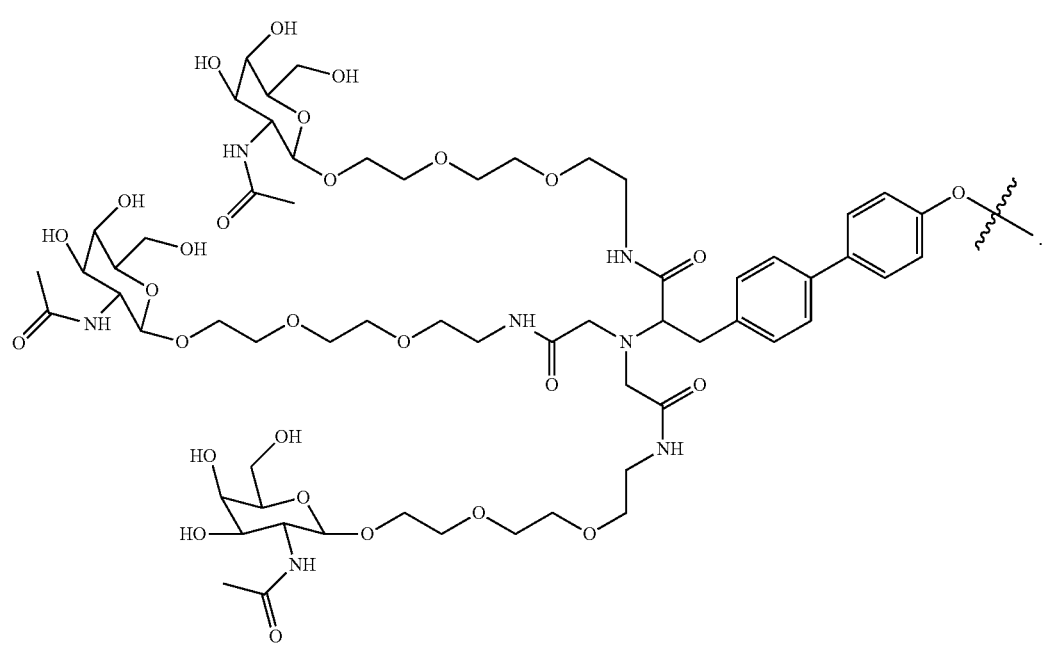

(Structure 1026)

In some embodiments, an expression-inhibiting oligomeric compound is linked to the targeting ligand and has the structure represented by the following:

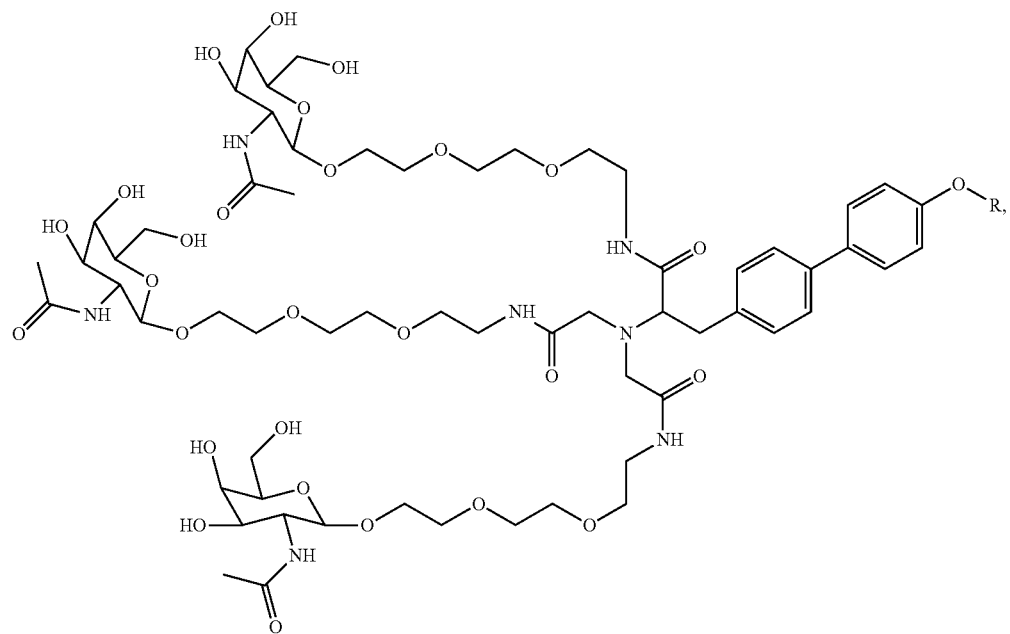

wherein R includes or consists of an expression-inhibiting oligomeric compound. (Structure 1026a).

In some embodiments, an expression-inhibiting oligomeric compound is linked to the targeting ligand and has the structure represented by the following:

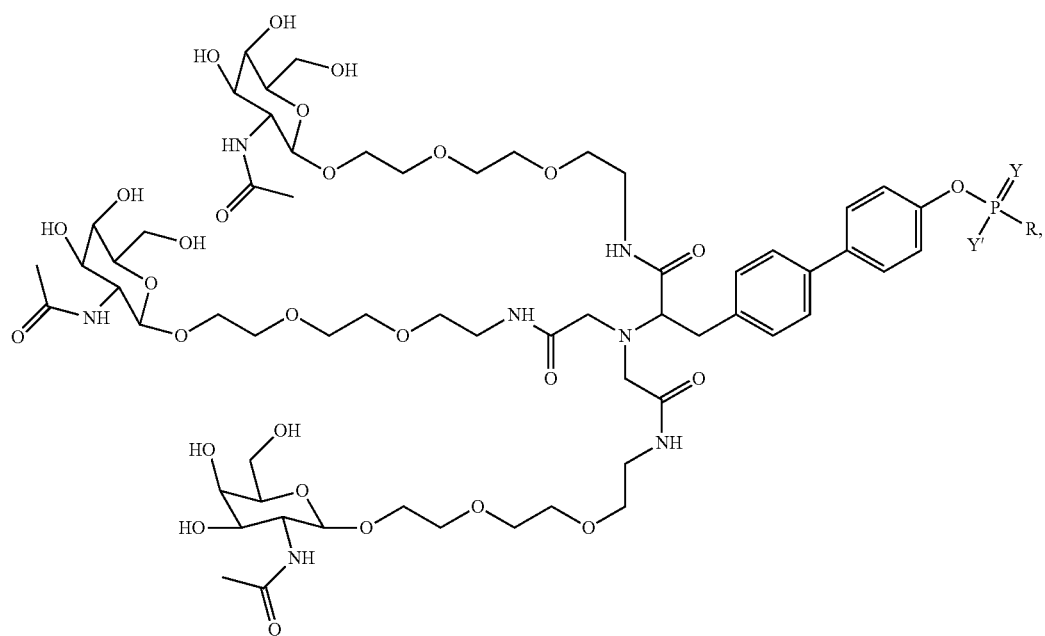

wherein R consists of or includes an expression-inhibiting oligomeric compound; Y is O or S; and Y' is O⁻, S⁻, or NH⁻. (Structure 1026a(i)).

In some embodiments, the targeting ligand is a phosphoramidite-containing compound having the structure represented by the following:

(Structure 1026b)

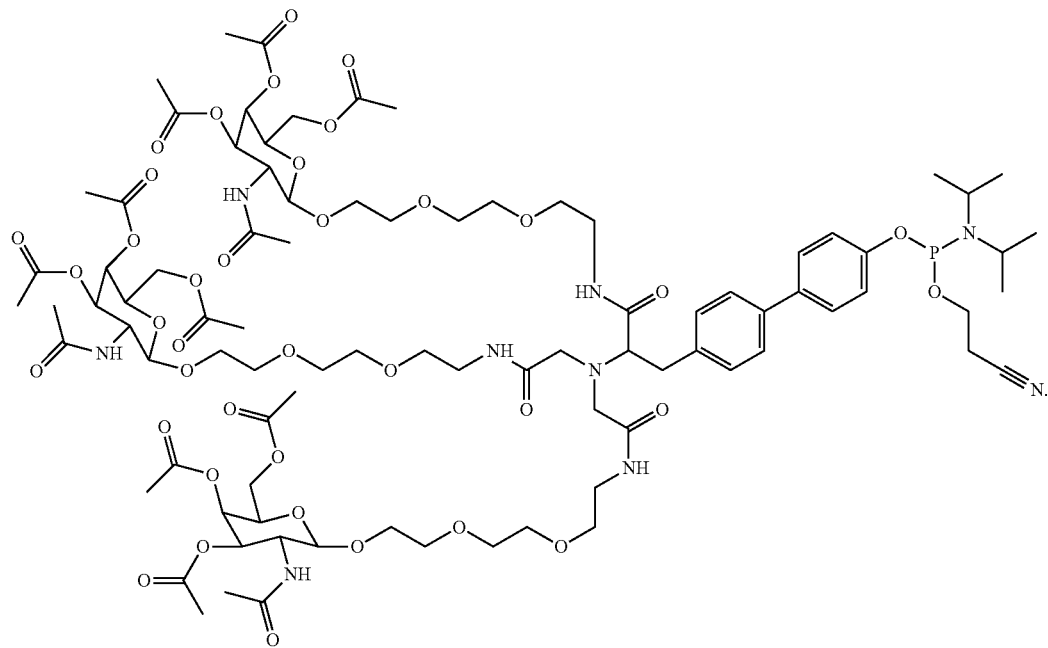

In some embodiments, the targeting ligand has the structure represented by the following:

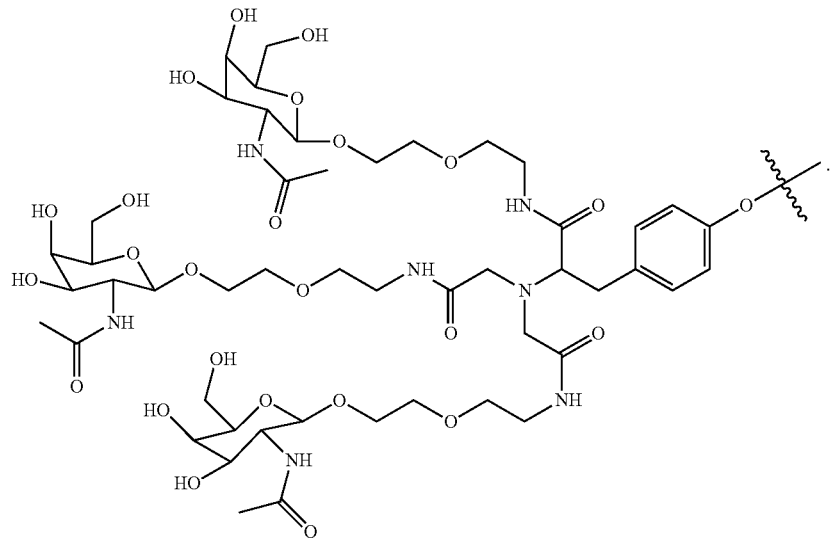

(Structure 1027)

In some embodiments, an expression-inhibiting oligomeric compound is linked to the targeting ligand and has the structure represented by the following:

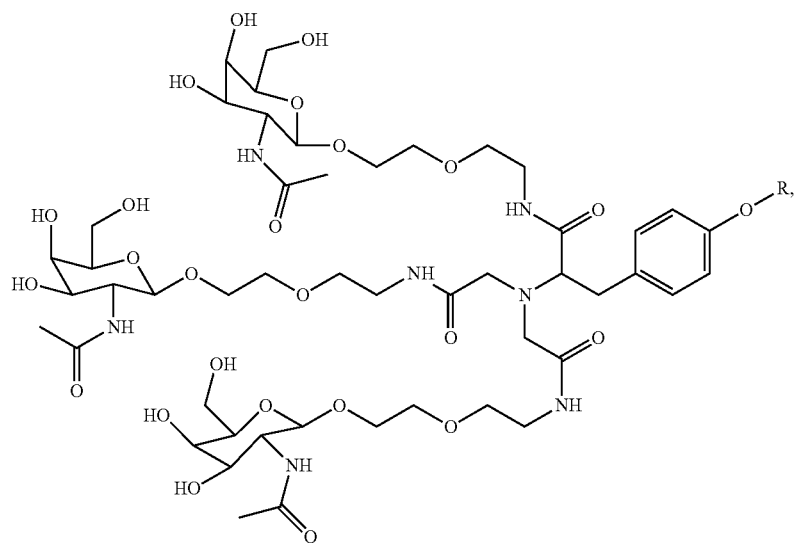

wherein R includes or consists of an expression-inhibiting oligomeric compound. (Structure 1027a).

In some embodiments, an expression-inhibiting oligomeric compound is linked to the targeting ligand and has the structure represented by the following:

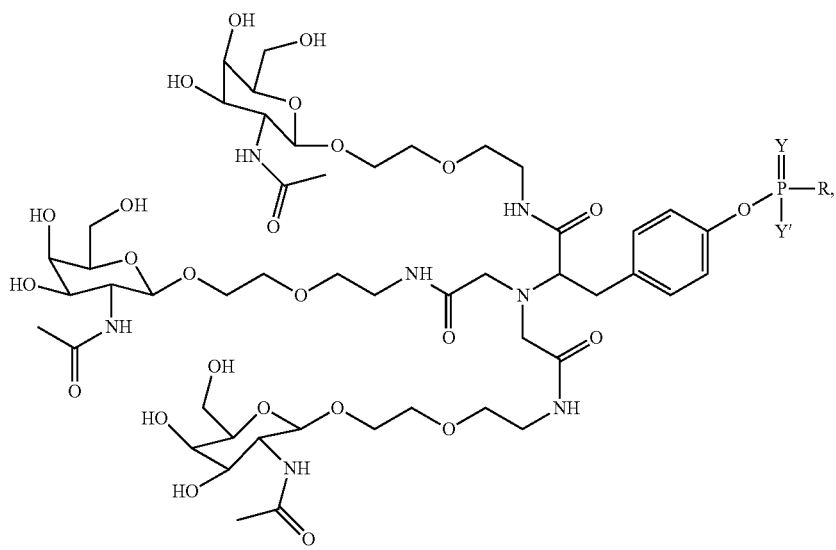

wherein R consists of or includes an expression-inhibiting oligomeric compound; Y is O or S; and Y' is O⁻, S⁻, or NH⁻. (Structure 1027a(i)).

In some embodiments, the targeting ligand is a phosphoramidite-containing compound having the structure represented by the following:

terminal galactose derivative may be linked to a tether through the C-1 carbon of the saccharide.

In some embodiments, the targeting ligand is comprised of three terminal galactosamines or galactosamine derivatives (such as N-acetyl-galactosamine) each having affinity for the asialoglycoprotein receptor. In some embodiments, (Structure 1027b)

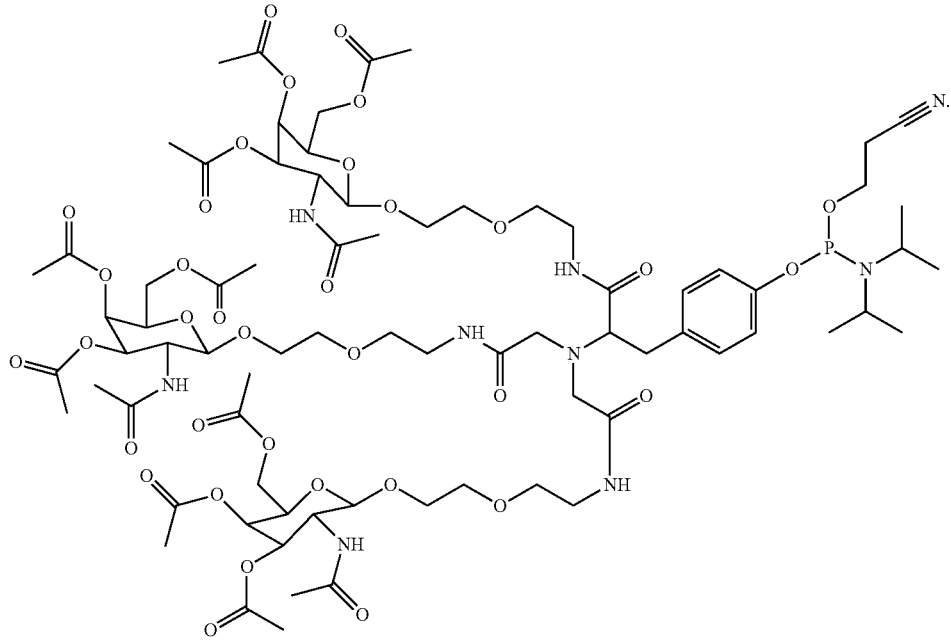

In some embodiments, the targeting ligand is in the form of a galactose cluster. As used herein, a galactose cluster includes a targeting ligand having two to four terminal galactose derivatives. As used herein, the term galactose derivative includes both galactose and derivatives of galactose having affinity for the asialoglycoprotein receptor equal to or greater than that of galactose. A galactose derivative is a saccharide sugar that is a type of targeting moiety. A the targeting ligand includes three terminal N-acetyl-galactosamines (GalNAc or NAG) as the targeting moieties.

In some embodiments, the targeting ligand is comprised of four terminal galactosamines or galactosamine derivatives (such as N-acetyl-galactosamine) each having affinity for the asialoglycoprotein receptor. In some embodiments, the targeting ligand includes four terminal N-acetyl-galactosamines (GalNAc or NAG) as the targeting moieties.

In some embodiments, each targeting moiety includes a galactosamine derivative that is N-acetyl-galactosamine. Other saccharides having affinity for the asialoglycoprotein receptor that may be used as targeting moieties may be selected from the list including: galactose, galactosamine, N-formyl-galactosamine, N-acetyl-galactosamine, N-propionyl-galactosamine, N-n-butanoylgalactosamine, and N-iso-butanoylgalactosamine. The affinities of numerous galactose derivatives for the asialoglycoprotein receptor have been studied (see for example: Iobst, S. T. and Drickamer, K. *J.B.C.* 1996, 271, 6686) or are readily determined using methods well known and commonly used in the art.

Terms commonly used in the art when referring to three terminal N-acetyl-galactosamines include tri-antennary, tri-valent, and trimer.

Terms commonly used in the art when referring to four terminal N-acetyl-galactosamines include tetra-antennary, tetra-valent, and tetramer.

Oligomeric Compounds

The targeting ligands disclosed herein can be linked to an oligomeric compound. In some embodiments, the oligomeric compound is an expression-inhibiting oligomeric compound. In some embodiments, the expression-inhibiting oligomeric compound is an RNAi agent. In some embodiments, the expression-inhibiting oligomeric compound is a double-stranded RNAi agent. In some embodiments the expression-inhibiting oligomeric compound is a single-stranded oligonucleotide. The expression-inhibiting oligomeric compounds may be synthesized using methods commonly used in the art.

The expression-inhibiting oligomeric compounds may include one or more modified nucleotides. A nucleotide base (or nucleobase) is a heterocyclic pyrimidine or purine compound which is a constituent of all nucleic acids and includes adenine (A), guanine (G), cytosine (C), thymine (T), and uracil (U). As used herein, the term "nucleotide" may include a modified nucleotide or nucleotide mimic, abasic site, or a surrogate replacement moiety. As used herein, a "modified nucleotide" is a nucleotide, nucleotide mimic, abasic site, or a surrogate replacement moiety other than a ribonucleotide (2'-hydroxyl nucleotide). In some embodiments a modified nucleotide includes a 2'-modified nucleotide (i.e. a nucleotide with a group other than a hydroxyl group at the 2' position of the five-membered sugar ring). Modified nucleotides include, but are not limited to: 2'-modified nucleotides, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides, (represented herein as NM or 2'-MOE), 2'-amino nucleotides, 2'-alkyl nucleotides, 3' to 3' linkages (inverted) nucleotides (represented herein as invdN, invN, invn, invX), non-natural base including nucleotides, locked nucleotides, bridged nucleotides, peptide nucleic acids, 2',3'-seco nucleotide mimics (unlocked nucleobase analogues, represented herein as $N_{UNA\ or}$ NUNA), locked nucleotide (represented herein as $N_{LNA}$ or NLNA), 3'-O-methoxy (2' internucleotide linked) nucleotide (represented herein as 3'-OMen), 2'-F-arabino nucleotides (represented herein as NfANA or $N_{fANA}$), morpholino nucleotides, vinyl phosphonate deoxyribonucleotide (represented herein as vpdN), vinyl phosphonate nucleotides, and abasic nucleotides (represented herein as X or Ab). It is not necessary for all positions in a given compound to be uniformly modified. Conversely, more than one modification may be incorporated in a single expression-inhibiting oligomeric compound or even in a single nucleotide thereof. The expression-inhibiting oligomeric compounds may be synthesized and/or modified by methods known in the art. Modification at each nucleotide is independent of modification of the other nucleotides.

Modified nucleobases include synthetic and natural nucleobases, such as 5-substituted pyrimidines, 6-azapyrimidines, N-2-, N-6-, and O-6-substituted purines (e.g., 2-aminopropyladenine), 5-propynyluracil, 5-propynylcytosine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine, 2-thiocytosine, 5-halouracil, 5-halocytosine, 5-propynyl uracil, 5-propynyl cytosine, 6-azo-uracil, 6-azo-cytosine, 6-azo-thymine, 5-uracil (pseudouracil), 4-thiouracil, 8-halo, 8-amino, 8-thiol, 8-thioalkyl, 8-hydroxyl and other 8-substituted adenines and guanines, 5-substituted uracils and cytosines (e.g., 5-halo uracils and cytosines (e.g., 5-bromouracil and 5-bromocytosine), 5-trifluoromethyl uracil, 5-trifluoromethyl cytosine), 7-methylguanine, 7-methyladenine, 8-azaguanine, 8-azaadenine, 7-deazaguanine, 7-deazaadenine, 3-deazaguanine, and 3-deazaadenine.

For the expression-inhibiting oligomeric compounds described herein, any modified nucleotides may be linked by phosphate-containing or non-phosphate-containing covalent internucleoside linkages. Modified internucleoside linkages or backbones include, but are not limited to, 5'-phosphorothioate group (represented herein as a lower case 's' before a nucleotide, as in sN, sn, sNf, or sdN), chiral phosphorothioates, thiophosphate, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, morpholino linkages, boranophosphates having normal 3'-5' linkages, 2'-5' linked analogs of boranophosphates, and boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, an expression-inhibiting oligomeric compound is a double-stranded RNAi agent, and includes a sense strand and an antisense strand that are at least partially complementary (at least 70% complementary) to each other. The antisense strand contains a region having a sequence that is perfectly complementary (100% complementary) or at least substantially complementary (at least 85% complementary) to a sequence in a target mRNA. The length of a double-stranded RNAi agent sense strand and antisense strand each can be 16 to 30 nucleotides in length. The sense and antisense strands can be either the same length or they can be different lengths. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In other embodiments, the sense and antisense strands are each independently 17-21 nucleotides in length. In some embodiments, both the sense and antisense strands are each 21-26 nucleotides in length. In some embodiments, both the sense and antisense strands are each 26 nucleotides in length. In some embodiments, the sense and antisense strands are each independently 17 to 26 nucleotides in length. In some embodiments, a double-stranded RNAi agent has a duplex length of about 16, 17, 18, 19, 20, 21, 22, 23 or 24 nucleotides. This region of perfect or substantial complementarity between the sense strand and the antisense strand is typically 15-25 (e.g., 15, 16, 17, 18, 19, 20, 21, 22, 23, 24, or 25 nucleotides in length) nucleotides in length and occurs at or near the 5' end of the antisense strand.

The expression-inhibiting oligomeric compounds that are conjugated to the ligands disclosed herein optionally and independently include an additional 1, 2, 3, 4, 5, or 6 nucleotides (as an extension) at the 3' end, the 5' end, or both the 3' and 5' ends of the core sequences. These additional nucleotides, if present, may or may not be complementary to the corresponding sequence in the targeted mRNA.

In some embodiments, when a double-stranded RNAi agent is conjugated to the targeting ligands disclosed herein, the additional sense strand additional nucleotides, if present, may or may not be identical to the corresponding sequence in the targeted mRNA. The additional antisense strand additional nucleotides, if present, may or may not be complementary to the corresponding additional nucleotides of the sense strand, if present.

Double-stranded RNAi agents can be formed by annealing an antisense strand with a sense strand.

In some embodiments, the targeting ligand is linked to an RNAi agent at the 3' or 5' end of either the sense strand or the antisense strand of the RNAi agent. In some embodiments, the targeting ligand is linked to 5' end of the sense strand. In some embodiments, the targeting ligand is linked to the 3' end of the sense strand. In some embodiments, the targeting ligand is linked to the RNAi agent via a labile, cleavable, or reversible bond. In some embodiments, the labile, cleavable, or reversible bond is included in a cleavable moiety added between the RNAi agent and the targeting ligand.

In some embodiments, the expression-inhibiting oligomeric compound is a single-stranded oligonucleotide. In some embodiments, the single-stranded oligonucleotide is utilizes the RNA interference mechanism to inhibit expression of the target mRNA. In some embodiments, the single-stranded oligonucleotides are active in reducing expression of the target nucleic acid through a mechanism other than RNA interference.

In some embodiments, the gene expression level and/or mRNA level of a target in a subject to whom a described targeting ligand conjugated to an expression-inhibiting oligomeric compound is administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to administration or to a subject not receiving the targeting ligand conjugate. The gene expression level and/or mRNA level in the subject may be reduced in a cell, group of cells, and/or tissue of the subject. In some embodiments, the protein level in a subject to whom a described targeting ligand conjugated to an expression-inhibiting oligomeric compound has been administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to being administered the targeting ligand conjugate or to a subject not receiving the targeting ligand conjugate. The protein level in the subject may be reduced in a cell, group of cells, tissue, blood, and/or other fluid of the subject. A reduction in gene expression, mRNA, or protein levels can be assessed by any methods known in the art. Reduction or decrease in mRNA level and/or protein level are collectively referred to herein as inhibiting, decreasing, or reducing the expression of the targeted gene.

Specific expression-inhibiting oligomeric compounds that can be used with the targeting ligands disclosed are known in the art. In particular, numerous references disclose expression-inhibiting oligomeric compounds that may be conjugated to the targeting ligands disclosed herein for delivery of the composition to the liver. Non-limiting examples include U.S. patent application Ser. No. 15/281,309, entitled Compositions and Methods for Inhibiting Gene Expression of LPA, which is incorporated herein by reference in its entirety, discloses various double-stranded expression-inhibiting oligomeric compounds targeting the human apolipoprotein(a) gene [LPA] (to inhibit expression of the apo(a) protein which is part of the lipoprotein(a) particle, and thereby the lipoprotein(a) particle (Lp(a))), that are suitable for use with the targeting ligands disclosed herein. The apo(a) gene [LPA] is expressed predominantly in the liver in humans and non-human primates. Similarly, for example, U.S. patent application Ser. No. 15/229,314, entitled RNAi Therapy for Hepatitis B Virus Infection, which is also incorporated herein by reference in its entirety, discloses various double-stranded expression-inhibiting oligomeric compounds targeting the hepatitis B virus, that are suitable for use with the targeting ligands disclosed herein. The Hepatitis B Virus is a strict hepatotrophic, double-stranded. DNA containing virus and is classified as one member of the Hepadnaviruses, belonging to the family of Hepadnaviridae. Further, as another example, U.S. patent application Ser. No. 15/229,314, entitled Compositions and Methods for Inhibiting Gene Expression of Factor XII, which is incorporated herein by reference in its entirety, discloses various double-stranded expression-inhibiting oligomeric compounds targeting the Factor XII (or Factor 12, F12) gene, that are suitable for use with the targeting ligands disclosed herein. Factor XII is a serine protease expressed predominantly in the liver and found in blood. Additionally, as another example U.S. patent application Ser. No. 14/740,307, entitled Compositions and Methods for Inhibiting Gene Expression of Alpha-1 AntiTrypsin, which is incorporated herein by reference in its entirety, discloses various double-stranded expression-inhibiting oligomeric compounds targeting the alpha-1 antitrypsin (or AAT) gene, that are suitable for use with the targeting ligands disclosed herein. AAT is a protease inhibitor belonging to the serpin superfamily, and normal AAT protein is primarily synthesized in the liver by hepatocytes and secreted into blood. Further, WO 2016/01123, entitled Organic Compositions to Treat APOC3-Related Diseases, which is incorporated herein by reference in its entirety, discloses various double-stranded expression-inhibiting oligomeric compounds targeting human apolipoprotein III (APOC3), that are suitable for use with the targeting ligands disclosed herein. Apolipoprotein C-III is a constituent of lipoproteins that is believed to inhibit hepatic uptake of triglyceride-rich particles. Additional references disclosing various therapeutic compounds, including expression-inhibiting oligomeric compounds, that may be suitable for use with the targeting ligands disclosed herein, can also be found in the art. These include, but are not limited to, compositions where targeting to the liver would be desirable.

Pharmaceutical Compositions and Formulations

The targeting ligands disclosed herein, when linked to an oligomeric compound, can be used to treat a subject (e.g., a human or mammal) having a disease or disorder that would benefit from administration of the compound. In some embodiments, the targeting ligands disclosed herein, when linked to an expression-inhibiting oligomeric compound, can be used to treat a subject (e.g., a human) having a disease or disorder that would benefit from reduction or inhibition in expression of the target mRNA. The subject is administered a therapeutically effective amount of any one or more expression-inhibiting oligomeric compounds, such as an RNAi agent, that is linked to a targeting ligand disclosed herein. The subject can be a human, patient, or human patient. The subject may be an adult, adolescent, child, or infant. The described pharmaceutical compositions including a targeting ligand linked to an expression-inhibiting oligomeric compound can be used to provide methods for the therapeutic treatment of diseases. Such methods include administration of a pharmaceutical composition described herein to a human being or animal.

The pharmaceutical compositions and methods disclosed herein may decrease the level of the target mRNA in a cell, group of cells, group of cells, tissue, or subject, including: administering to the subject a therapeutically effective amount of a herein described expression-inhibiting oligomeric compound that is linked to a targeting ligand, thereby inhibiting the expression of a target mRNA in the subject. In some embodiments, the subject has been previously identified as having a pathogenic upregulation of the target gene in the targeted cell or tissue.

In some embodiments, pharmaceutical compositions include at least one expression-inhibiting oligomeric compound linked to a targeting ligand. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering a composition including a targeting ligand as described herein linked to an expression-inhibiting oligomeric compound, such as an RNAi agent, to a subject to be treated. In some embodiments, one or more pharmaceutically acceptable excipients (including vehicles, carriers, diluents, and/or delivery polymers) are added to the pharmaceutical compositions including a targeting ligand linked to an expression-inhibiting oligomeric compound, thereby forming a pharmaceutical formulation suitable for in vivo delivery to a human.

In some embodiments, the described pharmaceutical compositions including a targeting ligand linked to an expression-inhibiting oligomeric compound are used for treating or managing clinical presentations associated with expression of a target mRNA. In some embodiments, a therapeutically or prophylactically effective amount of one or more of pharmaceutical compositions is administered to a subject in need of such treatment, prevention or management. In some embodiments, administration of any of the conjugated ligands covalently linked to an oligomeric compound can be used to decrease the number, severity, and/or frequency of symptoms of a disease in a subject.

The described pharmaceutical compositions including a targeting ligand linked to an expression-inhibiting oligomeric compound, can be used to treat at least one symptom in a subject having a disease or disorder that would benefit from reduction or inhibition in expression of a target mRNA. In some embodiments, the subject is administered a therapeutically effective amount of one or more pharmaceutical compositions including an expression-inhibiting oligomeric compound, such as an RNAi agent, linked to a targeting ligand described herein, thereby treating the symptom. In other embodiments, the subject is administered a prophylactically effective amount of one or more of expression-inhibiting oligomeric compounds thereby preventing the at least one symptom.

In some embodiments, the expression or level of a target mRNA in a subject to whom an expression-inhibiting oligomeric compound linked to a targeting ligand disclosed herein is administered is reduced by at least about 5%, for example, but at least about 10%, 15%, 20%, 25%, 30%, 35%, 40%, 45%, 50%, 55%, 60%, 65%, 70%, 75%, 80%, 85%, 90%, 95%, or 98% relative to the subject not receiving the pharmaceutical composition. The gene expression level in the subject may be reduced in a cell, group of cells, and/or tissue of the subject. In some embodiments, the level of mRNA is reduced. In other embodiments, the expressed protein level is reduced. In some embodiments, the level of protein in a subject to whom an expression-inhibiting oligomeric compound linked to a targeting ligand disclosed herein is administered is reduced by at least about 5%, for example, but at least about 10%, 15%, 20%, 25%, 30%, 35%, 40%, 45%, 50%, 55%, 60%, 65%, 70%, 75%, 80%, 85%, 90%, 95%, or 98% relative to the subject not receiving the pharmaceutical composition. Reduction in expression, mRNA levels, or protein levels can be assessed by any methods known in the art. Reduction or decrease in mRNA level and/or protein level are collectively referred to herein as a reduction or decrease in target RNA or inhibiting or reducing the expression of target mRNA.

The route of administration is the path by which an expression-inhibiting oligomeric compound is brought into contact with the body. In general, methods of administering drugs and nucleic acids for treatment of a mammal are well known in the art and can be applied to administration of the compositions described herein. The expression-inhibiting oligomeric compound linked to the herein described targeting ligands can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, there herein described pharmaceutical compositions and be administered via inhalation.

The pharmaceutical compositions including an expression-inhibiting oligomeric compound linked to a targeting ligand described herein can be delivered to a cell, group of cells, tumor, tissue, or subject using oligonucleotide delivery technologies known in the art. In general, any suitable method recognized in the art for delivering a nucleic acid molecule (in vitro or in vivo) can be adapted for use with a herein described compositions. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the herein described pharmaceutical compositions may comprise one or more pharmaceutically acceptable excipients. In some embodiments, the pharmaceutical compositions described herein can be formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical ingredient (API, therapeutic product, e.g., F12 RNAi agent) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

In conjunction with the methods of the present disclosure, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi agents may be used as "pharmaceutical compositions."

As used herein, "pharmacologically effective amount," "therapeutically effective amount," or simply "effective amount" refers to that amount of an RNAi agent to produce a pharmacological, therapeutic or preventive result.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 3 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

For treatment of disease or for formation of a medicament or composition for treatment of a disease, the pharmaceutical compositions described herein including an expression-inhibiting oligomeric compound, such as an RNAi agent, linked to a targeting ligand, can be combined with an excipient or with a second therapeutic agent or treatment including, but not limited to: a second or other expression-inhibiting oligomeric compound, a small molecule drug, an antibody, an antibody fragment, and/or a vaccine.

The described targeting ligands, when linked to expression-inhibiting oligomeric compounds, and when added to pharmaceutically acceptable excipients or adjuvants, can be packaged into kits, containers, packs, or dispensers. The pharmaceutical compositions described herein may packaged in pre-filled syringes or vials.

The above provided embodiments are now illustrated with the following, non-limiting examples.

EXAMPLES

The following examples are not limiting and are intended to illustrate certain embodiments disclosed herein.

Some of the abbreviations used in the following experimental details of the synthesis of the examples are defined below: h or hr=hour(s); min=minute(s); mol=mole(s); mmol=millimole(s); M=molar; µM=micromolar; g=gram (s); µg=microgram(s); rt or RT=room temperature; L=liter (s); mL=milliliter(s); wt=weight; $Et_2O$=diethyl ether; THF=tetrahydrofuran; DMSO=dimethyl sulfoxide; EtOAc=ethyl acetate; $Et_3N$ or TEa=triethylamine; i-$Pr_2$NEt or DIPEA or DIEA=diisopropylethylamine; $CH_2Cl_2$ or DCM=methylene chloride; $CHCl_3$=chloroform; $CDCl_3$=deuterated chloroform; $CCl_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DMAP=4-dimethylaminopyridine; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; HCl=hydrogen chloride or hydrochloric acid; NMM=N-methylmorpholine; $H_2$=hydrogen gas; KF=potassium fluoride; EDC-HCl=N-(3-Dimethylaminopropyl)-N'-ethylcarbodiimide hydrochloride; MTBE=methyl-tert-butyl ether; MeOH=methanol; Ar=argon; $SiO_2$=silica; $R_T$=retention time.

Additionally, examples of expression-inhibiting oligomeric compounds suitable for use with the targeting ligands disclosed herein are set forth in various Tables in the Examples that follow. The following notations are used to indicate modified nucleotides for sequences set forth in the Tables disclosed herein:

N=2'-OH (unmodified) ribonucleotide (capital letter without for d indication)
n=2'-OMe modified nucleotide
Nf=2'-fluoro modified nucleotide
dN=2'-deoxy nucleotides
$N_{UNA}$=2',3'-seco nucleotide mimics (unlocked nucleobase analogs)
$N_{LNA}$=locked nucleotide
$Nf_{ANA}$=2'-F-Arabino nucleotide
NM=2'-methoxyethyl nucleotide
X or Ab=abasic ribose
R=ribitol
(invdN)=inverted deoxyribonucleotide (3'-3' linked nucleotide)

(invAb)=inverted abasic nucleotide
(invX)=inverted abasic nucleotide
(invn)=inverted 2'-OMe nucleotide
s=phosphorothioate linked nucleotide
vpdN=vinyl phosphonate deoxyribonucleotide
(3'OMen)=3'-OMe nucleotide
(5Me-Nf)=5'-Me, 2'-fluoro nucleotide
cPrp=cyclopropyl phosphonate The compounds of the present disclosure can be made using synthetic chemical techniques known to those of skill in the art.

Example 1. Synthesis of Targeting Ligand Phosphoramidite-Containing Compound Structure 1005b, 1004b, and 1002b The Phosphoramidite-containing compound of Structure 1005b, Structure 1004b, and Structure 1002b were synthesized according to the following procedure, with the only difference being that 4-cis-hydroxycyclohexanecarboxylic acid (compound 8 herein) was used to synthesize compound Structure 1005b, 4-trans-hydroxycyclohexanecarboxylic acid (compound 8a herein) was used to synthesize compound Structure 1004b, and a mixture of 4-cis-hydroxycyclohexanecarboxylic acid (compound 8 herein) and 4-trans-hydroxycyclohexanecarboxylic acid (compound 8a herein) was used to synthesize compound Structure 1002b.

1) Preparation of 2-amino-3-[4-({[(benzyloxy)carbonyl]amino}methyl)phenyl]propanoic Acid (Compound 2).

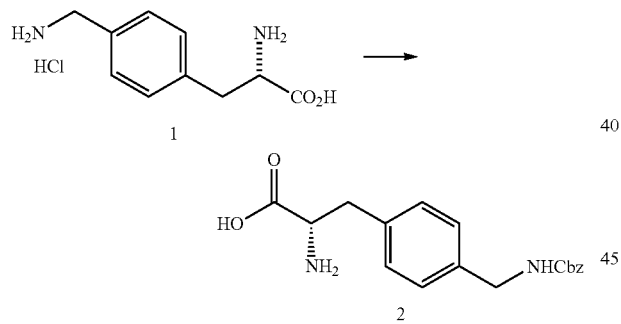

Copper carbonate basic (1.67 grams (g), 7.59 mmol) was added slowly to a solution of 1 (7.00 g, 30.34 mmol) in water (100 mL). The resulting mixture was heated to 80° C. until dissolution was observed. The resulting dark blue solution was cooled to 25-30° C. and then treated with sodium hydroxide (1.21 g, 30.34 mmol) as a solution in water (10 mL), which resulted in precipitation of the amino acid-copper complex. The suspension was stirred for 1 hour at ambient temperature before being treated with a solution of benzyl chloroformate (6.21 g, 36.41 mmol) in THF (20 mL) dropwise over 5 minutes. The mixture was stirred for 1-2 h, then filtered. The wet cake was triturated in EtOAc and filtered once more to aid in removal of water. The blue solids were then added to a flask containing 200 mL water and treated with 10 mL concentrated HCl. The slurry was stirred for 18 h, then filtered and washed with water which resulted in 4.5 g of compound 2 as a white solid (45% yield, 95 AP). $R_T$=5.8 min.

2) Preparation of Tri-Acid (Compound 3).

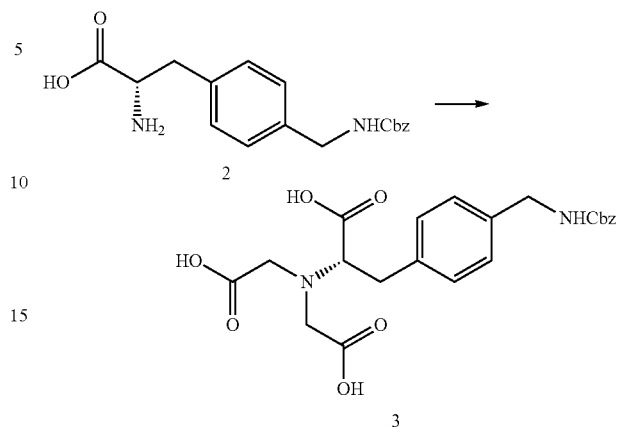

A slurry of 2 (6.00 g, 18.27 mmol) in 1.5M NaOH (100 mL) was heated to 60° C. at which point a solution was formed. The solution was then treated with a solution of bromoacetic acid (10.15 g, 73.20 mmol) dissolved in 1.5M NaOH (20 mL). The solution was stirred at 60° C. for 2 h (2=NMT 5% by HPLC). Once the reaction reached completion, the solution was cooled to 10° C. and 1M HCl was added until pH=1.7 was reached. The slurry was permitted to stand for 2-3 hours before being filtered and washed with deionized water. The solids were dried over vacuum resulting 3.01 g of tri-acid 3 (50%, 94 AP). $R_T$=6.94 min.

3) Preparation of TFP-Ester (Compound 4).

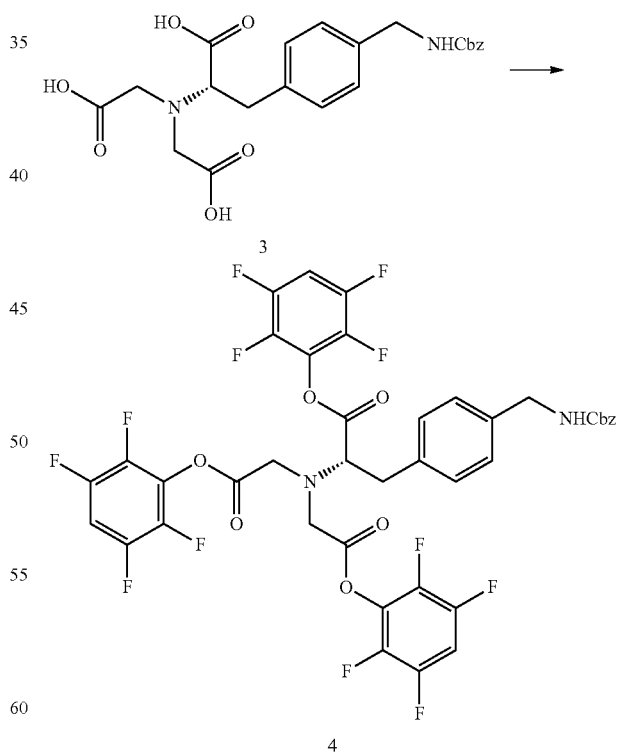

A solution of 3 (3.00 g, 6.75 mmol) and 2,3,5,6-tetrafluorophenol (3.99 g, 24.30 mmol) in DCM (50 mL) was cooled to 10° C. and treated with N-(3-dimethylaminopropyl)-N'-ethylcarbodiimide hydrochloride (4.66 g, 24.30 mmol) in portions over 5 minutes. The solution was then allowed to warm to ambient temperature over 20 minutes and stirred for 3 h. After completion (3<10 AP), the reaction mixture was washed with saturated sodium bicarbonate (20 mL), followed by brine (20 mL) and concentrated on a rotary evaporator. The resulting oil was purified on a flash column using a solvent gradient of 5-20% EtOAc/Hexanes resulting in 2.6 g of 4 as a colorless oil (40%, 94 AP). $R_T$=12.99 min.

4) Preparation of Amine Tosylate (Compound 5).

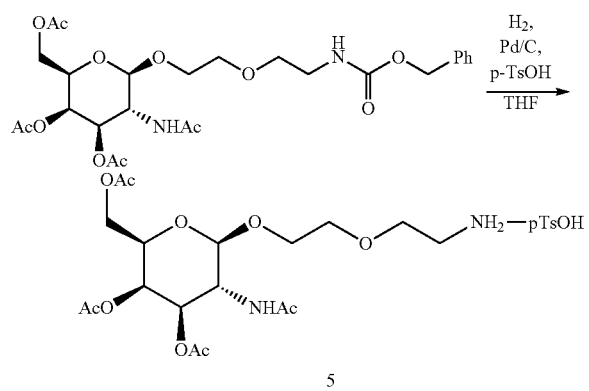

To an appropriately sized pressure reactor charge (10 volumes) of THF followed by CbZ protected amine (1.0 eq, NAG-Z) and p-TsOH-$H_2O$ (1.0 equiv). Degas the solution with nitrogen three times. Charge 10% Pd/C (5.0 wt %) and then degas with nitrogen three times. Degas with hydrogen three times. Charge hydrogen to a pressure of 40 to 50 psi. Stir at 20 to 30° C. for three hours then degas with nitrogen three times and sample for IPC assay (spec≤0.5% NAG-Z, if spec not met then stir under $H_2$ at 40 to 50 psi for 1 to 2 hr then reassay). Filter through diatomaceous earth to remove catalyst, washing with THF (4 volumes). Concentrate combined filtrate and wash under vacuum to about 2 volumes keeping Ti≤40° C. Dilute with DCM (3.8 volumes) and then reconcentrate to 2 volumes. Repeat DCM dilution and reconcentration then dilute with DCM (3.8 volumes). Sample for KF analysis (spec KF≤0.05%, if KF specification is not met then repeat concentration and dilution with DCM). After meeting the KF specification, concentrate the solution to a white foamy solid. Uncorrected yield of 100%. An analogous reaction substituting trifluoro acetic acid for p-TsOH-$H_2O$ may also be performed and can be used interchangeably.

5) Preparation of Tri-NAG (Compound 6).

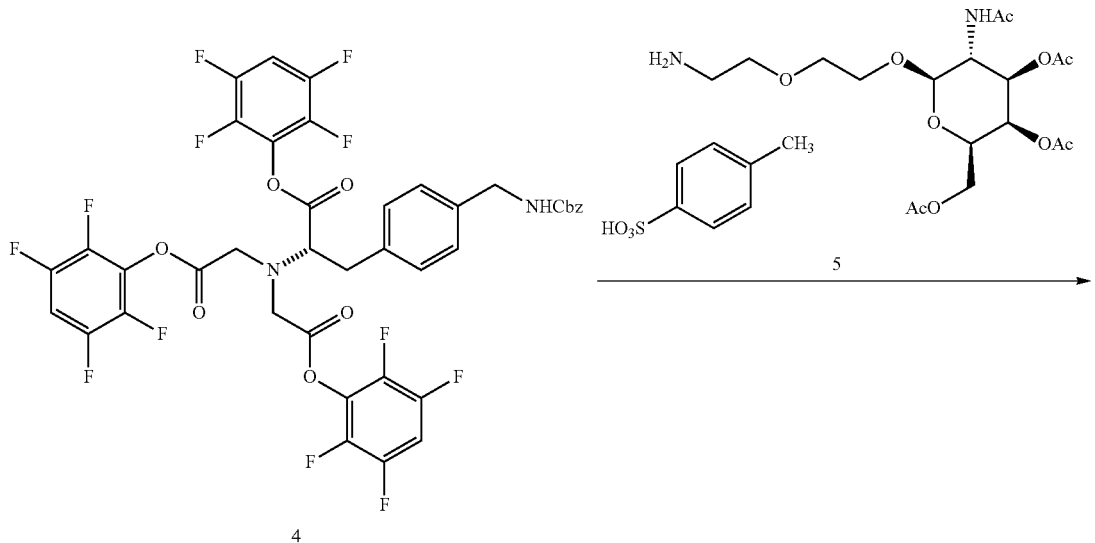

-continued

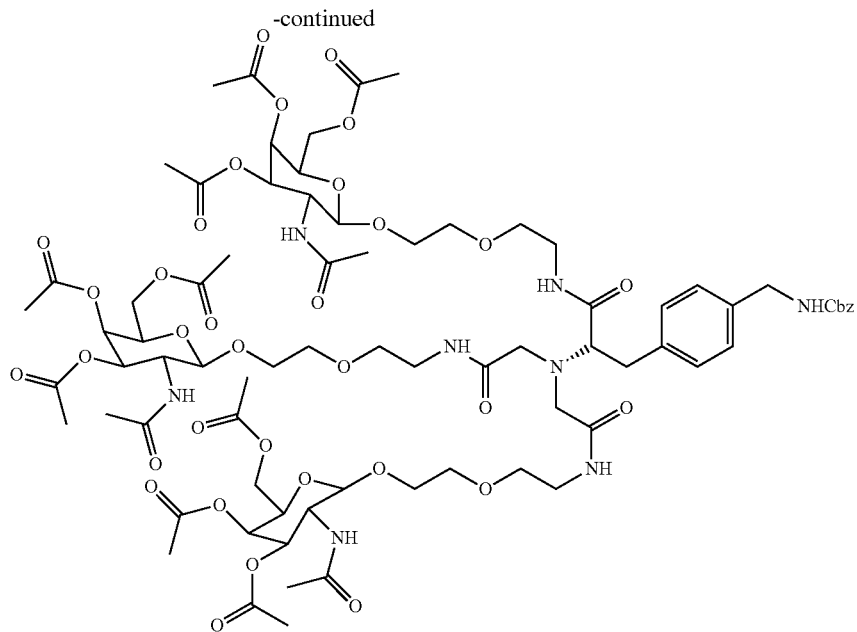

6

The activated ester 4 (2.15 g, 2.41 mmol) and amine tosylate 5 (4.10 g, 6.75 mmol) were dissolved in dichloromethane (22 mL) and cooled to 10° C. The solution was treated with triethylamine (1.37 g, 13.54 mmol) dropwise over 5 minutes and then allowed to warm to ambient temperature and held for 2 h. The reaction mixture was washed with saturated sodium bicarbonate (10 mL) followed by brine (10 mL). The solution was dried over magnesium sulfate, filtered and concentrated on a rotary evaporator to give a colorless oil. After workup, ~10% of the des-acyl impurity was found by HPLC. The impurity was re-acylated by stirring in neat acetic anhydride (90 mL) and triethylamine (6 mL) for 1 h. The acetic anhydride was then removed under reduced pressure and the resulting oil was re-dissolved in dichloromethane and washed with aqueous sodium bicarbonate. The solution was concentrated to an oil and purified via flash chromatography using gradient elution (2.5-25% MeOH/DCM) which gave 1.98 g 6 as a white solid (47%, 96 AP). $R_T$=7.57 min; des-Acyl impurity=7.18 min.

6) Preparation of Amine Salt (Compound 7).

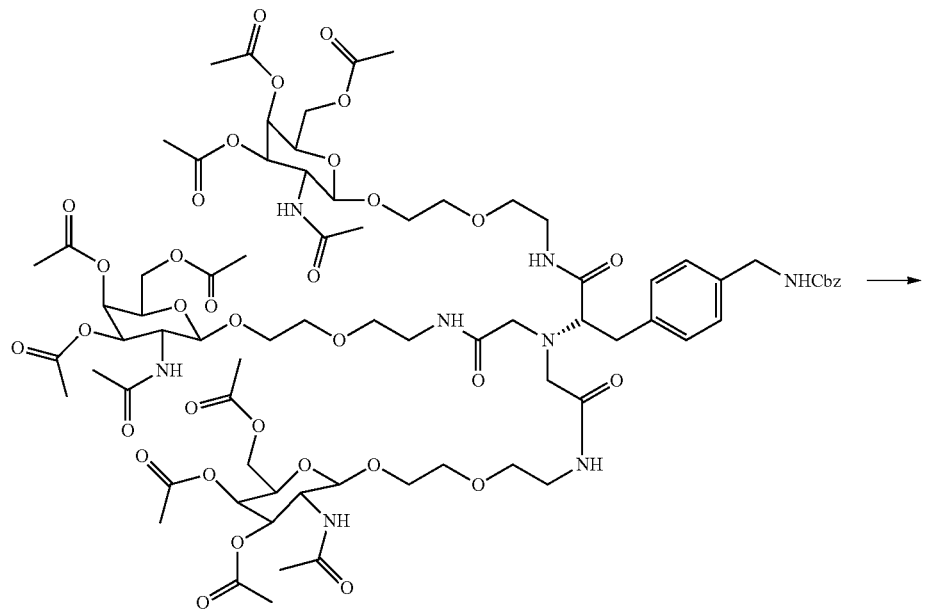

6

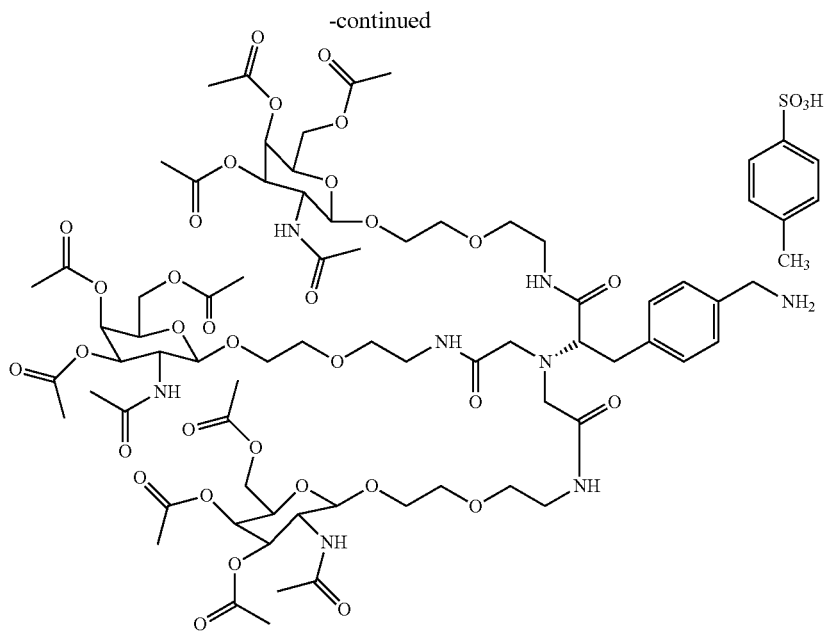

The protected amine 6 (1.98 g, 1.06 mmol) and p-toluenesulfonic acid monohydrate (202 mg, 1.06 mmol) were dissolved in absolute ethanol (30 mL) and placed under nitrogen atmosphere. To the flask was added 5% palladium on carbon (198 mg, 0.106 mmol) and the flask was placed under vacuum and back-filled with hydrogen several times. Once under hydrogen atmosphere, the reaction was allowed to stir at ambient temperature and found to be complete within 4 h or until the starting material was non detected by HPLC. The catalyst was filtered through a bed of celite and the filtrate was passed through a 0.2 micron membrane filter to remove fine particulates. The solution was concentrated to dryness under reduced pressure which resulted in 2.01 g of 7 as a grey solid (100%, 98 AP). $R_T$=5.82; p-toluenesulfonic acid $R_T$=2.4 and 3.1 min.

7) Preparation of Activated Linker (Compound 9 and 9a).

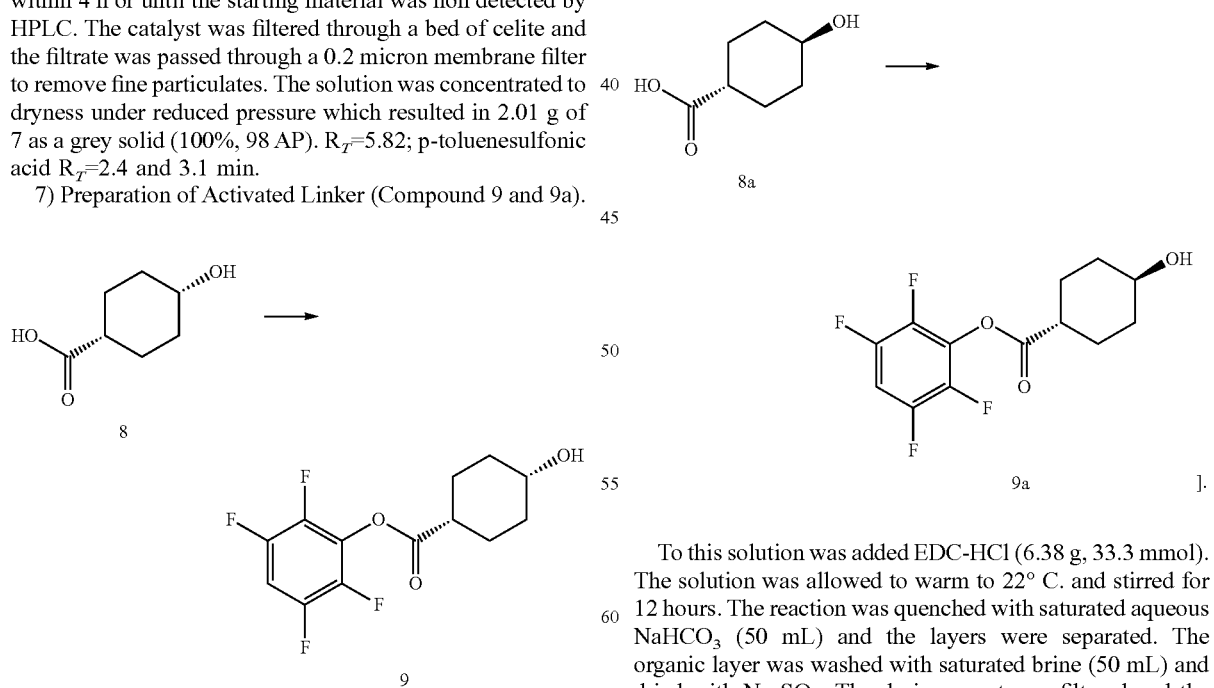

The cis-4-hydroxy cyclohexylcarboxylic acid 8 (for synthesizing Structure 1005) (4.00 g, 27.7 mmol) and 2,3,5,6-tetrafluorophenol (5.53 g, 33.3 mmol) were dissolved in 24 mL dichloromethane and cooled to 0° C. [As noted above, while cis-4-hydroxy cyclohexylcarboxylic acid (compound 8) is used as the linker to formulate Structure 1005, trans-4 hydroxy cyclohexylcarboxylic acid (compound 8b) may be substituted for the cis-isomer, which leads to the synthesis of Structure 1004b, following the same procedure for the remainder of the synthesis:

To this solution was added EDC-HCl (6.38 g, 33.3 mmol). The solution was allowed to warm to 22° C. and stirred for 12 hours. The reaction was quenched with saturated aqueous NaHCO$_3$ (50 mL) and the layers were separated. The organic layer was washed with saturated brine (50 mL) and dried with Na$_2$SO$_4$. The drying agent was filtered and the solution was concentrated to approximately 20 mL, which slowly solidified (seed crystals will help). The solids were slurried in 5% MTBE/Hexanes (50 mL) and filtered to yield 5.6 g of product 9 in 69% yield and 95% purity.

8) Linker Coupling (Preparation of Compound 10).

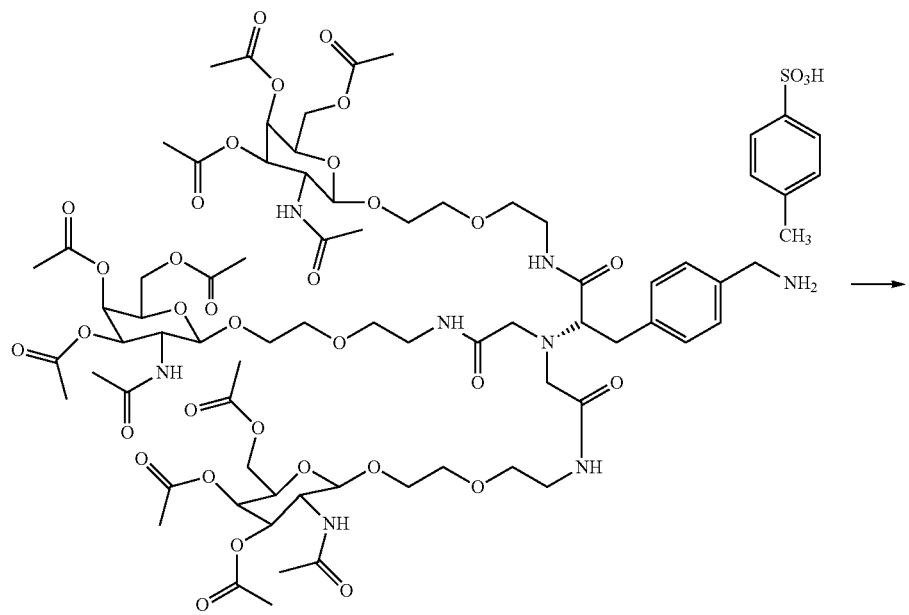

7

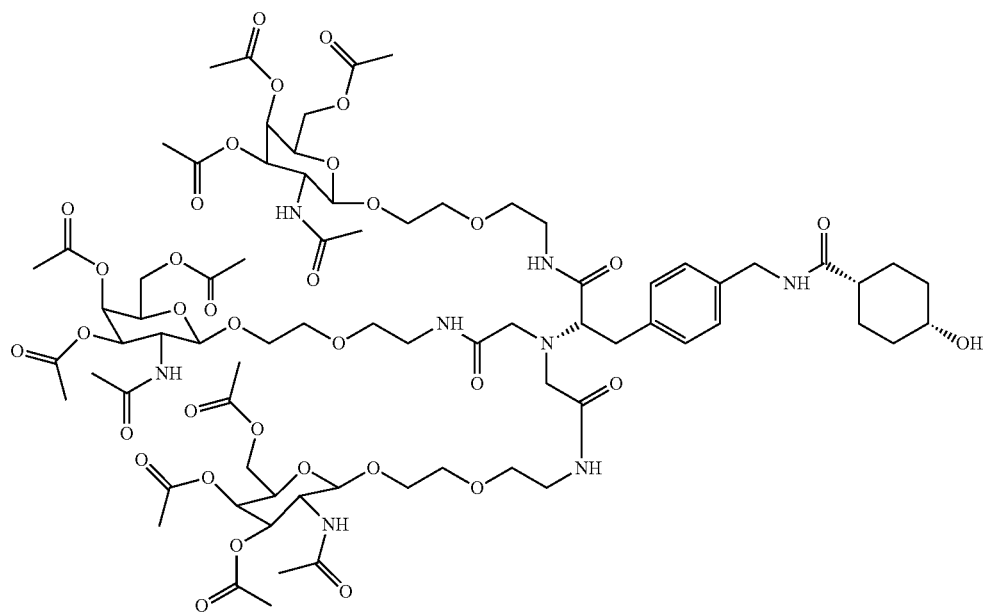

10

NAG amine salt 7 (5.00 g, 2.88 mmol) and 2,3,5,6-tetrafluorophenyl cis-4-hydroxycyclohexanecarboxylate 9 (1.68 g, 5.77 mmol) were dissolved in 25 mL dichloromethane and cooled to 0° C. To this solution was added triethylamine (1.60 mL, 11.55 mmol). The solution was allowed to warm to room temperature and stirred for 5 hours with monitoring by HPLC. The reaction was quenched with saturated aqueous $NaHCO_3$ (35 mL) and the layers were separated. The organic layer was washed with saturated brine (35 mL) and dried with $Na_2SO_4$. The drying agent was filtered and the solution was concentrated and purified via flash chromatography using gradient elution (0-20% MeOH/DCM) which gave 3.90 g of compound 10 as a white solid material (80%). $R_T$=6.16 min. Alternatively, it is possible to perform a direct coupling of the linker without the use of the TFP ester, as shown in Example 2, below.

9) Preparation of Compound 11.

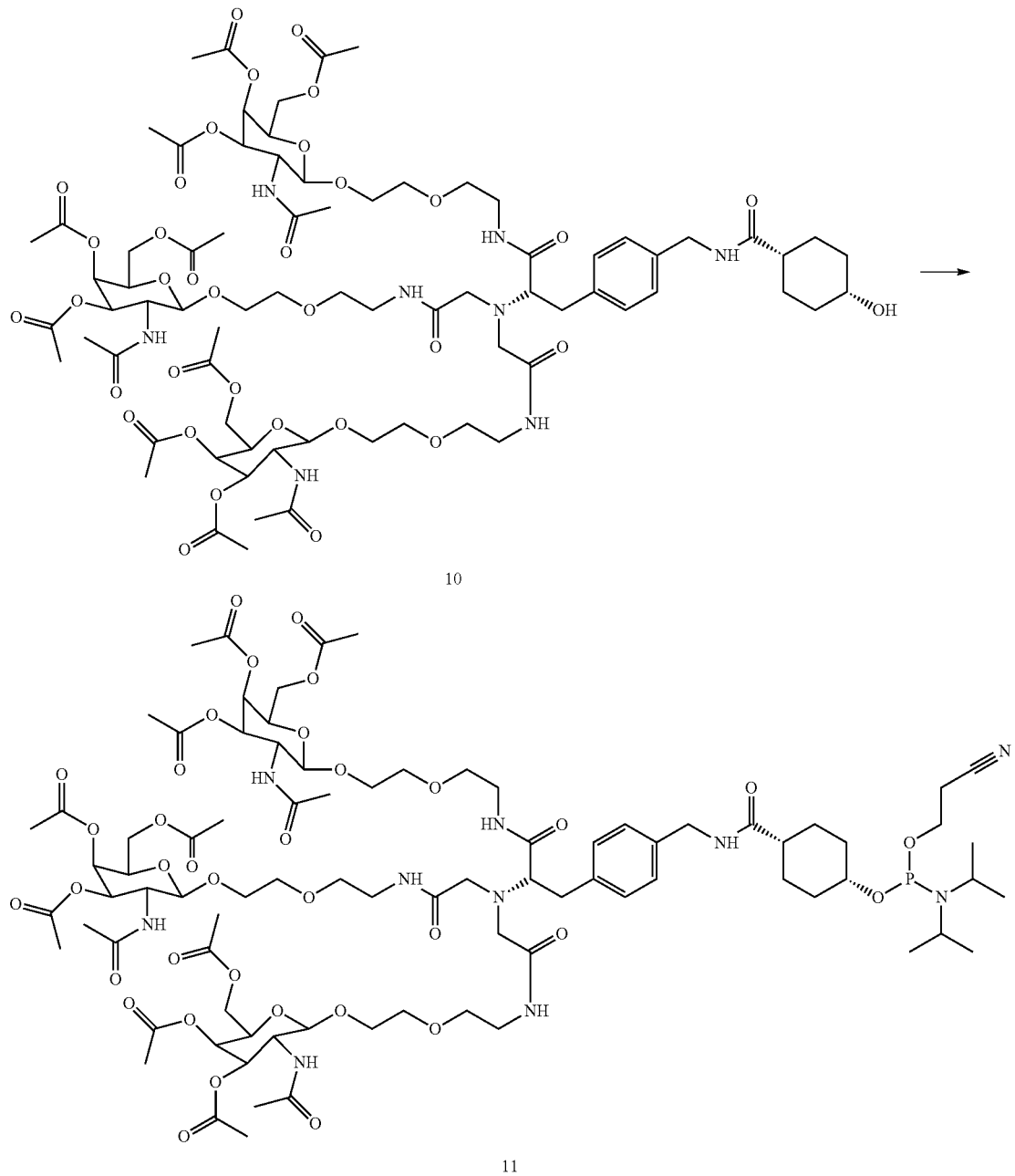

Compound 10 (1.87 g, 1.11 mmol) was dissolved in 20 mL dichloromethane and 2-cyanoethyl, N,N,N',N'-tetraisopropyl phosphoramidite (0.84 g, 2.77 mmol) was added. The resulting solution was cooled to 5° C. To this solution was added 4,5-dicyanoimidiazole (0.026 g, 0.22 mmol). The solution was allowed to warm to room temperature and stirred for 1 hour. The extent of conversion was then checked by HPLC (which indicated 2~% remaining starting material). Additional 2-cyanoethyl, N,N,N',N'-tetraisopropyl phosphoramidite (0.14 g, 0.46 mmol) was added and the reaction stirred for an additional 2.5 h (no significant change was observed by HPLC). The reaction was quenched with saturated aqueous NaHCO$_3$ (20 mL) and the layers were separated. The organic layer was washed with aqueous NaHCO$_3$ (20 mL) and saturated brine (2×20 mL) and dried with Na$_2$SO$_4$. The drying agent was filtered and the solution was concentrated to give 2.34 g of compound 11 as a white solid material.

A 100 mg of the crude 11 was purified by flash column chromatography by first eluting the silica gel-packed column with 2% triethylamine in dichloromethane for 30 min, followed by loading the crude 11 on the column and purifying using gradient elution (0-20% of 2% triethylamine:methanol/2% triethylamine:dichloromethane). The final product compound 11 (which has the chemical structure of Structure 1005b defined herein) was eluted in 2% triethylamine:dichloromethane (Fraction 2) to give 80 mg of white solid material.

FIG. 1 shows $^1$H NMR spectra for compound 11 (Structure 1005b herein).

Figure 1A:
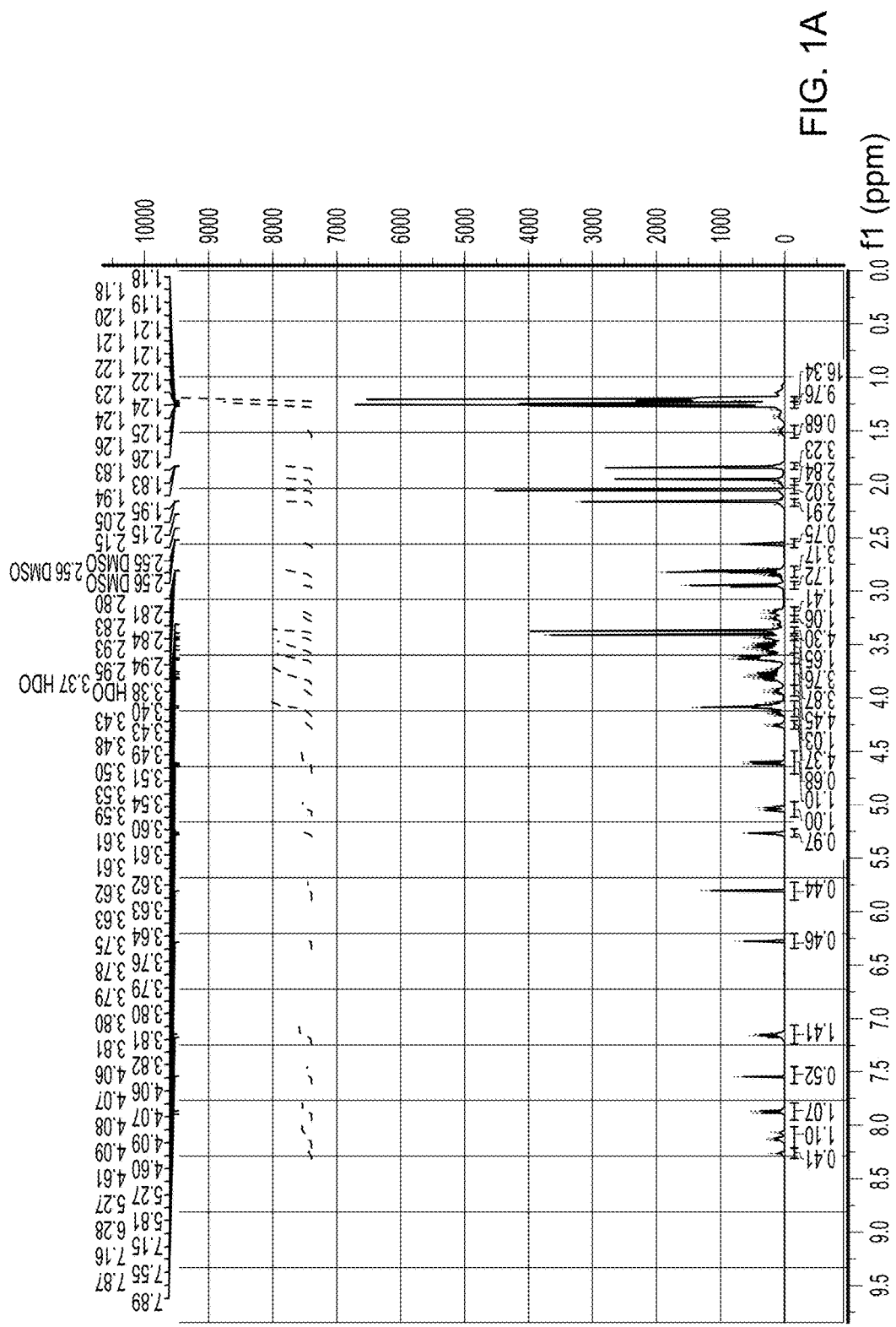
FIG. 1A is a $^1$H NMR spectra of Structure 1004b herein (which is described below in Example 1).

FIG. 1A shows $^1$H NMR spectra for the trans-isomer of compound 11 (Structure 1004b herein), following the alternative synthesis set forth in step 7, above.

Example 2. Synthesis of Targeting Ligand Phosphoramidite-Containing Compound Structure 1008b 1) Preparation of Tri-tert-butyl N—[N-(Benzyloxycarbonyl)-L-γ-glutamyl]-L-glutamate (compound 14)

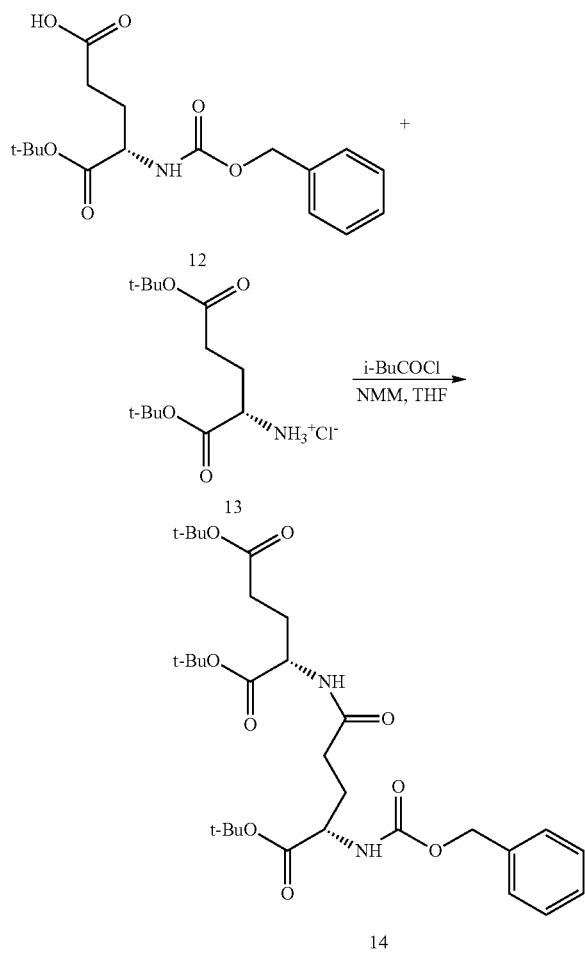

To a nitrogen-flushed, 250-mL 3-neck round-bottomed flask equipped with a thermocouple, magnetic stir bar, nitrogen inlet, and powder funnel was added 12 (10.00 g, 29.64 mmol) followed by THF (100 mL, 10 vol.). The resulting solution was stirred, and N-methylmorpholine (7.82 mL, 7.19 g, 71.15 mmol, 2.4 equivalents) was added (KF of reaction mixture: 163 ppm).

The powder funnel was replaced with a rubber septum, and the mixture was cooled using an ice bath to 0° C. Isobutyl chloroformate (iBuCOCl, 3.85 mL, 4.05 g, 29.64 mmol, 1.0 equivalents) was added to the reaction mixture dropwise over 10 minutes via syringe, maintaining a pot temperature of less than 4.0° C. Following addition, the mixture was stirred 40 minutes more, and the septum was replaced with a powder funnel. To the reaction mixture was added 13 (8.767 g, 29.64 mmol, 1.0 equivalents) portionwise over 15 minutes, maintaining a pot temperature of less than 4.0° C. (exothermic addition). Following addition of 13, the ice bath and powder funnel were removed, and the reaction was allowed to warm to ambient temperature over the course of the remaining steps. The clear, colorless solution was allowed to stand for 25 minutes following the addition of 13.

A sample of the reaction was taken 40 minutes after the start of addition of 13 and analyzed for percent conversion by RP-HPLC. There was found to be 23% remaining of 12, so after 60 minutes of reaction, additional iBuCOCl (1.16 mL, 1.21 g, 30 mol %) and 13 (2.63 g, 30 mol %) were added sequentially. The solution was allowed to stand for an additional 60 minutes, until a sample showed greater than 99% conversion by HPLC. Total reaction time was 2.5 hours from the start of the initial addition of 13.

The reaction solution was poured into a stirring solution of 0.5 M HCl$_{(aq)}$ (125 mL) chilled in an ice bath at 3° C. and stirred about 5 minutes. The quenched reaction mixture was extracted with ethyl acetate (100 mL, 10 vol.; check to make sure the aqueous layer is acidic for complete removal of NMM), and the organic phase was washed with brine (100 mL, 10 vol.), dried over Na$_2$SO$_4$, filtered over a coarse fritted funnel into a 500-mL round-bottomed flask, and concentrated in vacuo, affording a thick colorless oil. The oil was dissolved in MTBE (100 mL, 10 vol.) and concentrated in vacuo, once again yielding a thick colorless oil.

To the stirring oil (~600 rpm) was added hexanes (100 mL, 10 vol.). White haze appeared in the solution, which then disappeared upon further stirring. Seed crystals were added, and the mixture was allowed to stir for 40 minutes, during which time white crystals slowly formed. Within 20 minutes, additional hexanes (50 mL, 5 vol.) was added. After 40 minutes, the slurry was filtered over a coarse fritted funnel, washed 3× with hexanes (~10 mL each), and air-dried in the funnel for 1 hour, affording 14 as a fine white powder (15.64 g, 91%).

Figure 2:
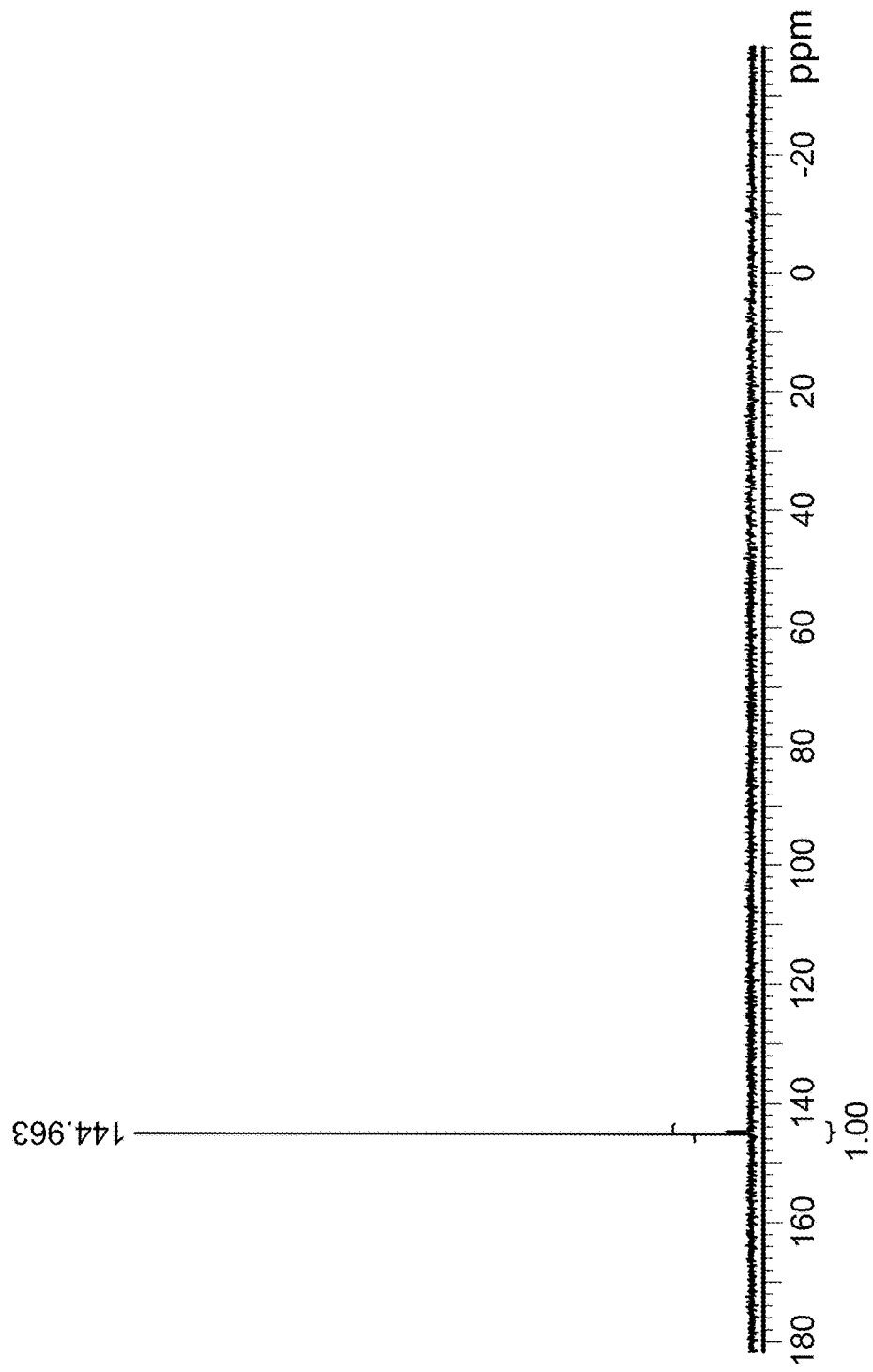
FIG. 2 is a $^{31}$P NMR spectra of compound 19 (which is described below in Example 2 and has the chemical structure of Structure 1008b herein.).
Figure 2A:
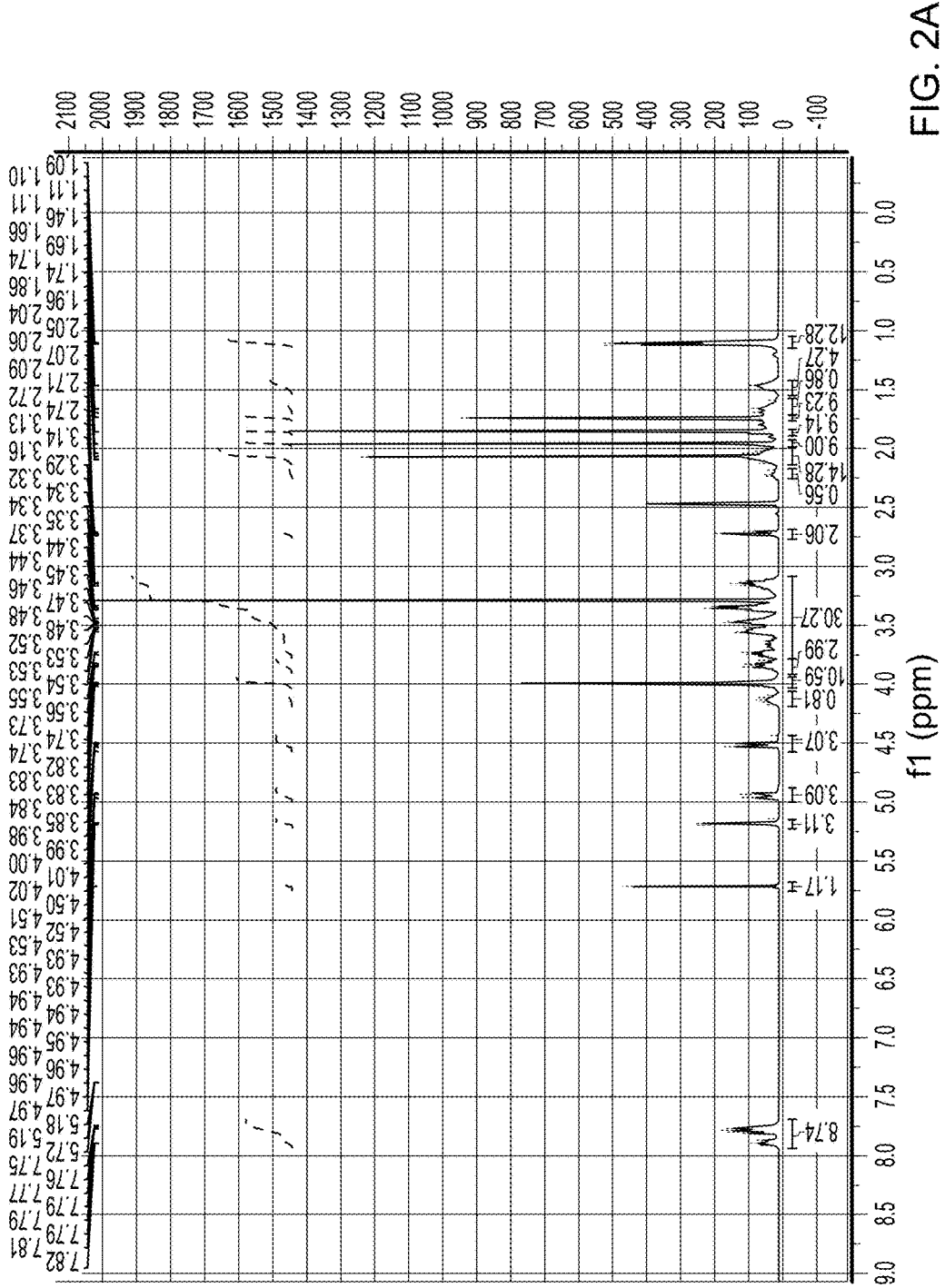
FIG. 2A is a $^1$H NMR spectra of Compound 19.
Figure 2B:
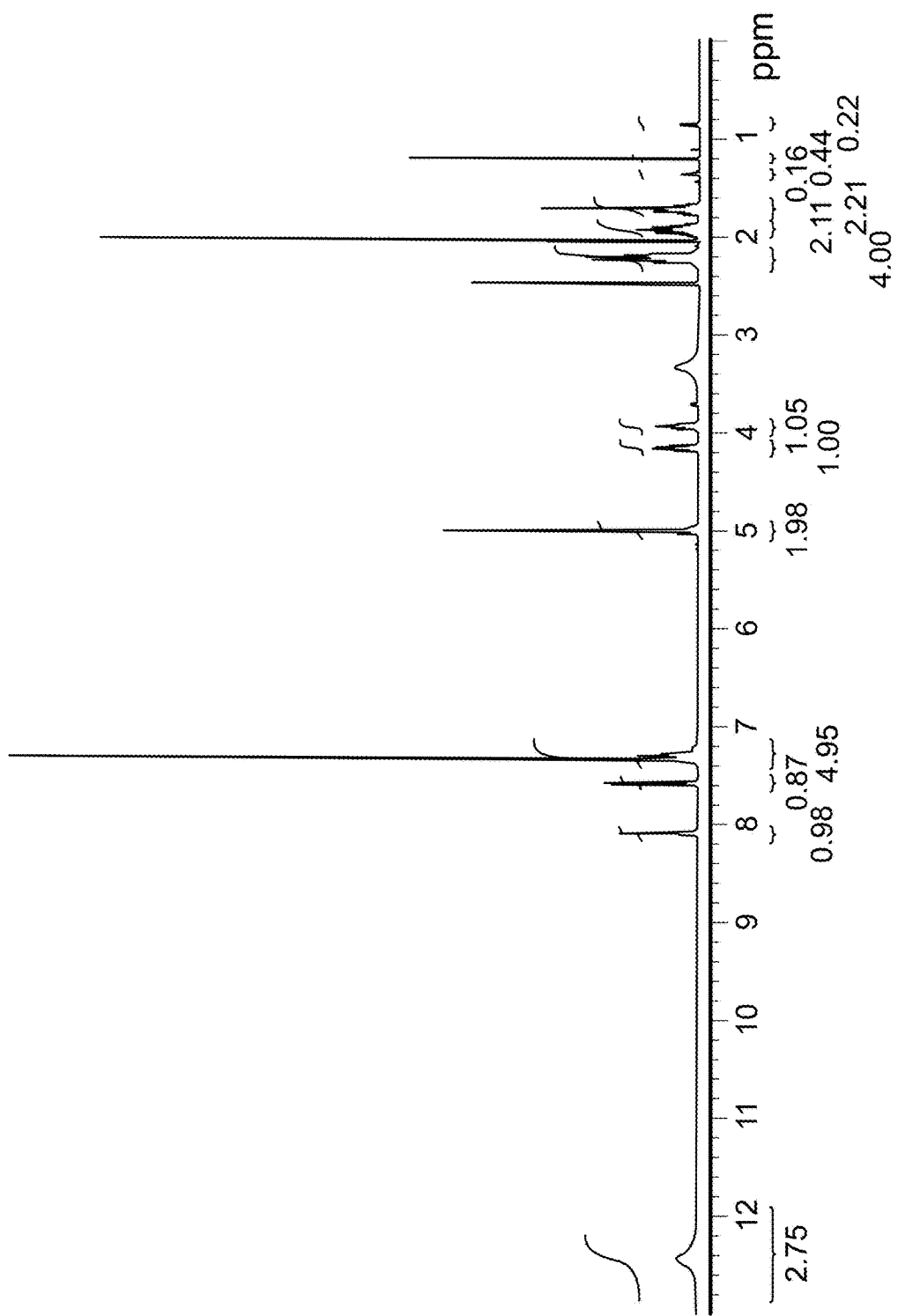
FIG. 2B is a $^1$H NMR spectra of Compound 14 (which is described below in Example 2).

FIG. 2B shows $^1$H NMR spectra for compound 14.

1) Preparation of N—[N-(Benzyloxycarbonyl)-L-γ-glutamyl]-L-glutamic Acid (Compound 15)

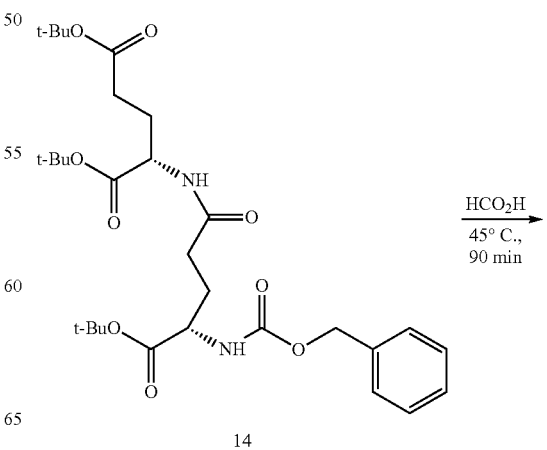

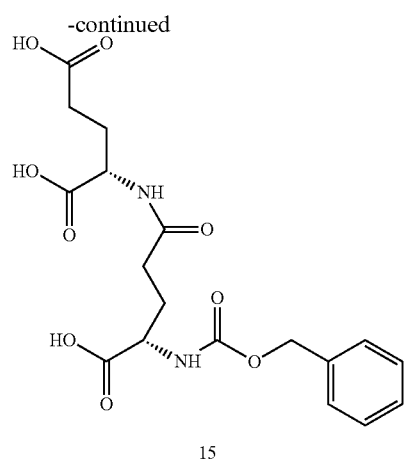

15

To a 3000-mL, 3-necked round-bottomed flask equipped with an overhead stirrer, powder funnel, thermocouple, and heating mantle was added 14 (72.57 g, 125.4 mmol) and formic acid (reagent grade, >95%, 1.45 L, 20 vol. equiv.). The powder funnel was replaced by a stopper with $N_2$ inlet, and the resulting solution was heated to 45° C. and stirred for 1 hour, with monitoring by RP-HPLC. The reaction was deemed complete when less than 2.0 area % of mono-t-butyl esters remained.

A sample of the reaction was taken 60 minutes after the addition of formic acid, and the sample was analyzed by RP-HPLC for the percentage of mono-t-butyl esters remaining. The analysis showed that 1.8% mono-t-Bu esters remained after 90 minutes, and the reaction was cooled to room temperature.

The reaction was diluted with toluene and acetonitrile (1500 mL each), and the mixture was concentrated in vacuo. Formic acid was azeotropically removed with 1:1 ACN:toluene (~600 mL), and twice with ACN (~500 mL each). The material was dried on high vacuum overnight to afford a white foamy solid (54.3 g, quantitative yield, 96.8 area % at 254 nm).

Figure 2C:
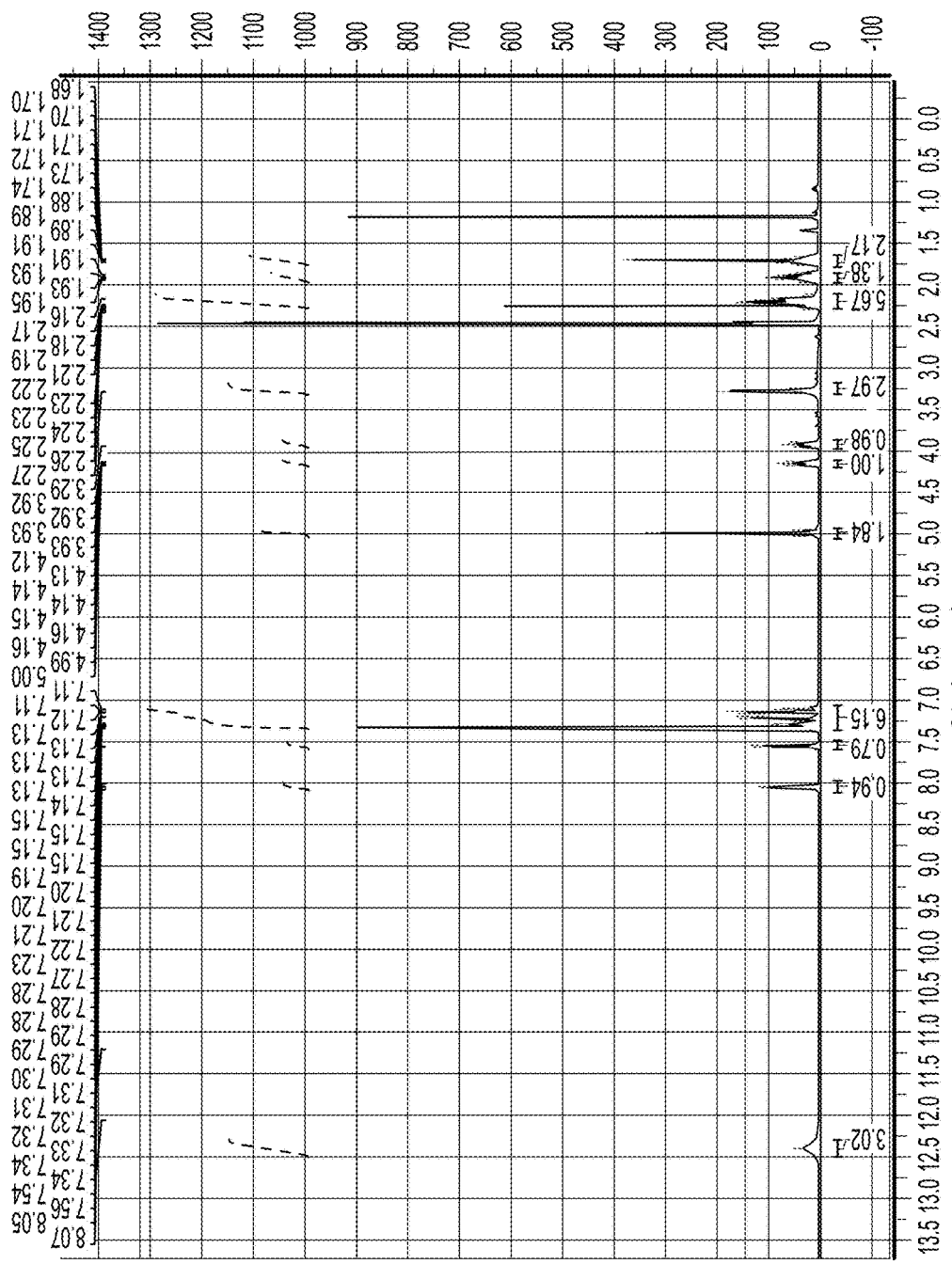
FIG. 2C is a $^1$H NMR spectra of Compound 15 (which is described below in Example 2).

FIG. 2C shows $^1$H NMR spectra for compound 15.

3) Preparation of Tri-NAG-bis-Glu-NHZ (Compound 16).

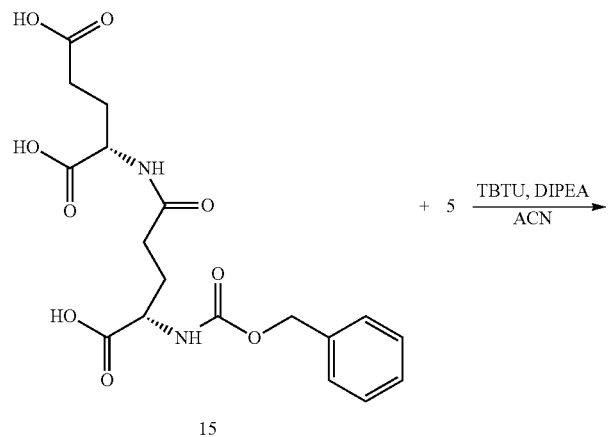

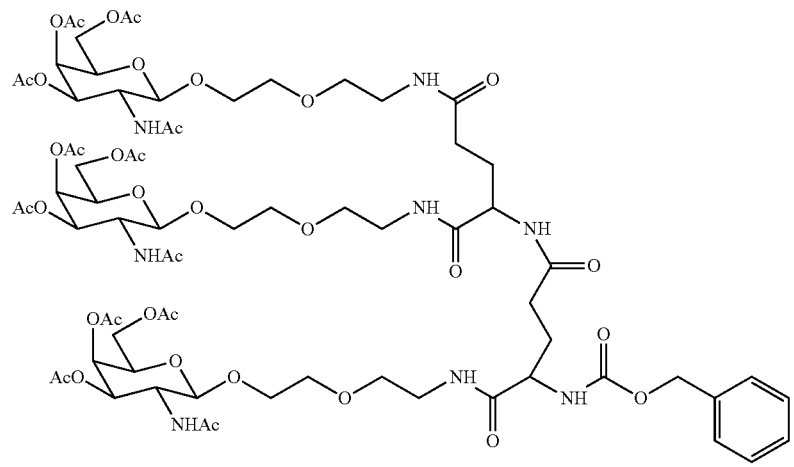

16

To a 1-liter round-bottomed flask was added NAG-amine p-tosylate salt (5, 59.19 g, 97.6 mmol, 4.13 equiv.) and Z-bis-Glu triacid (15, 10.01 g, 23.6 mmol purity corrected, 1.0 equiv.). The mixture was dissolved in acetonitrile (500 mL; KF of solution=1283 ppm) and concentrated in vacuo to remove water azeotropically. The residue was dissolved in fresh acetonitrile (400 mL) and transferred to a nitrogen-flushed 1-liter 3-neck round-bottomed flask containing a stir bar and equipped with a thermocouple. Water content was measured by KF (257 ppm).

To the stirring solution under nitrogen was added TBTU (28.20 g, 87.8 mmol, 3.7 equiv.) via a powder funnel.

330-g ISCO RediSep Rf Gold silica column. The crude material was loaded as a solution in $CHCl_3$ (~200 mL). A ramped gradient of Eluent A: $CHCl_3$; Eluent B: MeOH was utilized and a total of 36 fractions were collected (250-500 mL each). Product containing fractions were concentrated and yielded 18.75 g (97.0% purity) of 16. Mixed fractions yielded 12.2 g (78.8% purity) of 16.

Figure 2D:
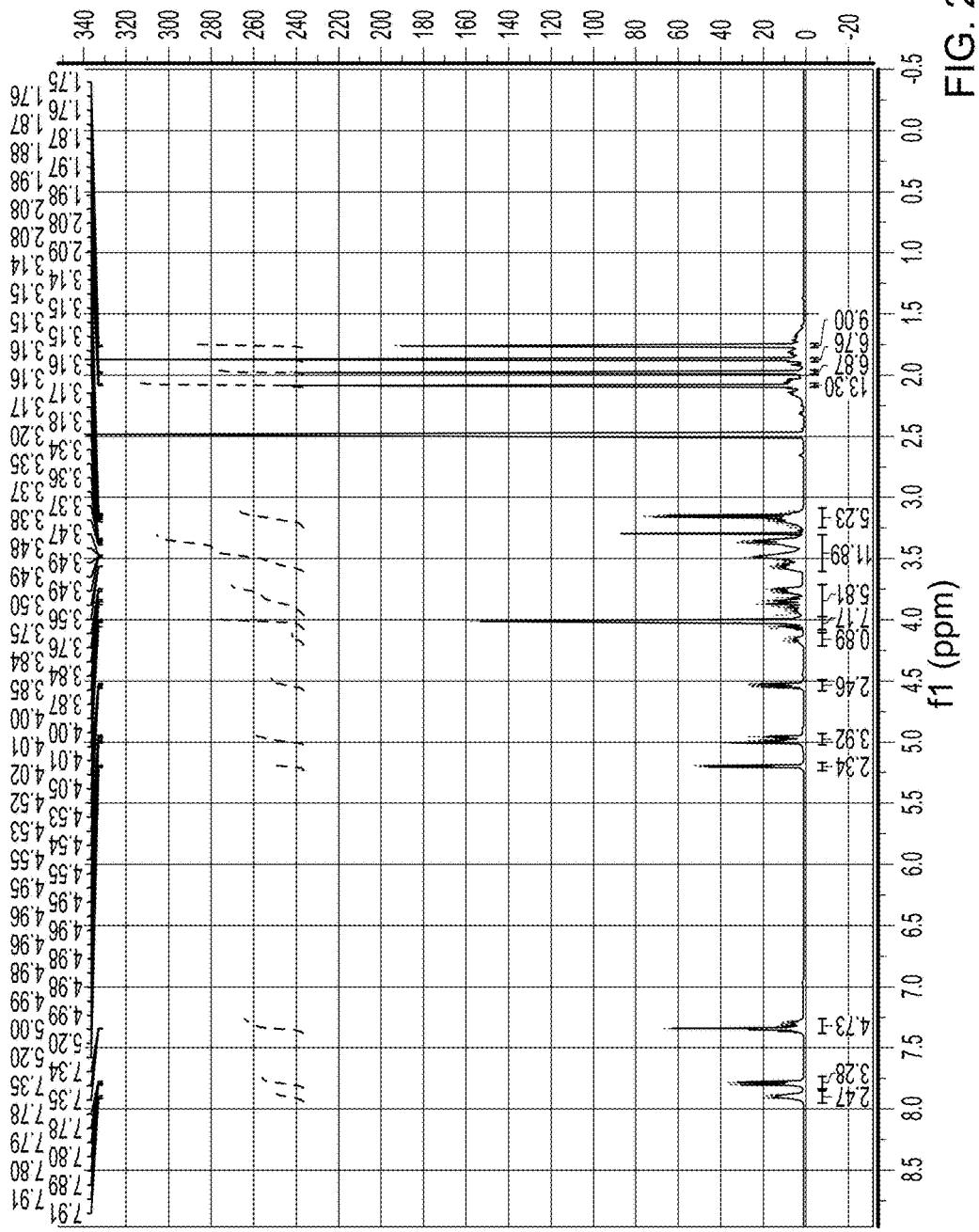
FIG. 2D is a $^1$H NMR spectra of Compound 16 (which is described below in Example 2).

FIG. 2D shows $^1$H NMR spectra for compound 16.

4) Preparation of Tri-NAG-bis-Glu-$NH_2$ (Compound 17).

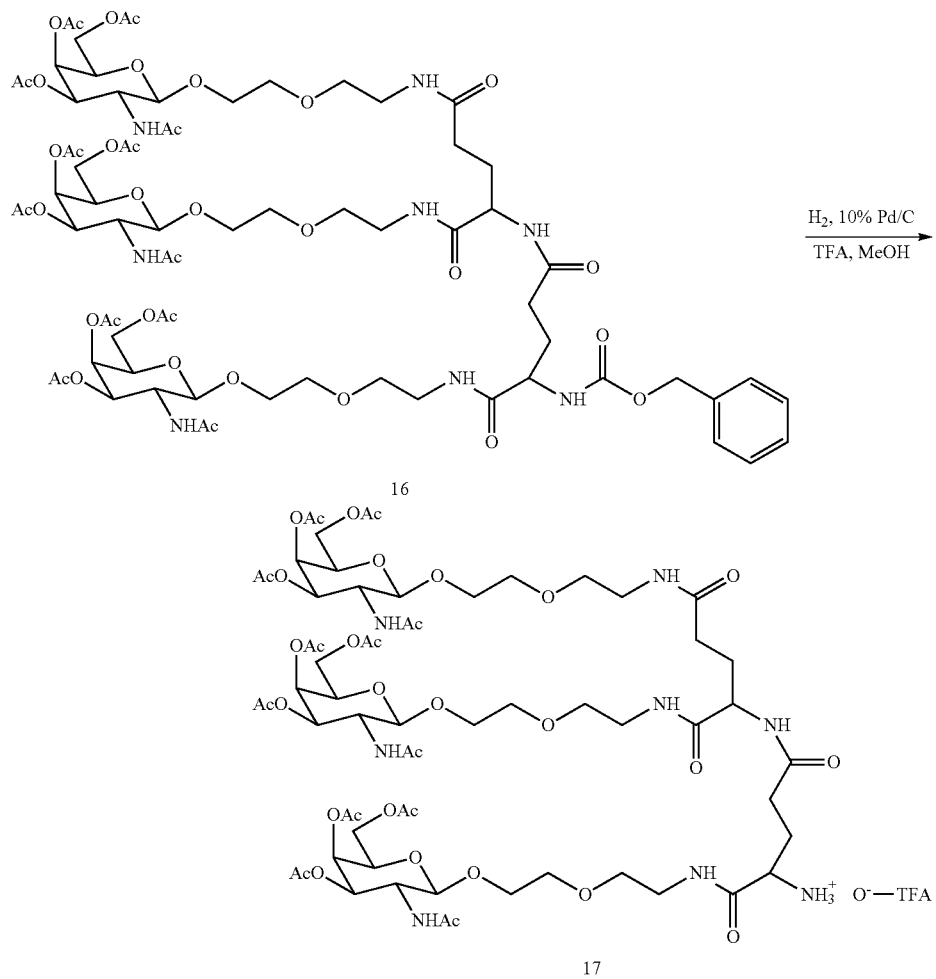

DIPEA (34.0 mL, 25.2 g, 8.0 equiv.) was added dropwise via syringe over 20 minutes, maintaining a reaction temperature below 25° C. (an exotherm of 5° C. was observed during the addition). The mixture was stirred for 2 hours from the start of DIPEA addition, with monitoring by HPLC. Analysis at 78 minutes showed complete consumption of starting material.

After two hours, the solvent was removed in vacuo. The resulting thick oil was dissolved in dichloromethane (1000 mL) and washed with 1.0 N $HCl_{(aq)}$ (3×500 mL) and saturated $NaHCO_{3(aq)}$ (3×500 mL). The organic layer was dried over $Na_2SO_4$, filtered, and concentrated in vacuo to afford an off-white waxy solid (33.5 g).

Flash column chromatography was performed on an ISCO CombiFlash automated purification system using a A 1000-mL 3-neck round-bottomed flask containing a stir bar was charged with methanol (200 mL, 13 vol.). To the stirring solvent was added compound 16 (15.44 g, 9.02 mmol purity-corrected), followed by additional methanol (200 mL, 13 vol.) and trifluoroacetic acid (1.40 mL, 18.1 mmol, 2.0 equiv.). The mixture was stirred about 10 minutes. To the mixture was added 10% Pd/C (50% wet basis, 1.547 g, 10% w/w). The headspace was flushed with hydrogen gas (balloon), and the mixture was allowed to stir at ambient temperature for 2 hours, with monitoring by RP-HPLC.

After 75 minutes, the reaction was sampled (100 µL) and mixed with 1:1 acetonitrile:$H_2O$ (900 µL) in a 1-mL syringe filter (10 mm, 0.1 µm GHP membrane). The HPLC chromatogram showed greater than 96 area % purity, with no remaining starting material. The reaction mixture was then flushed with nitrogen and filtered over a bed of Celite into a clean 1000-mL round-bottomed flask. The reaction vessel was rinsed with methanol (50 mL) and dichloromethane (50 mL), and the rinses were filtered also. The slightly cloudy filtrate was partially concentrated in vacuo. Additional rinses of the Celite bed were performed using methanol (50 mL) and dichloromethane (50 mL); these were combined with the residue and filtered over a 0.2-μm GHP membrane filter into another clean 1000-mL round-bottomed flask. The membrane was rinsed with acetonitrile (50 mL) so that the toluene byproduct could be removed azeotropically. The solution was concentrated in vacuo to afford 17 (14.15 g, 97.3 area % pure by HPLC) as an off-white foamy solid.

Figure 2E:
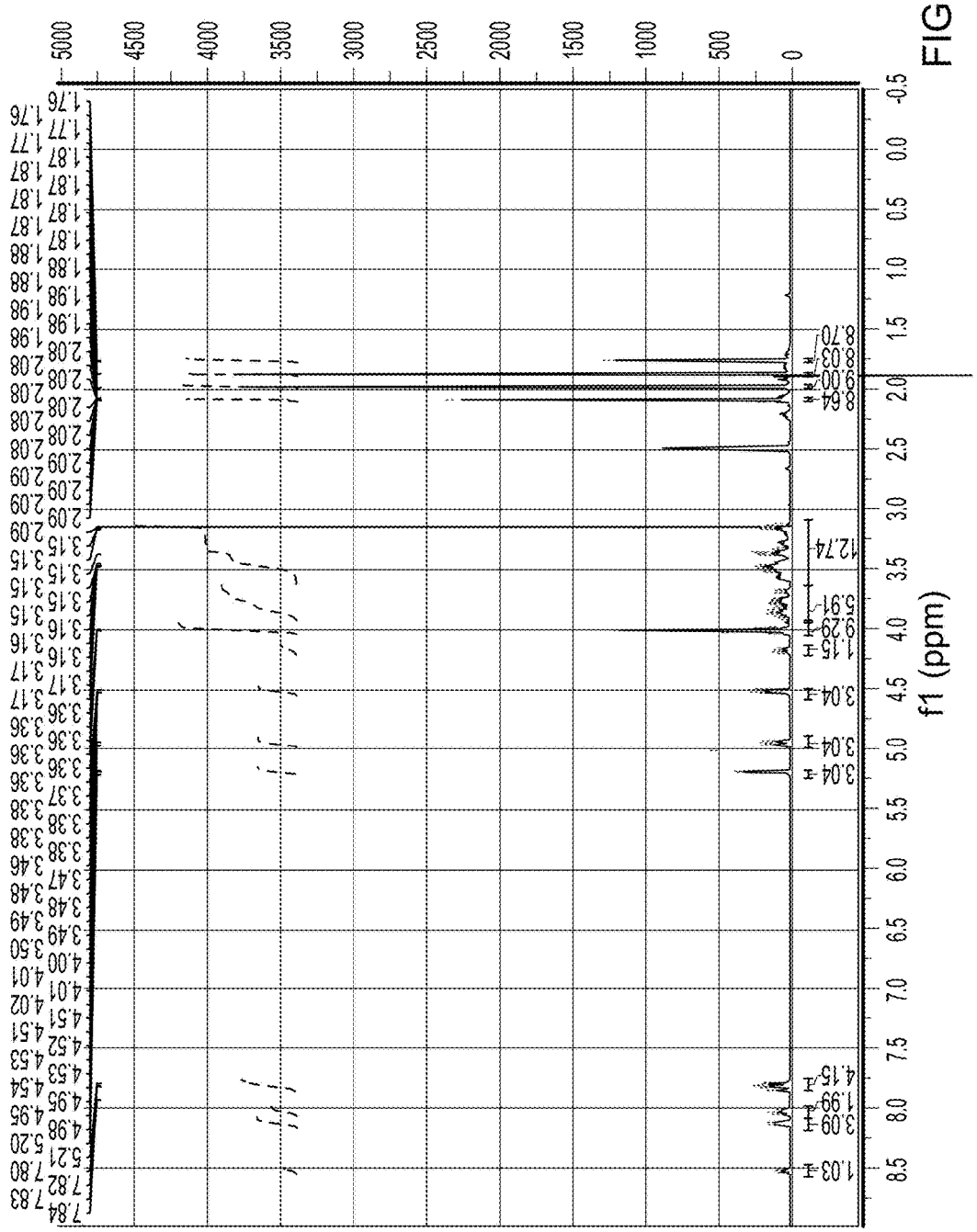
FIG. 2E is a $^1$H NMR spectra of Compound 17 (which is described below in Example 2).

FIG. 2E shows $^1$H NMR spectra for compound 17.

5) Preparation of Tri-NAG-bis-Glu-NH-linker (Compound 18).

12.6 mmol, 1.10 equiv.). The solution was cooled to −9° C. using an ice-brine bath, and DIPEA (6.97 mL, 5.17 g, 40.0 mmol, 3.5 equiv.) was added dropwise over 7 minutes, keeping the internal temperature below −5° C. An exotherm of 1.7° C. was observed during the addition. Once the addition of DIPEA was complete, the reaction was stirred at −9° C. for 90 minutes, at which point HPLC analysis (Method B) showed complete consumption of 17.

After 110 minutes, the reaction was quenched by addition of saturated NH$_4$Cl$_{(aq)}$ (400 mL). The layers were separated, and the aqueous layer was extracted with dichloromethane (2×200 mL). The combined organic layers were washed with a 1:1 mixture of saturated NaHCO$_{3(aq)}$ and brine (400 mL), dried over Na$_2$SO$_4$, filtered and concentrated in vacuo to approximately 125 mL. A small amount of methanol was used to ensure solubility. The resulting oil was added in a thin stream to a 3-L round-bottomed flask containing stirring

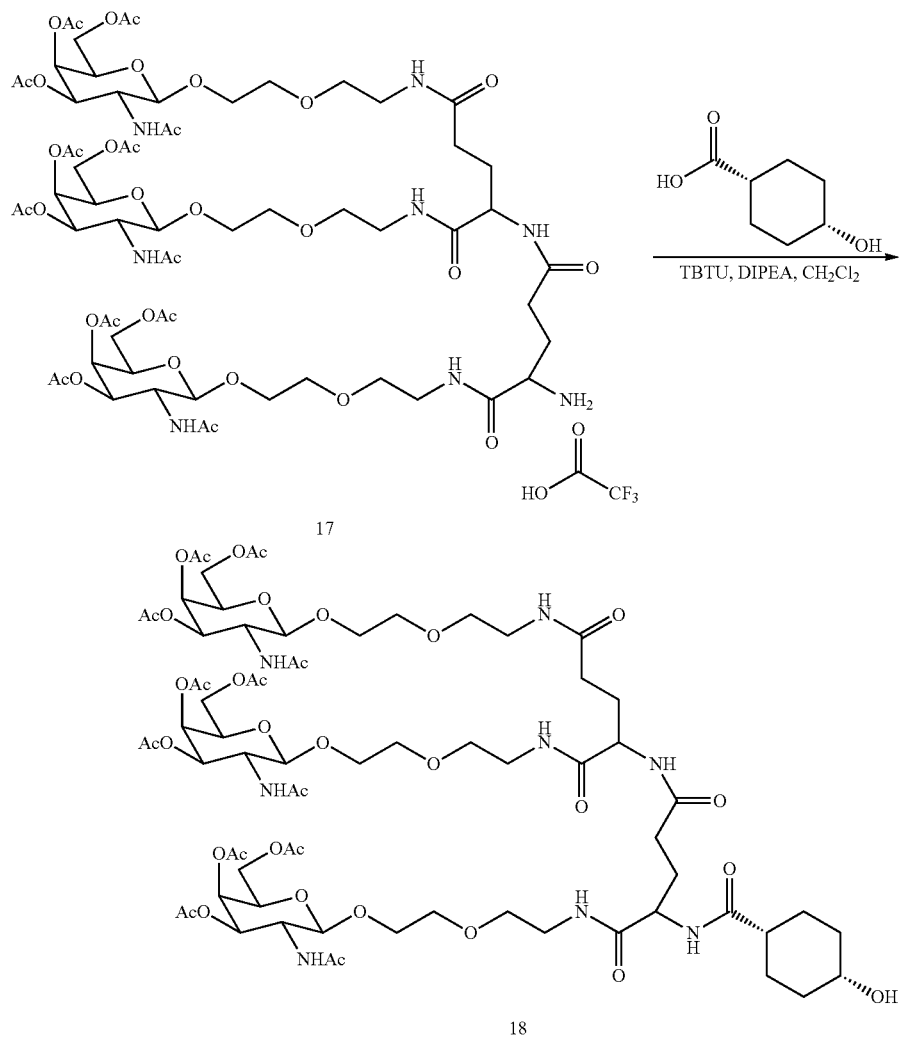

A 500 mL, 3-neck round-bottomed flask equipped with magnetic stirring, thermocouple, and nitrogen blanket was charged with 17 (93.7% pure, 20.00 g, 11.4 mmol) and dichloromethane (150 mL). To the stirring solution was added cis-4-hydroxycyclohexane-1-carboxylic acid (1.730 g, 12.0 mmol, 1.05 equiv.), followed by TBTU (4.036 g, MTBE (1600 mL), forming a white precipitate. Rinses of the source flask with dichloromethane (~20 mL) and MTBE (~200 mL) were added to the slurry, which was then allowed to age for 1 hour before being vacuum-filtered over a 600-mL coarse glass fritted funnel. The wet cake was re-slurried in MTBE (2×200 mL) in the funnel, filtered, and dried on a high-vacuum line to constant mass, affording crude 18 as a white powder (16.22 g, 86% uncorrected yield).

Crude 18 (17.16 g, combined with a previous lot) was purified on an ISCO CombiFlash EZPrep automated purification system using a 330-g ISCO RediSep Rf Gold silica column. The crude material was loaded as a solution in 8% MeOH/CH$_2$Cl$_2$ (~160 mL). A gradient of Eluent A: CH$_2$Cl$_2$; Eluent B: 50% MeOH:CH$_2$Cl$_2$ was utilized to produce 33 fractions. Product containing fractions were concentrated to afford 10.13 g (98.1% pure, 59% recovery) of 18. Mixed fractions were pooled to yield an additional 6.52 g (86.1% purity) of 18, which could be re-purified.

Figure 2F:
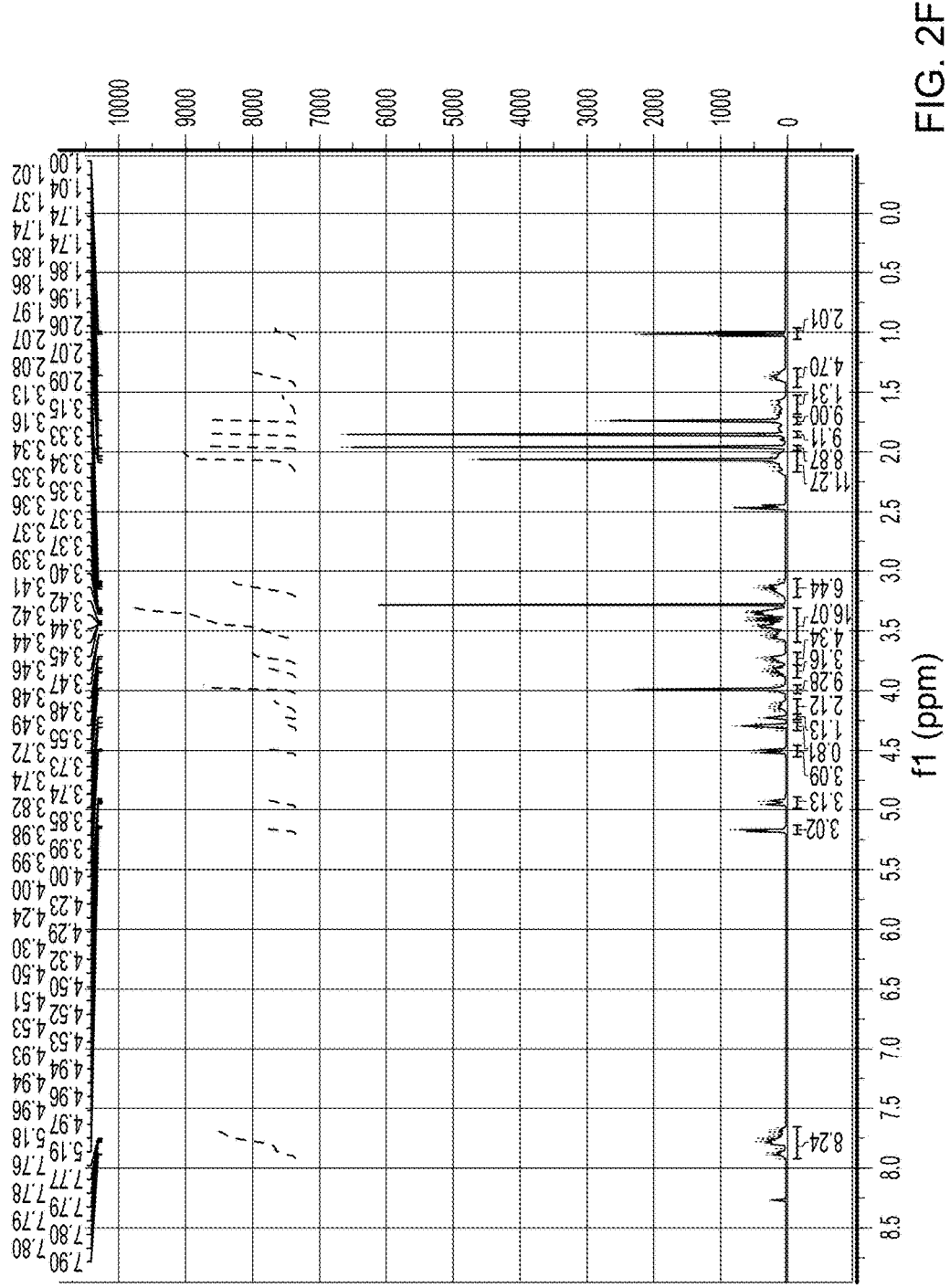
FIG. 2F is a $^1$H NMR spectra of Compound 18 (which is described below in Example 2).

FIG. 2F shows $^1$H NMR spectra for compound 18.

6) Preparation of Targeting Ligand Phosphoramidite (Compound 19)

(4.11 mL, 23.61 mmol) and a solution of 2-cyanoethyl-N,N-diisopropylchlorophosphorodiamidite (2.45 mL, 11.02 mmol) in anhydrous dichloromethane (5 mL) dropwise over 5 minutes. The reaction mixture was stirred at room temperature for 1 h while monitoring by HPLC (<1% SM remaining). The reaction was quenched with saturated aqueous NaHCO$_3$ (150 mL). The organic layer separated, washed with saturated aqueous NaHCO$_3$ (1×150 mL), and brine (1×150 mL), and dried with Na$_2$SO$_4$. The drying agent was filtered and the solution was concentrated and purified via flash chromatography by first treating the silica column with dichloromethane (+1% triethylamine) for 30 minutes followed by loading the crude final product, compound 19 (which has the chemical structure of Structure 1008 herein) on the column and purified using gradient elution (0-20%

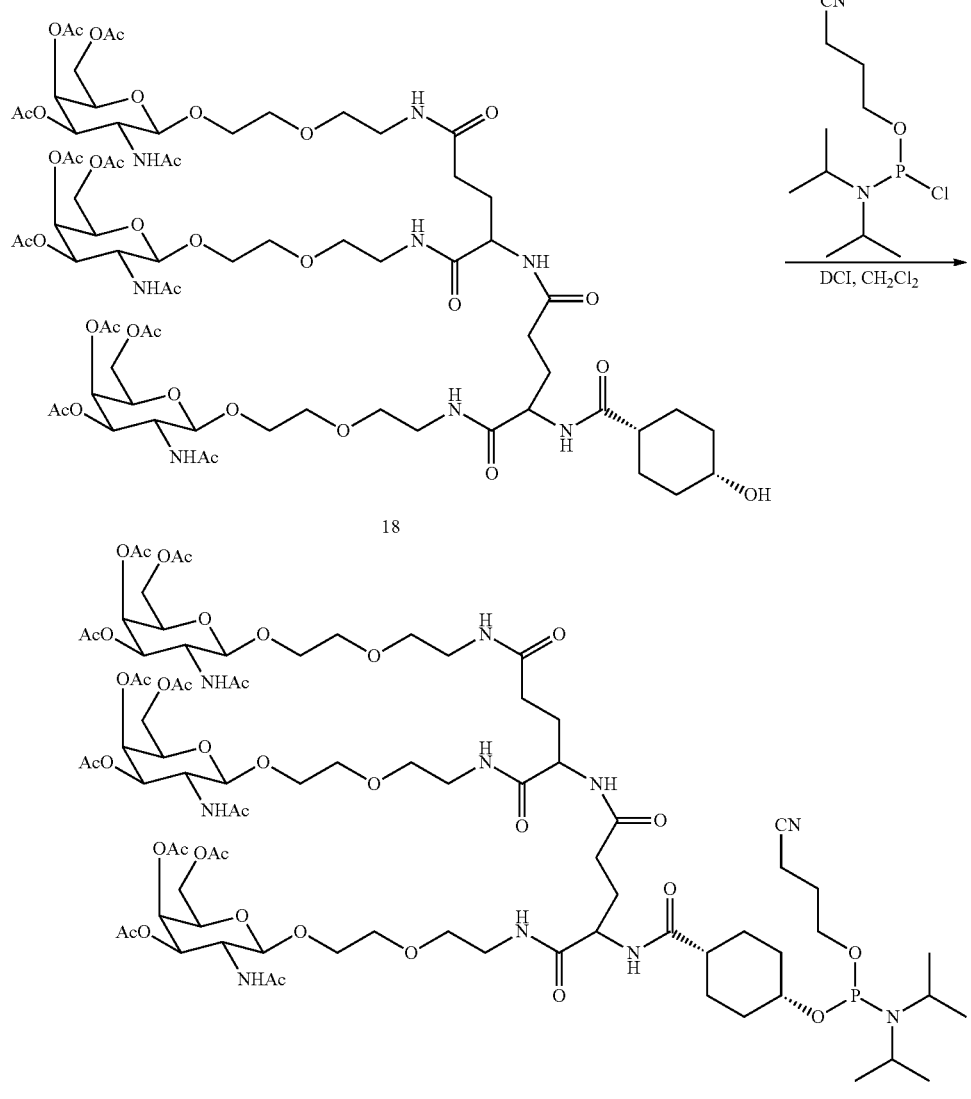

Compound 18 (13.0 g, 7.87 mmol) was dissolved in anhydrous dichloromethane (195 mL) and placed under nitrogen atmosphere. To this mixture, were added DIPEA MeOH (+1% TEA)/CH$_2$Cl$_2$ (+1% TEA)) over 30 min which gave 11.1 g of compound 19 as a white solid material (76% yield, purity 96.6%).

FIG. 2 shows $^{31}$P NMR spectra for Compound 19. FIG. 2A shows $^1$H NMR spectra for Compound 19. FIG. 2 and FIG. 2A are both consistent with the structure of Compound 19 (Structure 1008b herein).

Example 3. Synthesis of Targeting Ligand Phosphoramidite-Containing Compound Structure 1025

1) Preparation of Compound 21.

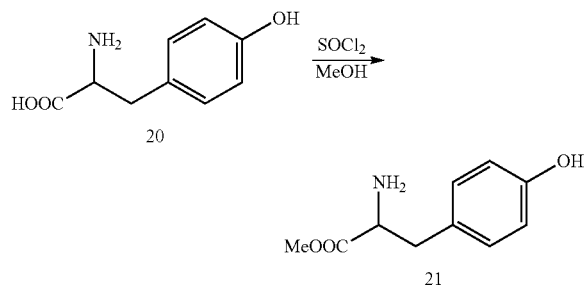

To a solution of compound 20 (40 g, 221 mmol, 1.00 eq) in MeOH (350 mL) was added SOCl$_2$ (52.5 g, 442 mmol, 32 mL, 2.00 eq) dropwise at 0-5° C. The solution was heated to 60° C. and stirred for 16 hrs. TLC (DCM/MeOH=5/1 with 5 drops HOAc, R$_f$=0.43) showed starting material consumed and LCMS (ET12452-6-P1A) showed product formed. The mixture was concentrated under vacuum to give crude compound 21 (52.4 g, crude) as a white solid. $^1$H NMR: (ET12452-6-p1c DMSO Bruker_B_400 MHz) δ 9.45 (s, 1H), 8.55 (br s, 3H), 7.00 (br d, J=8.0 Hz, 2H), 6.72 (d, J=8.0 Hz, 2H), 4.17 (br s, 1H), 3.67 (s, 3H), 3.01 (qd, J=14.2, 6.5 Hz, 2H).

2) Preparation of Compound 22.

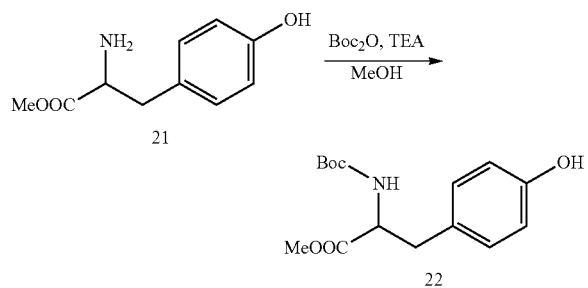

To a solution of compound 21 (52.4 g, 226 mmol, 1.00 eq) in MeOH (230 mL) was added TEA (68.7 g, 679 mmol, 94 mL, 3.00 eq), Boc$_2$O (59.2 g, 271 mmol, 62.4 mL, 1.20 eq) dropwise at 0° C., the mixture was stirred at 0° C. for 0.5 h, then stirred at 25° C. for 16 hrs. TLC (Petroleum ether/EtOAc=1/1, R$_f$=0.80) showed a new main spot formed and most starting material consumed. The mixture was concentrated, then purified by silica column (petroleum ether/EtOAc=1:1) to afford compound 22 (57.4 g, 86% yield) as a white solid. $^1$H NMR: (ET12452-8-p1g CDCl3 Bruker_B_400 MHz) δ 6.97 (d, J=8.5 Hz, 2H), 6.74 (br d, J=8.0 Hz, 2H), 5.65 (br s, 1H), 5.01 (br d, J=8.0 Hz, 1H), 4.49-4.59 (m, 1H), 3.72 (s, 3H), 2.92-3.09 (m, 2H), 1.43 (s, 9H).

3) Preparation of Compound 23.

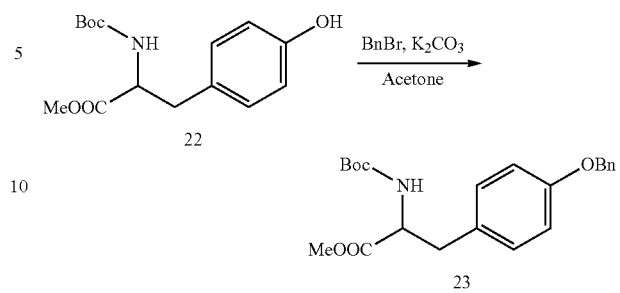

To a solution of compound 22 (35 g, 119 mmol, 1.00 eq) dissolved in Acetone (170 mL) was added K$_2$CO$_3$ (21.3 g, 154 mmol, 1.30 eq) and BnBr (24.3 g, 142 mmol, 16.9 mL, 1.20 eq), the reaction mixture was heated to reflux (60° C.) for 14 hrs. TLC (Petroleum ether/EtOAc=3/1, R$_f$=0.80) showed starting material consumed and a new spot formed. H$_2$O (500 mL) was added to the mixture at 5° C. and stirred for 0.5 h, then filtered and washed with H$_2$O (80 mL*3), dried under vacuum to give compound 23 (43 g, 88% yield, 93% purity) as a white solid. $^1$H NMR: (ET12452-9-p1a CDCl3 Bruker_B_400 MHz) δ 7.31-7.46 (m, 5H), 7.05 (d, J=8.5 Hz, 2H), 6.91 (d, J=9.0 Hz, 2H), 5.05 (s, 2H), 4.97 (br d, J=8.0 Hz, 1H), 4.50-4.60 (m, 1H), 3.72 (s, 3H), 2.96-3.11 (m, 2H), 1.43 (s, 9H).

4) Preparation of Compound 24.

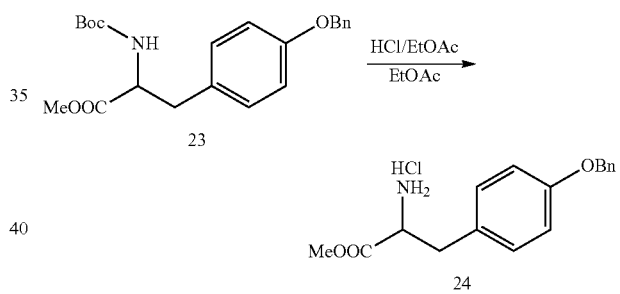

To a solution of compound 23 (43 g, 112 mmol, 1.00 eq) in EtOAc (215 mL) was added HCl/EtOAc (4 M, 215 mL, 7.71 eq) dropwise, the mixture was stirred for 9 hrs at 25° C. TLC (Petroleum ether/EtOAc=3/1, R$_f$=0.10) showed starting material consumed and a new pot formed. The mixture was filtered and washed with EtOAc (30 mL*3), dried under vacuum to give compound 24 (35 g, 97% yield, 99% purity) as a white solid. $^1$H NMR: (ET12452-12-p1a MeOD Varian_D_400 MHz) δ 7.40-7.45 (m, 2H), 7.34-7.39 (m, 2H), 7.29-7.33 (m, 1H), 7.17 (d, J=8.8 Hz, 2H), 7.00 (d, J=8.8 Hz, 2H), 5.09 (s, 2H), 4.26 (dd, J=7.3, 6.0 Hz, 1H), 3.81 (s, 3H), 3.07-3.23 (m, 2H).

5) Preparation of Compound 26.

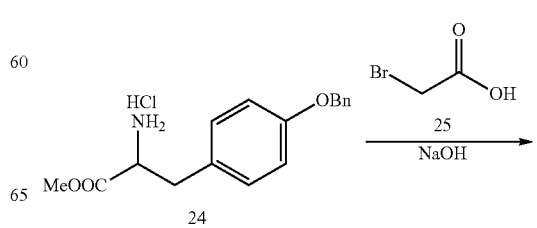

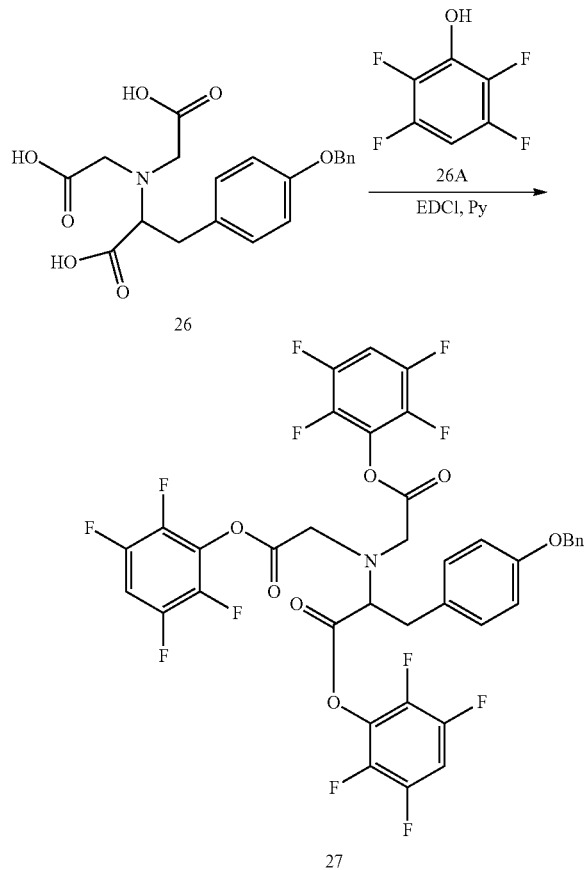

Compound 24 (15.5 g, 48.2 mmol, 1.00 eq) was dissolved in CH$_3$CN (40 mL) and NaOH (1.5 M, 70.6 mL, 2.20 eq), then compound 25 (13.4 g, 96.3 mmol, 6.94 mL, 2.00 eq) was added at 15° C., pH check: ~2.5. Then 4 N NaOH was added until pH=13. The solution was heated at 70° C. After 30 min, the pH dropped below 6, again adjusted with 4 N NaOH (pH 11-13). Additional compound 25 (6.69 g, 48.2 mmol, 3.47 mL, 1.00 eq) was added portionwise (twice) and pH was adjusted each time to 11-13. The mixture was heated at 70° C. for 14 hrs. LCMS (ET12452-30-P1A, Rt=0.749 min) showed product formed. The mixture was cooled to 15° C., then adjusted to pH 1 with 4N HCl, filtered and washed with H$_2$O (80 mL*2), dried. The residue was dissolved with THF (600 mL) and then concentrated for sixth with the batch of ET12452-27, ET12452-19, then stirred with DCM (500 mL) and filtered, the filter was dried to give compound 26 (35.5 g, 87% yield, 97% purity) as a white solid. $^1$H NMR: (ET12452-30-p1r MeOD Varian_D_400 MHz) δ 7.40-7.45 (m, 2H), 7.36 (t, J=7.4 Hz, 2H), 7.27-7.32 (m, 1H), 7.17 (d, J=8.4 Hz, 2H), 6.91 (d, J=8.6 Hz, 2H), 5.49 (s, 1H), 5.05 (s, 2H), 3.71 (t, J=7.6 Hz, 1H), 3.61 (s, 4H), 3.07 (dd, J=14.1, 7.5 Hz, 1H), 2.86-2.96 (m, 1H), 2.03 (s, 2H).

6) Preparation of Compound 27.

To the solution of compound 26 (15 g, 38.7 mmol, 1.00 eq), compound 26A (25.7 g, 155 mmol, 4.00 eq) in Pyridine (250 mL) was added EDCI (29.7 g, 155 mmol, 4.00 eq) at 5° C. The mixture was stirred at 30° C. for 12 hrs. LCMS (ET12452-59-P1A, Rt=1.053 min) showed mostly product. The mixture was concentrated, then dissolved with DCM (200 mL), washed with sat. NaHCO$_3$ (80 mL*4), brine (80 mL*2), dried over Na$_2$SO$_4$, filtered and concentrated. The residue was purified by silica column (Petroleum ether/EtOAc=3:1, Rf=0.75) to afford product with compound 26A, then dissolved with DCM (200 mL), washed with sat. NaHCO$_3$ (80 mL*4) and brine (80 mL*2), dried over Na$_2$SO$_4$, filtered and concentrated to give compound 27 (19.8 g, 61% yield) as an off-white gum. $^1$H NMR: (ET12452-59-p1 g CDCl3 Bruker_B_400 MHz) δ 7.36-7.46 (m, 4H), 7.30-7.35 (m, 1H), 7.24 (d, J=8.7 Hz, 2H), 6.97-7.07 (m, 3H), 6.94 (d, J=8.7 Hz, 2H), 5.05 (s, 2H), 4.13-4.26 (m, 5H), 3.25 (d, J=7.5 Hz, 2H), 2.06 (s, 1H), 1.25-1.29 (m, 1H)

7) Preparation of Compound 27-2.

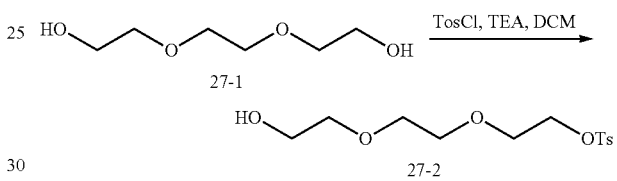

Compound 27-1 (230 g, 1.53 mol, 205 mL, 1.00 eq) was dissolved in dry DCM (1.6 L) under an N$_2$ atmosphere. The solution was cooled to 0° C. with an ice bath and TEA (232 g, 2.3 mol, 318 mL, 1.50 eq) was added. Subsequently TosCl (233 g, 1.22 mol, 0.80 eq) in DCM (500 mL) was added to the cooled reaction mixture. After addition, the solution was allowed to warm to 20° C. and was stirred for 5 hrs. TLC (petroleum ether/EtOAc=1:1, R$_f$=0.15) showed starting material consumed and HPLC (ET12452-15-P1L, R$_t$=1.71 min) showed 2 peaks. The reaction mixture was quenched by addition H$_2$O (500 mL) at 0° C., and then the 2 reactions were extracted with CH$_2$Cl$_2$ (800 mL). The combined organic layers were washed with H$_2$O (1 L) and brine (1 L), dried over Na$_2$SO$_4$, filtered and concentrated. The residue was purified by silica column (petroleum ether/EtOAc=1:1) to give compound 27-2 (338 g, 36% yield) as a yellow oil. $^1$H NMR: (ET12452-15-p1z1 CDCl3 Bruker_B_400 MHz) δ 7.79 (d, J=8.0 Hz, 2H), 7.34 (d, J=8.5 Hz, 2H), 4.12-4.19 (m, 2H), 3.67-3.72 (m, 4H), 3.60 (s, 4H), 3.55-3.58 (m, 2H), 2.44 (s, 3H), 2.32 (s, 1H)

8) Preparation of Compound 27-3A.

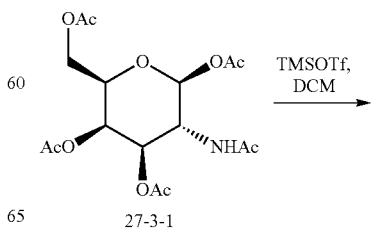

-continued

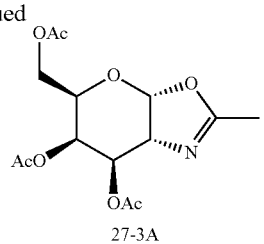

27-3A

Compound 27-3-1 (230 g, 591 mmol, 1.00 eq) suspended in DCM (700 mL) at 20° C. and TMSOTf (197 g, 886 mmol, 160 mL, 1.50 eq) was added under N$_2$. The color of the mixture changed to pink. The mixture was heated to 50° C. and stirred for 1.5 hrs. Then the reaction mixture was cooled to 20° C. and stirred for 14 hrs. TLC (DCM/MeOH=20:1, Rf=0.6) showed starting material consumed. The mixture was poured into aq. NaHCO$_3$ (600 mL) at 0~5° C. and stirred for 15 min. The color of the mixture changed to yellow. The mixture was extracted with DCM (500 mL), washed with aq.NaHCO$_3$ (500 mL), water (500 mL*2) and brine (500 mL), dried over Na$_2$SO$_4$, filtered and concentrated to afford compound 27-3A (189 g, crude, 92% purity) as a brown oil. $^1$H NMR: (ET12452-28-p1c CDCl3 Varian_D_400 MHz) δ 6.00 (d, J=6.6 Hz, 1H), 5.47 (t, J=3.0 Hz, 1H), 4.91 (dd, J=7.5, 3.3 Hz, 1H), 4.17-4.28 (m, 2H), 4.08-4.14 (m, 1H), 3.97-4.03 (m, 1H), 2.13 (s, 3H), 2.05-2.09 (m, 9H)

9) Preparation of Compound 27-4A.

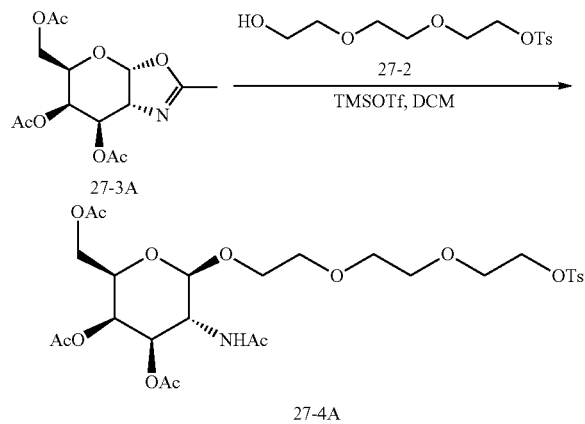

To a mixture of compound 27-3A (189 g, 574 mmol, 1.00 eq), compound 7-2 (140 g, 460 mmol, 0.80 eq) and 4 A MOLECULAR SIEVE (150 g) in DCM (1.5 L) was added TMSOTf (63.8 g, 287 mmol, 51.9 mL, 0.50 eq) under N$_2$ atmosphere, the mixture was stirred at 25° C. for 8 hrs. TLC (DCM/MeOH=20:1, Rf=0.46) showed starting material consumed and LCMS (ET12452-35-P1A, Rt=0.76 min) showed product formed. The mixture was filtered to remove the sieves, then quenched with cold NaHCO$_3$ aqueous (1000 mL), extracted with DCM (800 mL*2), the separated organic layers were washed with sat. NaHCO$_3$ (800 mL), H$_2$O (800 mL*2) and brine (800 mL), dried over Na$_2$SO$_4$, filtered and concentrated. Then purified by silica column (DCM/MeOH=20:1) to afford compound 27-4A (285 g, 73% yield) as a yellow oil. $^1$H NMR: (ET12452-35-p1g CDCl3 Varian_D_400 MHz) δ 7.81 (d, J=8.4 Hz, 2H), 7.37 (d, J=8.2 Hz, 2H), 6.30 (br d, J=9.5 Hz, 1H), 5.28-5.35 (m, 1H), 5.08 (dd, J=11.2, 3.3 Hz, 1H), 4.81 (d, J=8.6 Hz, 1H), 4.09-4.29 (m, 5H), 3.86-3.98 (m, 3H), 3.68-3.81 (m, 3H), 3.56-3.66 (m, 5H), 2.46 (s, 3H), 2.16 (s, 3H), 2.04 (s, 3H), 1.98 (s, 3H), 1.95 (s, 3H)

10) Preparation of Compound 27-4.

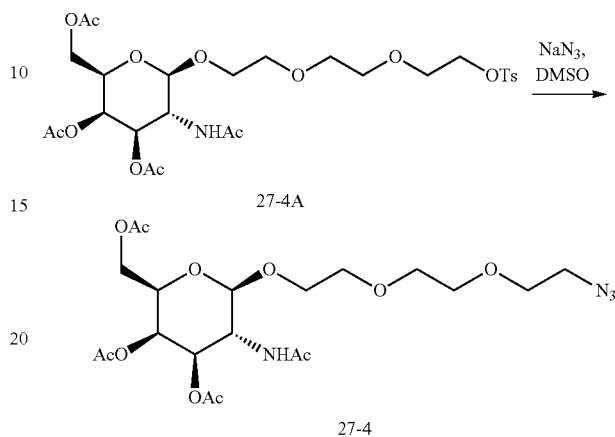

To a solution of compound 27-4A (285 g, 450 mmol, 1.00 eq) in DMSO (1.4 L) was added NaN$_3$ (38.1 g, 586 mmol, 1.30 eq) at 10° C., the mixture was stirred at 60° C. for 16 hrs. LCMS (ET12452-37-P1A, Rt=0.67 min) showed product formed and starting material consumed. The mixture was poured into H$_2$O (1500 mL), extracted with EtOAc (1 L*5), washed with H$_2$O (800 mL*3) and brine (800 mL*3), dried over Na$_2$SO$_4$, filtered and concentrated to give compound 27-4 (168 g, crude) as a red oil. $^1$H NMR: (ET12452-37-p1c CDCl3 Bruker_B_400 MHz) δ 6.12 (br d, J=9.4 Hz, 1H), 5.32 (d, J=2.9 Hz, 1H), 5.06 (dd, J=11.3, 3.4 Hz, 1H), 4.78 (d, J=8.7 Hz, 1H), 4.08-4.27 (m, 5H), 3.82-3.94 (m, 3H), 3.61-3.77 (m, 10H), 3.45-3.50 (m, 2H), 2.16 (s, 3H), 2.05 (d, J=1.5 Hz, 5H), 1.99 (d, J=4.5 Hz, 6H), 1.26 (t, J=7.2 Hz, 2H)

11) Preparation of Compound 27A.

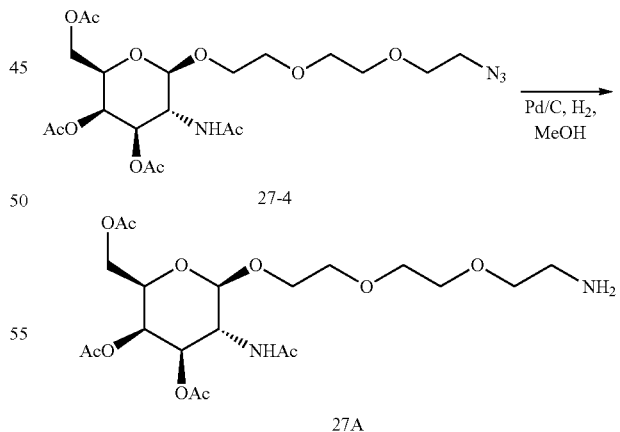

To a solution of compound 27-4 (79 g, 156 mmol, 1.00 eq) in EtOAc/MeOH (4:1) (640 mL) was added Pd(OH)$_2$/C (7.9 g), the mixture was stirred at 15° C. for 4 hrs under H$_2$ (30 psi) atmosphere. TLC (DCM/MeOH=20:1) showed starting material consumed and LCMS (ET12452-53-P1C, Rt=2.55 min) showed product formed. The 2 parallel reactions were filtered with Celite and washed with DCM (500 mL*5) and MeOH (200 mL*3), concentrated to give compound 27A (140 g, crude) as a dark-brown oil. ¹H NMR: (ET12452-53-p1c CDCl3 Varian_D_400 MHz) δ 7.02 (br d, J=9.3 Hz, 1H), 5.29-5.34 (m, 1H), 5.09 (dd, J=11.2, 3.3 Hz, 1H), 4.80 (d, J=8.6 Hz, 1H), 4.09-4.24 (m, 3H), 3.82-3.95 (m, 3H), 3.52-3.70 (m, 10H), 2.91 (td, J=5.2, 2.8 Hz, 1H), 2.15 (s, 3H), 2.05 (s, 4H), 1.98 (d, J=6.4 Hz, 6H).

12) Preparation of Compound 28.

CH₃CN was evaporated off, then diluted with DCM (400 mL) and washed with sat. NaHCO₃ (100 mL*4). Organic layer was separated and washed with 0.1M HCl/saturated brine (1:1, 100 mL*4), dried over Na₂SO₄, filtered and concentrated. The residue was purified by silica column (DCM/MeOH=10:1, Rf=0.45) to give product, then further purified by p-HPLC (column: Phenomenex Gemini C18 250*50 mm*10 um; mobile phase: [water (10 mM

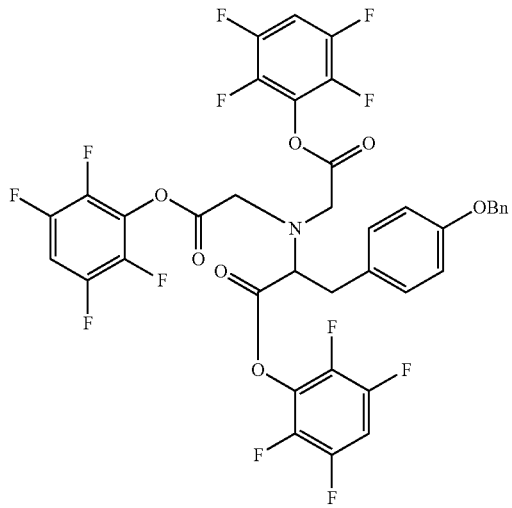

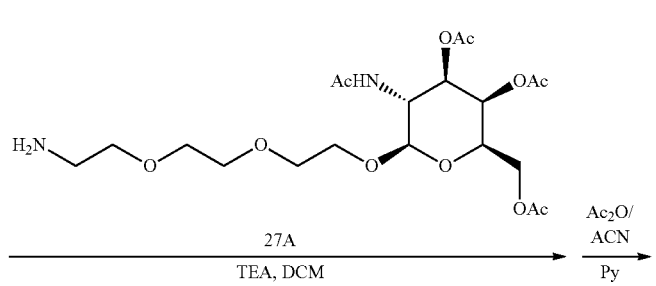

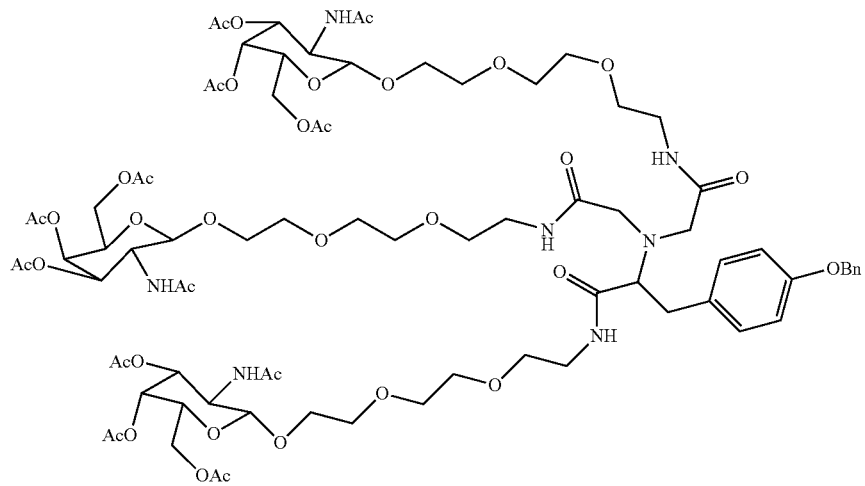

TEA (12.1 g, 119 mmol, 16.5 mL, 5.00 eq) was added to a stirred solution containing compound 27 (19.8 g, 23.8 mmol, 1.00 eq) and compound 27A (57 g, 119 mmol, 5.00 eq) in DCM (160 mL). It was stirred at 30° C. for 16 hrs. LCMS (ET12452-64-P1A, Rt=1.21 min) showed product formed. Diluted with DCM (100 mL) and washed with saturated NaHCO₃/saturated brine (1:1, 2×80 mL). Organic layer was dried over Na₂SO₄, filtered and concentrated to give crude product as a brown solid.

The crude product was dissolved in Ac₂O (42 mL), CH₃CN (62.5 mL) and Py (82.3 g, 1.04 mol, 84 mL, 23.96 eq), the mixture was stirred at 25° C. for 12 hrs. HPLC (ET12452-65-P1A, Rt=2.54 min) showed most product.

NH₄HCO₃)-ACN]; B %: 25%-55%, 23 min) to give compound 28 (28.8 g, 58% yield, 98% purity) as a yellow solid. ¹H NMR: (ET12452-65-p1j DMSO Varian_D_400 MHz) δ 8.00-8.09 (m, 3H), 7.81 (d, J=9.0 Hz, 3H), 7.29-7.45 (m, 5H), 7.10 (d, J=8.6 Hz, 2H), 6.89 (d, J=8.4 Hz, 2H), 5.21 (d, J=3.3 Hz, 3H), 5.04 (s, 2H), 4.97 (dd, J=11.2, 3.3 Hz, 3H), 4.54 (d, J=8.4 Hz, 3H), 4.02 (s, 9H), 3.83-3.92 (m, 3H), 3.73-3.81 (m, 3H), 3.53-3.61 (m, 4H), 3.44-3.52 (m, 17H), 3.42 (br d, J=4.4 Hz, 2H), 3.35-3.40 (m, 6H), 3.07-3.27 (m, 11H), 2.74-2.87 (m, 2H), 2.09 (s, 9H), 1.99 (s, 10H), 1.89 (s, 9H), 1.77 (s, 9H).

13) Preparation of Compound 29.

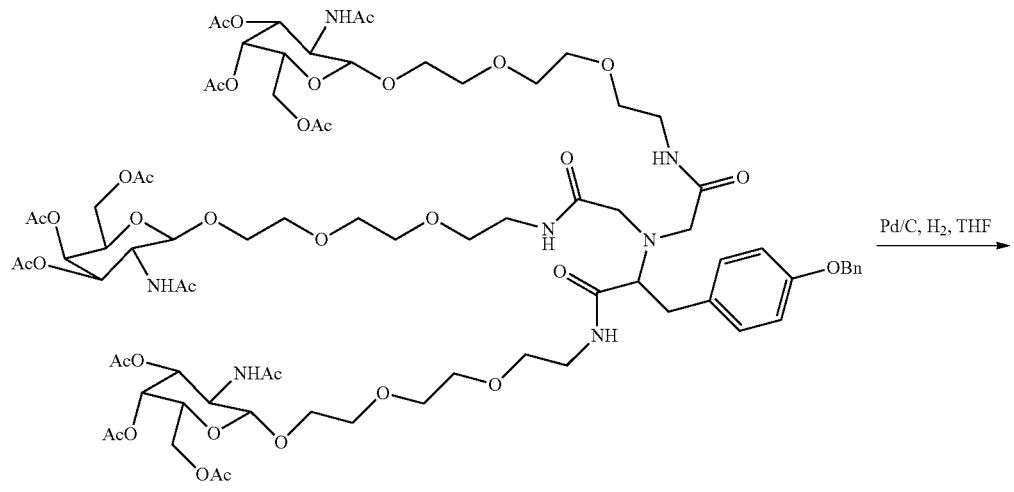

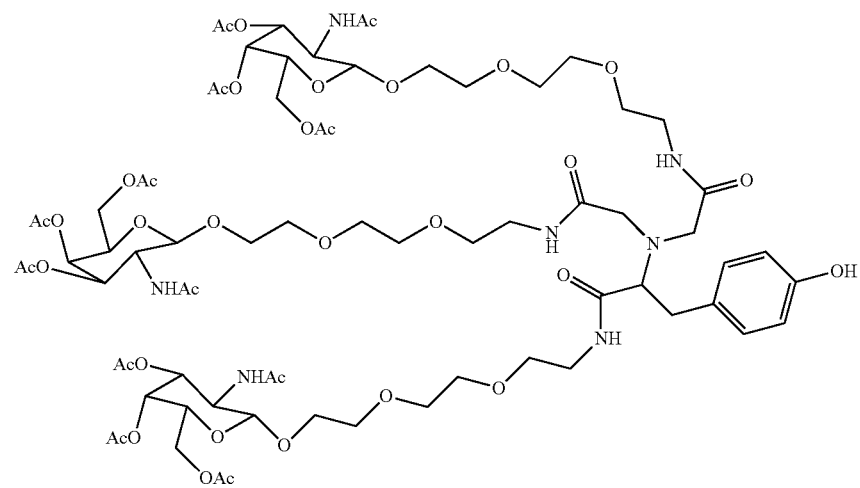

To a solution of compound 28 (9.7 g, 5.48 mmol, 1.00 eq) in THF (250 mL) was added dry Pd/C (5.5 g, 5.48 mmol), the mixture was stirred at 40° C. for 6.5 hrs under H₂ atmosphere (50 psi). TLC (DCM/MeOH=10:1, Rf=0.3) showed starting material consumed. The 2 parallel reactions were filtered and washed with THF (300 mL*4) and DCM (200 mL*3), concentrated. The residue was purified by p-HPLC (column: Phenomenex luna C18 250*50 mm*10 um; mobile phase: [water (0.1% TFA)-ACN]; B %: 15%-45%, 20 min) with the batch of ET12452-78 to afford compound 29 (14 g, 63% yield) as a white solid. $^1$H NMR: (ET12452-80-p1j DMSO Varian_D_400 MHz) δ 9.19 (s, 1H), 7.99-8.10 (m, 3H), 7.83 (d, J=9.3 Hz, 3 H), 6.95 (d, J=8.4 Hz, 2H), 6.62 (d, J=8.4 Hz, 2H), 5.76 (s, 2H), 5.21 (d, J=3.3 Hz, 3H), 4.97 (dd, J=11.2, 3.3 Hz, 3H), 4.54 (d, J=8.6 Hz, 3H), 4.03 (s, 9H), 3.83-3.92 (m, 3H), 3.73-3.81 (m, 3H), 3.53-3.61 (m, 4H), 3.44-3.52 (m, 16H), 3.43 (br d, J=4.4 Hz, 3H), 3.36-3.39 (m, 3H), 3.26-3.33 (m, 4H), 3.05-3.24 (m, 9H), 2.65-2.82 (m, 2H), 2.10 (s, 9H), 2.00 (s, 9H), 1.89 (s, 9H), 1.77 (s, 9H).

14) Preparation of Compound 30.

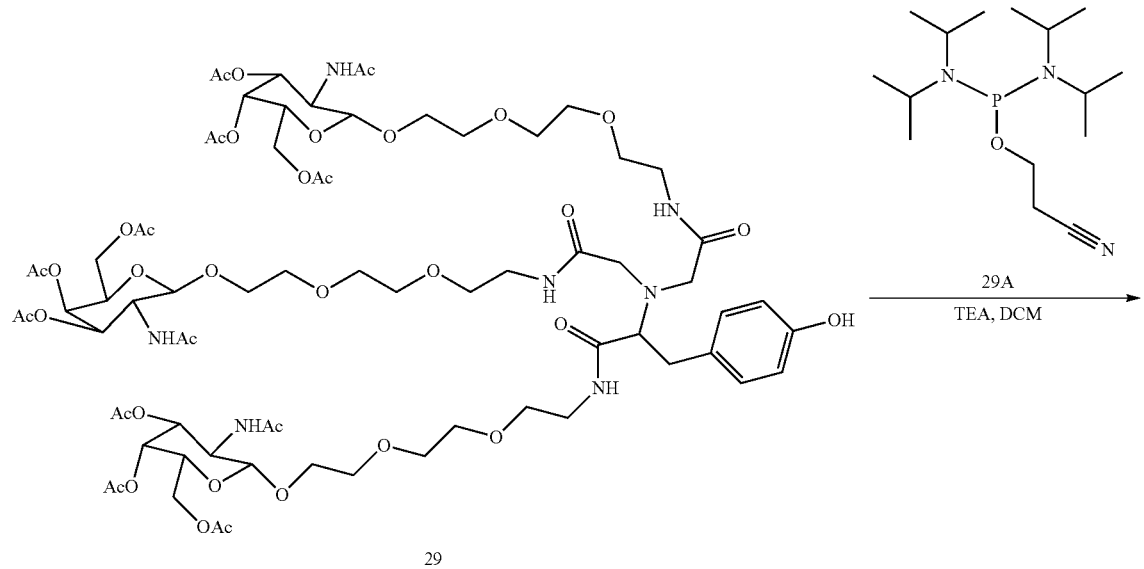

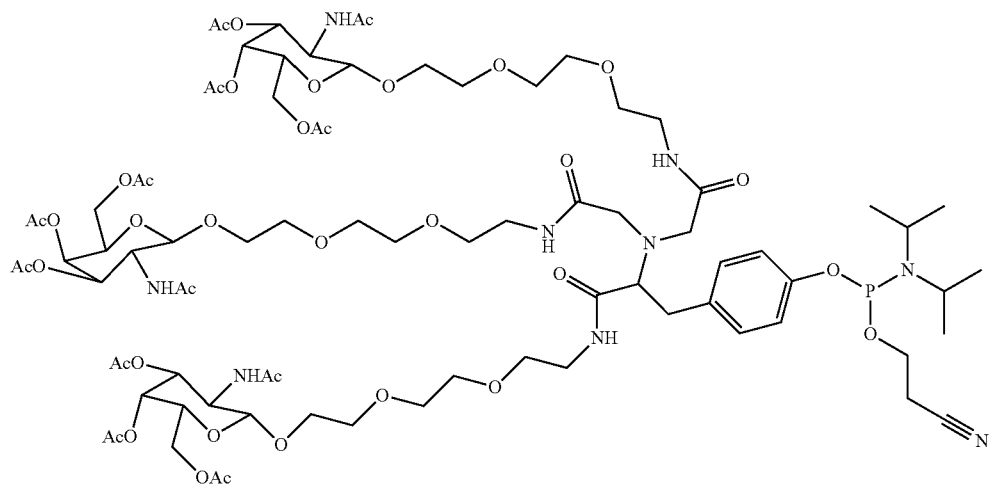

Compound 29 (8 g, 4.77 mmol, 1.00 eq) was dissolved in DCM (65 mL) and compound 29A (2.88 g, 9.54 mmol, 3 mL, 2.00 eq) was added. The resulting solution was cooled to 5° C. To this solution was added 2H-tetrazole (0.45 M, 11.7 mL, 1.10 eq). The solution was allowed to warm to 15° C. and stirred for 3.5 hrs. TLC (DCM/MeOH=5:1, Rf=0.52) showed starting material consumed and HPLC (ET12452-82-P1A, Rt=2.69 min) showed product formed. Diluted with DCM (50 mL), quenched with NaHCO$_3$ (30 mL), the aqueous was extracted with DCM (30 mL*2), the combined organic layers was washed with sat. NaHCO$_3$ (30 mL*2), H$_2$O (30 mL) and brine (30 mL*2), dried over Na$_2$SO$_4$, filtered and concentrated. The residue was dissolved with DCM (30 mL), then Hexane (150 mL) was added dropwise at 0° C. and stirred for 15 min, then chilled, the organic layer was poured off and the oil was dissolved with DCM (30 mL) again and added Hexane (150 mL) dropwise, the procedure was repeated for 7 times, dried under vacuum to afford compound 30 (5.5 g, 55% yield) as a white solid. $^1$H NMR: (ET12452-83-p1b DMSO Varian_D_400 MHz) δ 7.97-8.09 (m, 3H), 7.78 (d, J=9.3 Hz, 3H), 7.06 (d, J=8.2 Hz, 2H), 6.86 (d, J=8.2 Hz, 2H), 5.73 (s, 2H), 5.18 (d, J=3.3 Hz, 3H), 4.94 (dd, J=11.1, 3.4 Hz, 3H), 4.51 (d, J=8.4 Hz, 3H), 3.99 (s, 9H), 3.79-3.89 (m, 4H), 3.70-3.78 (m, 4H), 3.59-3.69 (m, 2H), 3.49-3.58 (m, 4H), 3.44 (s, 16H), 3.40 (br d, J=4.2 Hz, 3H), 3.32-3.37 (m, 5H), 3.24-3.28 (m, 1H), 3.05-3.22 (m, 9H), 2.78 (br t, J=5.8 Hz, 4H), 2.07 (s, 9H), 1.96 (s, 9H), 1.86 (s, 9H), 1.74 (s, 9H), 1.15 (d, J=6.8 Hz, 6H), 1.09 (d, J=6.8 Hz, 6H).

Figure 3:
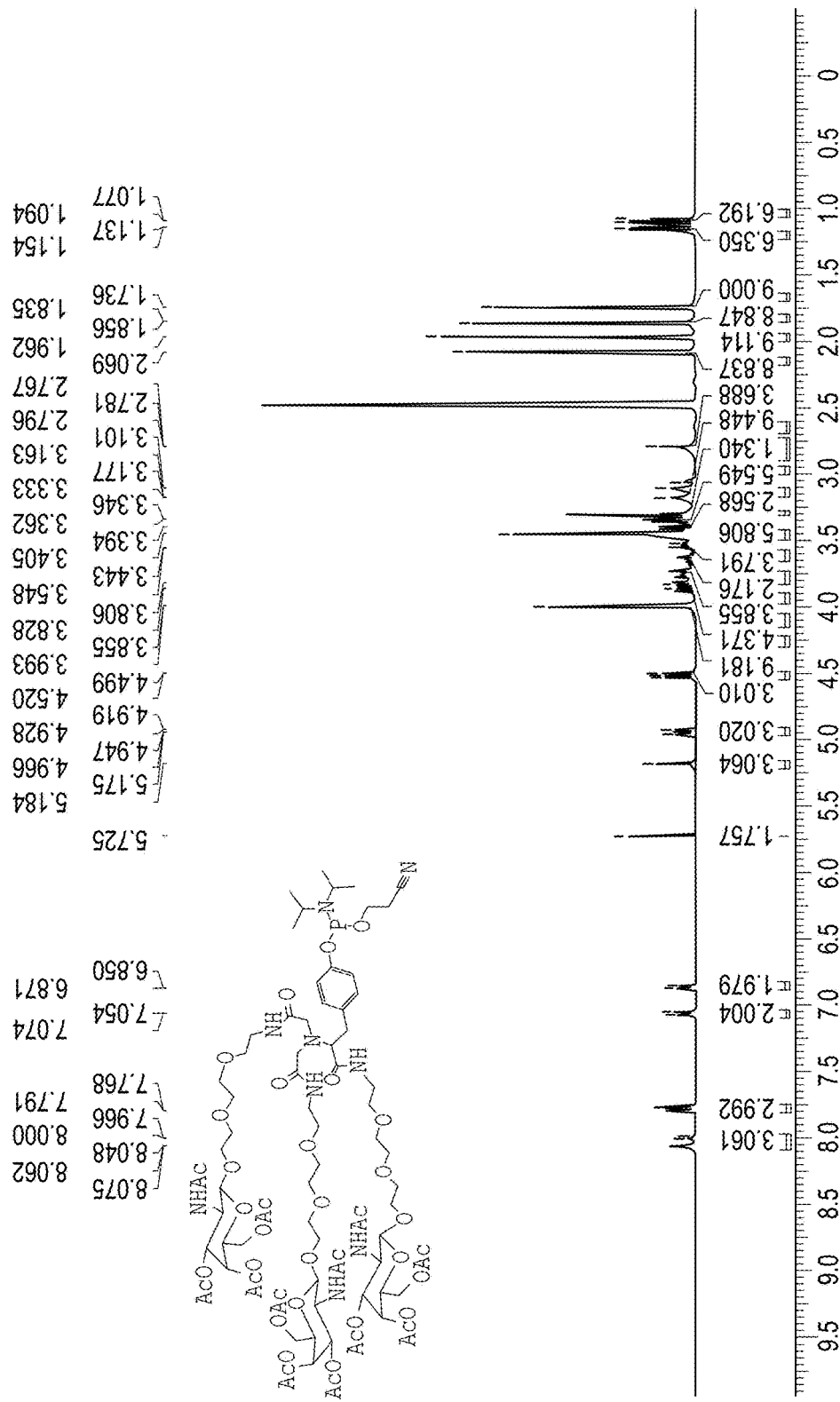
FIG. 3 is a $^1$H NMR spectra of Compound 30 (which is described below in Example 3).

FIG. 3 shows $^1$H NMR spectra for compound 30 (Structure 1025b herein).

Example 4: Synthesis of Targeting Ligand Phosphoramidite-Containing Compound Structure 1014b 1) Preparation of Compound 32.

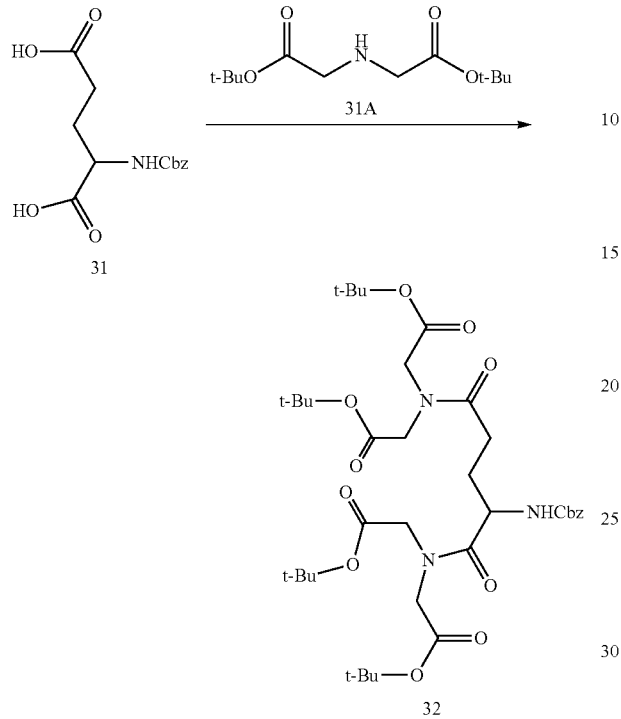

A solution of compound 31 (24.71 g, 87.85 mmol, 1.00 eq), compound 31A, EDCI (39.07 g, 203.82 mmol, 2.32 eq), Pyridine (19.39 g, 245.11 mmol, 19.79 mL, 2.79 eq) in ACN (260.00 mL) was stirred at 25° C. for 2 hrs. TLC (petroleum ether/ethyl acetate=1/1, desired product; Rf=0.7) showed desired product formed. The mixture was added to 300 mL EtOAc, washed with NaHCO$_3$ (100 mL*2), 100 mL brine, dried with Na$_2$SO$_4$, filtered and concentrated to give a residue. The crude product was purified with a silica column (petroleum ether/ethyl acetate=100/1~3/1) to give compound 32 (60.00 g, 79.25 mmol, 90.20% yield, 97.19% purity) as a yellow oil. $^1$H NMR: (ET12600-89-p1a DMSO Varian_D_400 MHz) δ ppm 7.52 (d, J=8.4 Hz, 1H), 7.27-7.38 (m, 5H), 4.99 (s, 2H), 4.26-4.42 (m, 3H), 3.80-4.15 (m, 8H), 2.27 (br s, 2H), 1.78-1.88 (m, 1H), 1.66 (br dd, J=14.4, 7.2 Hz, 1H), 1.37-1.41 (m, 35H)

2) Preparation of Compound 33.

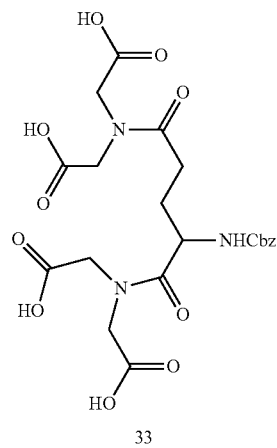

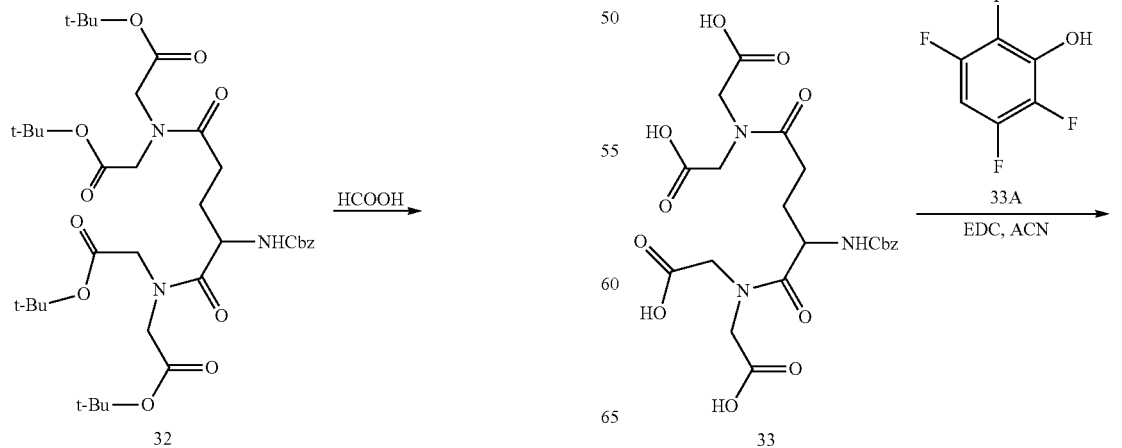

A solution of compound 32 (45.00 g, 61.15 mmol, 1.00 eq) in FORMIC ACID (800.00 mL) was stirred at 45° C. for 6 hr. LCMS (et12600-90-p1a, MS=511) showed the desired product formed. The mixture was concentrated to give a residue. The residue was washed with 1000 mL DCM to give compound 33 (30.00 g, 54.71 mmol, 89.47% yield, 93.27% purity) as a white solid. $^1$H NMR: (ET12600-90-p1a DMSO Bruker_B_400 MHz) δ 12.75 (br s, 3H), 7.53 (br d, J=8.4 Hz, 1H), 7.29-7.38 (m, 5H), 4.99 (d, J=3.6 Hz, 2H), 4.27-4.38 (m, 2H), 4.12 (br s, 2H), 3.84-4.07 (m, 6H), 2.30 (br t, J=7.2 Hz, 2H), 2.07 (s, 1H), 1.59-1.88 (m, 2H), 1.39 (t, J=5.6 Hz, 1H).

3) Preparation of Compound 34.

-continued

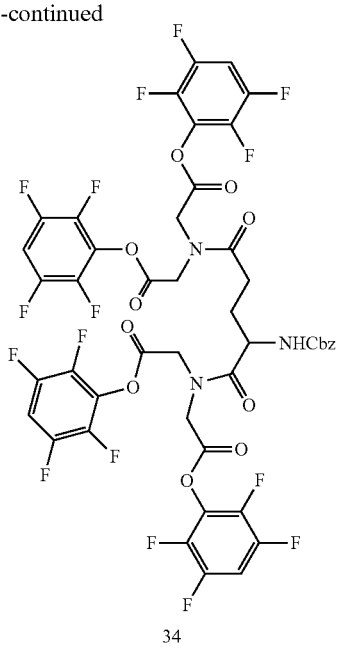

34

To a solution of compound 33 (15 g, 29.33 mmol, 1.00 eq), compound 33A (29.22 g, 175.98 mmol, 6.00 eq), Pyridine (11.60 g, 146.65 mmol, 11.84 mL, 5.00 eq) in ACN (90 mL) was added EDCI (28.11 g, 146.65 mmol, 5.00 eq), then the mixture was stirred for 25° C. for 1 hrs. TLC (petroleum ether/ethyl acetate=3/1) showed desired product formed. The mixture was added 500 mL DCM, washed with NaHCO$_3$ (200 mL*2), 100 mL brine, dried with Na$_2$SO$_4$, filtered and concentrate to give a residue. Purified with silica column (petroleum ether/ethyl acetate=4/1) to give compound 34 (28 g) as a yellow solid.

4) Preparation of Compound 35.

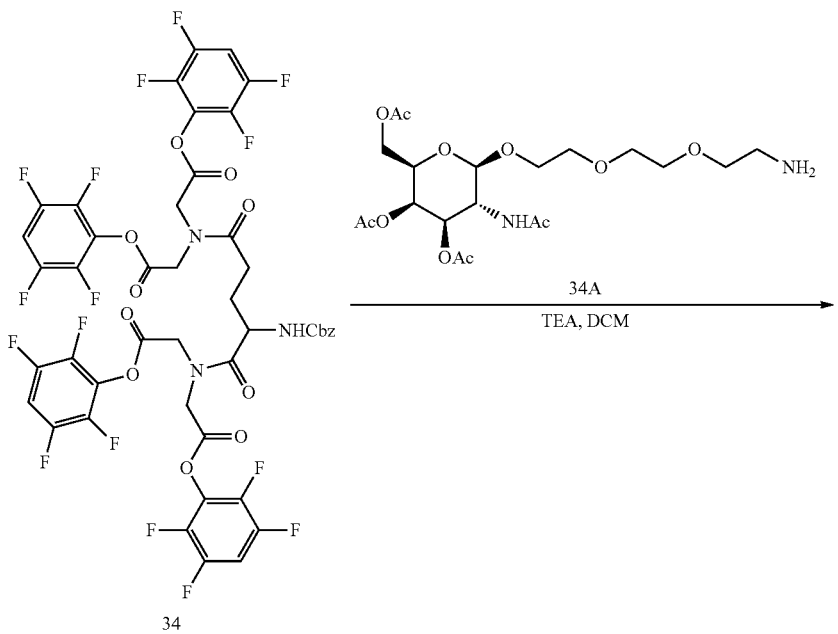

34

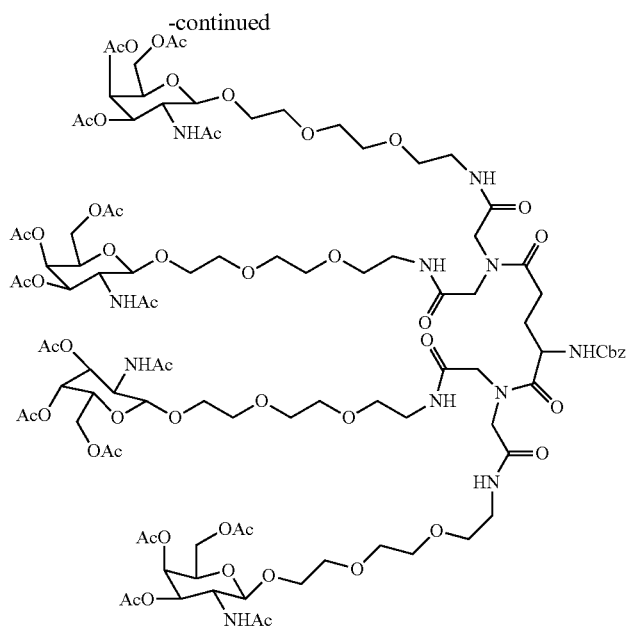

35

To a solution of compound 34 (16.57 g, 15.01 mmol, 1 eq), compound 34A in DCM (140 mL) was added TEA (9.12 g, 90.08 mmol, 12.49 mL, 6.00 eq), then the mixture was stirred at 25° C. for 16 hrs. LCMS (et12600-98-p1g) showed desired product formed. The mixture was poured onto 200 mL DCM, washed with 100 mL NaHCO$_3$, 100 mL brine, dried with Na$_2$SO$_4$, filtered and concentrated to give a residue. Purified with prep-HPLC (column: Phenomenex Gemini C18 250*50 10u; mobile phase: [water (10 mM NH$_4$HCO$_3$)-ACN]; B %: 15%-45%, 20 min) to give compound 5 (11 g, 4.65 mmol, 30.98% yield, 99.5% purity) as a yellow solid. $^1$H NMR: (ET12600-98-p1a1 DMSO Varian_D_400 MHz) δ 8.65-8.71 (m, 1H), 8.51 (br s, 1H), 8.18-8.25 (m, 1H), 8.11 (br s, 1H), 7.80 (d, J=8.8 Hz, 4H), 7.47 (br d, J=7.6 Hz, 1H), 7.28-7.40 (m, 5H), 5.75 (s, 4H), 5.22 (d, J=3.2 Hz, 4H), 4.95-5.03 (m, 6H), 4.55 (d, J=8.4 Hz, 4H), 3.98-4.06 (m, 15H), 3.88 (dt, J=11.2, 8.8 Hz, 7H), 3.78 (dt, J=10, 5.2 Hz, 5H), 3.54-3.62 (m, 6H), 3.46-3.53 (m, 25H), 3.41 (q, J=5.6 Hz, 9H), 3.23 (br dd, J=11.6, 5.6 Hz, 8H), 2.10 (s, 12H), 2.00 (s, 12H), 1.89 (s, 12H), 1.77 (s, 12H).

5) Preparation of Compound 36.

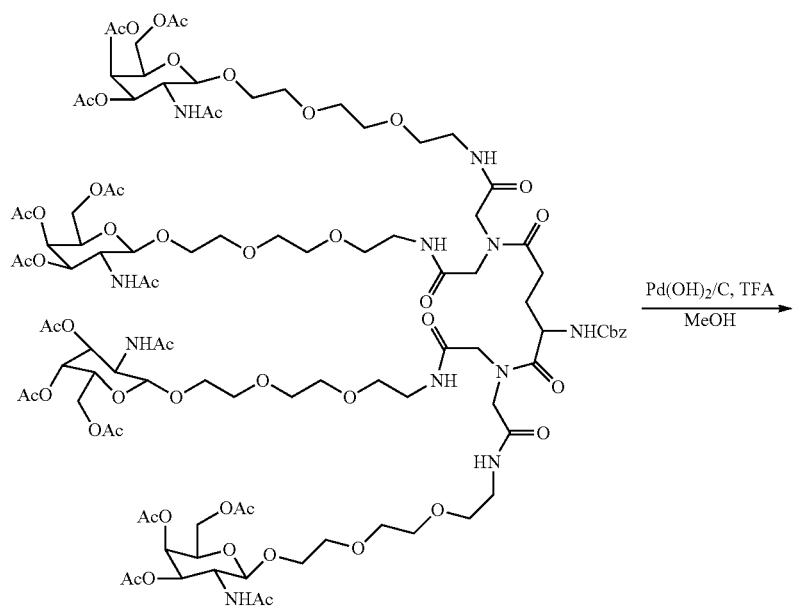

35

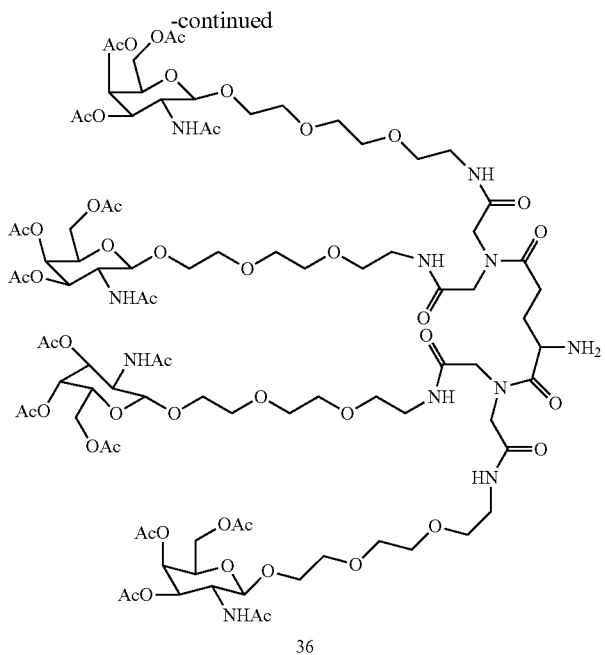

36

To a solution of compound 35 (10 g, 4.25 mmol, 1 eq), TFA (484.52 mg, 4.25 mmol, 314.62 uL, 1 eq) in MeOH (10 mL) was added 10% Pd(OH)$_2$/C (3.00 g), then the mixture was stirred at 20° C. for 4 hrs under H$_2$ (50 Psi). LCMS (et12600-107-p1a, Rt=2.195) showed desired product formed the mixture was filtered and concentrated to give compound 36 (8 g, 3.60 mmol, 84.84% yield) as a yellow solid. $^1$H NMR: (ET12600-107-p1a DMSO Varian_D_400 MHz) δ 8.68 (br t, J=5.2 Hz, 1H), 8.46 (br t, J=5.2 Hz, 1H), 8.21-8.27 (m, 1H), 8.15 (br d, J=5.6 Hz, 2H), 7.84 (br d, J=9.2 Hz, 4H), 5.22 (d, J=3.2 Hz, 4H), 4.98 (dd, J=11.2, 3.2 Hz, 4H), 4.56 (d, J=8.4 Hz, 4H), 4.24 (br s, 1H), 3.99-4.14 (m, 23H), 3.84-3.94 (m, 7H), 3.74-3.83 (m, 5H), 3.55-3.62 (m, 5H), 3.51 (s, 25H), 3.38-3.46 (m, 9H), 3.20-3.30 (m, 9H), 3.17 (d, J=5.2 Hz, 14H), 2.11 (s, 12H), 2.00 (s, 13H), 1.89 (s, 12H), 1.78 (s, 12H).

6) Preparation of Compound 37.

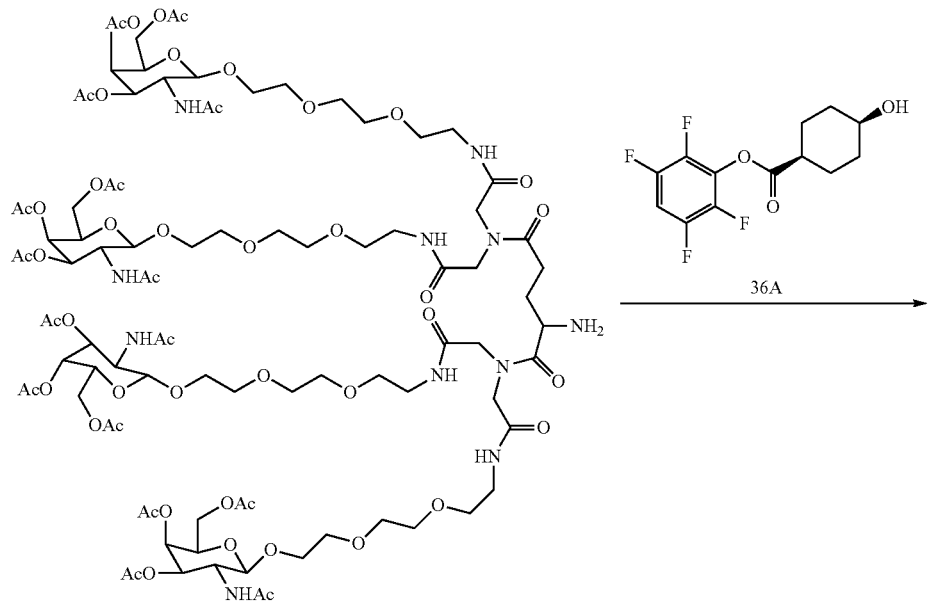

36

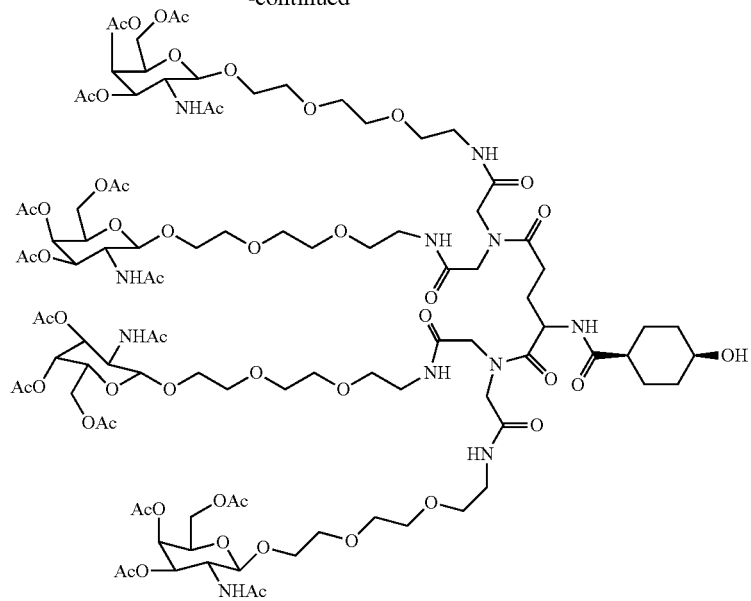

37

For batches was in parallel. To a solution of compound 36 (2 g, 857.18 umol, 1.00 eq, TFA), compound 36A (626.23 mg, 2.14 mmol, 2.50 eq) in DCM (6 mL) was added TEA (312.26 mg, 3.09 mmol, 427.75 uL, 3.60 eq), then the mixture was stirred at 25° C. for 16 hrs. LCMS showed desired product formed. All the reaction mixture was combined, dissolved in 200 mL DCM, poured onto 30 mL NaHCO$_3$, washed with 30 mL brine, dried with Na$_2$SO$_4$, filtered and concentrated to give a residue. Purified with prep-HPLC (column: Phenomenex Gemini C18 250*50 10u; mobile phase: [water (10 mM NH$_4$HCO$_3$)-ACN]; B %: 15%-45%, 20 min) to give compound 37 (7.5 g, 3.20 mmol, 93.27% yield) as a white solid. $^1$H NMR: (ET12600-111-p1a DMSO Varian_D_400 MHz) δ 8.66 (s, 1H), 8.51 (br s, 1H), 8.20 (s, 1H), 8.08 (s, 1H), 7.91 (br d, J=7.2 Hz, 1H), 7.80 (d, J=9.2 Hz, 4H), 5.22 (d, J=3.2 Hz, 4H), 4.98 (dd, J=11.2, 3.2 Hz, 4H), 4.55 (d, J=8.4 Hz, 4H), 4.47 (br s, 1H), 4.30 (s, 1H), 4.25 (d, J=3.2 Hz, 1H), 4.03 (s, 11H), 3.97 (br s, 2H), 3.84-3.92 (m, 7H), 3.73-3.82 (m, 6H), 3.55-3.62 (m, 5H), 3.47-3.54 (m, 24H), 3.41 (q, J=5.6 Hz, 9H), 3.23 (br dd, J=11.2, 5.6 Hz, 8H), 2.19 (br s, 1H), 2.10 (s, 12H), 2.00 (s, 13H), 1.89 (s, 12H), 1.77 (s, 13H), 1.61 (br s, 3H), 1.40 (br d, J=11.2 Hz, 4H).

8) Preparation of Compound 38.

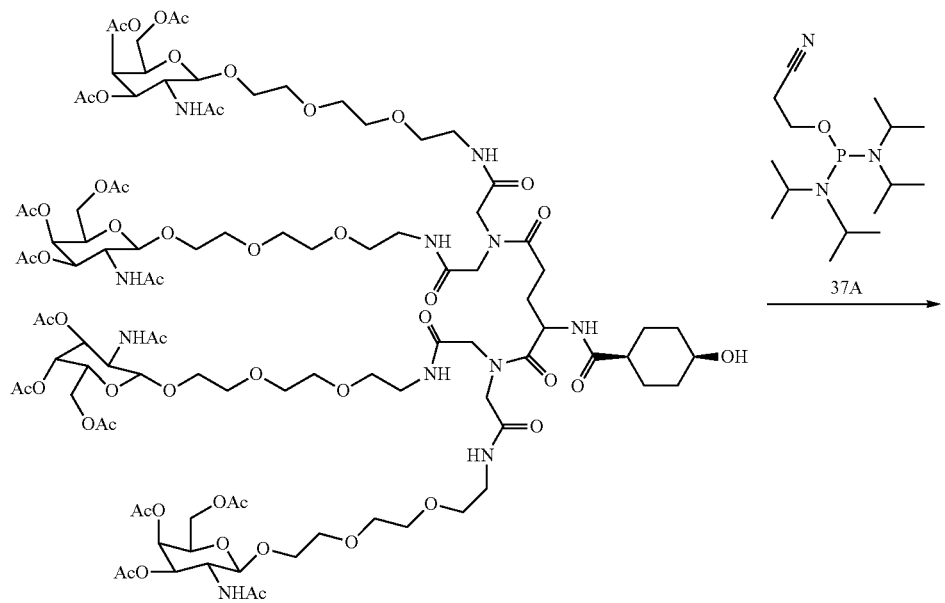

37

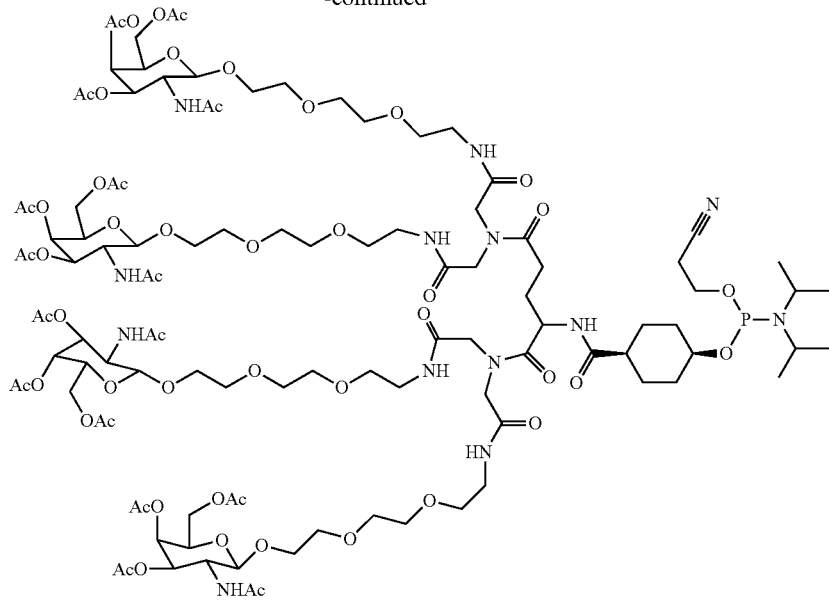

38

Compound 37 (4.4 g, 1.88 mmol, 1 eq) in DCM (26.4 mL) and compound 37A (1.13 g, 3.75 mmol, 1.19 mL, 2 eq) was added. The resulting solution was cooled to 5° C. To this solution was added 2H-tetrazole (0.45 M, 4.59 mL, 1.1 eq). The solution was allowed to warm to 20° C. and stirred for 2 hr. The mixture was dissolved in 100 mL DCM, quenched with 20 mL NaHCO$_3$, extracted with DCM (50 mL*2), washed with 20 mL NaHCO$_3$, 20 mL brine, dried with Na$_2$SO$_4$, filtered and concentrated to give a residue. The residue was dissolved with DCM (25 mL, 0.2% TEA), then Hexane (125 mL, 0.2% TEA) was added dropwise at 0° C. and stirred for 15 min, then chilled, the organic layer was poured off and the oil was dissolved with DCM (30 mL) agained and added Hexane (150 mL) dropwise, the procedure was rapeated for 3 times, dried under vacuum. 20 mL of DCM was added to the white solid, it was dried under vacuum at 30° C. to give 38 (4.8 g, 1.83 mmol, 67.34% yield, 97.15% purity) as a white solid. LCMS: [M-iPr$_2$N]$^+$/2, 1222.8. $^1$H NMR: (DMSO, Varian_400 MHz) δ 8.67 (br s, 1H), 8.52 (br s, 1H), 8.20 (br s, 1H), 8.08 (br s, 1H), 7.98 (br d, J=7.6 Hz, 1H), 7.79 (br d, J=9.2 Hz, 4H), 5.21 (d, J=3.2 Hz, 4H), 4.98 (dd, J=11.2, 3.2 Hz, 4H), 4.55 (d, J=8.4 Hz, 4H), 4.47 (br s, 1H), 4.29 (br d, J=17.6 Hz, 1H), 3.94-4.11 (m, 16H), 3.83-3.94 (m, 8H), 3.78 (br dd, J=10.4, 5.2 Hz, 6H), 3.64-3.74 (m, 3H), 3.54-3.63 (m, 8H), 3.50 (br s, 26H), 3.36-3.44 (m, 9H), 3.14-3.29 (m, 9H), 2.75 (t, J=5.6 Hz, 2H), 2.15-2.27 (m, 4H), 2.10 (s, 13H), 2.00 (s, 13H), 1.82-1.95 (m, 15H), 1.77 (s, 14H), 1.59-1.73 (m, 4H), 1.45 (br d, J=14.4 Hz, 4H), 1.14 (d, J=6.4 Hz, 12H).

Figure 4:
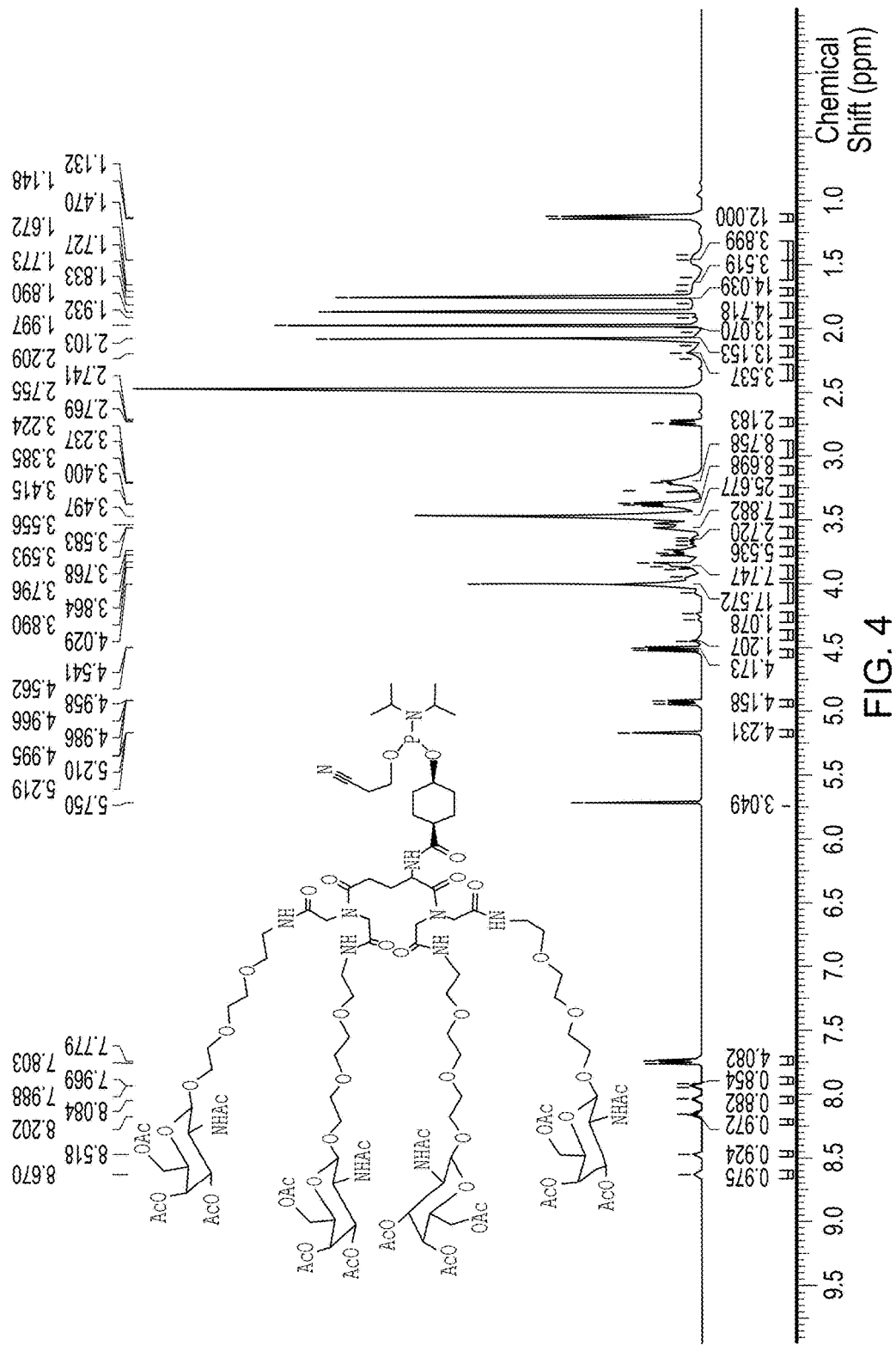
FIG. 4 is a $^1$H NMR spectra of Compound 38 (which is described below in Example 4).

FIG. 4 shows $^1$H NMR spectra for compound 38 (Structure 1014b herein).

Example 5: Synthesis of Targeting Ligand Phosphoramidite Compound Structure 1006b and 1007b The phosphoramidite-containing compound of Structure 1006b and Structure 1007b were synthesized according to the following same procedure, with the only difference being that 4-cis-hydroxycyclohexanecarboxylic acid (compound 8 herein) was used to synthesize Structure 1006b, and 4-trans-hydroxycyclohexanecarboxylic acid (compound 8a herein) was used to synthesize Structure 1007b.

1) Preparation of Compound 41.

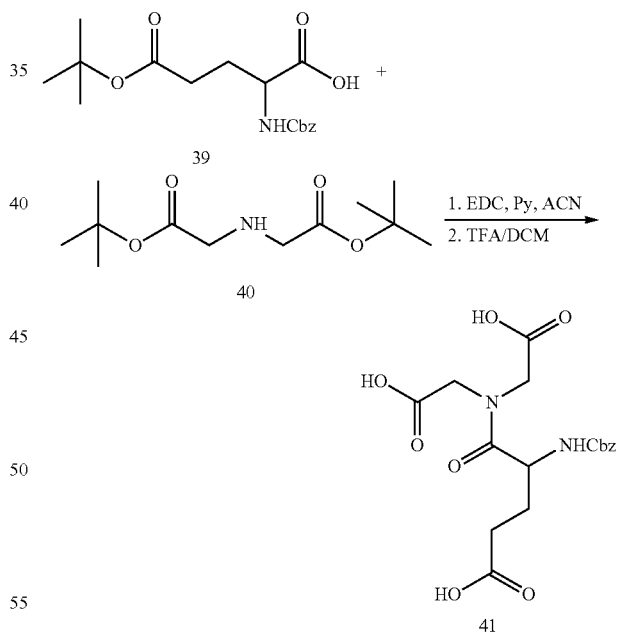

A solution of Z-Glu-(OtBu)-OH 39 (445 mg, 1.32 mmol), Di-tert-butyl iminodiacetate 40 (340 mg, 1.39 mmol), EDC (319 mg, 1.66 mmol, 1.23 eq) and Py (3 eq, 0.33 mL) in ACN (3 mL) was stirred at RT for 1 h, diluted with ethyl acetate and washed with NaHCO3 (2×). Organic layer was dried MgSO$_4$ and evaporated. Next the crude was dissolved in DCM (5 mL) and TFA (5 mL) was added. It was stirred at RT for 16 h and then evaporated. Ethyl acetate was added and evaporated 4× until foam/precipitate was formed. The crude 41 was used directly in TFP activation step. R$_t$=3.78 min, 90% pure. LCMS (ES, M/z): 379.0 [M+H]$^+$.

2) Preparation of Compound 42.

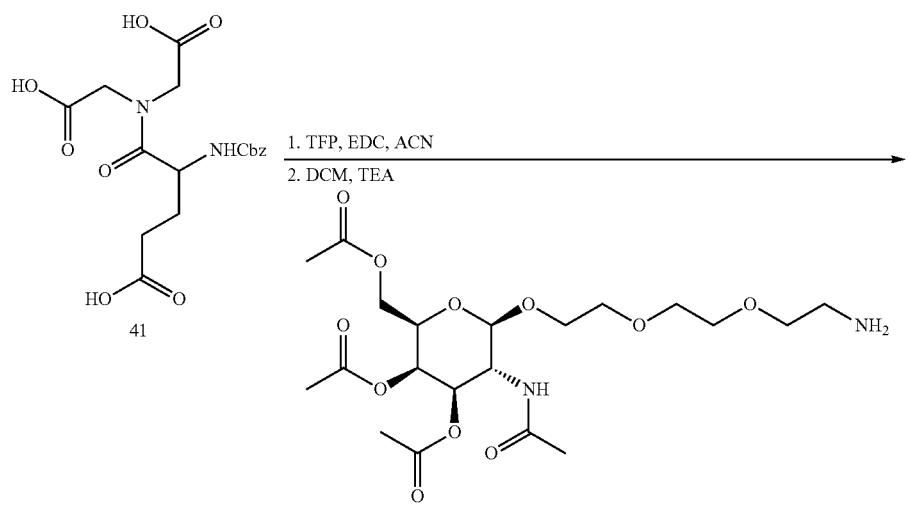

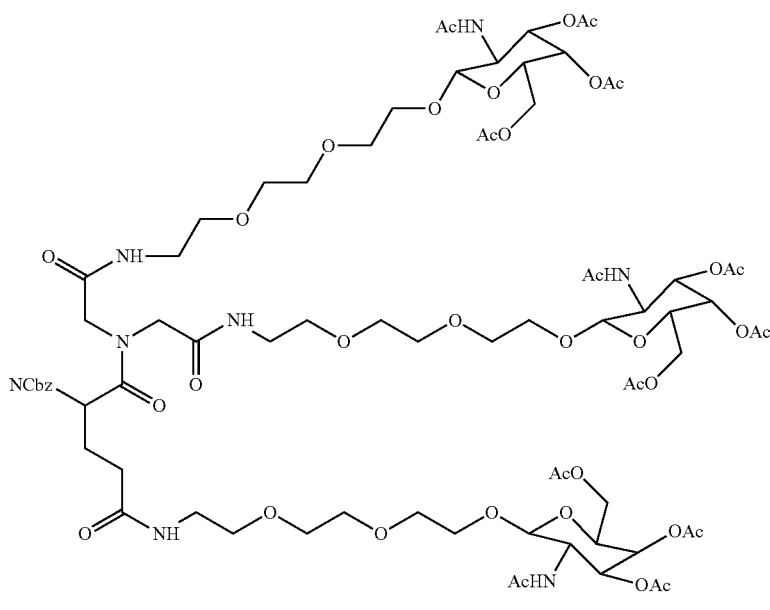

A solution of crude tri-acid 41 (~1.30 mmol), TFP (7 eq, 9.10 mmol, 1.51 g), TEA (4 eq, 0.723 mL) and EDC (3.3 eq, 4.29 mmol, 0.82 g) in ACN (3.5 mL) was stirred at RT for 1 h, diluted with DCM (250 mL) and washed with saturated NaHCO$_3$ (2×100 mL). Organic phase was dried over Na$_2$SO$_4$, concentrated and purified on silica column. Product activated tri-TFP ester was eluted with AcOEt in hex (5-20%) to give 550 mg of product, with a trace of TFP. R$_t$=7.06 min.

TEA (400 uL, 2.9 mmol) was added to a stirred solution containing tri-TFP ester (540 mg, 0.642 mmol) and GalNac-Peg$_3$-NH$_2$×TsOH (2.89 mmol, 1.88 g) in DCM (6 mL). It was stirred at RT for 16 h, diluted with DCM (200 mL) and washed with saturated NaHCO$_3$/saturated brine (1:1, 2×150 mL). Organic layer was dried over Na$_2$SO$_4$, evaporated leaving a white solid. The solid was dissolved in DCM and purified on silica column. Elution with MeOH in DCM (0-10%) gave 748 mg, 95.4% pure and ~100 mg, 80% pure tri-GalNAc 42, 36% yield, 2-steps. LCMS (ES, M/z): 1777.5 [M]$^+$, R$_t$=4.67 min.

3) Preparation of compound 43.

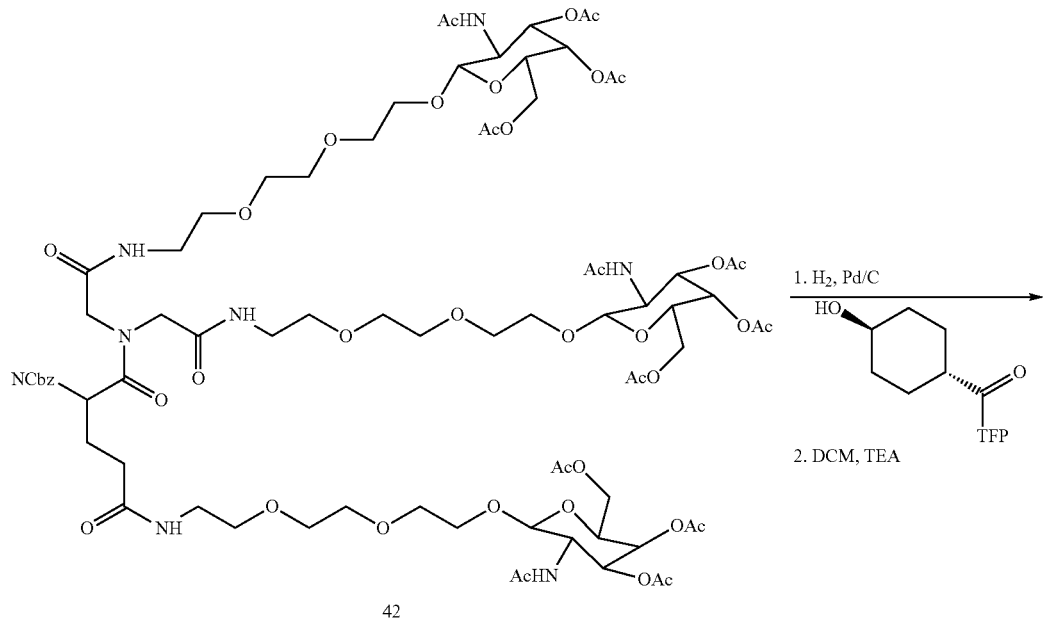

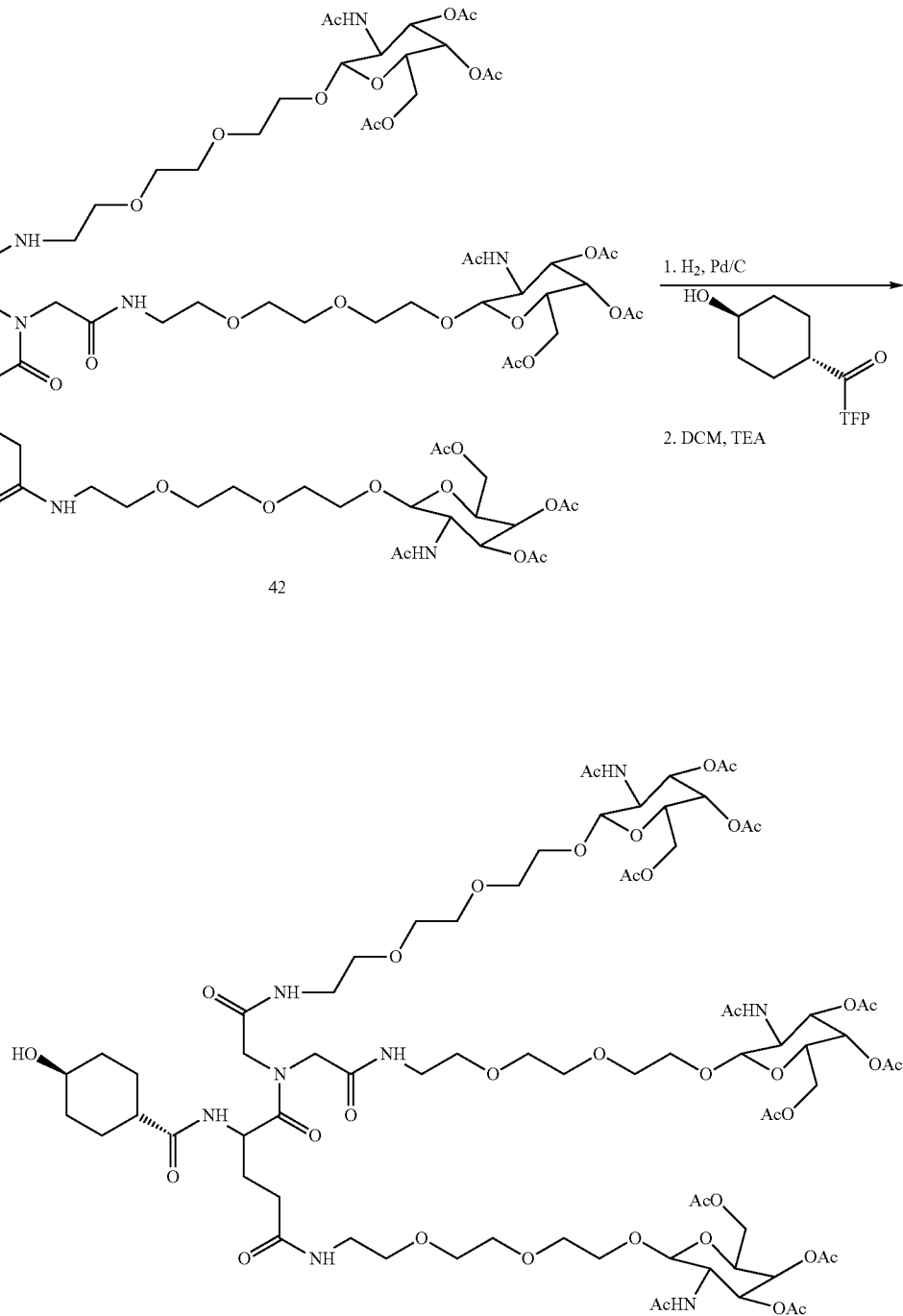

10% Pd/C, activated matrix (30 mg) was added to a solution of Cbz protected amine 42 (715 mg, 0.402 mmol) and TsOH (74.5 mg, 0.402 mmol) in THF (4 mL) and TFE (4 mL). Next, hydrogen atmosphere (balloon) was established by pulling vacuum and back filling with hydrogen. It was stirred under hydrogen atmosphere for 24 h, filtered through Celite, washed with DCM (2×10 mL) and evaporated leaving the alcohol C as a white solid. LCMS (ES, M/z): 1644.2 [M+H]$^+$, R$_t$=4.67 min.

The deprotected intermediate (0.4 mmol) and TFP ester of 4-cis-Hydroxycyclohexanecarboxylic acid (350 mg, 1.20 mmol) ware dissolved in DCM (2.5 mL) and TEA (3.5 eq, 0.195 mL) was added. It was stirred at RT for 16 h. Next it was diluted with DCM (100 mL), washed with saturated NaHCO$_3$/saturated brine (1:1, 100 mL×2). Organic phase was dried over Na$_2$SO$_4$, concentrated and purified on silica column. Product was eluted with MeOH in DCM (2-20%) to give 430 mg of >95% pure 43, 61% yield. R$_t$=4.20 min. LCMS: (ES, M/z): 1771.26 [M+H]$^+$.

4) Preparation of Compound 44.

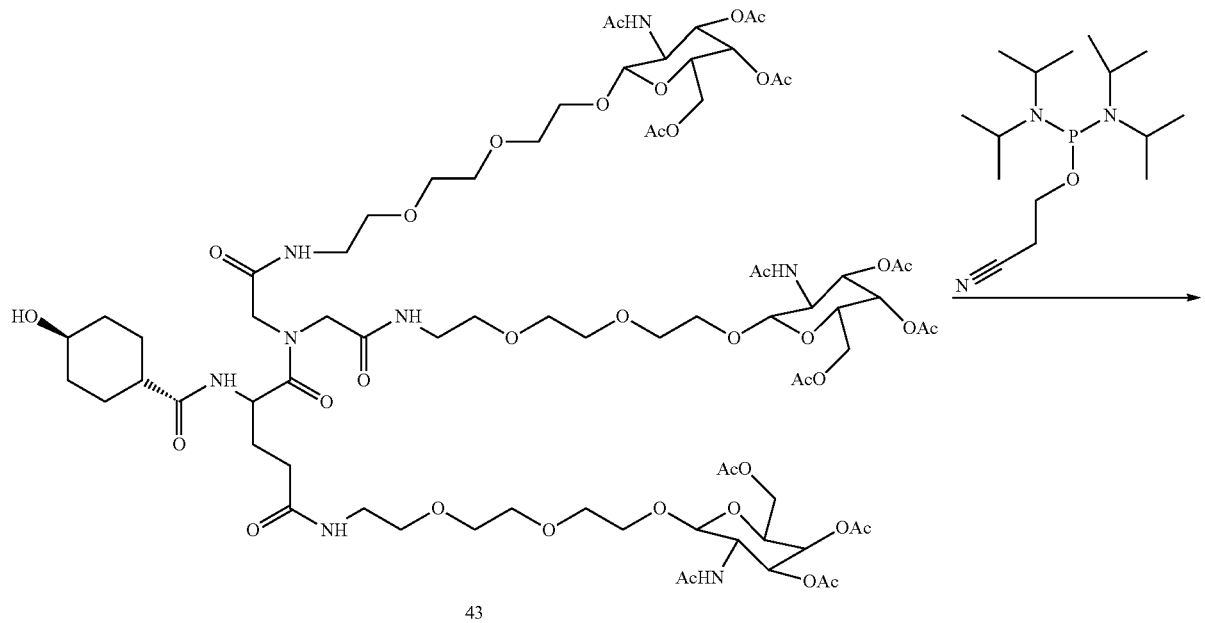

2-Cyanoethyl N,N,N',N'-tetraisopropylphosphorodiamidite (1.5 eq, 110 uL, 0.343 mmol) was added at 0° C. to a stirred solution of alcohol 43 (405 mg, 0.229 mmol, vacuum dried) and tetrazole (0.50 eq, 0.25 mL, 0.112 mmol, 0.45M in ACN) in anhydrous DCM (2.4 mL). It was stirred at RT for 1, and additional tetrazole (0.125 ml) and 2-Cyanoethyl N,N,N',N'-tetraisopropylphosphorodiamidite (0.10 mL) were added. Stirring continued for 30 min, next it was diluted with DCM (200 mL) and washed with saturated NaHCO$_3$/saturated brine (1:1, 200 mL). Organic layer was dried over Na$_2$SO$_4$/MgSO$_4$, evaporated, than dissolved in anhydrous DCM and evaporated again leaving a white solid 44, 408 mg, HPLC purity 92%, 83% yield. LCMS: (ES, M/z): 1870.4 [M-iPr$_2$N]$^+$.

Figure 5:
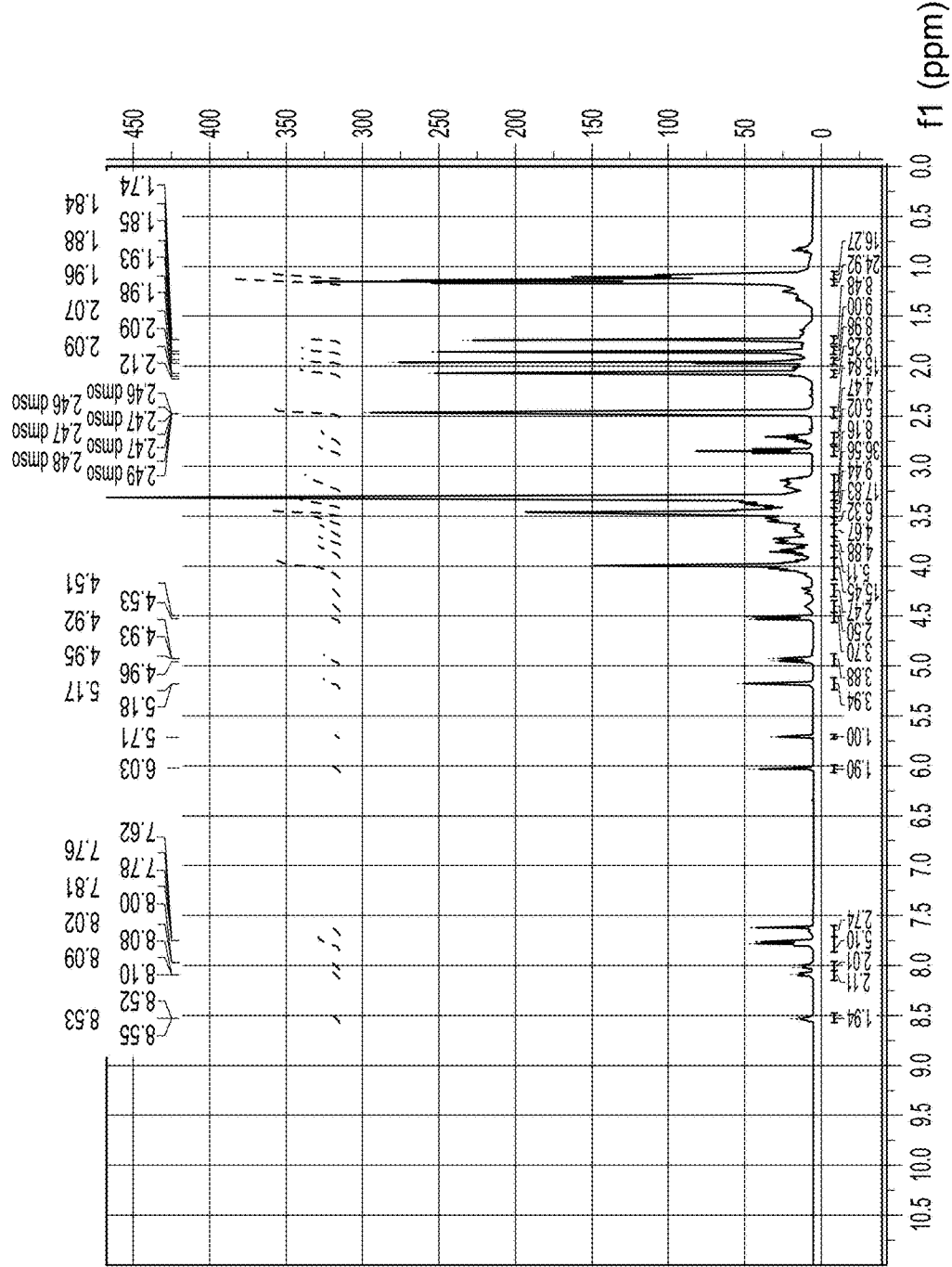
FIG. 5 is a $^1$H NMR spectra of Compound 44 (which is described below in Example 5).

FIG. 5 shows $^1$H NMR spectra for compound 44 (Structure 1007b herein).

Example 6: Synthesis of Targeting Ligand Phosphoramidite-Containing Compound Structure 1027b 1) Preparation of Compound 45.

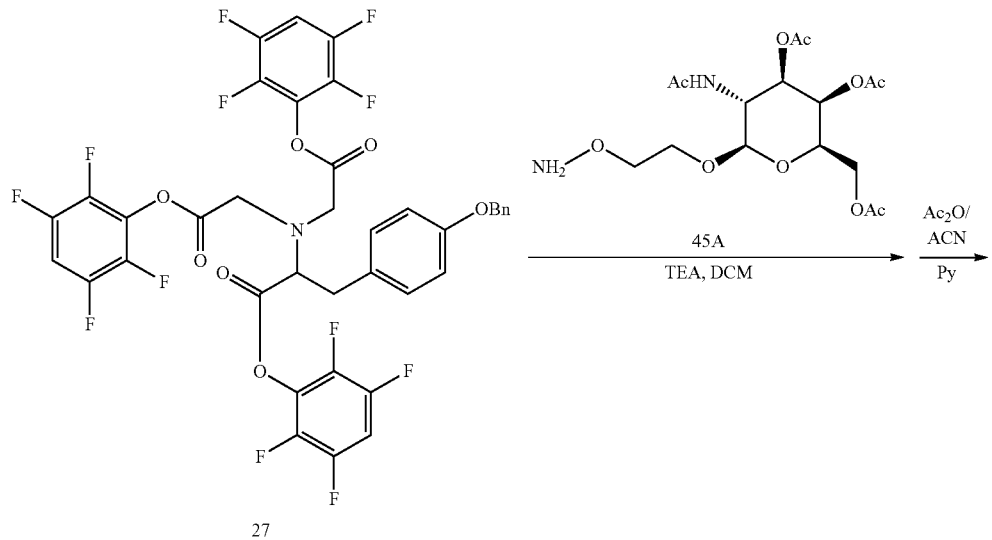

27

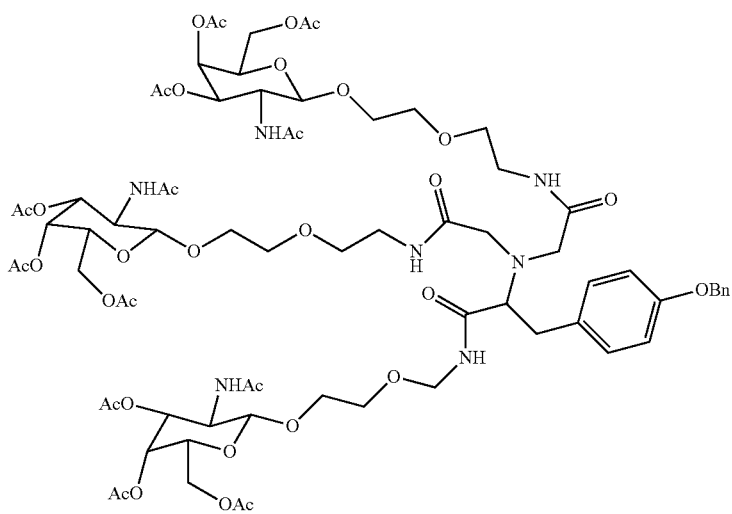

45

TEA (5.3 mmol, 0.735 mL, 4.00 eq) was added to a stirred solution containing compound 27 (1.1 g, 1.32 mmol, 1.00 eq) and compound 45A (3.20 g, 5.29 mmol, 4.00 eq) in DCM (9 mL). It was stirred at 30° C. for 16 hrs. Diluted with DCM (100 mL) and washed with saturated $NaHCO_3$/saturated brine. Organic layer was dried over $Na_2SO_4$, filtered and concentrated to give crude product as a brown solid.

The crude product was dissolved in $Ac_2O$ (3 mL), $CH_3CN$ (6 mL) and Py (6 mL) and the mixture was stirred at 25° C. for 16 hrs. $CH_3CN$ was evaporated off, then it was diluted with DCM and washed with sat. $NaHCO_3$ four times. Organic layer was separated and washed with 0.1M HCl/saturated brine, dried over $Na_2SO_4$, filtered and concentrated. The residue was purified by silica column (DCM/MeOH=10:1, Rf=0.45) to give product 45 (1.47 g, 68% yield, 96% purity) as a white solid.

4) Preparation of Compound 46.

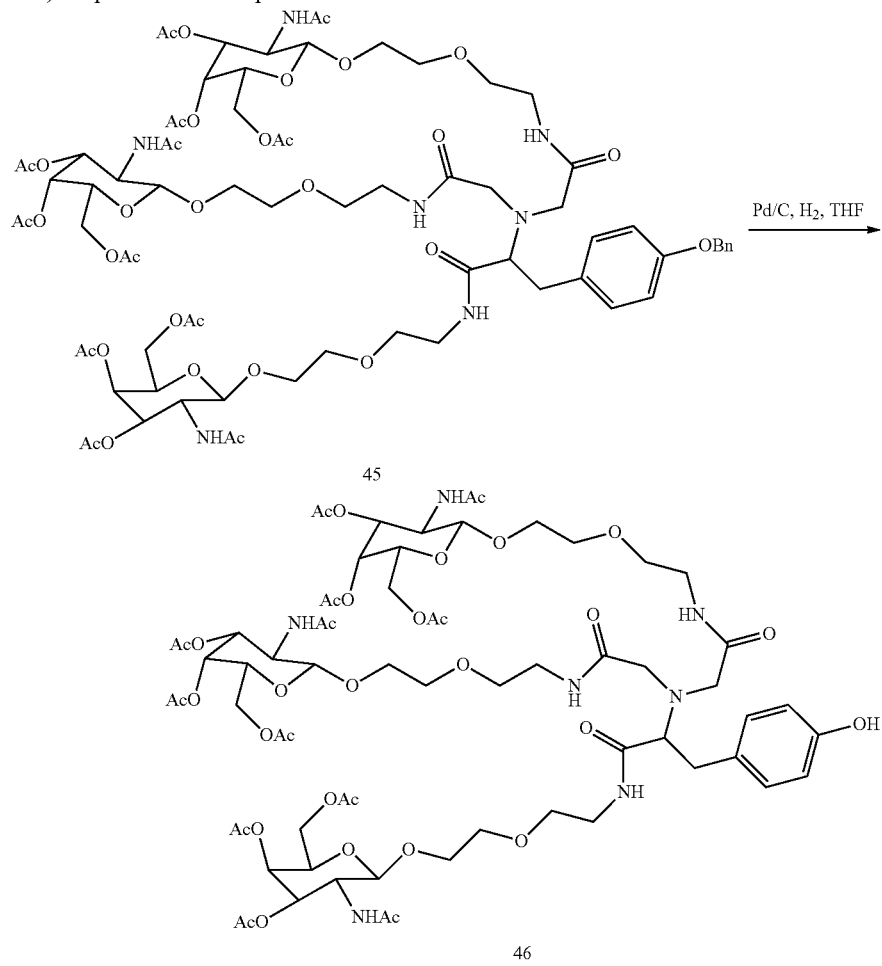

To a solution of compound 45 (1.425 g, 0.871 mmol, 1.00 eq) in THF/TFE (1:1, 5 mL) was added 10% Pd/C (24 mg), and the mixture was stirred at 40° C. for 30 h under $H_2$ atmosphere. TLC (DCM/MeOH=10:1, Rf=0.3) showed starting material consumed. It was filtered, washed with THF (5 mL×3), DCM (5 mL×3) and concentrated. The residue was purified on silica column. Eluted with DCM/MeOH to give compound 46 (1.013 g, 75% yield, 95% pure) as a white solid. LCMS: (ES, M/z): 1547.5 $[M+H]^+$.

5) Preparation of Compound 47.

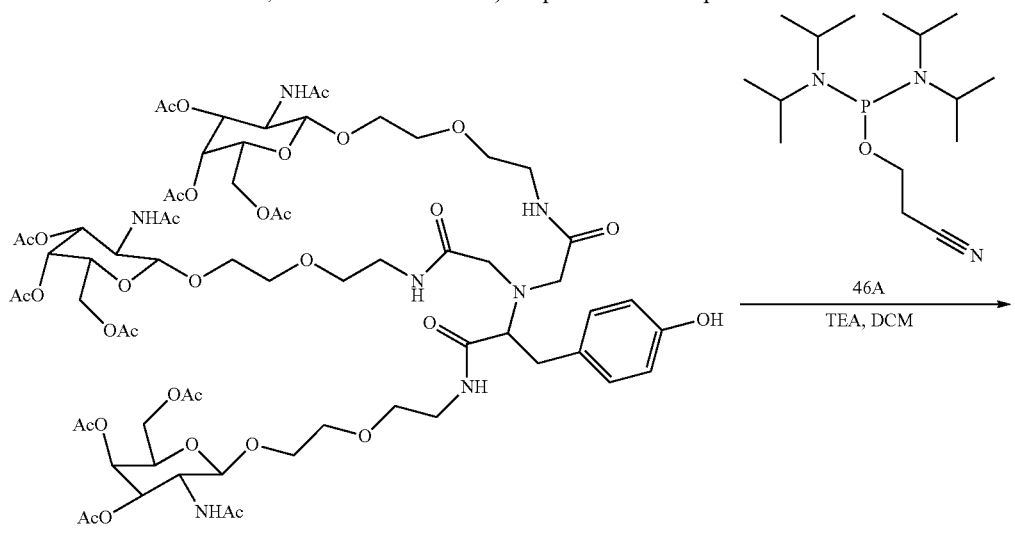

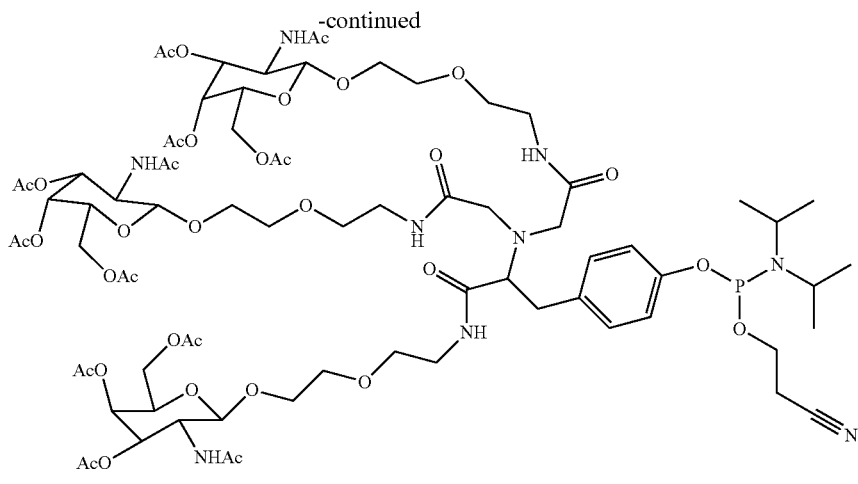

47

Compound 46 (970 mg, 0.627 mmol, 1.00 eq) was dissolved in DCM (4.2 mL) and compound 46A (0.941 mmol, 0.298 mL, 1.5 eq) was added. The resulting solution was cooled to 5° C. and dicyanoimidazole (DCI) (23.1 mg, 0.188 mmol, 0.3 eq). The solution was allowed to warm to 15° C. and stirred for 2 hrs. TLC (DCM/MeOH=5:1, Rf=0.52) showed starting material consumed and HPLC showed product formed. It was diluted with DCM (50 mL), washed with sat. NaHCO$_3$ (30 mL), H$_2$O (30 mL) and brine (30 mL), dried over Na$_2$SO$_4$, filtered and concentrated. The residue was dissolved with DCM (2 mL) and added to hexane (120 mL). The white precipitate was filtered off to afford compound 47 (0.975 g, 93% pure, 82% yield) as a white solid. LCMS: (ES, M/z): 1747.5 [M+H]+.

Figure 6:
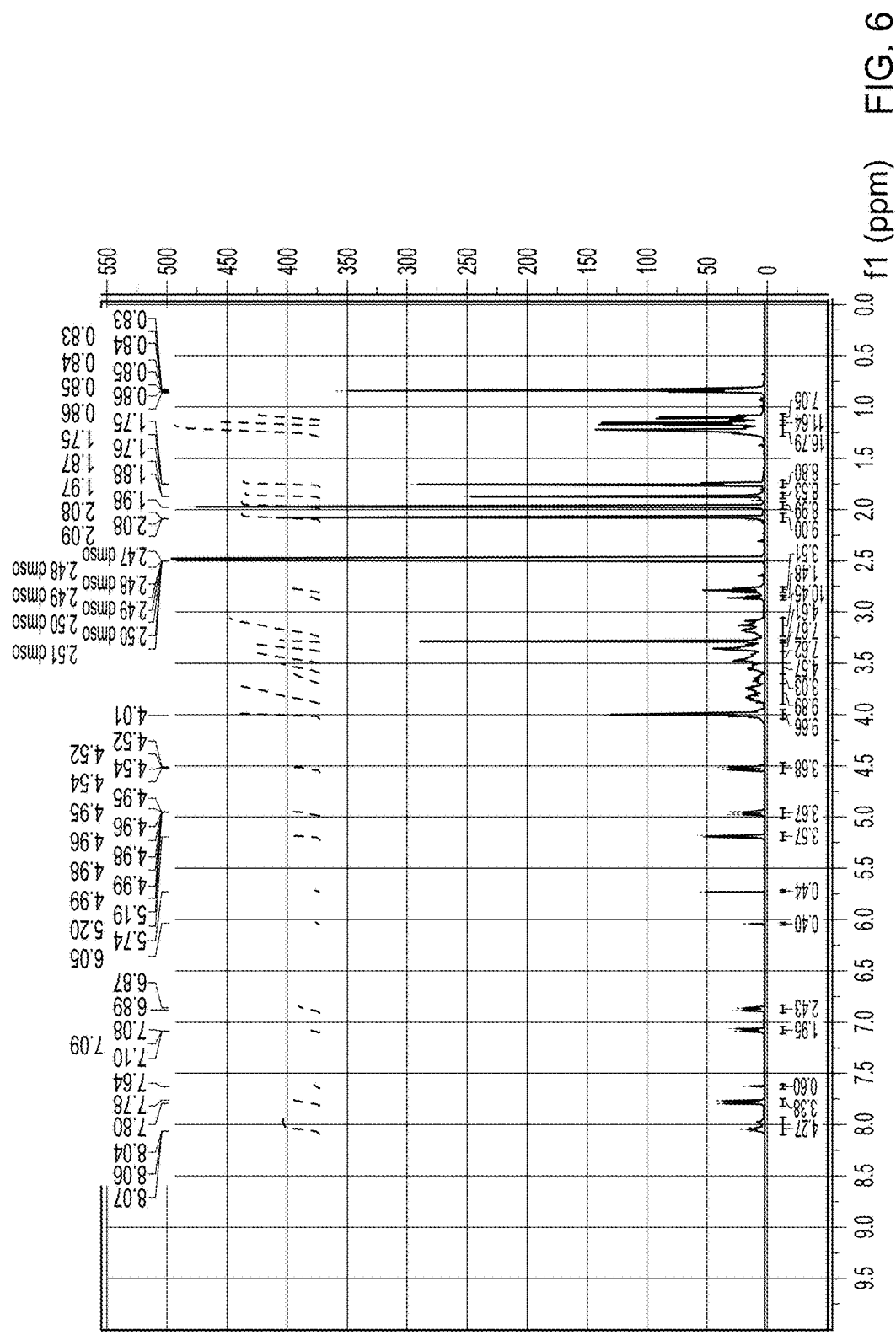
FIG. 6 is a $^1$H NMR spectra of Compound 47 (which is described below in Example 6).

FIG. 6 shows $^1$H NMR spectra for Compound 47 (Structure 1027b herein).

Example 7. Synthesis of Targeting Ligand Phosphoramidite-Containing Compound Structure 1026b 1) Preparation of Tri-Acid 49.

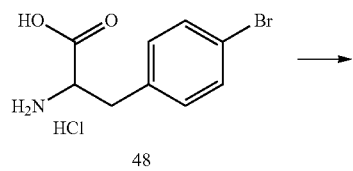

48

-continued

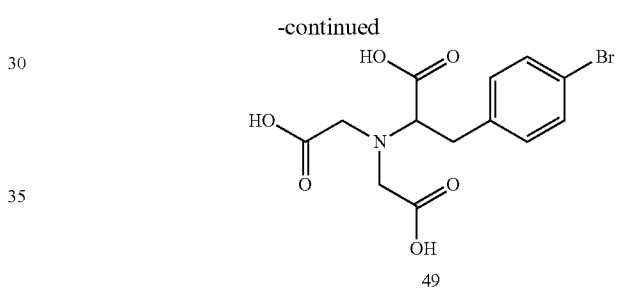

49

To a solution of 4-bromo-DL-phenylalanine hydrochloride (5.0 g, 17.8 mmol) in 1.5M NaOH (100 mL) was added bromoacetic acid (8.17 g, 58.8 mmol). The solution was heated to 60° C. for 1 hour, keeping the pH above 12 by addition of sodium hydroxide pellets. Upon completion, the reaction was cooled to 15° C. and the pH was adjusted to 1.75-2.00 and the oily suspension was aged for 2 hours until a filterable solid was observed. The solids were filtered and washed with water several times resulting in isolation of a white solid (6.0 g, 93% yield).

2) Preparation of Biaryl Tri-Acid 50.

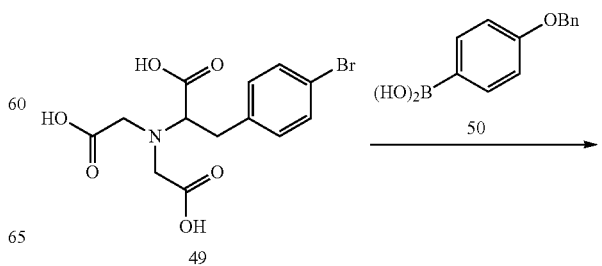

49

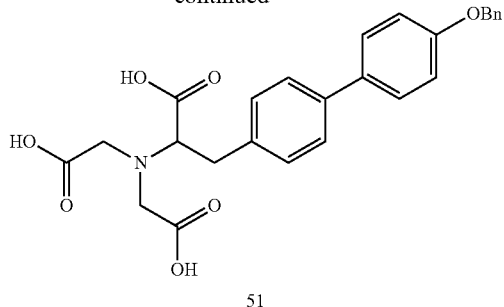

51

The aryl bromide 49 (4.2 g, 11.6 mmol) and boronic acid 50 (2.8 g, 12.2 mmol) were dissolved in a 1:1 mixture of DMF/water (168 mL) and degassed for 10 minutes. The solution was treated with potassium carbonate (8.0 g, 116.2 mmol) and PdCl$_2$(dppf) (0.476 g, 0.6 mmol) and the reaction vessel was placed under nitrogen atmosphere and heated to 40° C. for 5 hours. Upon completion, the pH was adjusted to 12 and the aqueous phase was washed 2× (20 mL) ethyl acetate. The pH was then adjusted to 1.75-2.00 and cooled to 15° C. The resulting solids were filtered and washed with water several times to remove any inorganics to provide 51 (4.8 g, 89% yield).

1) Preparation of Tri-TFP Ester 52.

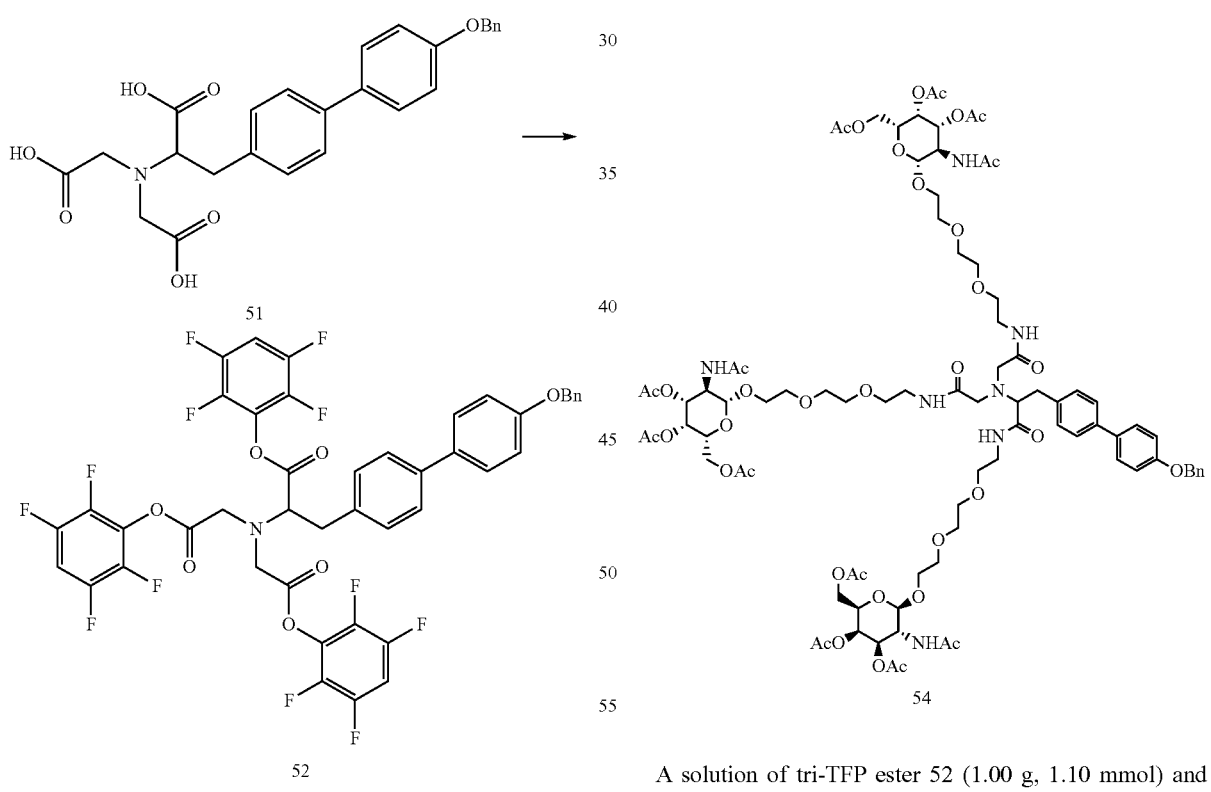

A slurry of triacid 51 (5.0 g, 10.7 mmol) and tetrafluorophenol (6.5 g, 38.8 mmol) in dichloromethane (50 mL) were cooled to 0° C. and treated with EDC hydrochloride (7.45 g, 38.8 mmol). The slurry was warmed to ambient and stirred for 18 hours. Upon reaction completion the reaction was washed with water and the organic layer was concentrated to an oil and purified on a silica column resulting in TFP ester 52 (1.63 g, 16% yield).

2) Preparation of Tri-NAG Protected Alcohol 54.

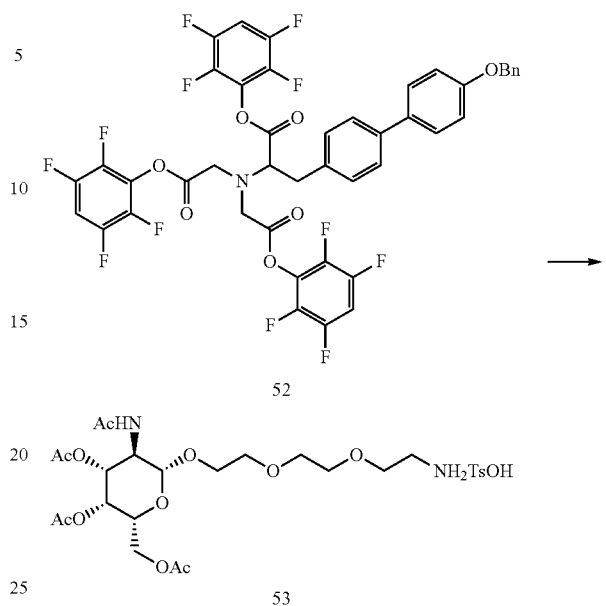

A solution of tri-TFP ester 52 (1.00 g, 1.10 mmol) and NAG-amine tosylate 53 (2.15 g, 3.33 mmol) in dichloromethane (5 mL) were cooled to 0° C. and treated with triethylamine (0.66 g, 6.6 mmol). The solution was allowed to warm to ambient over 2 hours. Upon completion, the reaction mixture was washed with water and concentrated to an oil. The crude oil was dissolved in acetic anhydride (30 mL) and the solution was treated with 1 mL triethylamine. After 3 hours, the organics were removed under high vacuum resulting in an oil 54 (1.7 g, 85% yield).

3) Preparation of Phenol 55.
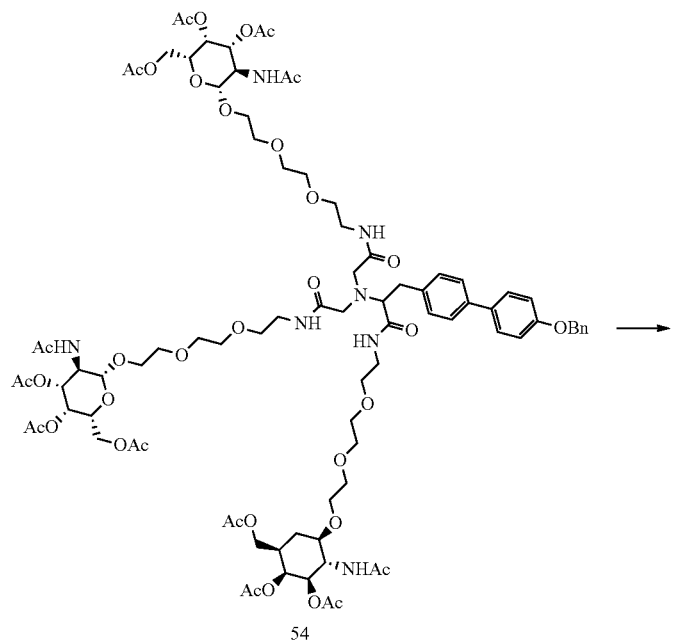
54
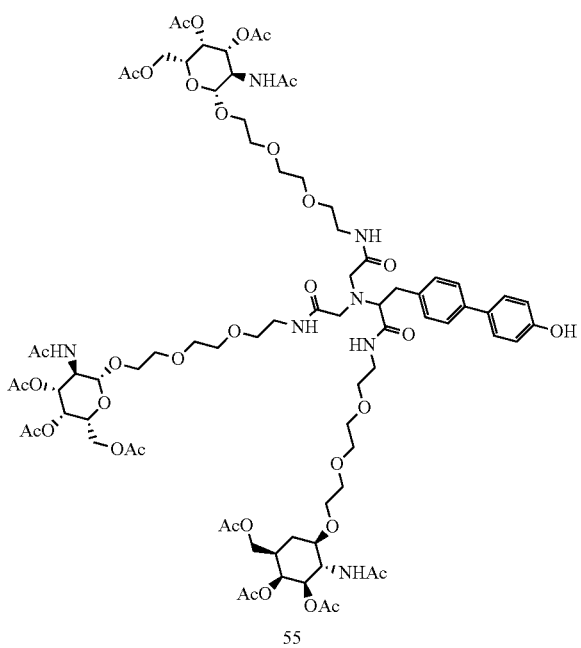
55
The benzyl-protected alcohol 54 (2.0 g, 1.08 mmol) was dissolved in ethanol (23 mL) and placed under nitrogen atmosphere. To the solution was added 10% Pd/C (0.7 g, 30 mol %). The slurry was stirred for 8 hours at ambient and the catalyst was removed via celite pad. The organics were removed under high vacuum resulting in a white solid 55 (1.4 g, 74% yield).

4) Preparation of Compound 56.

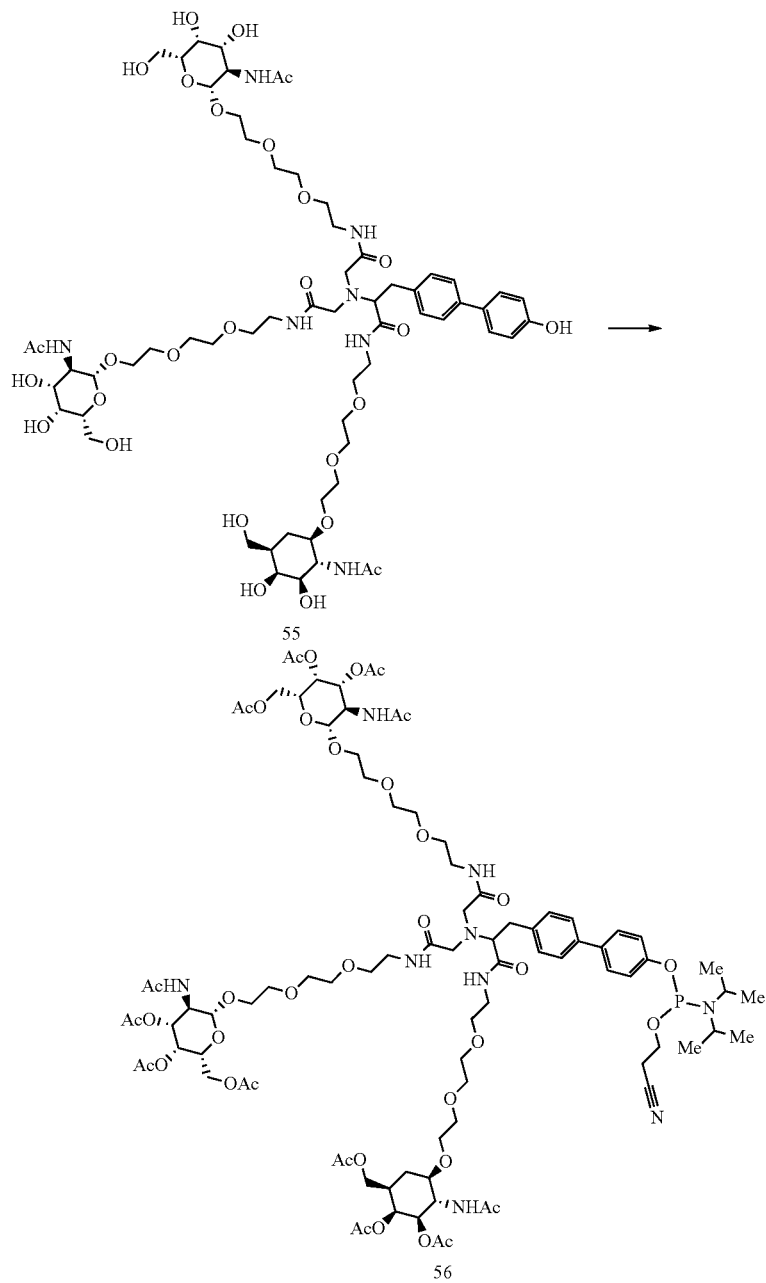

A solution of phenol 55 (1.3 g, 0.74 mmol) and phosphoramidite reagent (0.364 mg, 1.11 mmol) in dichloromethane (10 mL) were cooled to 0° C. and treated with 4,5-dicyanoimidazole and then allowed to warm to ambient over 2 hours. Upon completion, the reaction mixture was washed with saturated sodium bicarbonate (10 mL), followed by water (10 mL) and the organic layer was dried over sodium sulfate. The organics were concentrated under reduced pressure resulting in a white solid (1.4 g, 93% yield).

Compound 56 of Example 7 is Structure 1026b herein.

Figure 7:
FIG. 7 is a photograph of a PEG linker-GalNAc phosphoramidite-containing compound in a bottle (which is described below in Example 7).

Example 8. Physical Properties of Targeting Ligand Phosphoramidite-Containing Compounds Certain GalNAc ligand phosphoramidite compounds that do not have the rigid linker structure disclosed herein have shown a propensity to gel in many common solvents. Attached at FIG. 7 is a photograph illustrating the behavior of a GalNAc structure having the same targeting moiety (N-acetyl-galactosamine), tether, and branch point group as Structure 1008b, but includes a PEG linker instead of the rigid linker of Structure 1008b disclosed herein. The PEG linker-GalNAc phosphoramidite compound was held for 12 hours in a 3:1 mixture of ACN:DMF at 0.1 M dilution over molecular sieves. The PEG linker-GalNAc shows significant gelling in this highly polar solvent system. For this PEG linker-GalNAc phosphoramidite compound, it is necessary to use up to 1:1 mixture of ACN:DMF to maintain solubility.

Figure 8:
FIG. 8 is a photograph of Structure 1008b phosphoramidite-containing compound in a bottle (which is described below in Example 7).

Attached at FIG. 8 is a photograph depicting phosphoramidite compound Structure 1008b being fully dissolved in 0.05 M in acetonitrile, without the need for a highly polar solvent such as DMF. Unlike PEG linker-GalNAc constructs, the phosphoramidite compounds that include the rigid linker of Structure 1008b are not at risk or require a highly polar solvent to maintain solubility. Despite being dissolved in the bottle at a lower concentration, this illustrates that the structures comprising the rigid linkers disclosed herein are more soluble in common solvents typically used for oligonucleotide synthesis, and do not require the addition of a highly polar solvent to prevent gelling.

Example 9. Purity of Targeting Ligand Phosphoramidite-Containing Compounds

As noted above in Example 2, FIG. 2A shows a $^{31}$P NMR spectra of the phosphoramidite compound of Structure 1008b. FIG. 2A shows a single peak exhibiting the correct shift for phosphoramidite. No other peaks, including hydrolysis peaks, are shown, which indicate a highly pure compound.

Figure 9:
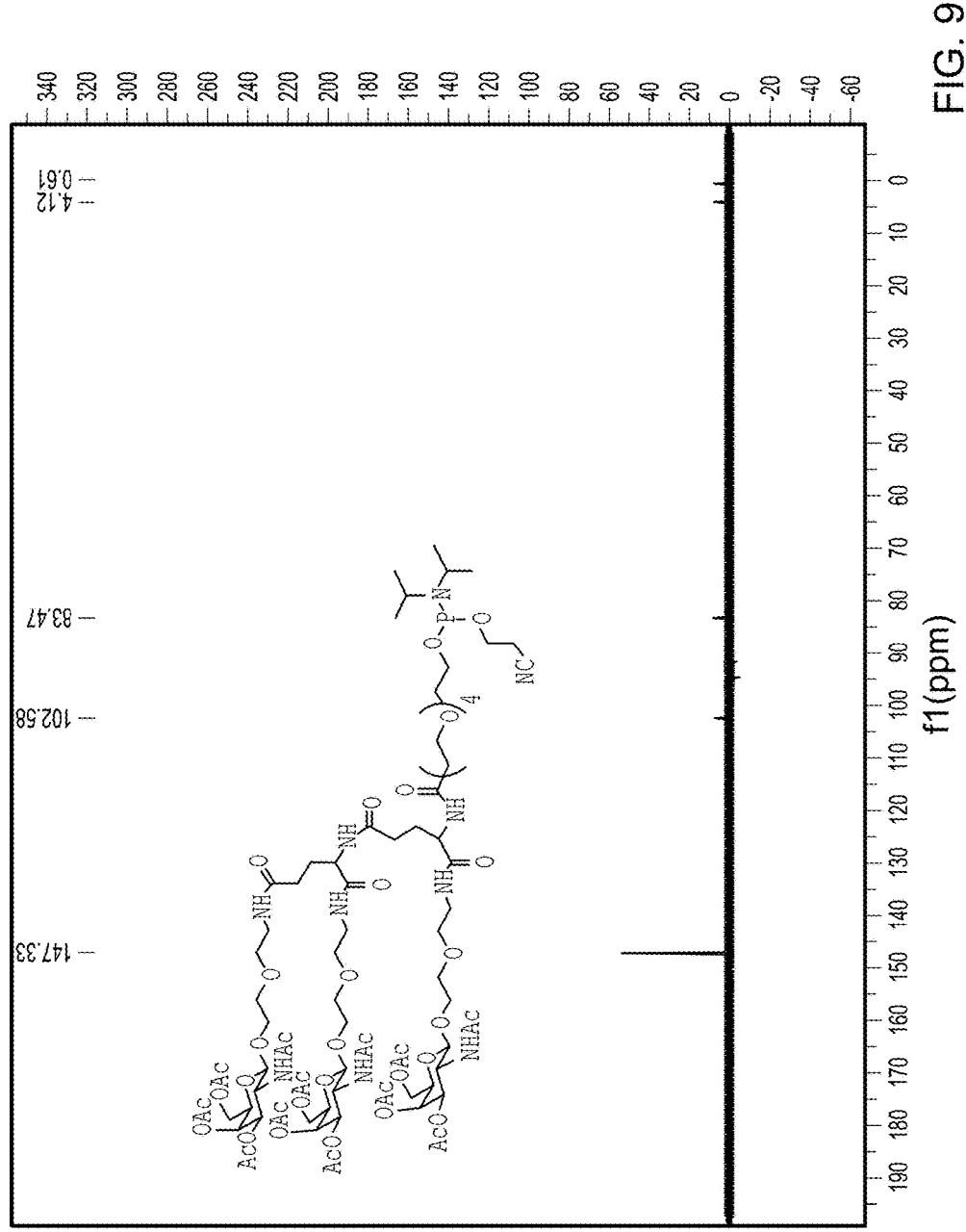
FIG. 9 is a $^{31}$P NMR spectra of a PEG linker-GalNAc Structure (which is described below in Example 8).

FIG. 9 shows a $^{31}$P NMR spectra of a PEG linker-GalNAc Structure, that otherwise includes the same branch point, tether, and targeting moiety as Structure 1008b. The chemical structure of the phosphoramidite for which the spectra of FIG. 9 was obtained is depicted on FIG. 9.

FIG. 9 shows multiple impurity peaks, which include what appear to be hydrolyzed byproduct.

Example 10. Oligonucleotide Composition Synthesis

A. Synthesis.

RNAi agents was synthesized according to phosphoramidite technology on solid phase used in oligonucleotide synthesis. Depending on the scale, either a MerMade96E® (Bioautomation) or a MerMade12® (Bioautomation) was used. Syntheses were performed on a solid support made of controlled pore glass (CPG, 500 Å or 600 Å, obtained from Prime Synthesis, Aston, Pa., USA). All RNA and 2'-modified RNA phosphoramidites were purchased from Thermo Fisher Scientific (Milwaukee, Wis., USA). Specifically, the following 2'-O-methyl phosphoramidites were used: (5'-O-dimethoxytrityl-N$^6$-(benzoyl)-2'-O-methyl-adenosine-3'-O-(2-cyanoethyl-N,N-diisopropy-lamino) phosphoramidite, 5'-O-dimethoxy-trityl-N$^4$-(acetyl)-2'-O-methyl-cytidine-3'-O-(2-cyanoethyl-N,N-diisopropyl-amino) phosphoramidite, (5'-O-dimethoxytrityl-N$^2$-(isobutyryl)-2'-O-methyl-guanosine-3'-O-(2-cyano-ethyl-N,N-diisopropylamino)phosphoramidite, and 5'-O-dimethoxy-trityl-2'-O-methyl-uridine-3'-O-(2-cyanoethyl-N,N-diisopropylamino)phosphoramidite. The 2'-deoxy-2'-fluoro-phosphoramidites carried the same protecting groups as the 2'-O-methyl RNA amidites. Targeting ligand containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for two hours at 30° C. The solution was evaporated and the solid residue was reconstituted in water (see below).

C. Purification.

Crude oligomers were purified by anionic exchange HPLC using a TKSgel SuperQ-5PW 13u column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 medium with a running buffer of 100 mM ammonium bicarbonate, pH 6.7 and 20% Acetonitrile.

D. Annealing.

Complementary strands were mixed by combining equimolar RNA solutions (sense and antisense) in 0.2×PBS (Phosphate-Buffered Saline, 1×, Corning, Cellgro) to form the RNAi agents. This solution was placed into a thermomixer at 70° C., heated to 95° C., held at 95° C. for 5 min, and cooled to room temperature slowly. Some RNAi agents were lyophilized and stored at −15 to −25° C. Duplex concentration was determined by measuring the solution absorbance on a UV-Vis spectrometer in 0.2×PBS. The solution absorbance at 260 nm was then multiplied by a conversion factor and the dilution factor to determine the duplex concentration. Unless otherwise stated, all conversion factor was 0.037 mg/(mL·cm). For some experiments, a conversion factor was calculated from an experimentally determined extinction coefficient.

Example 11. Comparison of 3' and 5' Sense Strand Attachment Sites for GalNAc Targeting Ligands Using F12 Expression-Inhibiting Oligomeric Compounds in Wild Type Mice To assess differences in the site of attachment of GalNAc ligands between the 3' and 5' terminal end of the sense strand, expression-inhibiting oligomeric compounds (double-stranded RNAi agents) directed to F12 (referred to as F12 RNAi agents herein) were prepared having the sequences set forth in the following Table 1:

TABLE 1

F12 expression-inhibiting oligomeric compounds (RNAi agent duplexes) of Example 11.

| | 5' → 3' | SEQ ID NO: |
|---|---|---|
| Duplex ID: AD02803 | | |
| Sense Strand Sequence: (AM03628-SS) | uAuAugscsccaagaAfaGfugaaagacca(NAG15) | 1 |
| Antisense Strand Sequence: (AM03157-AS) | usGfsgucuuUfcAfcuuUfcuugggcsuscuAu | 2 |
| Duplex ID: AD02807 | | |
| Sense Strand Sequence: (AM03632-SS) | (NAG18)uauaugscsccaagaAfaGfugaaagacc(invdA) | 3 |
| Antisense Strand Sequence: (AM03157-AS) | usGfsgucuuUfcAfcuuUfcuugggcsuscuAu | 4 |

In Table 1, above, the following notations are used:
(NAG15) =

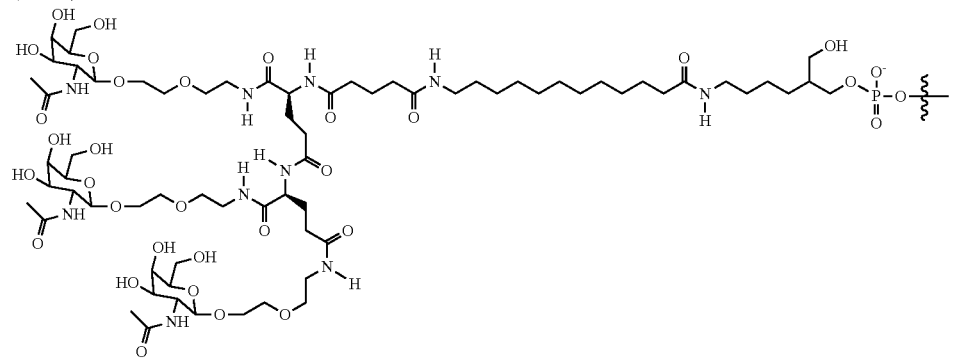

(NAG18) =

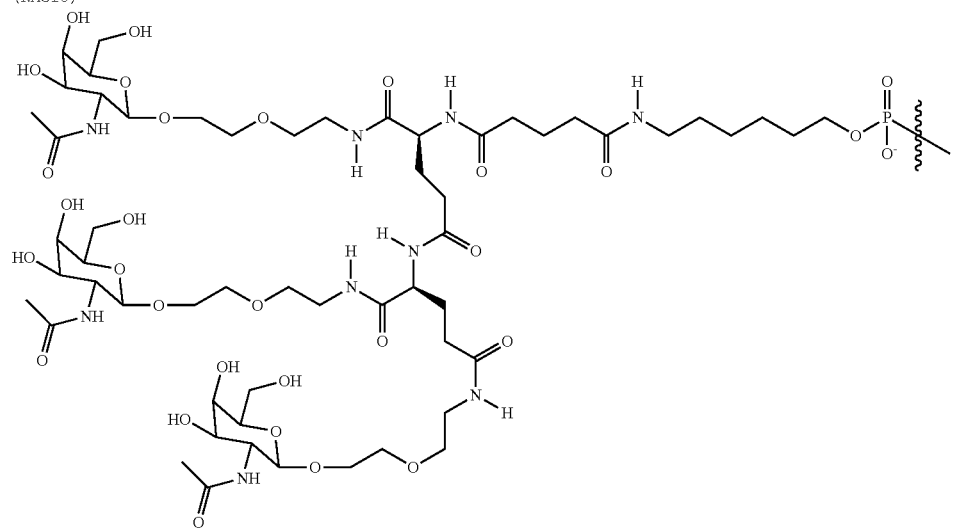

Each strand of the F12 RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

The F12 RNAi agents linked to the respective GalNAc ligands (i.e., (NAG15) or (NAG18)) were combined in a pharmaceutically acceptable buffer as known in the art for subcutaneous (SC) injection.

The F12 RNAi agents linked to the respective GalNAc ligands (i.e., (NAG15) or (NAG18)) were delivered via SC injection. On day 1, a SC injection was administered into the loose skin on the back between the shoulders of 200 µl solution/20 g mouse containing either saline or a 3 mg/kg (mpk) dose of one of two F12 RNAi agents (AD02803 or AD02807) in buffered saline. There were three (3) wild type mice per treatment group. As shown above, AD02803 includes (NAG15) attached to the 3' terminal end of the sense strand, while AD 2807 includes (NAG18) attached to the 5' terminal end of the sense strand.

Serum samples from treated mice were taken on days 8, 15, 22 and 29 to monitor knockdown. Knockdown was measured by quantifying circulating mouse F12 protein (mF12) levels in serum by an internally developed mF12 alphaLISA® (Perkin Elmer). Expression at a specific bleed date was normalized to the mean of the saline control group for that same date.

Figure 10:
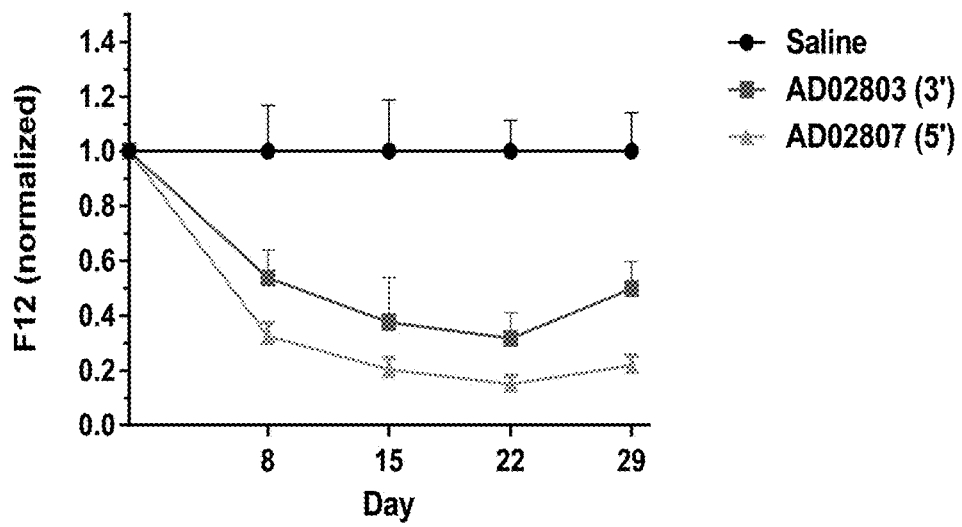
FIG. 10 is a graph illustrating normalized mouse Factor 12 (mF12) protein levels in wild type mice (which is described below in Example 11).

FIG. 10 shows the results from this study. At nadir (day 22), AD02803 showed approximately 70% reduction in circulating F12 levels, while AD02807 showed a greater than 80% reduction. The data also show a difference in length of knockdown effect, as at day 29 AD02803-treated mice showed a faster return to baseline as compared to AD02807-treated mice. These data support that the linkage of a GalNAc ligand on the 5' end of the sense strand outperforms linkage at the 3' sense strand.

Example 12. Further Comparison of 3' and 5' Sense Strand Attachment Sites for GalNAc Targeting Ligands Using F12 Expression-Inhibiting Oligomeric Compounds in Wild Type Mice To further assess the site of attachment of GalNAc ligands on the 3' and 5' terminal ends of the sense strand of double-stranded expression-inhibiting oligomeric compounds (double-stranded RNAi agents), compositions directed to the F12 gene were prepared having the sequences set forth in the following Table 2:

automation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

The F12 RNAi agents linked to the respective GalNAc ligand (i.e., (NAG20)) were combined in a pharmaceutically acceptable buffer as known in the art for subcutaneous (SC) injection.

The F12 RNAi agents linked to the respective GalNAc ligand (i.e., (NAG20)) were delivered via SC injection. On day 1, a SC injection was administered into the loose skin on the back between the shoulders of 200 µl solution/20 g mouse containing either saline or a 3 mg/kg (mpk) dose of one of the two RNAi agents (AD02815 or AD02816) in buffered saline. There were three (3) wild type mice per treatment group. As shown above in Table 2, AD02815 includes (NAG20) attached to the 5' end of the sense strand, while AD02816 includes (NAG20) attached to the 3' terminal end of the sense strand.

Serum samples from treated mice were taken on days 8, 15, 22 and 29 to monitor knockdown. Knockdown was measured by quantifying circulating mouse F12 protein (mF12) levels in serum by an internally developed mF12 alphaLISA® (Perkin Elmer). Expression at a specific bleed date was normalized to the mean of the saline control group for that same date.

TABLE 2

| F12 expression-inhibiting oligomeric compounds (RNAi agent duplexes) of Example 12. | |
|---|---|
| 5' → 3' | SEQ ID NO: |
| Duplex ID: AD02815 | |
| Sense Strand Sequence: (NAG20)uauaugscsccaagaAfaGfugaaagacc(invdA) (AM03640-SS) | 5 |
| Antisense Strand Sequence: usGfsgucuuUfcAfcuuUfcuugggcsuscuAu (AM03157-AS) | 6 |
| Duplex ID: AD02816 | |
| Sense Strand Sequence: uAuAugscsccaagaAfaGfugaaagacca(NAG20) (AM03641-SS) | 7 |
| Antisense Strand Sequence: usGfsgucuuUfcAfcuuUfcuugggcsuscuAu (AM03157-AS) | 8 |

In Table 2 above the following notations are used:
(NAG20) =

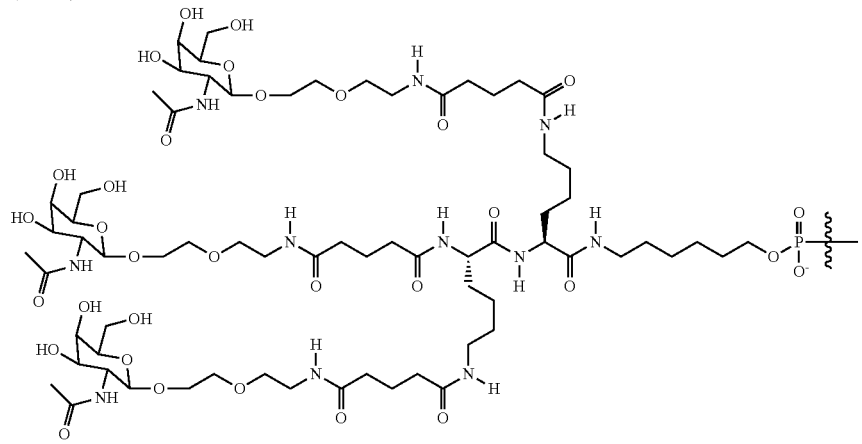 [SMILES: *P(=O)([O-])OCCCCCCNC(=O)[C@H](CCCCNC(=O)CCCC(=O)NCCOCCOC1OC(CO)C(O)C(O)C1NC(C)=O)NC(=O)[C@H](CCCCNC(=O)CCCC(=O)NCCOCCOC1OC(CO)C(O)C(O)C1NC(C)=O)NC(=O)CCCC(=O)NCCOCCOC1OC(CO)C(O)C(O)C1NC(C)=O]

Figure 11:
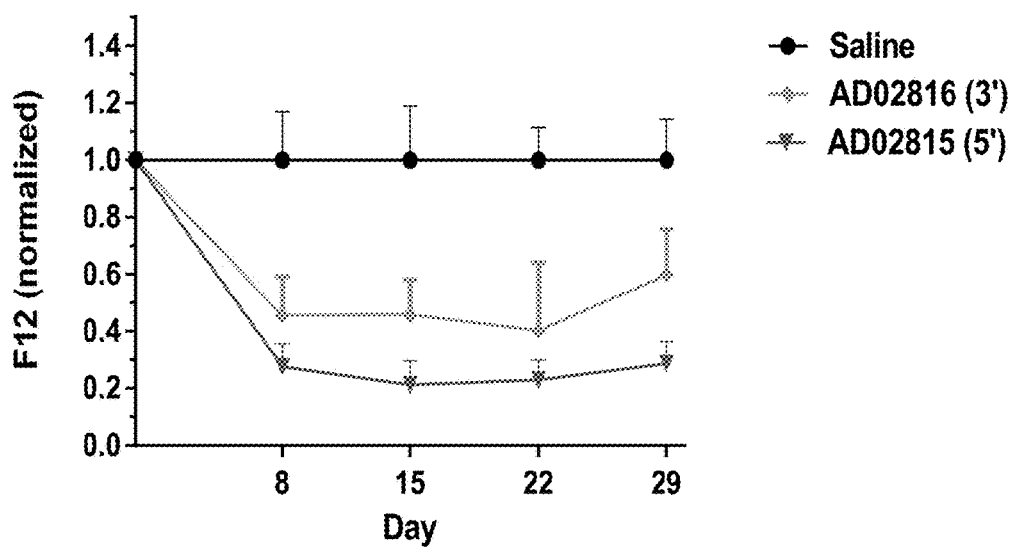
FIG. 11 is a graph illustrating normalized mouse Factor 12 (F12) protein levels in wild type mice (which is described below in Example 12).

Each strand of the F12 RNAi agents was synthesized according to phosphoramidite technology on solid phase used in oligonucleotide synthesis using either a MerMade96E® (Bioautomation) or a MerMade12® (Bioautomation), FIG. 11 shows the results from this experiment. At nadir (day 22), AD02816 showed approximately 60% reduction in circulating F12 protein levels, while AD02815 showed a 79% reduction. The data also show a difference in length of knockdown effect. At day 29, AD02816-treated mice show 40% knockdown while AD02815-treated mice show 71% knockdown from saline levels. These data support linkage of a GalNAc ligand at the 5' terminal end of the sense strand.

Example 13. Lp(a) Expression-Inhibiting Oligomeric Compounds (Double-Stranded RNAi Agents) Linked to Targeting Ligands of Structure 1003 in Lp(a) Transgenic (Tg) Mice Lp(a) expression-inhibiting oligomeric compounds (double-stranded Lp(a) RNAi agents) were prepared having the sequences set forth in the following Table 3:

TABLE 3

LP(a) expression-inhibiting oligomeric compounds (RNAi agent duplexes) of Example 13.

| 5' → 3' | SEQ ID NO: |
|---|---|
| Duplex ID: AD03547 | |
| Sense Strand Sequence: (NAG29)uauauaasuuaucgaGfGfcucauucucsa(invAb) (AM04498-SS) | 9 |
| Antisense Strand Sequence: usGfsasGfaAfuGfaGfccuCfgAfuAfausuAUAUA (AM04507-AS) | 10 |
| Duplex ID: AD03549 | |
| Sense Strand Sequence: (NAG25)uauauaasuuaucgaGfGfcucauucucsa(invAb) (AM04502-SS) | 11 |
| Antisense Strand Sequence: usGfsasGfaAfuGfaGfccuCfgAfuAfausuAUAUA (AM04507-AS) | 12 |

In Table 3, above, the following notations are used:
(NAG25) =

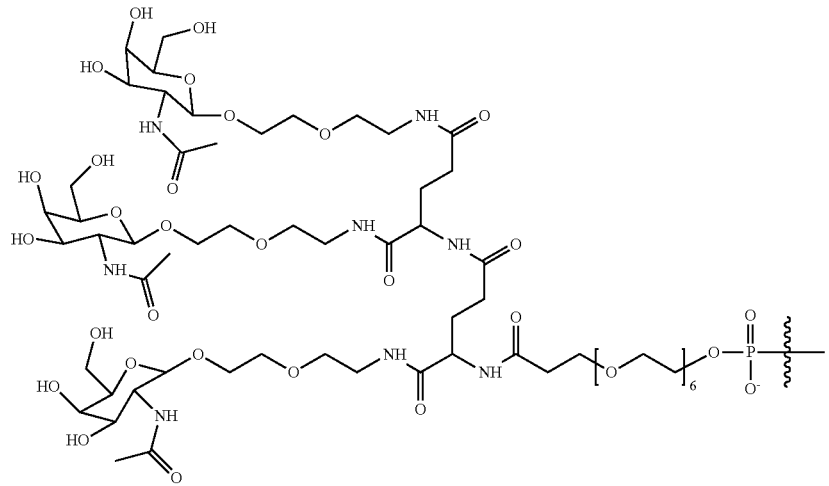

TABLE 3-continued

Lp(a) expression-inhibiting oligomeric compounds (RNAi agent duplexes) of Example 13.

5' → 3'    SEQ ID NO:

(NAG29) =

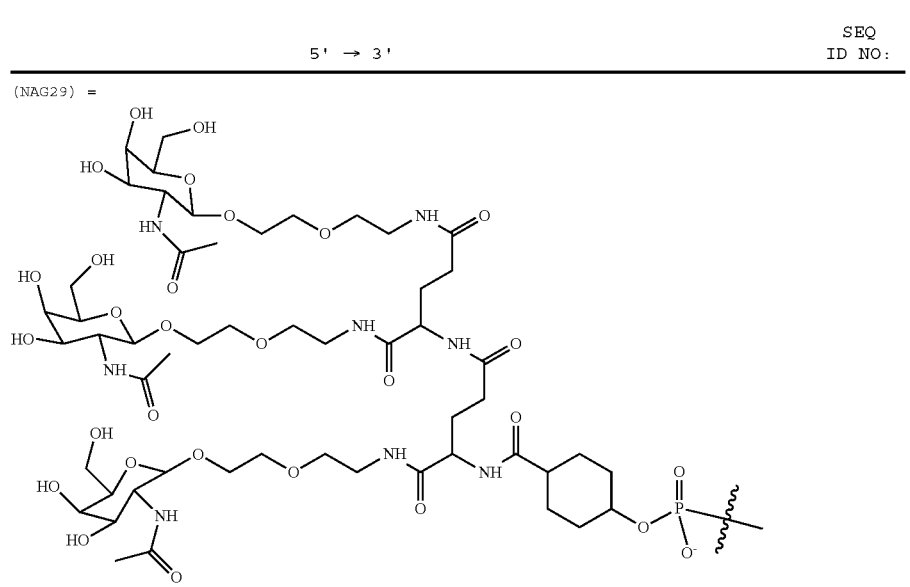

(NAG29) has the chemical structure represented by Structure 1003 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

Lp(a) transgenic (Tg) mice (Frazer K A et al 1995, *Nature Genetics* 9:424-431) were used to evaluate the efficacy of double-stranded RNAi agents with conjugated N-acetyl-galactosamine ligands in vivo. This mouse expresses human apo(a) from a YAC containing the full LPA gene (encoding apo(a) protein) with additional sequences both 5' and 3', as well as the human apoB-100, thereby producing humanized Lp(a) particles (hereinafter referred to as "Lp(a) Tg mice.") (Callow M J et al 1994, *PNAS* 91:2130-2134).

The Lp(a) RNAi agents linked to the respective GalNAc ligands (i.e., (NAG25) or (NAG29)) were combined in a pharmaceutically acceptable buffer as known in the art for subcutaneous (SC) injection.

The Lp(a) RNAi agents linked to the respective GalNAc ligands (i.e., (NAG25) or (NAG29)) at the 5' end of the sense strand were delivered via SC injection. On day 1, a SC injection was administered into the loose skin on the back between the shoulders of 200 μl solution/20 g mouse containing either saline or a 1 mg/kg (mpk) dose of the respective Lp(a) RNAi agent (AD03547 or AD03549) in buffered saline. There were four (4) Lp(a) Tg mice per treatment group.

Serum samples from treated mice were taken on days -1 (pre-dose), 5, 11, 16, 22, 29, and 36. Knockdown was determined by calculating circulating Lp(a) particle levels in serum. Lp(a) particle levels were measured on a Cobas® Integra 400 (Roche Diagnostics) according to the manufacturer's recommendations. For normalization, Lp(a) level for each animal at a time point was divided by the pre-dose level of expression in that animal (in this case at day -1) to determine the ratio of expression "normalized to day -1." Expression at a specific time point was then normalized to the saline control group by dividing the "normalized to day -1" ratio for an individual animal by the mean "normalized to day -1" ratio of all mice in the saline control group. This resulted in expression for each time point normalized to that in the control group. Experimental error is given as standard deviation.

Figure 12:
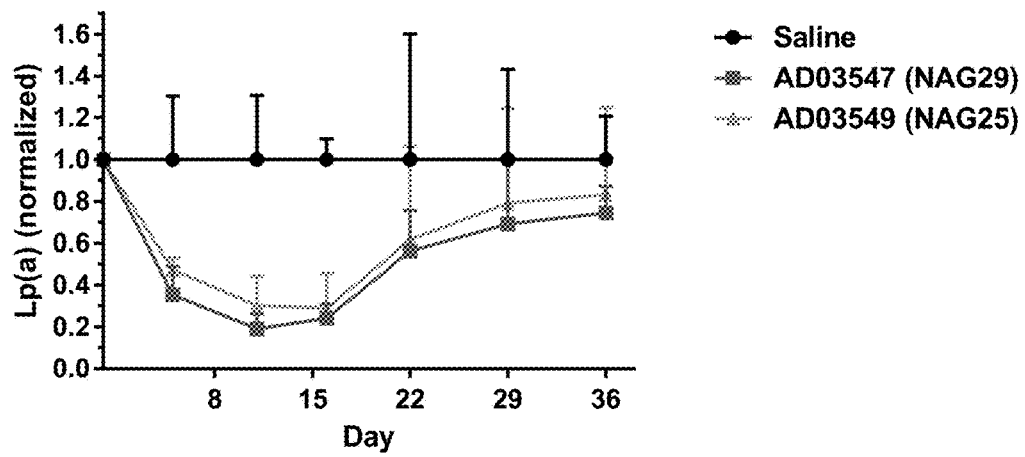
FIG. 12 is a graph illustrating normalized lipoprotein(a) (Lp(a)) particle levels in Lp(a) transgenic (Tg) mice (which is described below in Example 13).

Results are shown in FIG. 12. AD03549 (NAG25) showed 71% knockdown at nadir (day 16), and AD03547 (NAG29) showed 81% knockdown at nadir (day 11). Both triggers showed similar recovery curves after nadir, with less than 26% knockdown on day 36. These data support that the GalNAc ligands shown in Example 13 are comparable in both initial knockdown activity and duration of knockdown in Lp(a) Tg mice with a single 1 mg/kg dose.

Example 14. Apo(a) Knockdown in Apo(a) Transgenic (Tg) Mice Following Administration of Lp(a) Expression-Inhibiting Oligomeric Compounds (Double-Stranded RNAi Agents) Linked to Targeting Ligand Structures 1002 and 1004

Lp(a) expression-inhibiting oligomeric compounds (double-stranded Lp(a) RNAi agents) were prepared having the sequences set forth in the following Table 4:

TABLE 4

LP(a) expression-inhibiting oligomeric compounds (RNAi agent duplexes) of Example 14.

| | 5' → 3' | SEQ ID NO: |
|---|---|---|
| Duplex ID: AD03536 | | |
| Sense Strand Sequence: (AM04496-SS) | (NAG25)(invAb)GfcCfcCfuUfAfUfuGfuUfaUfaCfgausu(invAb) | 13 |
| Antisense Strand Sequence: (AM03972-AS) | usCfsgsUfaUfaAfCfAfauaAfgGfgGfcusu | 14 |
| Duplex ID: AD03538 | | |
| Sense Strand Sequence: (AM04499-SS) | (NAG28)(invAb)GfcCfcCfuUfAfUfuGfuUfaUfaCfgausu(invAb) | 15 |
| Antisense Strand Sequence: (AM03972-AS) | usCfsgsUfaUfaAfCfAfauaAfgGfgGfcusu | 16 |
| Duplex ID: AD03540 | | |
| Sense Strand Sequence: (AM04500-SS) | (NAG30)(invAb)GfcCfcCfuUfAfUfuGfuUfaUfaCfgausu(invAb) | 17 |
| Antisense Strand Sequence: (AM03972-AS) | usCfsgsUfaUfaAfCfAfauaAfgGfgGfcusu | 18 |

In Table 4, above, the following notations are used:
(NAG28) =

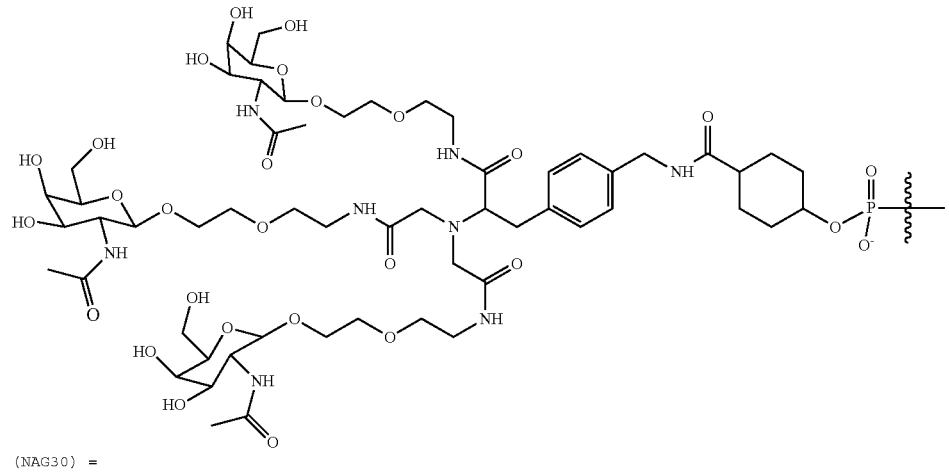

(NAG30) =

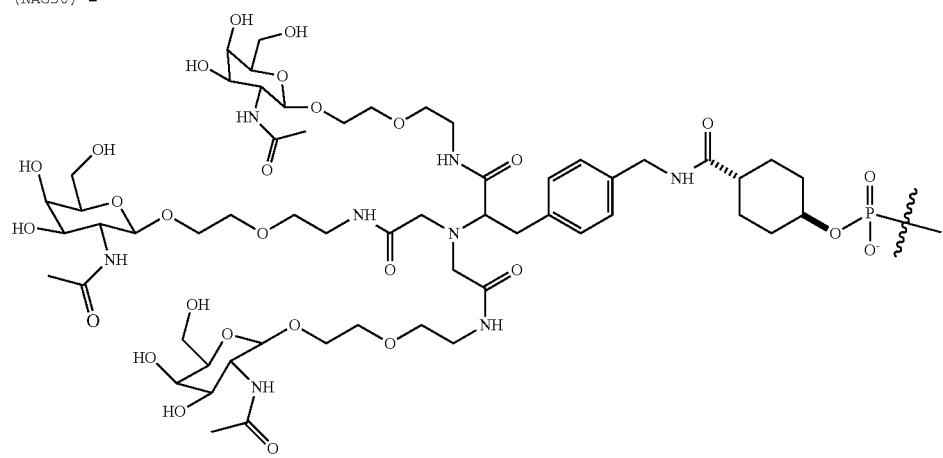

Additionally, (NAG25) has the same chemical structure as shown in Example 13, above.

(NAG28) has the chemical structure represented by Structure 1002 herein. (NAG30) has the chemical structure represented by Structure 1004 herein. (NAG28) includes a mixture of the cis- and trans-isomers, while (NAG30) is exclusively the trans-isomer.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

Apo(a) transgenic (Tg) mice were used to evaluate the efficacy of double-stranded RNAi agents with conjugated N-acetyl-galactosamine ligands in vivo. Apo(a) Tg mice (Frazer K A et al 1995, *Nature Genetics* 9:424-431) express human apo(a) from a YAC containing the full LPA gene (encoding apo(a) protein) with additional sequences both 5' and 3' (hereinafter referred to as "apo(a) Tg mice").

The Lp(a) RNAi agents linked to the respective GalNAc ligands (i.e., (NAG25), (NAG28), or (NAG30)) were combined in a pharmaceutically acceptable buffer as known in the art for subcutaneous (SC) injection.

The Lp(a) RNAi agents linked to the respective GalNAc ligands (i.e., (NAG25), (NAG28), or (NAG30)) at the 5' end of the sense strand were delivered via SC injection. On day 1, a SC injection was administered into the loose skin on the back between the shoulders of 200 µl solution/20 g mouse containing either saline or a 0.5 mg/kg (mpk) dose of the RNAi agent (AD03536, AD03538, or AD03540) in buffered saline. There were three (3) apo(a) Tg mice per treatment group.

Serum samples from treated mice were taken on days −1 (pre-dose), 8, 15, 22, and 29. Knockdown was determined by assaying serum from the mice using an ELISA for apo(a) (Abcam). For normalization, apo(a) level for each animal at a time point was divided by the pre-treatment level of expression in that animal (in this case at day −1) to determine the ratio of expression "normalized to day −1". Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard error of the mean.

Figure 13:
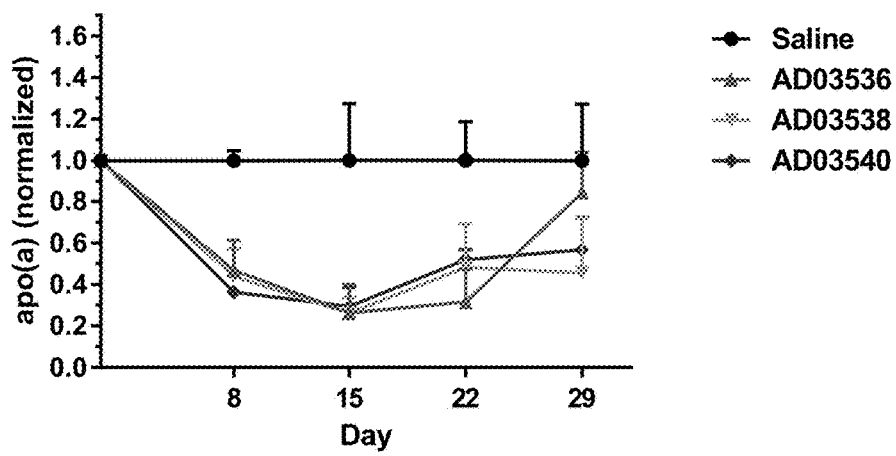
FIG. 13 is a graph illustrating normalized apo(a) levels in apo(a) transgenic (Tg) mice (which is described below in Example 14).

Results are shown in FIG. 13. Nadir was day 15 for all RNAi agents tested. At nadir, AD03536 showed 74% knockdown of apo(a) protein, AD03538 showed 74% knockdown of apo(a) protein, and AD03540 showed 71% knockdown of apo(a) protein. At day 29, all of the RNAi agents show >48% knockdown of apo(a) protein levels except for AD03536 (containing NAG25) which shows only 16% knockdown. These data support that the NAG structures behave similarly with respect to initial knockdown activity, with the RNAi agents containing the linker structures NAG28 and NAG30 showing numerically greater knockdown at day 29.

Example 15. Lp(a) Knockdown in Lp(a) Tg Mice Following Administration of Lp(a) Expression-Inhibiting Oligomeric Compounds (Double-Stranded RNAi Agents) Linked to Targeting Ligands of Structures 1005 and 1008

Lp(a) expression-inhibiting oligomeric compounds (double-stranded Lp(a) RNAi agents) were prepared having the sequences set forth in the following Table 5:

TABLE 5

LP(a) expression-inhibiting oligomeric compounds (RNAi agent duplexes) of Example 15.

| | 5' → 3' | SEQ ID NO: |
|---|---|---|
| Duplex ID: AD03536 | | |
| Sense Strand Sequence: (AM04496-SS) | (NAG25)(invAb)GfcCfcCfuUfAfUfuGfuUfaUfaCfgausu(invAb) | 19 |
| Antisense Strand Sequence: (AM03972-AS) | usCfsgsUfaUfaAfCfAfauaAfgGfgGfcusu | 20 |
| Duplex ID: AD03629 | | |
| Sense Strand Sequence: (AM04611-SS) | (NAG31)(invAb)GfcCfcCfuUfAfUfuGfuUfaUfaCfgausu(invAb) | 21 |
| Antisense Strand Sequence: (AM03972-AS) | usCfsgsUfaUfaAfCfAfauaAfgGfgGfcusu | 22 |
| Duplex ID: AD04170 | | |
| Sense Strand Sequence: (AM05341-SS) | (NAG37)(invAb)GfcCfcCfuUfAfUfuGfuUfaUfaCfgausu(invAb) | 23 |

TABLE 5-continued

LP(a) expression-inhibiting oligomeric compounds (RNAi agent duplexes) of Example 15.

| 5' → 3' | SEQ ID NO: |
|---|---|
| Antisense Strand Sequence: usCfsgsUfaUfaAfCfAfauaAfgGfgGfcusu (AM03972-AS) | 24 |

In Table 5, above, the following notations are used:
(NAG31) =

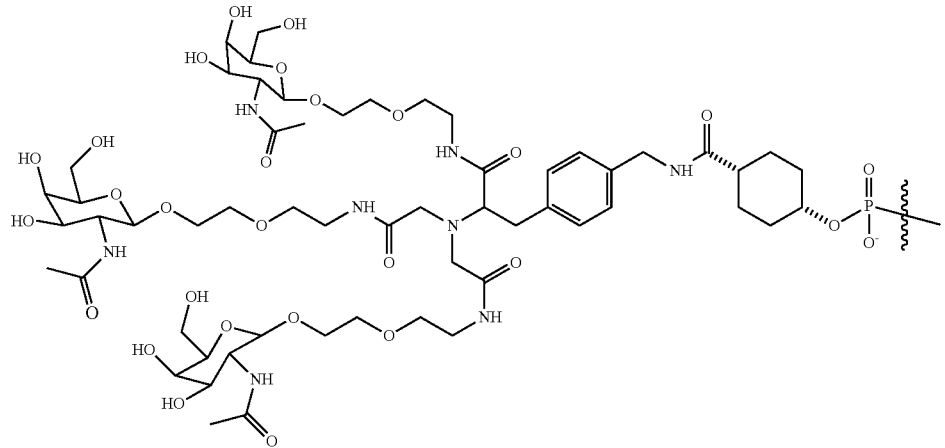

(NAG37) =

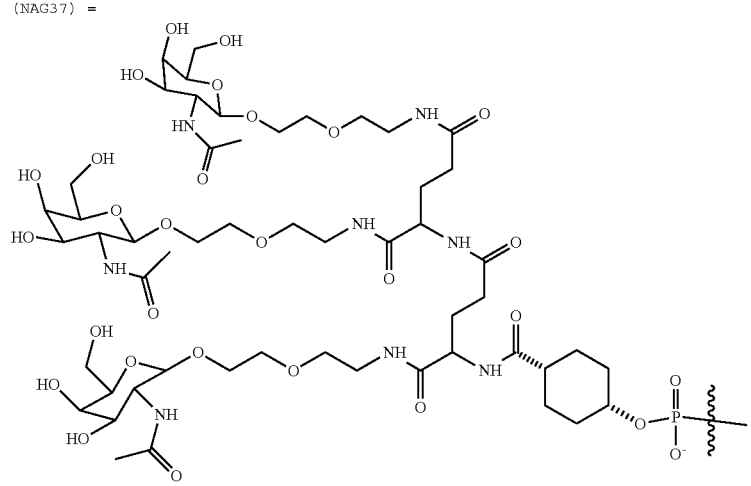

Additionally, (NAG25) is the same structure as shown in Example 13, above.

(NAG31) has the chemical structure represented by Structure 1005 herein. (NAG37) has the chemical structure represented by Structure 1008 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

Lp(a) Tg mice were used to evaluate the efficacy of double-stranded RNAi agents with conjugated N-acetylgalactosamine ligands in vivo.

The Lp(a) RNAi agents linked to the respective GalNAc ligands (i.e., (NAG25), (NAG31) or (NAG37)) were combined in a pharmaceutically acceptable buffer as known in the art for subcutaneous (SC) injection.

The Lp(a) RNAi agents linked to the respective GalNAc ligands (i.e., (NAG25), (NAG31), or (NAG37)) were delivered via SC injection. On day 1, a SC injection was administered into the loose skin on the back between the shoulders of 200 μl solution/20 g mouse containing either saline or a 3 mg/kg (mpk) dose of the RNAi agent (AD03536, AD03629, or AD04170) in buffered saline. There were four (4) Lp(a) Tg mice per treatment group.

Serum samples from treated mice were taken on days −1 (pre-dose), 8, 15, 22, 29, and 36. Knockdown was determined by calculating circulating Lp(a) particle levels in serum. Lp(a) particle levels were measured on a Cobas® Integra 400 (Roche Diagnostics) according to the manufacturer's recommendations. For normalization, Lp(a) level for each animal at a time point was divided by the pre-dose level of expression in that animal (in this case at day −1) to determine the ratio of expression "normalized to day −1."

Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard deviation.

Figure 14:
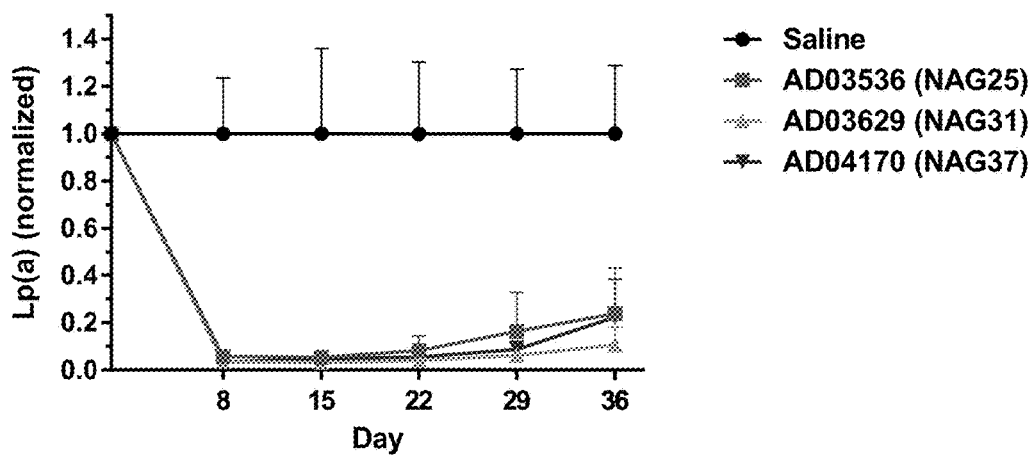
FIG. 14 is a graph illustrating normalized Lp(a) particle levels in Lp(a) Tg mice (which is described below in Example 15)

Resulting data are shown in FIG. 14. AD03536 showed 95% knockdown of Lp(a) levels at nadir (day 15), and maintained knockdown of 76% at day 36. AD03629 showed 97% knockdown of Lp(a) levels at nadir (day 8), and maintained knockdown of 90% at day 36. AD04170 showed 97% knockdown of Lp(a) levels at nadir (day 8), and maintained knockdown of 78% at day 36.

Example 16. F12 Knockdown in Wild Type Mice Following Administration of F12 Expression-Inhibiting Oligomeric Compounds (Double-Stranded RNAi Agents) Linked to Targeting Ligands of Structures 1005, 1008, 1025, and 1027

F12 expression-inhibiting oligomeric compounds (double-stranded F12 RNAi agents) were prepared that were conjugated at the 5' terminal end via a phosphorothioate linkage to GalNAc targeting ligands (NAG25)s [AD04162]; (NAG37)s [AD04623]; (NAG31)s [AD04512]; (NAG33)s [AD04650] or (NAG38)s [AD04651]. Each of the double-stranded RNAi agents were directed to F12.

The following notations are used for the GalNAc targeting ligand structures:

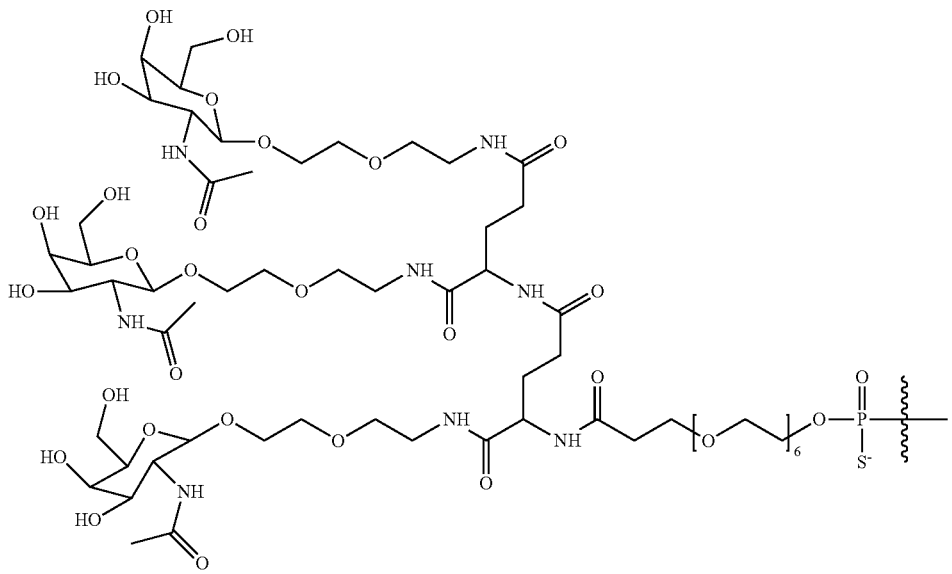

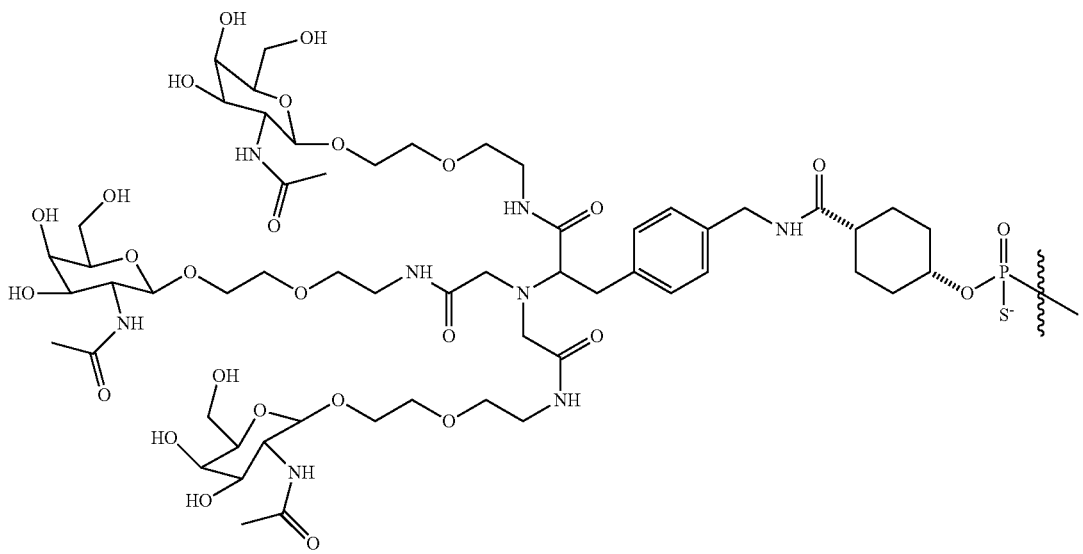

(NAG33)s =
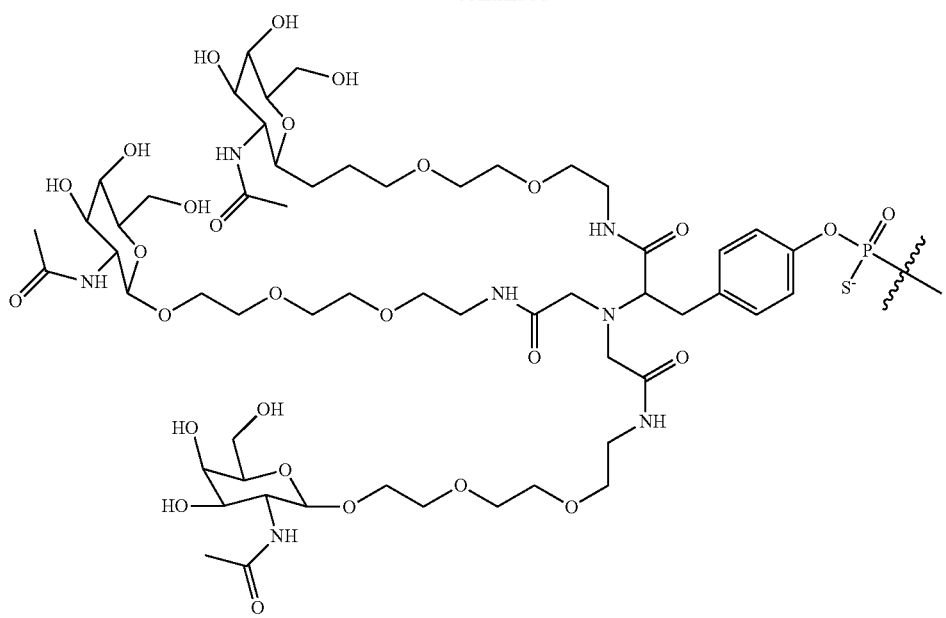
(NAG37)s =
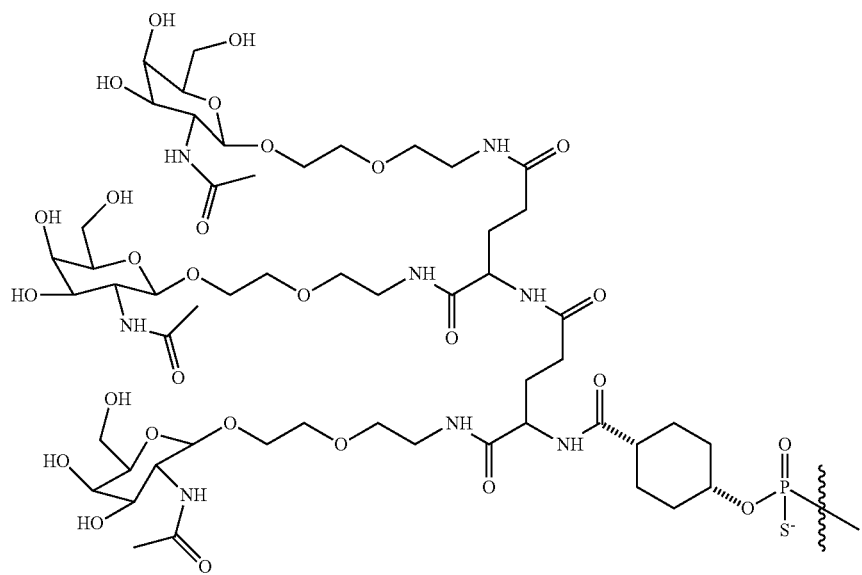

(NAG38)s =

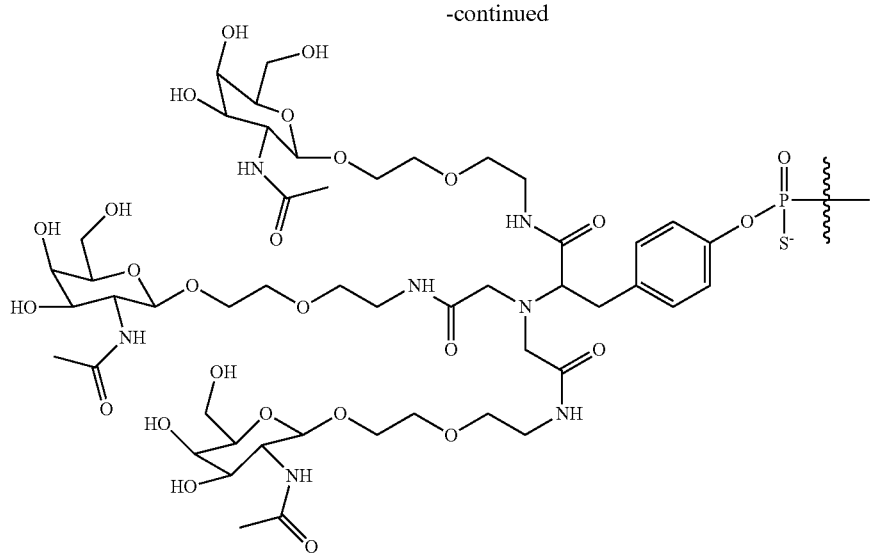

(NAG31)s has the chemical structure represented by Structure 1005 herein. (NAG33)s has the chemical structure represented by Structure 1025 herein. (NAG37)s has the chemical structure represented by Structure 1008 herein. (NAG38)s has the chemical structure represented by Structure 1027 herein. The sequences and modification patterns were identical for AD04162, AD04623, AD04512, AD04650, and AD04651, with the only difference in the compositions being the GalNAc targeting ligand structure located at the 5′ terminal end of the sense strand of each F12 RNAi agent, as shown above.

Each strand of the F12 RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

The F12 RNAi agents conjugated to the respective GalNAc targeting ligands (i.e., (NAG25)s, (NAG31)s, (NAG33)s, (NAG37)s, or (NAG38)s) were combined in a pharmaceutically acceptable buffer as known in the art for subcutaneous (SC) injection.

The F12 RNAi agents linked to the respective GalNAc ligands (i.e., (NAG25)s, (NAG31)s, (NAG33)s, (NAG37)s, or (NAG38)s) were delivered via SC injection. On day 1, a SC injection was administered into the loose skin on the back between the shoulders of 200 ul solution/20 g mouse containing either saline or a 1 mg/kg (mpk) dose of one of five duplexes (AD04162, AD04623, AD04512, AD04650 and AD04651) in buffered saline. There were four (4) wild type mice per treatment group. As shown above, AD04162 includes the structure (NAG25)s, AD04623 includes the structure (NAG37)s, AD04512 includes the structure (NAG31)s, AD04650 includes the structure (NAG33)s, and AD04651 includes the structure (NAG38)s. All GalNAc targeting ligands were attached at the 5′ terminal end of the sense strand of each respective RNAi agent Serum samples from treated mice were taken on days −1 (pre-dose), 8, 15 and 22 to monitor knockdown. Knockdown was measured by quantifying circulating mouse F12 protein (mF12) levels in serum by an internally developed mF12 alphaLISA® (Perkin Elmer). mF12 levels for each animal at a respective time point was divided by the pre-treatment level of expression in that animal to determine the ratio of expression "normalized to pre-dose". Expression at a specific time point was then normalized to the saline control group by dividing the "normalized to day pre-dose" ratio for an individual animal by the mean "normalized to day pre-dose" ratio of all mice in the saline control group. This resulted in expression for each time point normalized to that in the control group. Experimental error is given as standard deviation.

Figure 15:
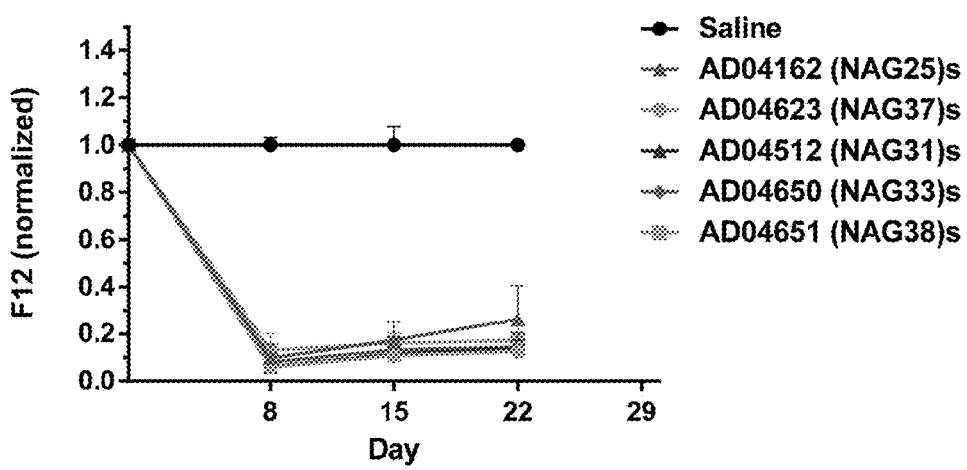
FIG. 15 is a graph illustrating normalized mouse F12 protein levels in wild type mice (which is described below in Example 16).

Results from this study are shown in FIG. 15. Nadir was day 8 for all RNAi agents tested. At nadir, AD04162 showed 90% knockdown of mF12, AD04623 showed 94% knockdown of mF12, AD04512 showed 94% knockdown of mF12, AD04650 showed 92% knockdown of mF12 and AD04651 showed 87% knockdown at of mF12. At day 22, all of the RNAi agents show >82% knockdown of mF12 levels except for AD04162 (containing NAG25) which shows only 74% knockdown. These data support that the NAG structures behave similarly with respect to initial knockdown activity, with the RNAi agents containing the rigid linker structures or linker replacement moieties disclosed herein (i.e., NAG31, NAG33, NAG37 and NAG38) showing numerically greater mF12 knockdown at day 22.

Example 17. Lp(a) Expression-Inhibiting Oligomeric Compounds (Double-Stranded RNAi Agents) Linked to Targeting Ligands of Structures 1004 and 1005 in Lp(a) Tg Mice Lp(a) expression-inhibiting oligomeric compounds (double-stranded RNAi agents) were prepared having the sequences set forth in the following Table 6:

TABLE 6

LP(a) expression-inhibiting oligomeric compounds
(RNAi agent duplexes) of Example 17.

| Duplex ID: AD03629 | 5'→3' | SEQ ID NO: |
|---|---|---|
| Sense Strand Sequence: (AM04611-SS) | (NAG31)(invAb)GfcCfcCfuUfAfUfuGfuUfaUfaCfgausu(invAb) | 25 |
| Antisense Strand Sequence: (AM03972-AS) | usCfsgsUfaUfaAfCfAfauaAfgGfgGfcusu | 26 |
| Sense Strand Sequence: (AM04500-SS) | (NAG30)(invAb)GfcCfcCfuUfAfUfuGfuUfaUfaCfgausu(invAb) | 27 |
| Antisense Strand Sequence: (AM03972-AS) | usCfsgsUfaUfaAfCfAfauaAfgGfgGfcusu | 28 |

In Table 6, (NAG30) is the same chemical structure as shown in Example 14, above, and (NAG31) is the same chemical structure as shown in Example 15, above.

NAG30 has the chemical structure represented by Structure 1004 herein. NAG31 has the chemical structure represented by Structure 1005 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

Lp(a) Tg mice as described herein were used to evaluate the efficacy of double-stranded RNAi agents with conjugated N-acetyl-galactosamine ligands in vivo.

The Lp(a) RNAi agents linked to the respective GalNAc ligands (i.e., NAG30 or NAG31) were combined in a pharmaceutically acceptable buffer as known in the art for subcutaneous (SC) injection.

The Lp(a) RNAi agents linked to the respective GalNAc ligands (i.e., NAG30 or NAG31) at the 5' end of the sense strand were delivered via SC injection. On day 1, a SC injection was administered into the loose skin on the back between the shoulders of 200 μl solution/20 g mouse containing either saline or a 1 mg/kg (mpk) dose of the Lp(a) RNAi agent (AD03629 or AD03540) in buffered saline. There were four (4) Lp(a) Tg mice per treatment group.

Serum samples from treated mice were taken on days −1 (pre-dose), 8, 15, 22, 29, 36 and 43. Knockdown was determined by calculating circulating Lp(a) particle levels in serum. Lp(a) particle levels were measured on a Cobas® Integra 400 (Roche Diagnostics) according to the manufacturer's recommendations. For normalization, Lp(a) level for each animal at a time point was divided by the pre-dose level of expression in that animal (in this case at day −1) to determine the ratio of expression "normalized to day −1." Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard deviation.

Figure 16:
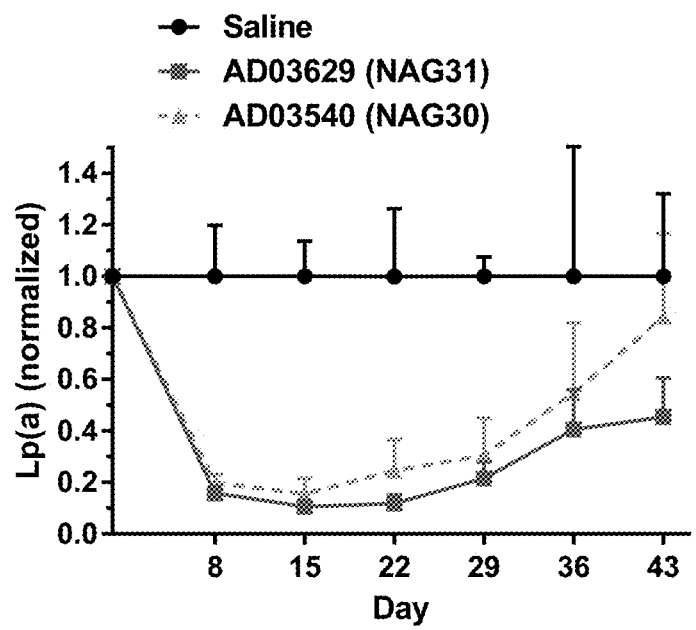
FIG. 16 is a graph illustrating normalized Lp(a) particle levels in Lp(a) Tg mice (which is described below in Example 17).

Results are shown in FIG. 16. Nadir was day 15 for both RNAi agents studied. AD03629 showed 89% knockdown of Lp(a) levels at nadir, while AD03540 showed 85% knockdown of Lp(a) levels at nadir. Both RNAi agents showed similar recovery curves to day 36. However, at day 43, while AD03540 showed 16% knockdown of Lp(a) levels, AD03629 showed 55% knockdown of Lp(a) levels.

Example 18. Apo(a) Knockdown in Apo(a) Tg Mice Following Administration of Lp(a) Expression-Inhibiting Oligomeric Compounds Linked to Targeting Ligand Structures 1007, 1025, and 1026

Lp(a) expression-inhibiting oligomeric compounds (double-stranded RNAi agents) were prepared having the sequences set forth in the following Table 7:

TABLE 7

LP(a) expression-inhibiting oligomeric compounds (RNAi agent duplexes) of Example 18.

| | 5' → 3' | SEQ ID NO: |
|---|---|---|
| Duplex ID: AD03721 | | |
| Sense Strand Sequence: (AM04742-SS) | (NAG33)(invAb)GfcCfcCfuUfAfUfuGfuUfaUfaCfgausu(invAb) | 29 |

TABLE 7-continued

LP(a) expression-inhibiting oligomeric compounds (RNAi agent duplexes) of Example 18.

| | 5' → 3' | SEQ ID NO: |
|---|---|---|
| Antisense Strand Sequence: (AM03972-AS) Duplex ID: AD03722 | usCfsgsUfaUfaAfCfAfauaAfgGfgGfcusu | 30 |
| Sense Strand Sequence: (AM04743-SS) | (NAG34)(invAb)GfcCfcCfuUfAfUfuGfuUfaUfaCfgausu(invAb) | 31 |
| Antisense Strand Sequence: (AM03972-AS) Duplex ID: AD03723 | usCfsgsUfaUfaAfCfAfauaAfgGfgGfcusu | 32 |
| Sense Strand Sequence: (AM04744-SS) | (NAG35)(invAb)GfcCfcCfuUfAfUfuGfuUfaUfaCfgausu(invAb) | 33 |
| Antisense Strand Sequence: (AM03972-AS) | usCfsgsUfaUfaAfCfAfauaAfgGfgGfcusu | 34 |

In Table 7, above, the following notations are used:

(NAG33) =

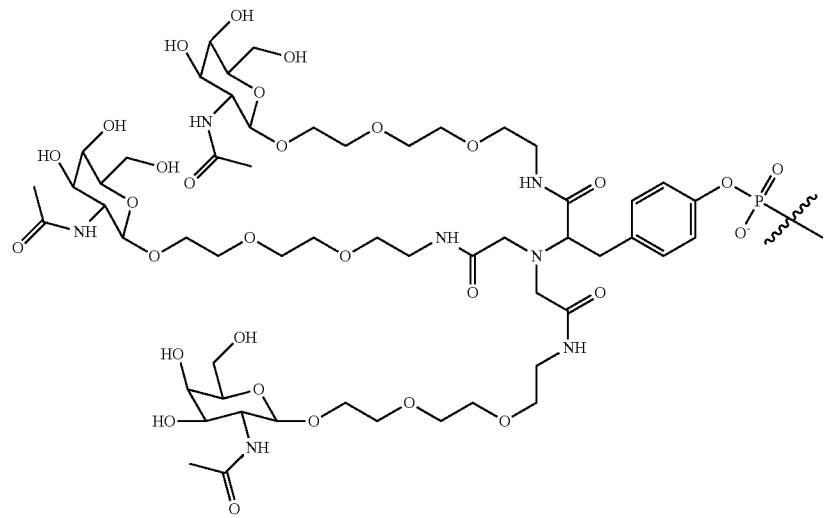 [SMILES: *P(=O)([O-])Oc1ccc(CC(C(=O)NCCOCCOCCOC2OC(CO)C(O)C(O)C2NC(C)=O)N(CC(=O)NCCOCCOCCOC2OC(CO)C(O)C(O)C2NC(C)=O)CC(=O)NCCOCCOCCOC2OC(CO)C(O)C(O)C2NC(C)=O)cc1]

(NAG34) =

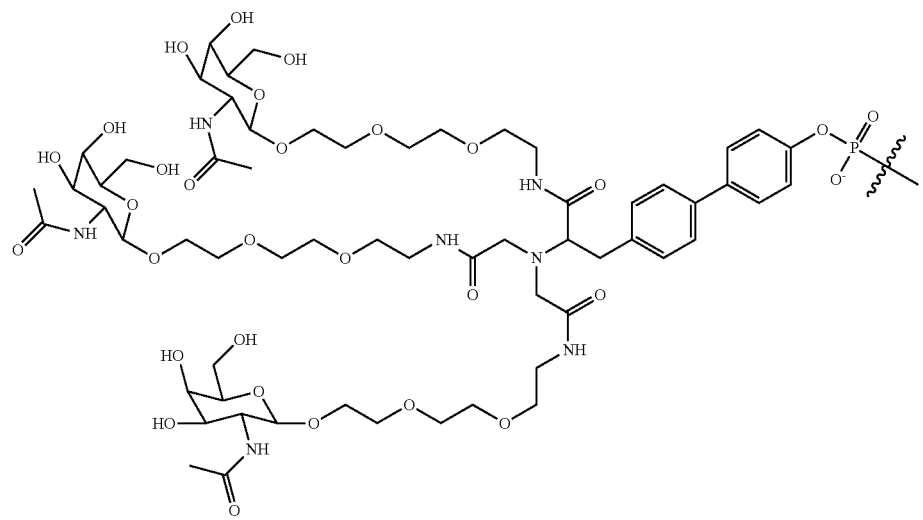 [SMILES: *P(=O)([O-])Oc1ccc(-c2ccc(CC(C(=O)NCCOCCOCCOC3OC(CO)C(O)C(O)C3NC(C)=O)N(CC(=O)NCCOCCOCCOC3OC(CO)C(O)C(O)C3NC(C)=O)CC(=O)NCCOCCOCCOC3OC(CO)C(O)C(O)C3NC(C)=O)cc2)cc1]

TABLE 7-continued

LP(a) expression-inhibiting oligomeric compounds (RNAi agent duplexes) of Example 18.

5' → 3'  SEQ ID NO:

(NAG35) =

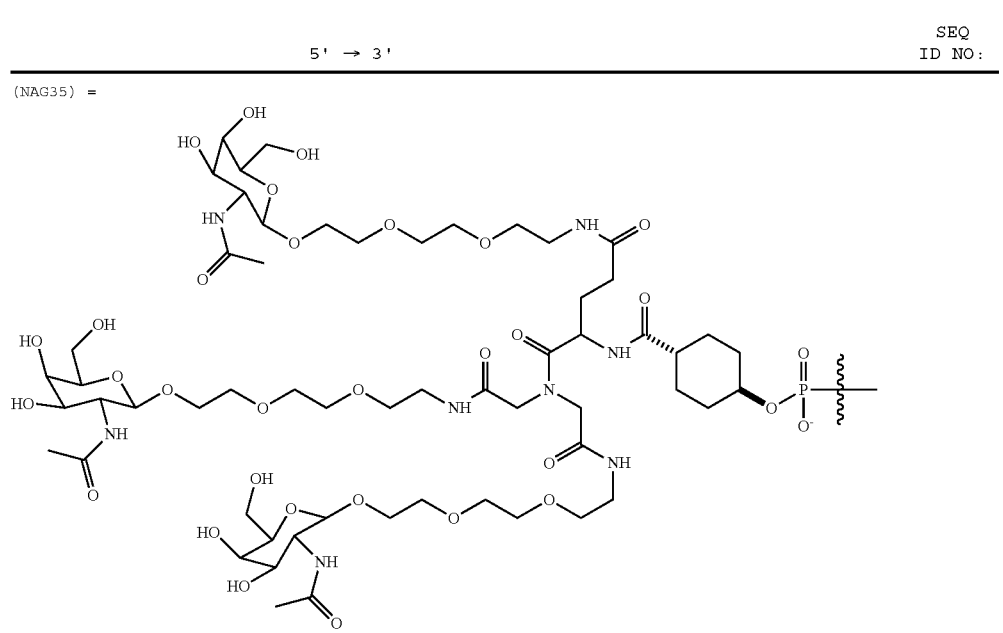

(NAG33) has the chemical structure represented by Structure 1025 herein. (NAG34) has the chemical structure represented by Structure 1026 herein. (NAG35) has the chemical structure represented by Structure 1007 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

Apo(a) transgenic (Tg) mice were used to evaluate the efficacy of double-stranded RNAi agents with conjugated N-acetyl-galactosamine ligands in vivo.

The Lp(a) RNAi agents linked to the respective GalNAc ligands (i.e., NAG33, NAG34 or NAG35) were combined in a pharmaceutically acceptable buffer as known in the art for subcutaneous (SC) injection.

Lp(a) RNAi agents conjugated to the respective GalNAc targeting ligands (i.e., NAG33, NAG34 or NAG35) were administered by SC injection. On day 1, a SC injection was administered into the loose skin on the back between the shoulders of 200 µl solution/20 g mouse containing either saline or a 1 mg/kg (mpk) dose of the RNAi agent (AD03721, AD03722, or AD03723) in buffered saline. There were three (3) apo(a) Tg mice per treatment group.

Serum samples from treated mice were taken on days −1 (pre-dose), 8, 15, 22, and 29. Knockdown was determined by assaying circulating apo(a) protein levels in serum. Human apo(a) protein levels in serum were monitored by assaying serum from the mice using an ELISA for apo(a) (Abcam). For normalization, apo(a) level for each animal at a time point was divided by the pre-treatment level of expression in that animal (in this case at day −1) to determine the ratio of expression "normalized to day −1". Expression at a specific time point was then normalized to the saline control group by dividing the "normalized to day −1" ratio for an individual animal by the mean "normalized to day −1" ratio of all mice in the saline control group. Experimental error is given as standard error of the mean.

Figure 17:
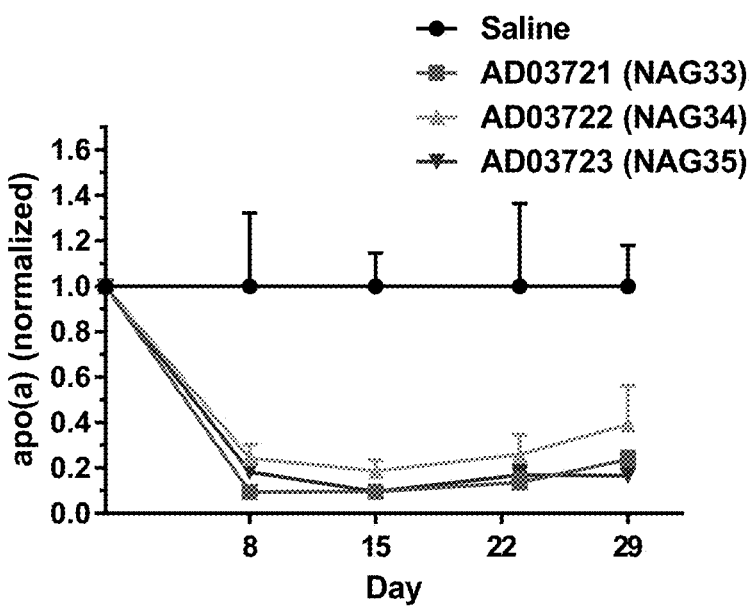
FIG. 17 is a graph illustrating normalized apo(a) levels in apo(a) Tg mice (which is described below in Example 18).

Resulting data are shown in FIG. 17. Nadir was day 15 for all RNAi agents studied. AD03721 showed 91% knockdown of apo(a) protein levels at nadir, AD03722 showed 81% knockdown of apo(a) protein levels at nadir, while AD03723 showed 90% knockdown of apo(a) protein levels at nadir. Recovery of apo(a) protein levels after treatment showed similar trajectories, with both AD03721 and AD03723-treated mice showing nearly identical knockdown at each timepoint, whereas AD03722-treated mice showed numerically less knockdown at each timepoint tested. For example, at Day 29, AD03721-treated mice showed 76% knockdown of apo(a) levels, AD03723-treated mice showed 83% knockdown of apo(a) levels, while AD03722-treated mice showed 61% knockdown of apo(a) levels. These data support that the NAG33, NAG34 and NAG35 structures all show knockdown activity, with the RNAi agents containing structures NAG33 and NAG35 showing numerically greater a knockdown at day 29.

Example 19. Dose Response of LP(a) Expression-Inhibiting Oligomeric Compounds (Double-Stranded RNAi Agents) Linked to Targeting Ligands of Structure 1008, Dosed at 1 Mg/Kg and 3 mg/kg in Lp(a) Tg Mice Lp(a) transgenic mice as described herein were used to evaluate the efficacy of double-stranded RNAi agents with conjugated N-acetyl-galactosamine ligands in vivo. RNAi agents directed to Lp(a) having Duplex ID: AD04170, as set forth above in Example 15, were manufactured. As set forth above, Lp(a) Duplex ID: AD04170 includes a (NAG37) targeting ligand (Structure 1008) attached at the 5' terminal end of the sense strand.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

The Lp(a) RNAi agents linked to targeting ligand Structure 1008 were combined in a pharmaceutically acceptable buffer as known in the art for subcutaneous (SC) injection.

The Lp(a) RNAi agents linked to targeting ligand Structure 1008 were administered by subcutaneous (SC) injection. On day 1, a SC injection was made into the loose skin on the back between the shoulders of 200 µl solution/20 g mouse containing a dose of either saline, 1 mg/kg (mpk) of the RNAi agent in buffered saline, or 3 mg/kg (mpk) of the RNAi agent in buffered saline.

Control serum (pre-treatment) samples were taken from the mice pre-injection on day −1. Lp(a) particle levels were determined on a Cobas® Integra 400 (Roche Diagnostics) according to the manufacturer's recommendations. For normalization, Lp(a) levels for each animal at a time point was divided by the pre-treatment level of expression in that animal (in this case at day −1) to determine the ratio of expression "normalized to day −1." Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard deviation.

Figure 18:
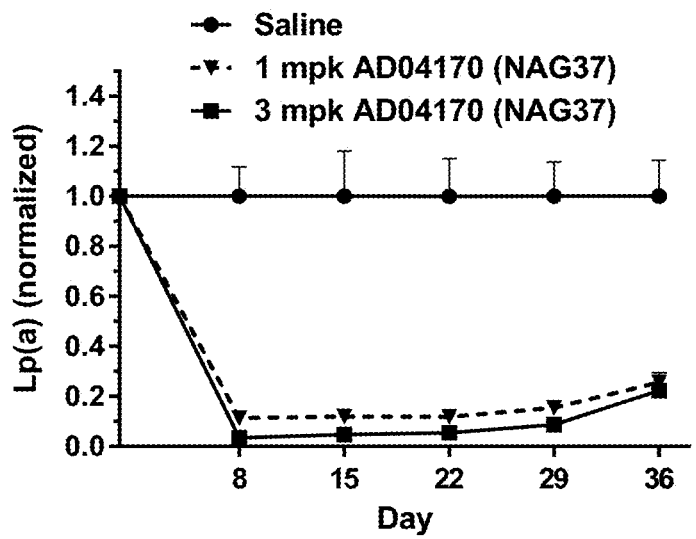
FIG. 18 is a graph illustrating normalized Lp(a) particle levels in Lp(a) Tg mice (which is described below in Example 19).

Results are shown in FIG. 18. As shown in FIG. 18, a dose-dependent relationship is apparent for the Lp(a) RNAi agent across all time points.

Example 20: LP(a) Expression-Inhibiting Oligomeric Compounds (Double-Stranded RNAi Agents) Linked to Targeting Ligands of Structures 1003 and 1004 in Cynomolgus Monkeys Lp(a) expression-inhibiting oligomeric compounds (double-stranded RNAi agents) were prepared having the sequences set forth in the following Table 8:

combining equimolar RNA solutions (sense and antisense) in 0.2×PBS (Phosphate-Buffered Saline, 1×, Corning, Cellgro) to form the duplexes, following the methods generally described in Example 10 herein.

The Lp(a) RNAi agents conjugated to targeting ligands disclosed herein having Structure 1003 or Structure 1004, were made and combined in a pharmaceutically acceptable buffer as known in the art for subcutaneous (SQ) injection.

Control serum (pre-treatment) samples were taken from the cynomolgus monkeys pre-injection on day −14, −7, and day 1 (pre-dose). Lp(a) particle levels were determined on a Cobas® Integra 400 (Roche Diagnostics) according to the manufacturer's recommendations. For normalization, Lp(a) levels for each animal at a time point was divided by the average of the pre-treatment levels of expression in that animal (in this case at days −14, −7, and day 1 (pre-dose)) to determine the ratio of expression "normalized to pre-dose." Experimental error is given as standard deviation.

On day 1, cynomolgus macaque (*Macaca fascicularis*) primates were injected subcutaneously with Lp(a) RNAi agents linked to targeting ligands disclosed herein with 3 mg/kg of either Lp(a) RNAi agent AD03668 or Lp(a) RNAi agent AD03547. Two (2) monkeys were dosed per treatment group.

Figure 19:
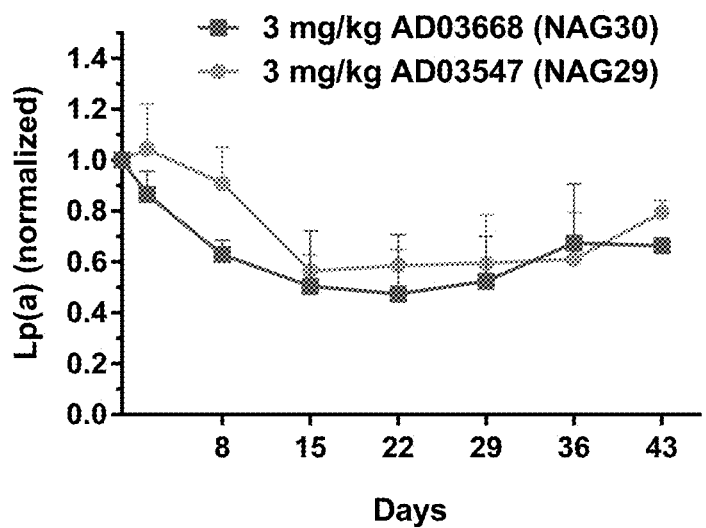
FIG. 19 is a graph illustrating normalized Lp(a) particle levels in cynomolgus monkeys (which is described below in Example 20).

Results are reported in FIG. 19. Lp(a) RNAi triggers conjugated to either Structure 1003 (AD03547) or Structure 1004 (AD03668) showed knockdown in cynomolgus monkeys.

Example 21: F12 Expression-Inhibiting Oligomeric Compounds (Double-Stranded RNAi Agents) Linked to Targeting Ligands of Structure 1008 in Cynomolgus Monkeys F12 RNAi agents having varying sequences directed to F12 and linked to GalNAc targeting ligand Structure 1008 [(NAG37)s] at the 5' end of the sense strand, were made and combined in a pharmaceutically acceptable buffer as known in the art for subcutaneous (SC) injection. (NAG37)s has the chemical structure as shown in Example 16, above.

TABLE 8

Lp(a) expression-inhibiting oligomeric compounds (RNAi agent duplexes) of Example 20.

| Duplex ID: AD03668 | 5'→3' | SEQ ID NO: |
|---|---|---|
| Sense Strand Sequence: (AM04500-SS) | (NAG30)(invAb)GfcCfcCfuUfAfUfuGfuUfaUfaCfgausu(invAb) | 35 |
| Antisense Strand Sequence: (AM04501-AS) | cPrpTMsCfsgsUfaUfaAfCfAfauaAfgGfgGfcusu | 36 |

Lp(a) RNAi agent AD03547 is the same as shown in Example 13, and is conjugated to (NAG29). Lp(a) RNAi agent AD3668 was conjugated to (NAG30). (NAG30) has the chemical structure shown in Example 14. (NAG29) is represented by Structure 1003 herein. (NAG30) is represented by Structure 1004 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by On day 1, cynomolgus macaque (*Macaca fascicularis*) primates were injected subcutaneously with 3 mg/kg of one of six (6) different Lp(a) RNAi agents having different sequence structures and different modification patterns: AD04623, AD04624, AD04625, AD04626, AD04627, or AD04628. Two (2) monkeys were dosed per treatment group.

Serum samples from treated cynomolgus monkeys were taken on day −7 and day 1 (pre-dose), and on days 8, 15 and 22 to monitor knockdown. Knockdown was measured by quantifying circulating cyno F12 protein (cF12) levels in serum by a human F12 ELISA kit (Molecular Innovations).

cF12 levels for each animal at a respective time point was divided by the pre-treatment level (average of day −7 and day 1) of expression in that animal to determine the ratio of expression "normalized to pre-dose". Experimental error is given as standard deviation.

Figure 20:
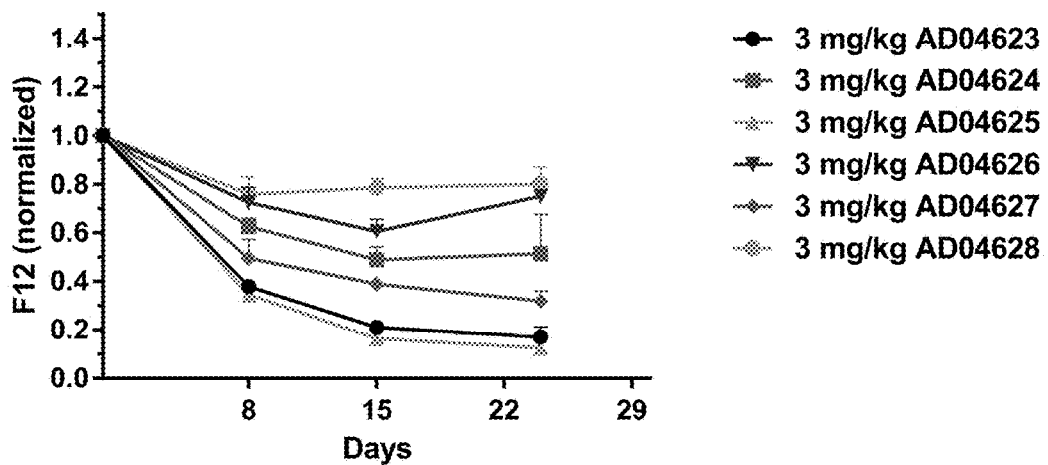
FIG. 20 is a graph illustrating normalized cF12 protein levels in cynomolgus monkeys (which is described below in Example 21).

FIG. 20 shows the results. Each of the F12 RNAi agents linked to NAG37 (Structure 1008) showed knockdown in cynomolgus monkeys, with AD04625 and AD04623 showing the greatest knockdown across all time points measured.

Example 22. Alpha-1 Antitrypsin Expression-Inhibiting Oligomeric Compounds (Double-Stranded RNAi Agents) Linked to Targeting Ligands of Structure 1008 in PiZ Transgenic Mice To evaluate RNAi agents directed to the alpha-1 antitrypsin (AAT) gene in vivo, a transgenic PiZ mouse model (PiZ mice) was used. PiZ mice harbor the human PiZ AAT mutant allele and model human AATD (Carlson et al., Journal of Clinical Investigation 1989). AAT expression-inhibiting oligomeric compounds (double stranded RNAi agents) were prepared having the sequences set forth in the following Table 9:

TABLE 9

AAT expression-inhibiting oligomeric compounds (RNAi agent duplexes) of Example 22.

| Duplex ID: AD04663 | 5'→3' | SEQ ID NO: |
|---|---|---|
| Sense Strand Sequence: (AM05968-SS) | (NAG37)s(invAb)sucaacaAfAfCfccuuugucuus(invAb) | 37 |
| Antisense Strand Sequence: (AM05969-AS) | asAfsgsAfcAfaAfgGfgUfuUfgUfuGfausu | 38 |

(NAG37)s has the chemical structure as shown in Example 16, above.

The AAT RNAi agent was prepared in a pharmaceutically acceptable saline buffer and administered by subcutaneous (SC) injection into the loose skin on the back between the shoulders of 200 μl solution/20 g mouse to PiZ mice to evaluate knockdown of AAT gene expression. Each mouse received a single SC dose of 3 mg/kg (mpk) of AD04463. Three mice were dosed with the AAT RNAi agent (n=3).

Plasma samples were drawn and analyzed for AAT (Z-AAT) protein levels on days −1, day 1 (pre-dose), day 8, and day 15. AAT levels were normalized to day 1 (pre-dose) AAT plasma levels. Protein levels were measured by quantifying circulating human Z-AAT levels in plasma by an ELISA kit.

Figure 21:
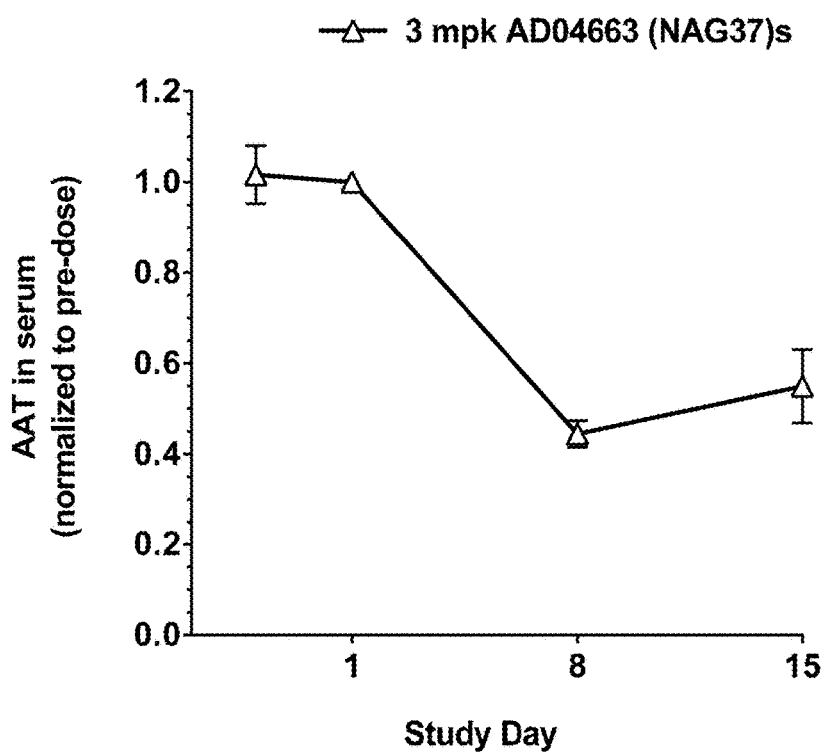
FIG. 21 is a graph illustrating normalized AAT (Z-AAT) protein levels in PiZ transgenic mice (which is described below in Example 22).

The average normalized AAT (Z-AAT) levels are shown in FIG. 21. The AAT RNAi agent linked to the targeting ligand of Structure 1008 herein showed knockdown in PiZ transgenic mice.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:
1. A targeting ligand comprising a structure selected from the group consisting of:
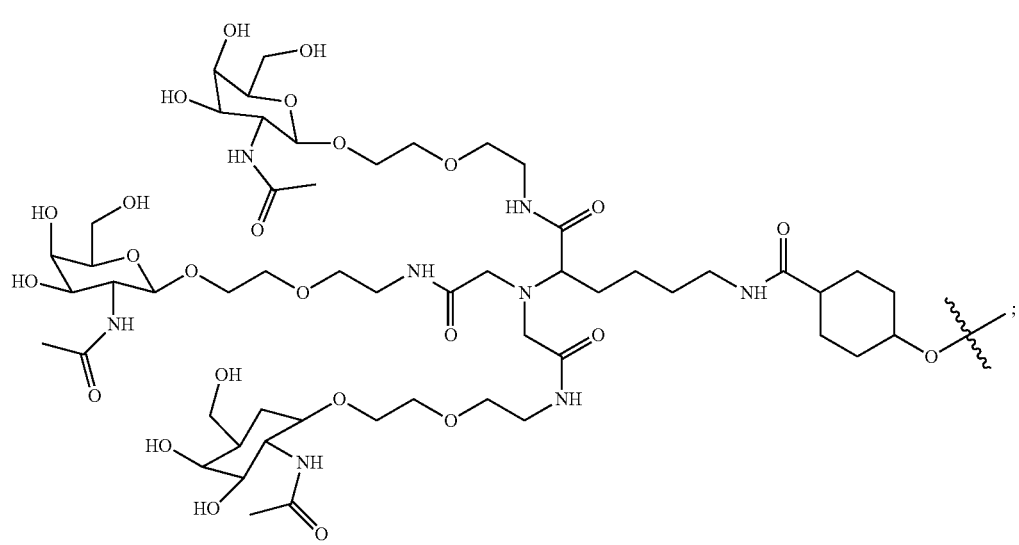
(Structure 1001)
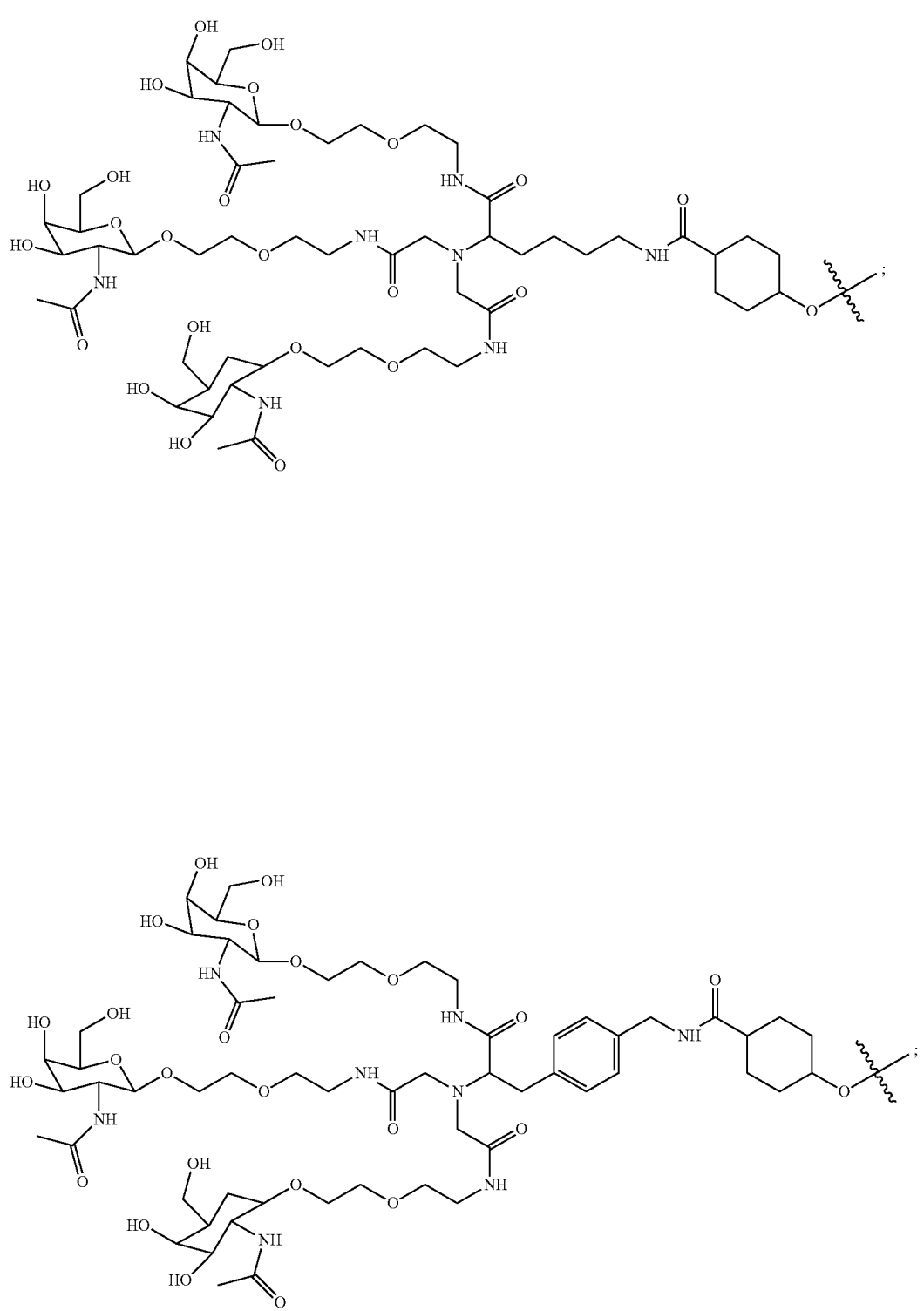
(Structure 1002)

(Structure 1003)
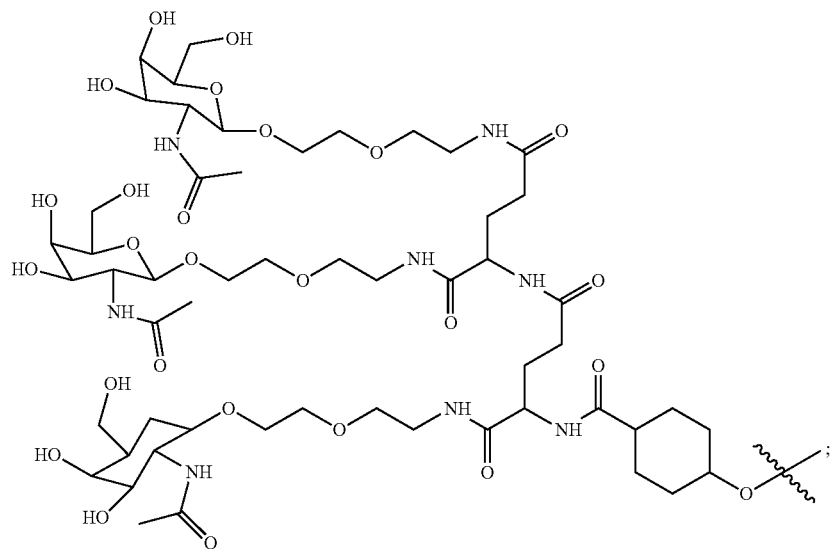
(Structure 1004)
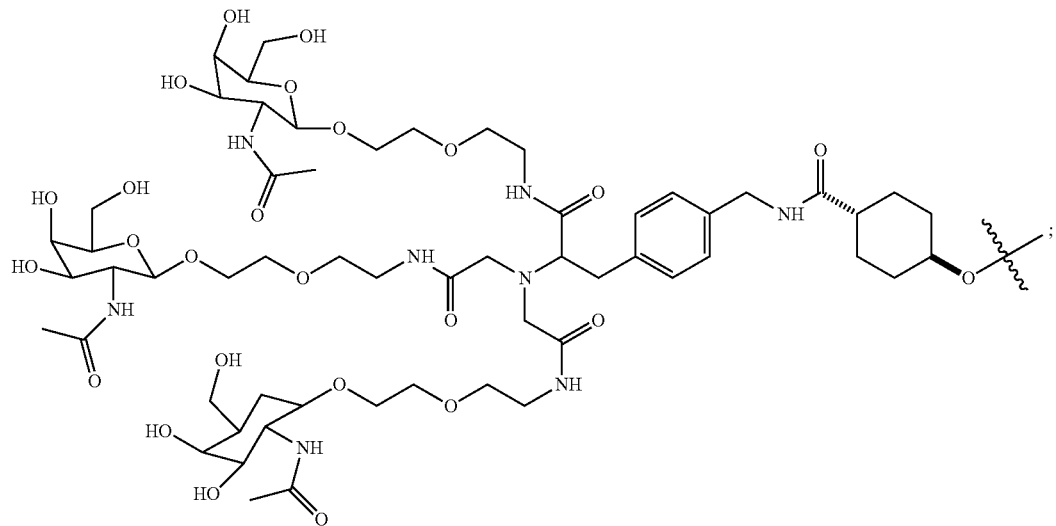
(Structure 1005)
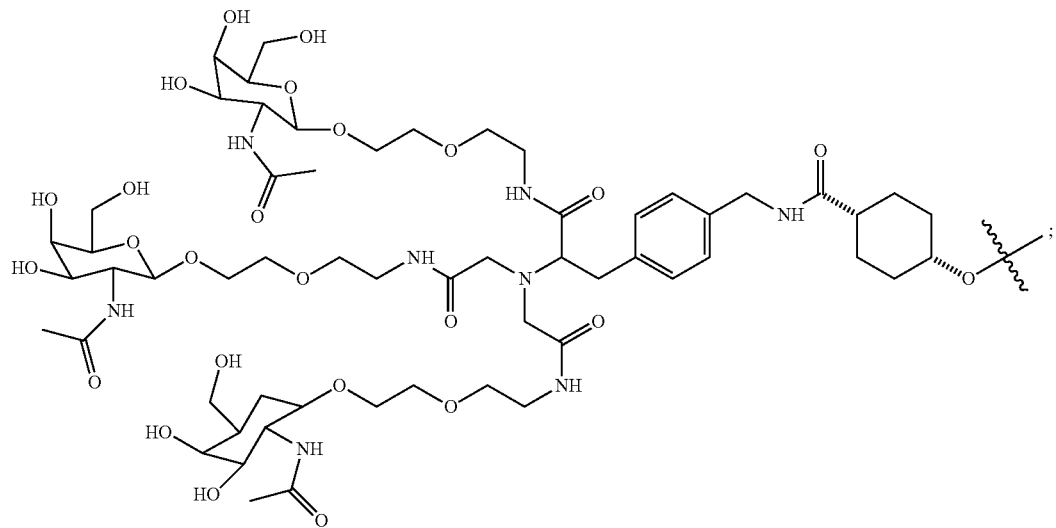

-continued
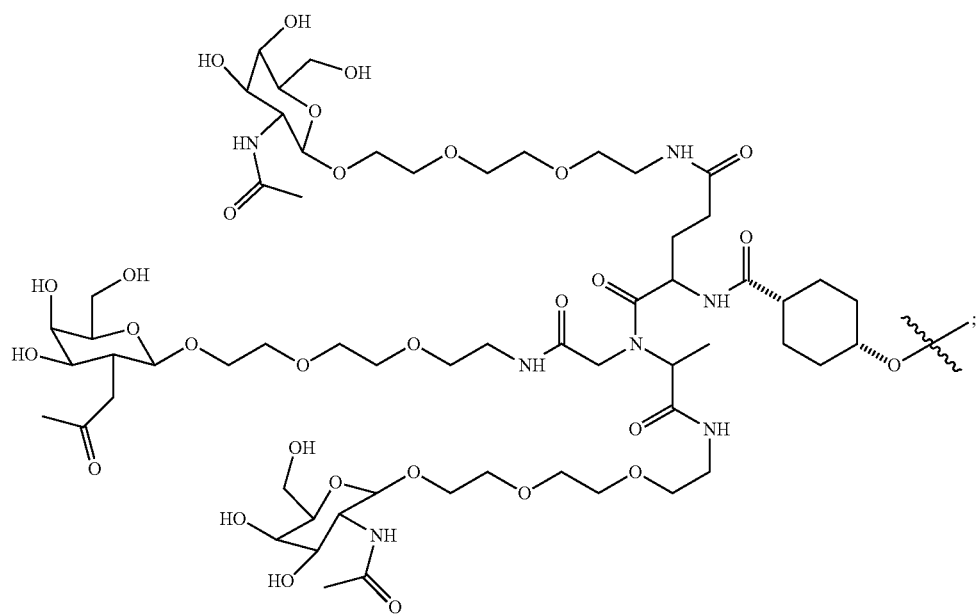
(Structure 1006)
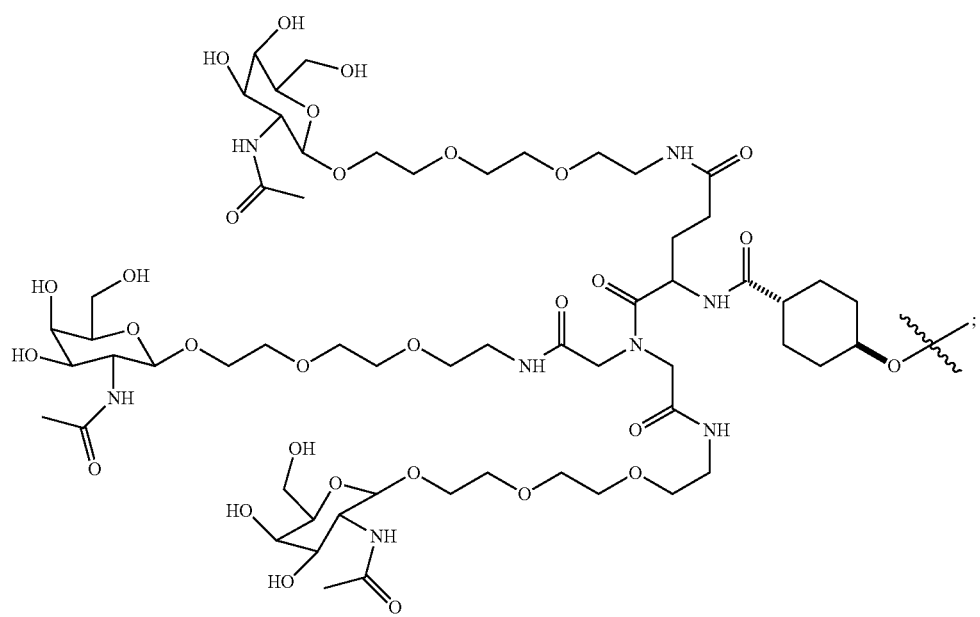
(Structure 1007)

(Structure 1008)
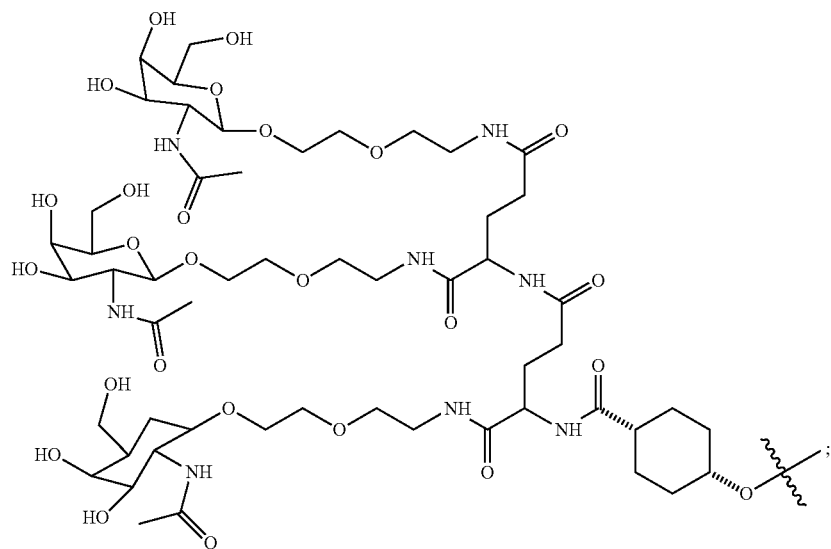
(Structure 1009)
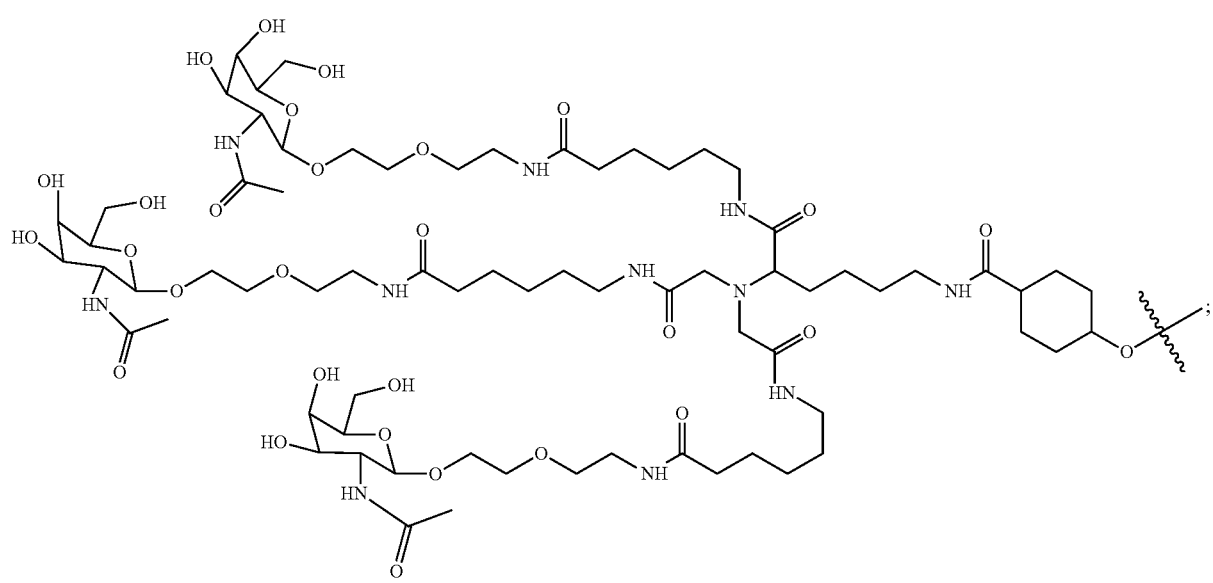

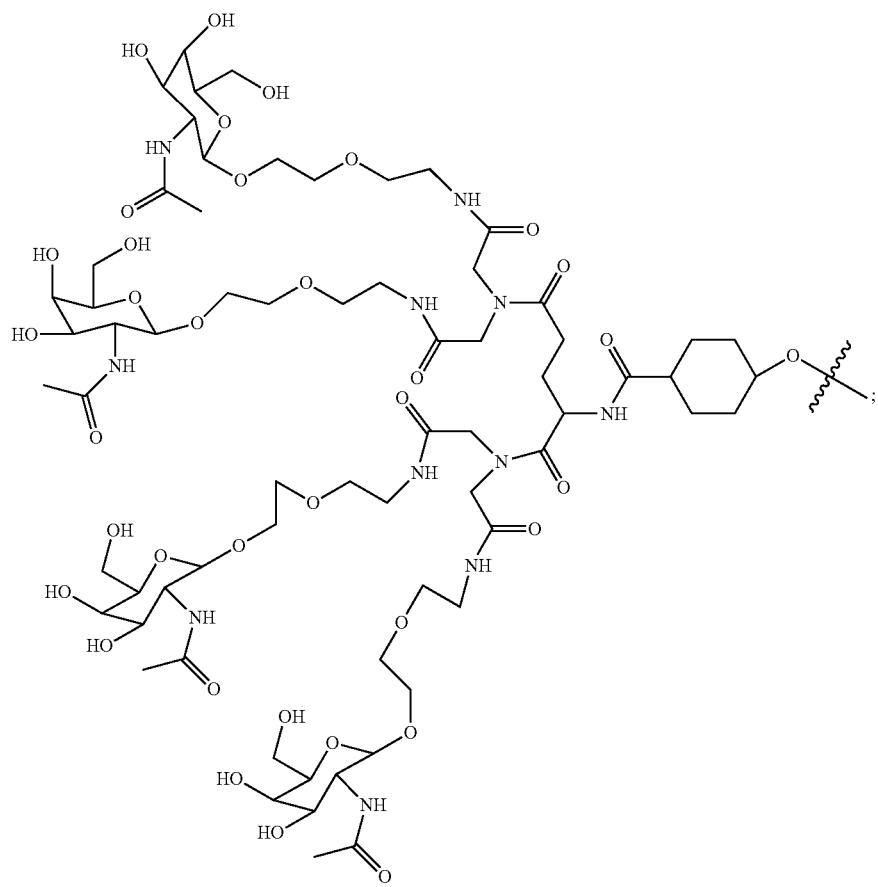
(Structure 1012)
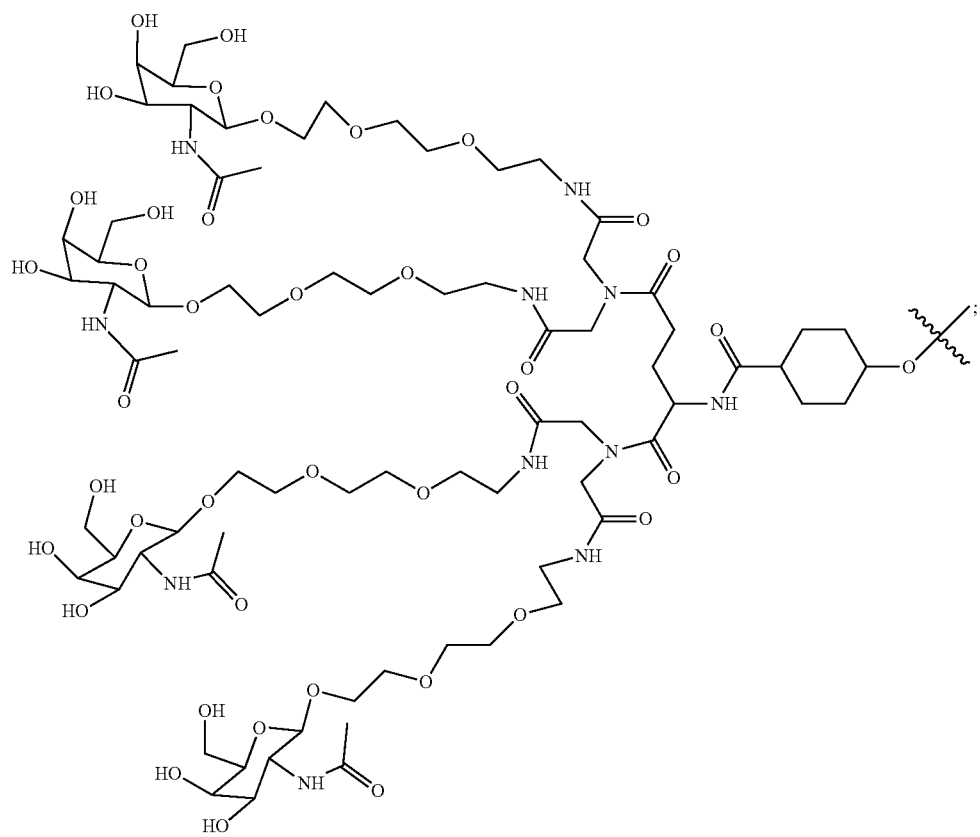
(Structure 1014)

-continued
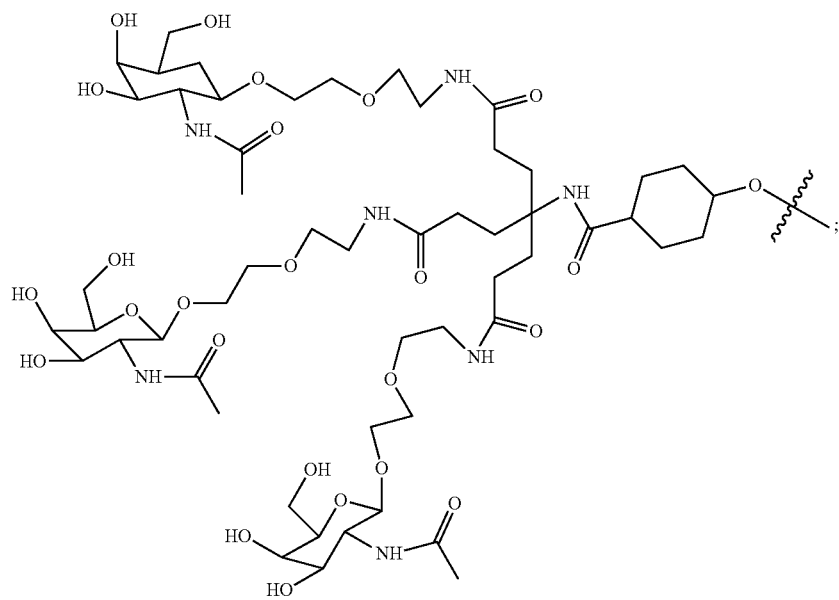
(Structure 1016)
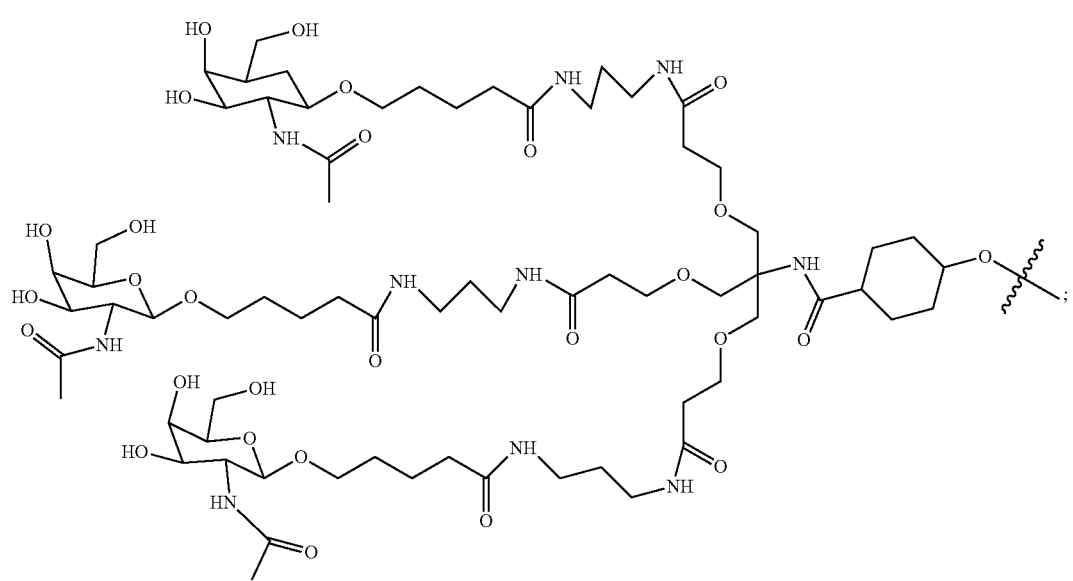
(Structure 1018)

-continued
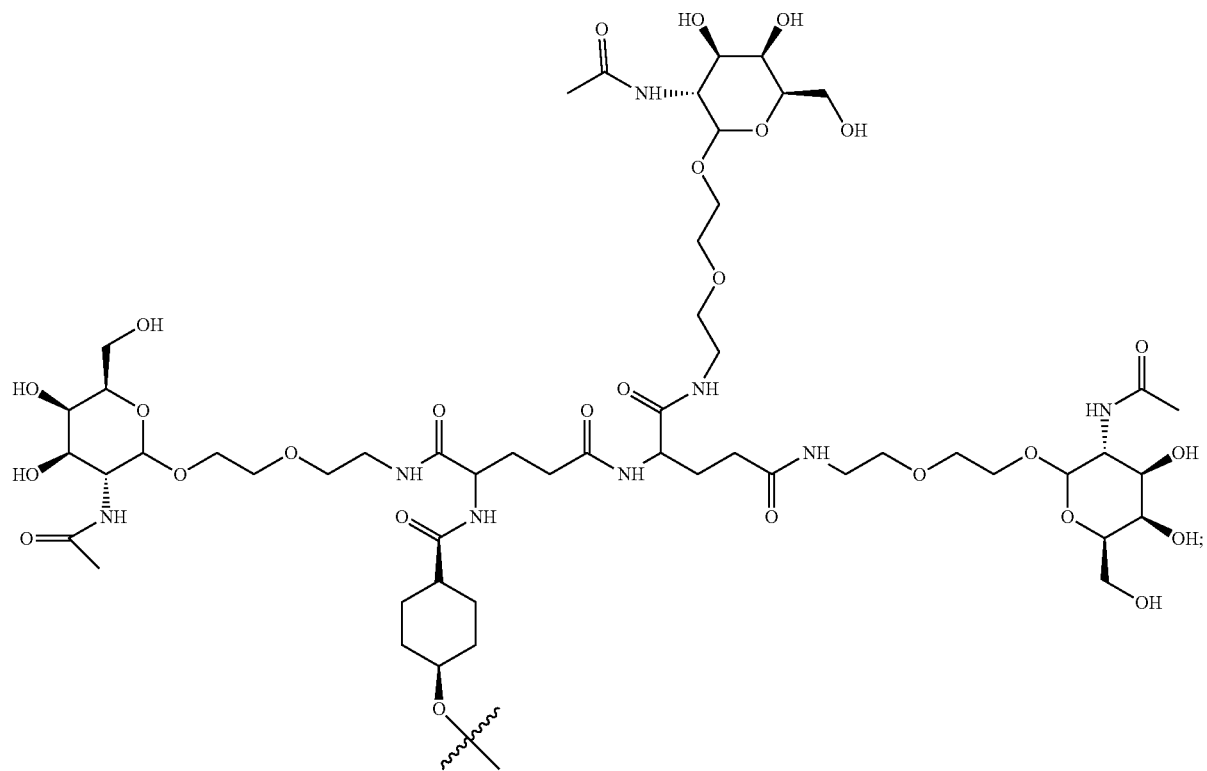
(Structure 1019)
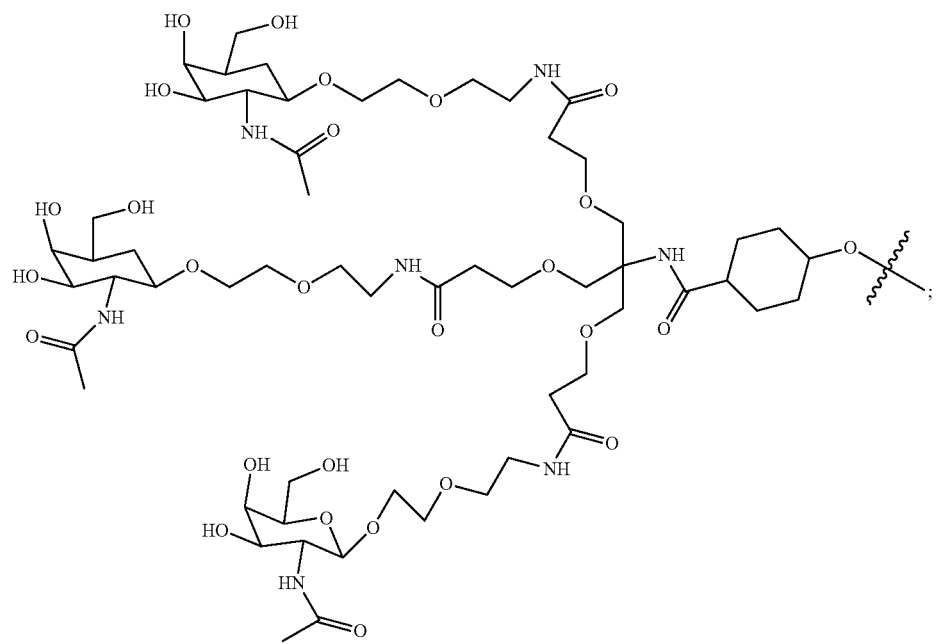
(Structure 1021)

(Structure 1023)
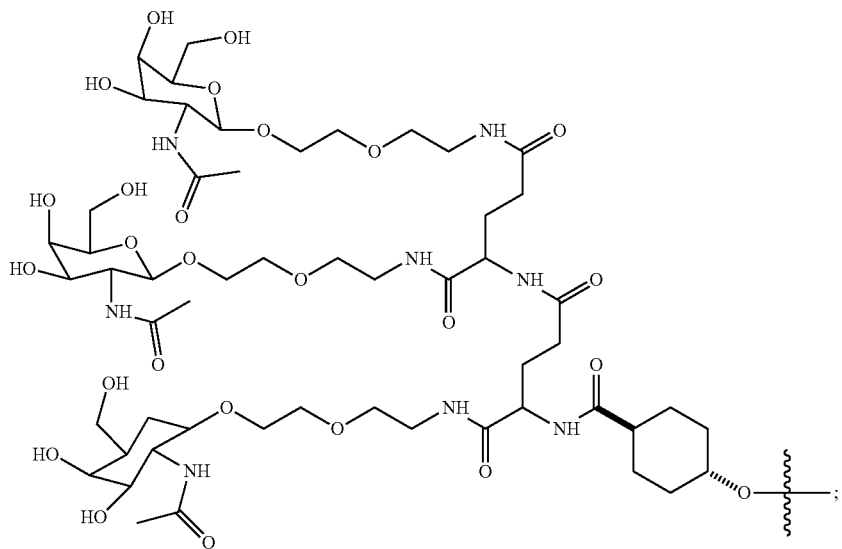
and
(Structure 1024)
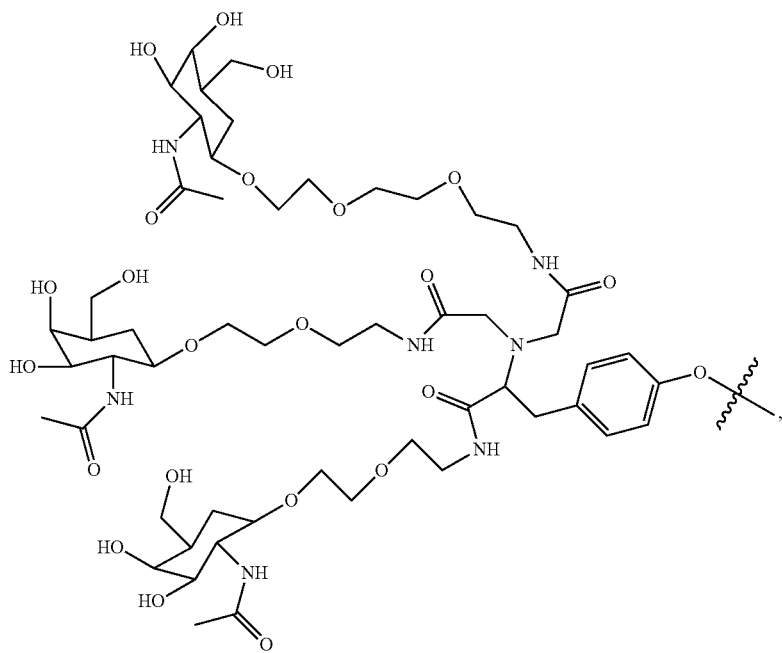
wherein the targeting ligand is linked to an RNAi agent.
2. The targeting ligand of claim 1, wherein the RNAi agent is double-stranded.
3. The targeting ligand of claim 2, wherein the RNAi agent includes one or more modified nucleotides.
4. The targeting ligand of claim 1, wherein the structure is selected from the group consisting of:

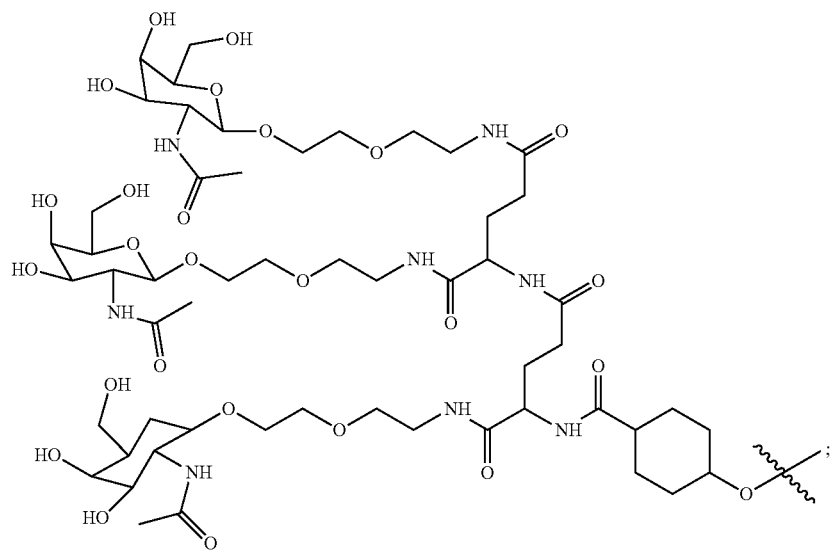
(Structure 1003)
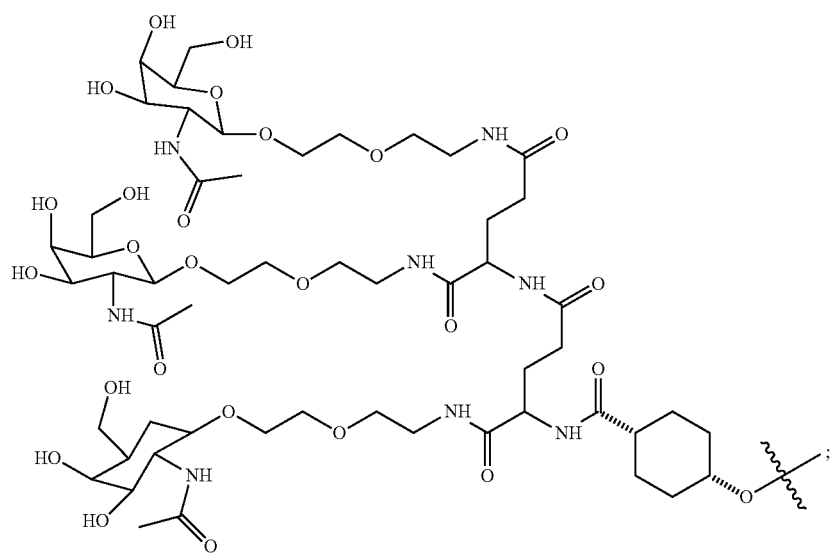
(Structure 1008) and
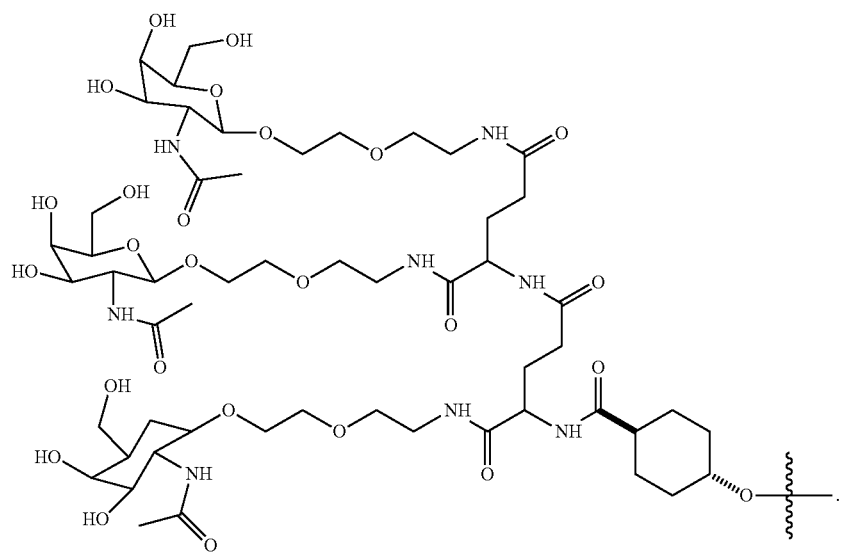
(Structure 1023)

5. The targeting ligand of claim 2, wherein the double-stranded RNAi agent is linked to the targeting ligand at the 5' terminal end of the sense strand of the RNAi agent.

6. The targeting ligand of claim 5, wherein the RNAi agent is linked to the linker of the targeting ligand via a phosphate group, phosphorothioate group, or a phosphonate group.

7. A composition comprising a targeting ligand linked to an expression-inhibiting oligomeric compound, wherein the structure of the targeting ligand and expression-inhibiting oligomeric compound is represented by the structure selected from the group consisting of:

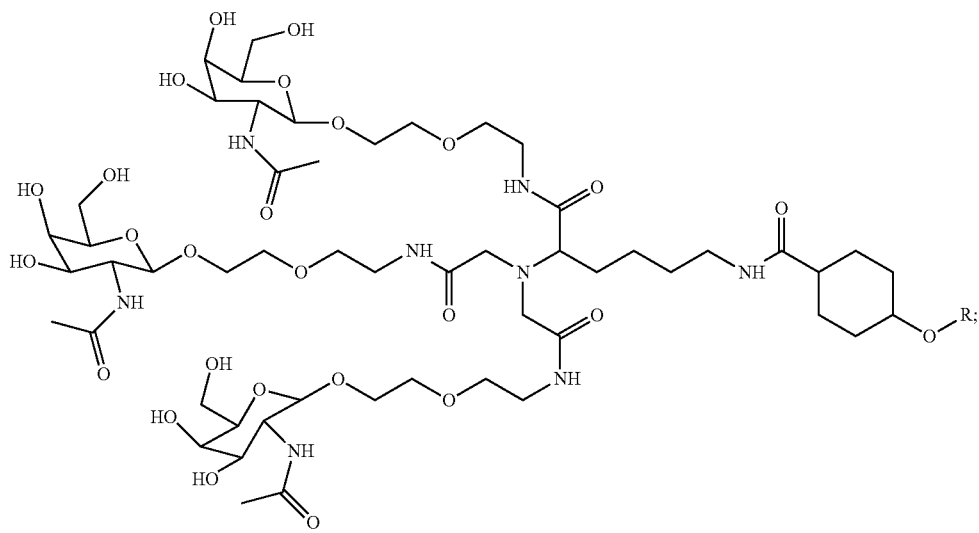

(Structure 1001a)

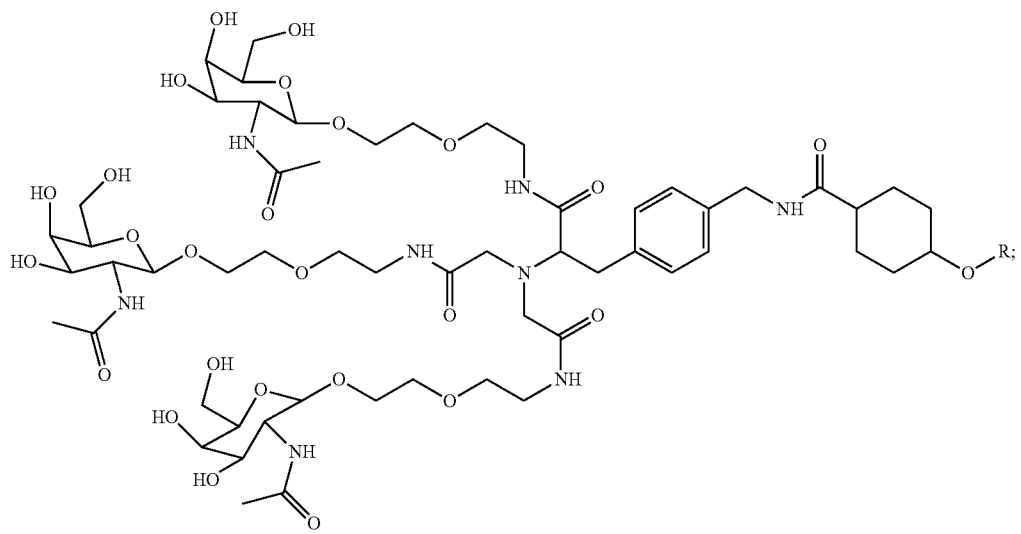

(Structure 1002a)

(Structure 1003a)
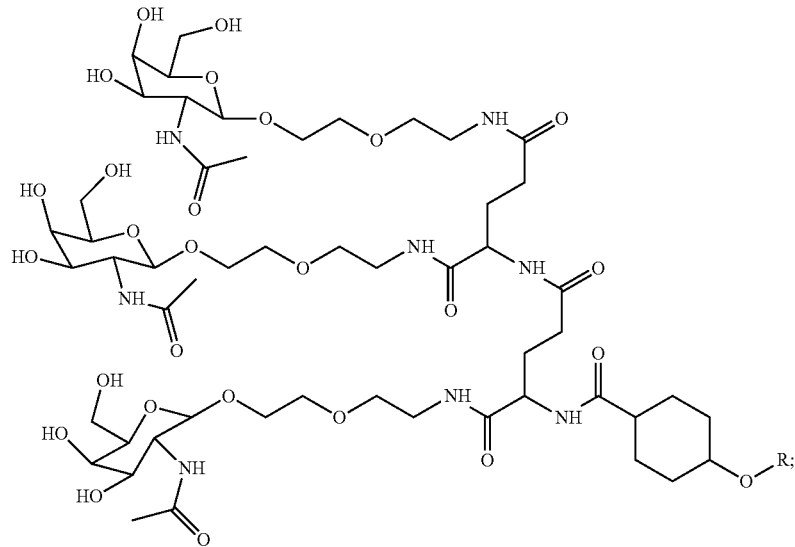
(Structure 1004a)
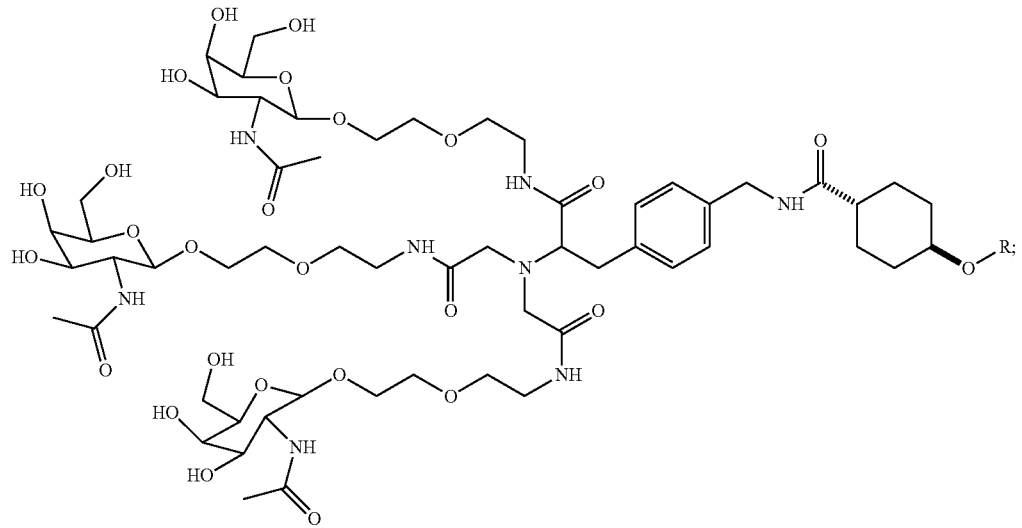
(Structure 1005a)
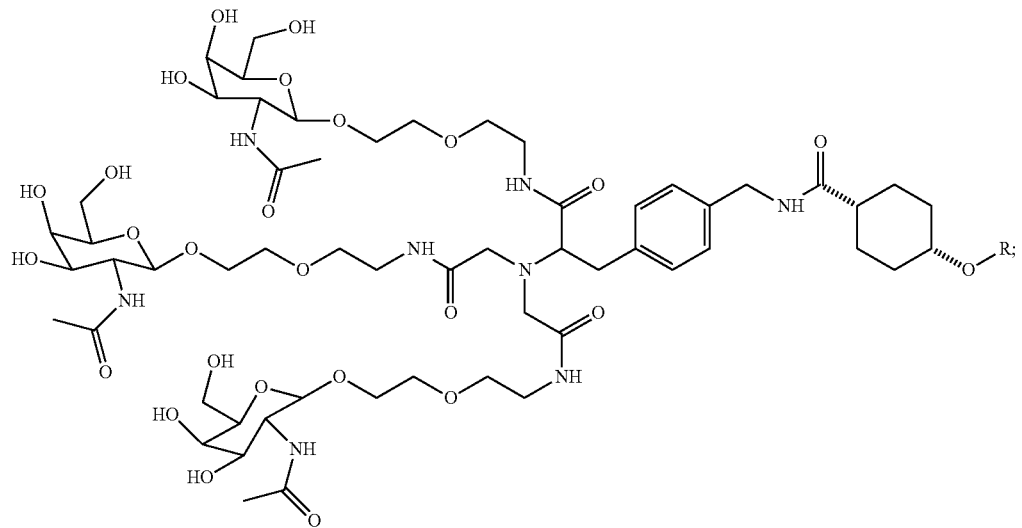

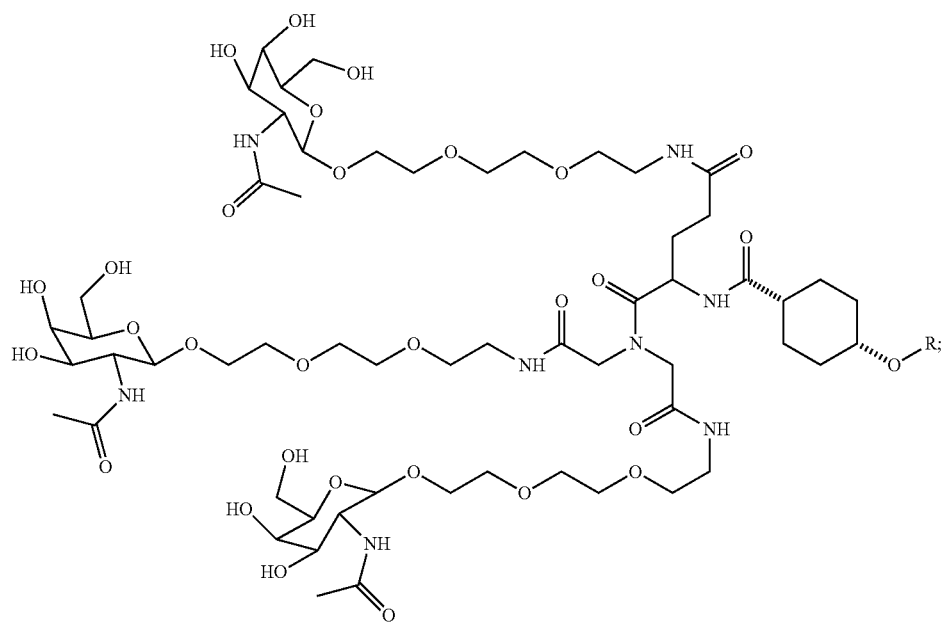
(Structure 1006a)
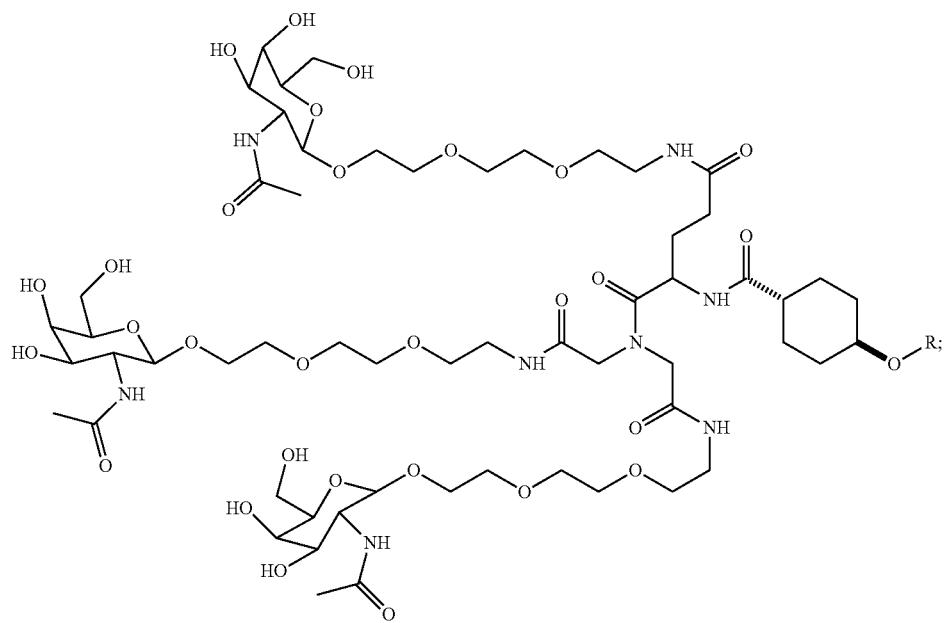
(Structure 1007a)

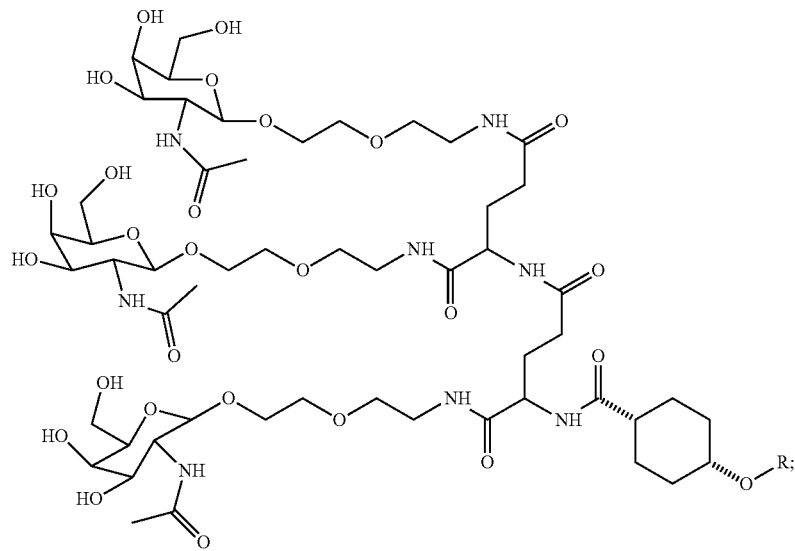
(Structure 1008a)
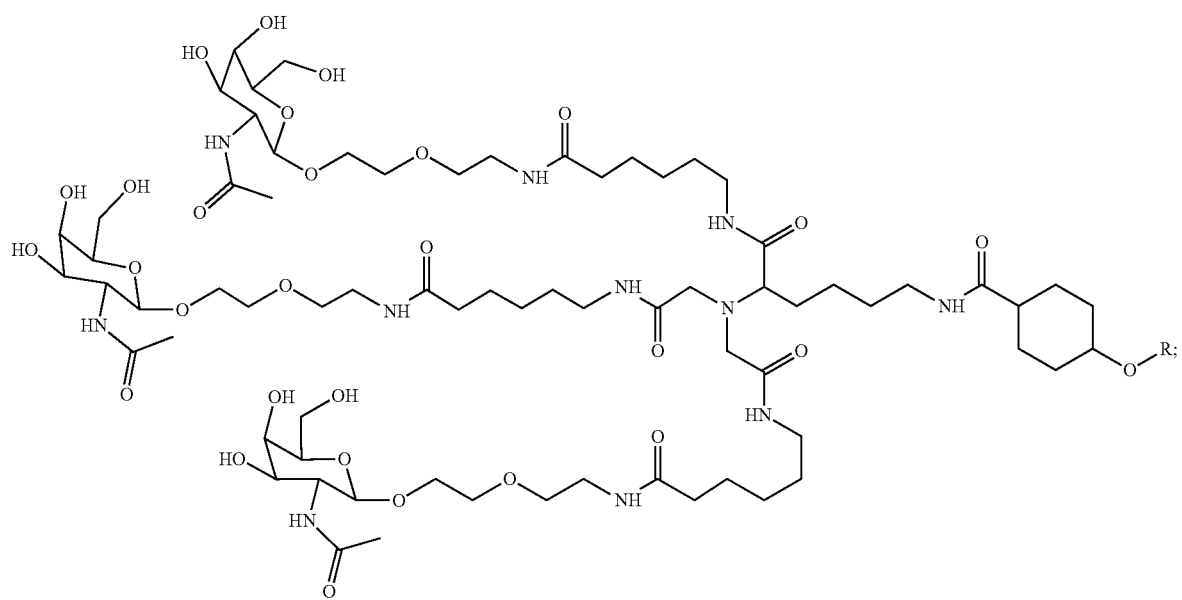
(Structure 1009a)

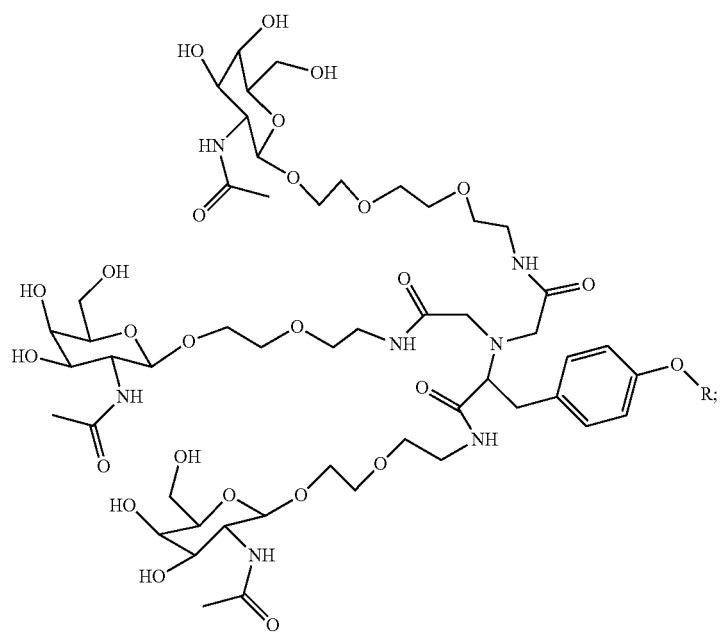
(Structure 1024a)
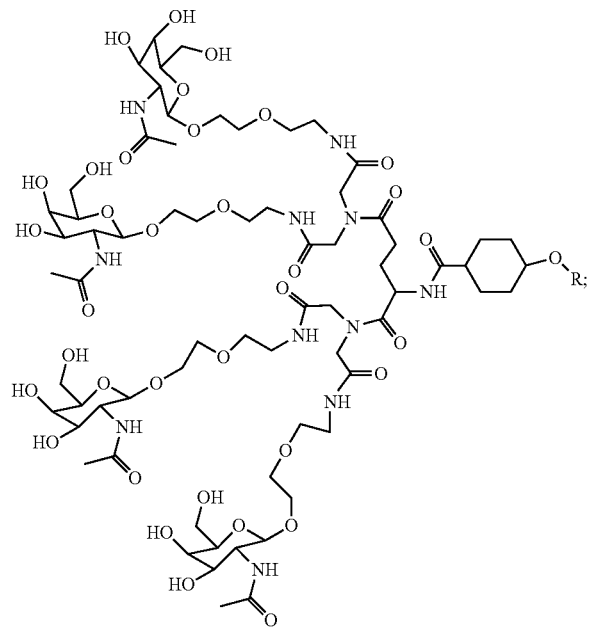
(Structure 1012a)

(Structure 1014a)
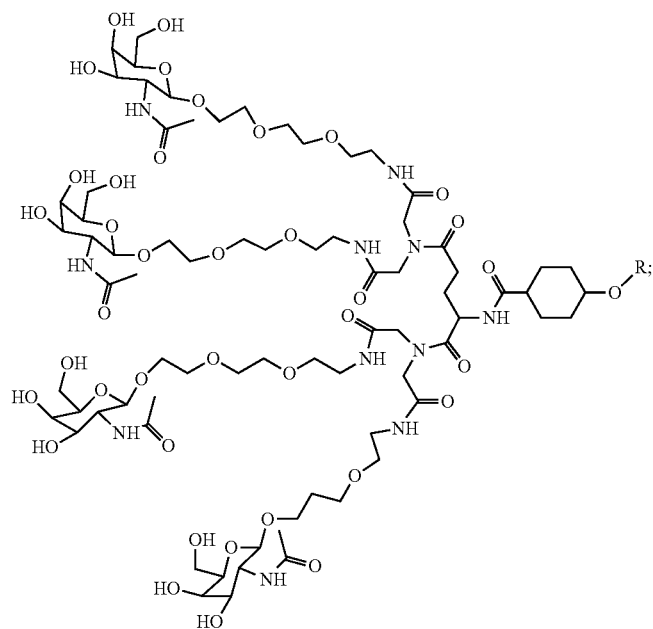
(Structure 1016a)
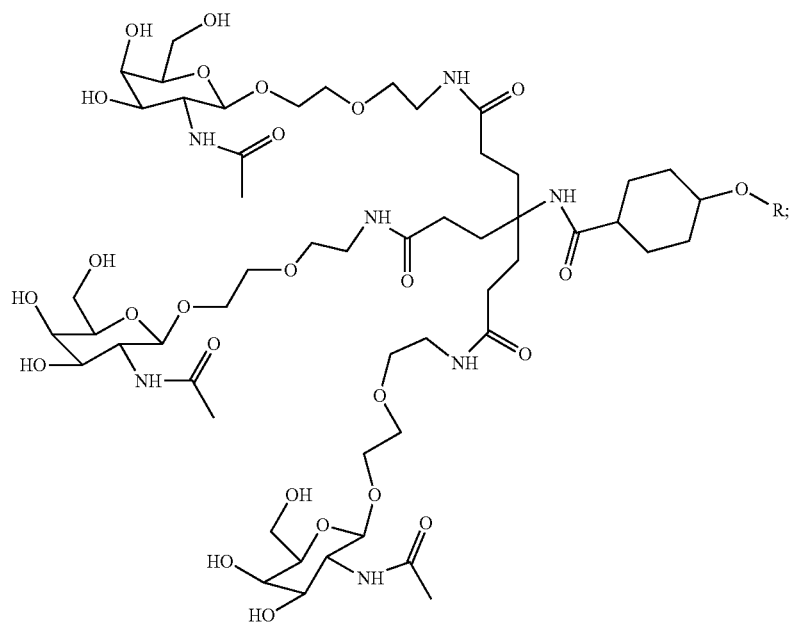

-continued
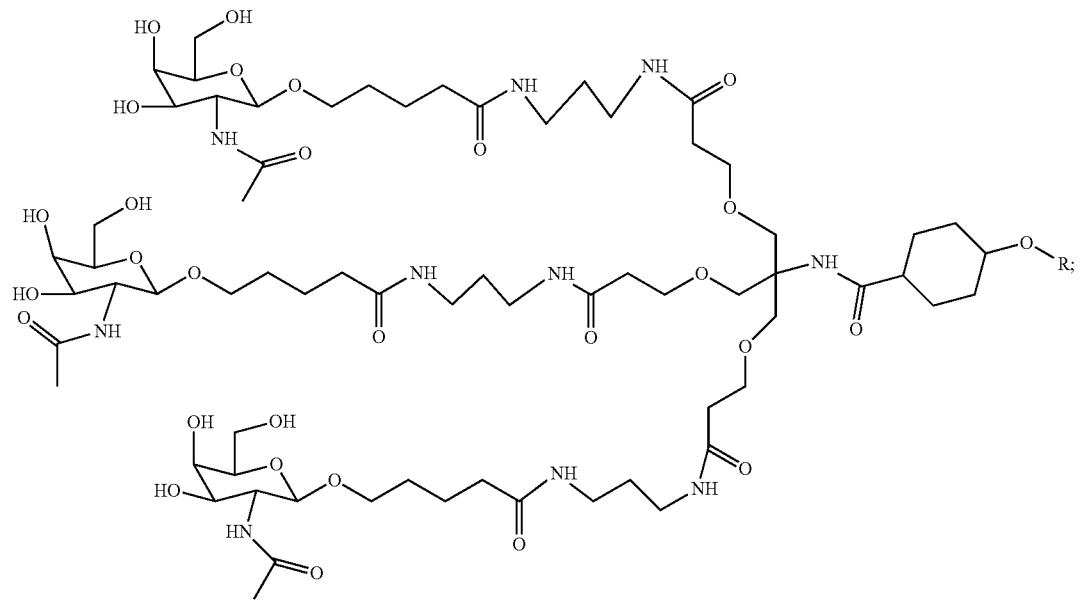
(Structure 1018a)
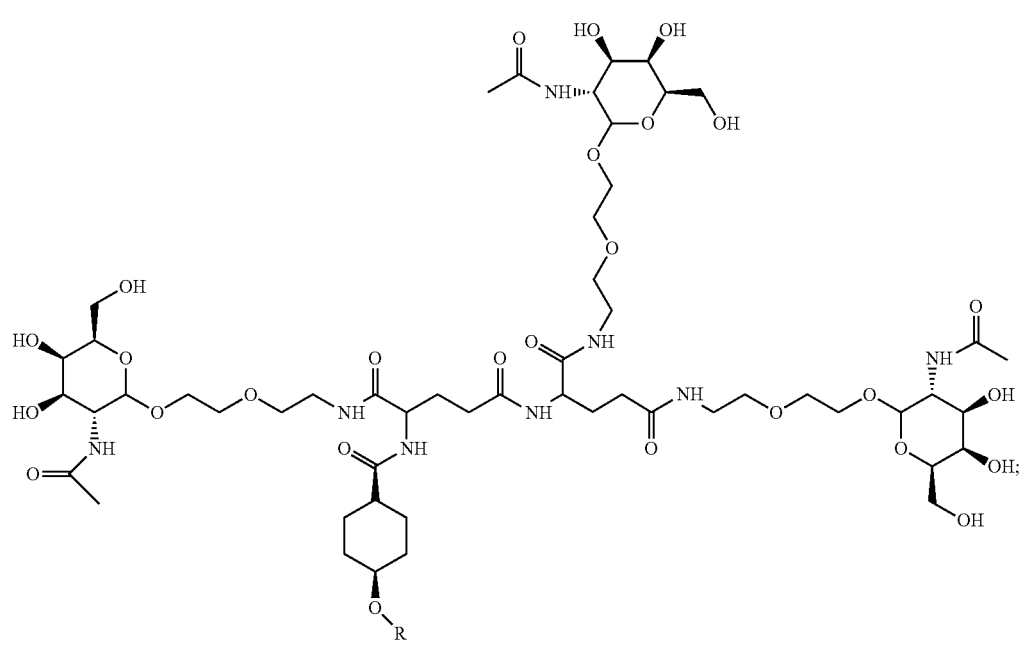
(Structure 1019a)

-continued

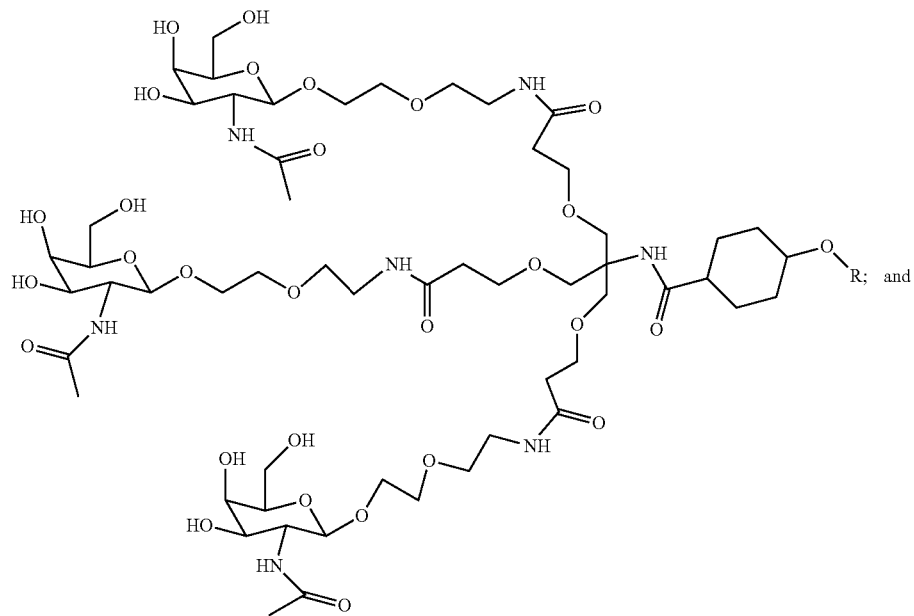

(Structure 1021a)

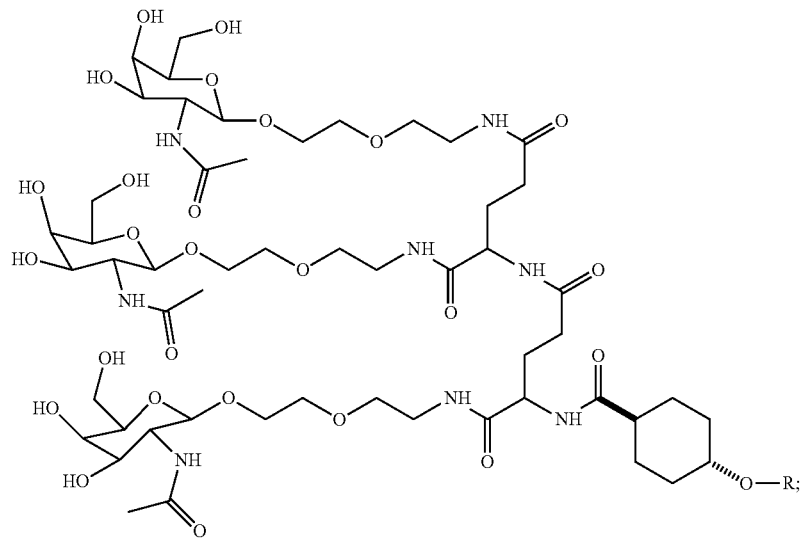

(Structure 1023a)

wherein R in each structure comprises the expression-inhibiting oligomeric compound, wherein the expression-inhibiting oligomeric compound comprises an RNAi agent, and wherein the targeting ligand is linked to the RNAi agent via a phosphate group, phosphorothioate group, or a phosphonate group.

8. The composition of claim 7, wherein the RNAi agent is a double-stranded RNAi agent.

9. The composition of claim 8, wherein the targeting ligand is linked to the 5' terminal end of the sense strand of the RNAi agent.

10. A compound having the structure selected from the group consisting of:

(Structure 1001b)
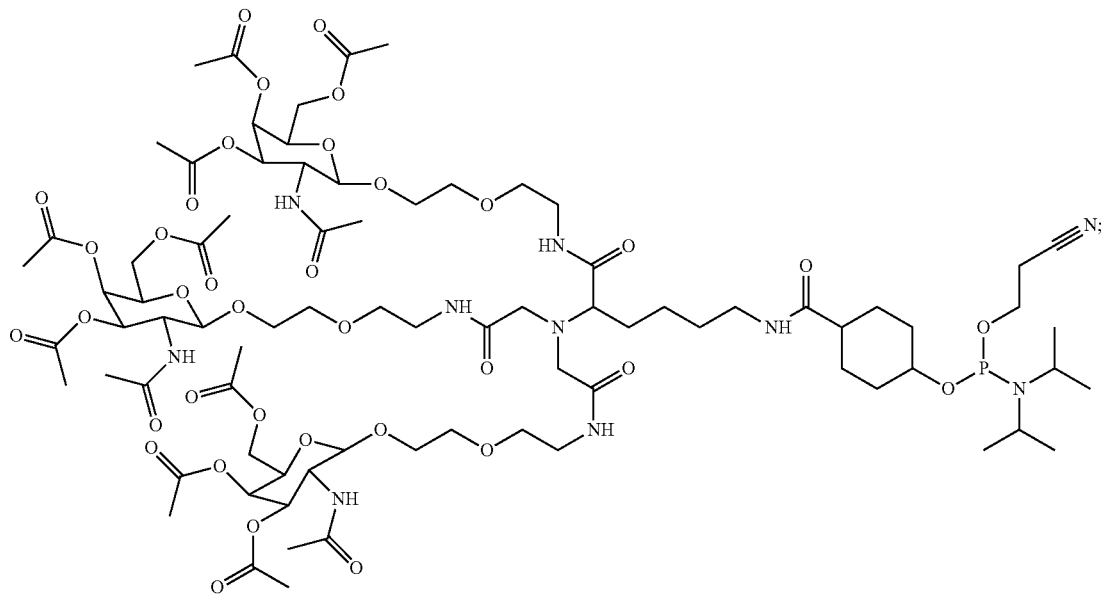
(Structure 1002b)
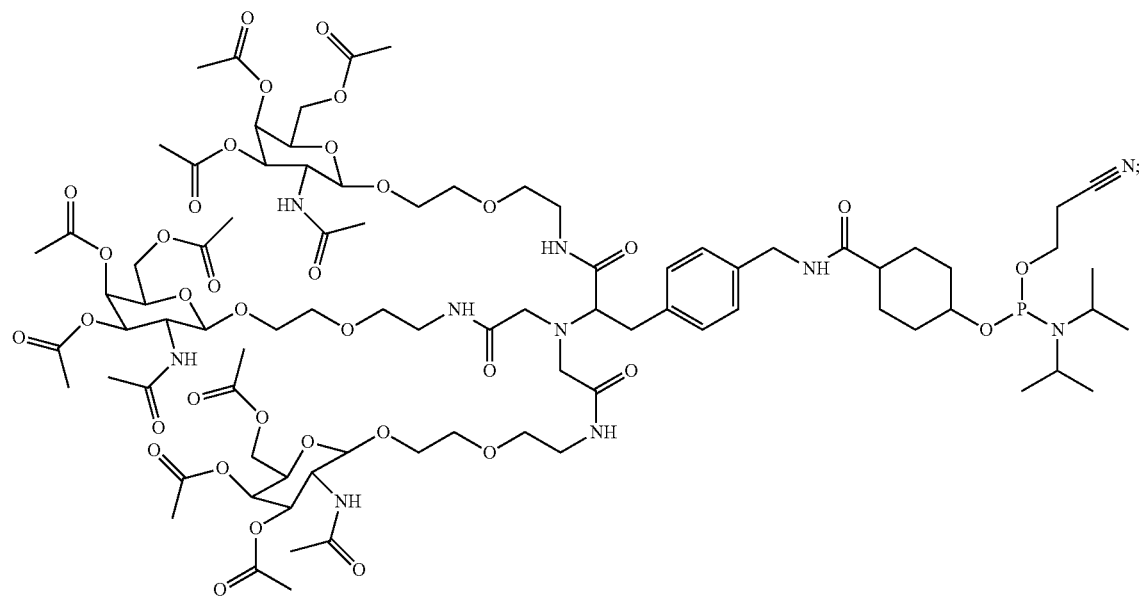

-continued
(Structure 1003b)
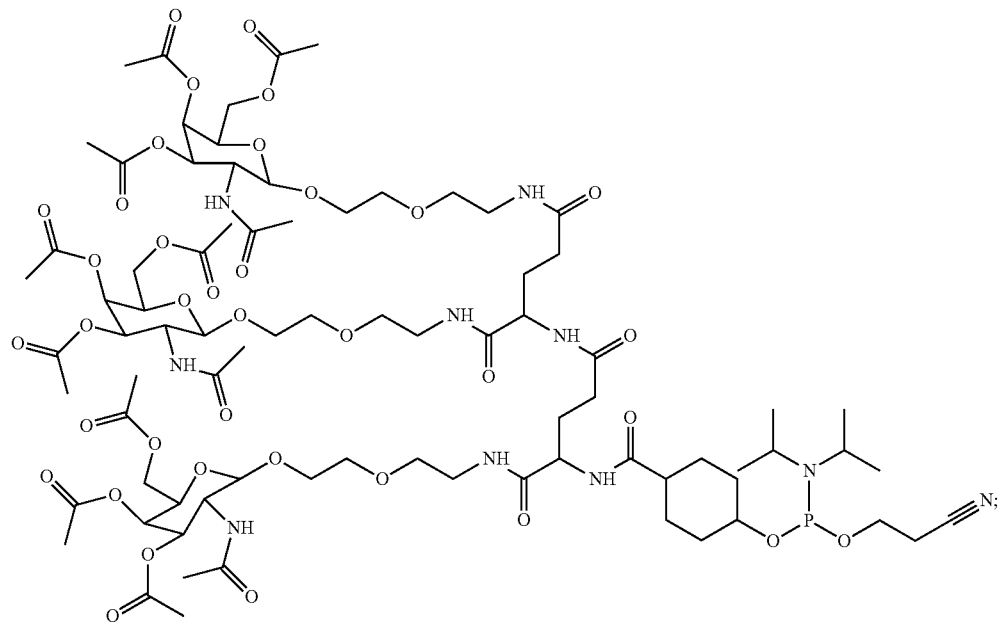
(Structure 1004b)
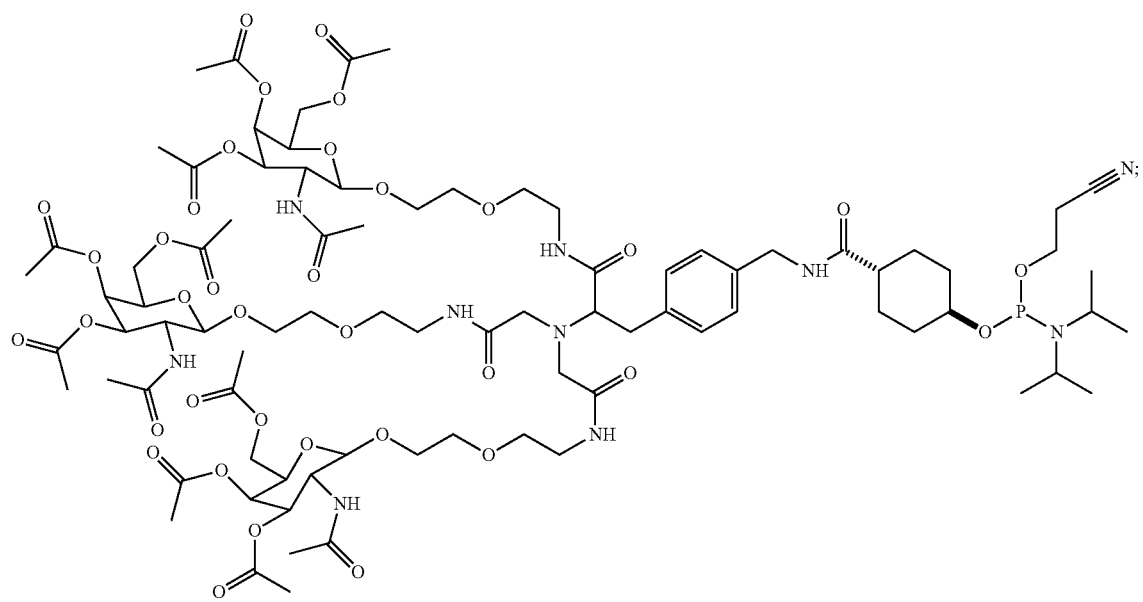

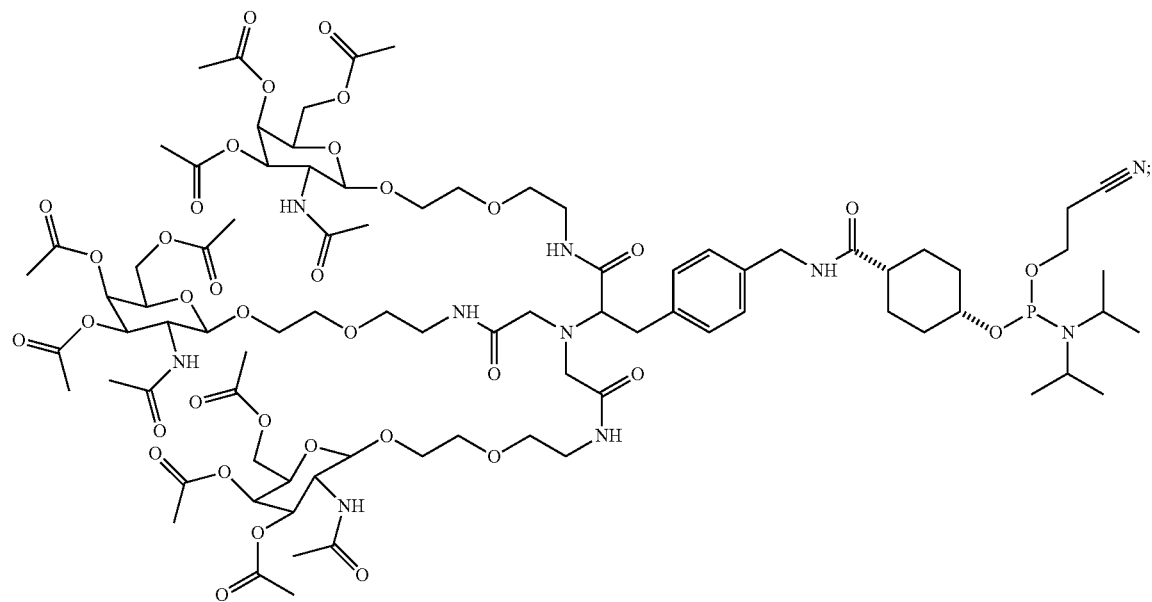
(Structure 1005b)
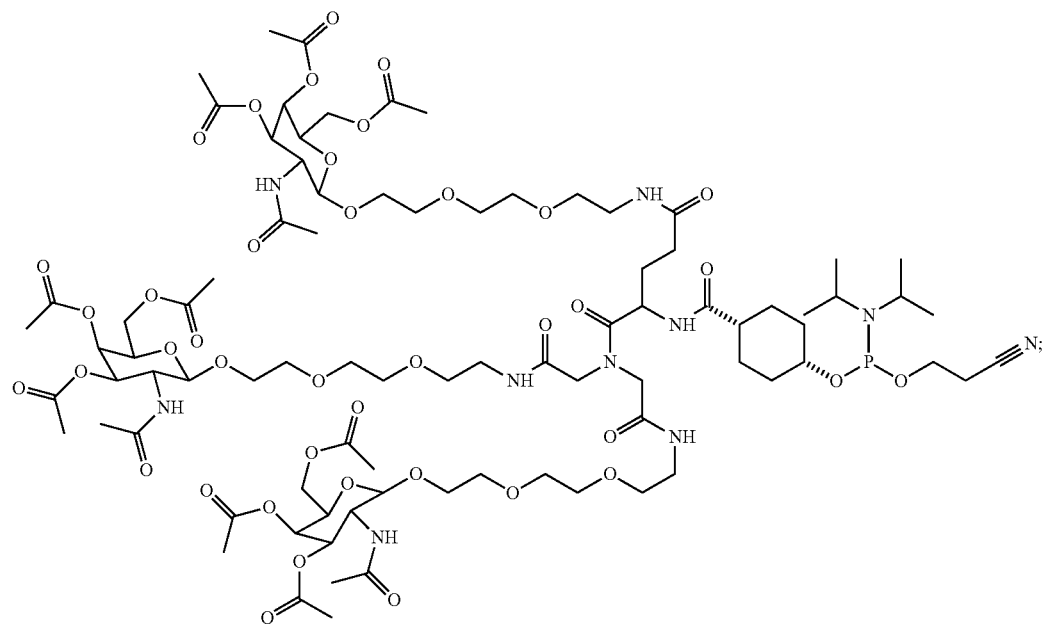
(Structure 1006b)

-continued
(Structure 1007b)
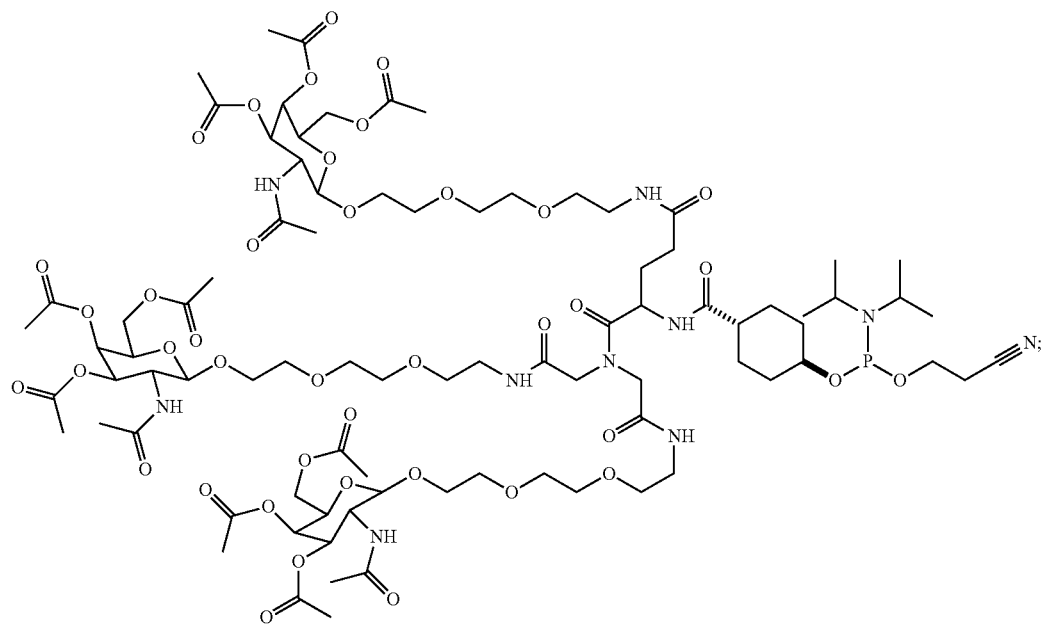
(Structure 1008b)
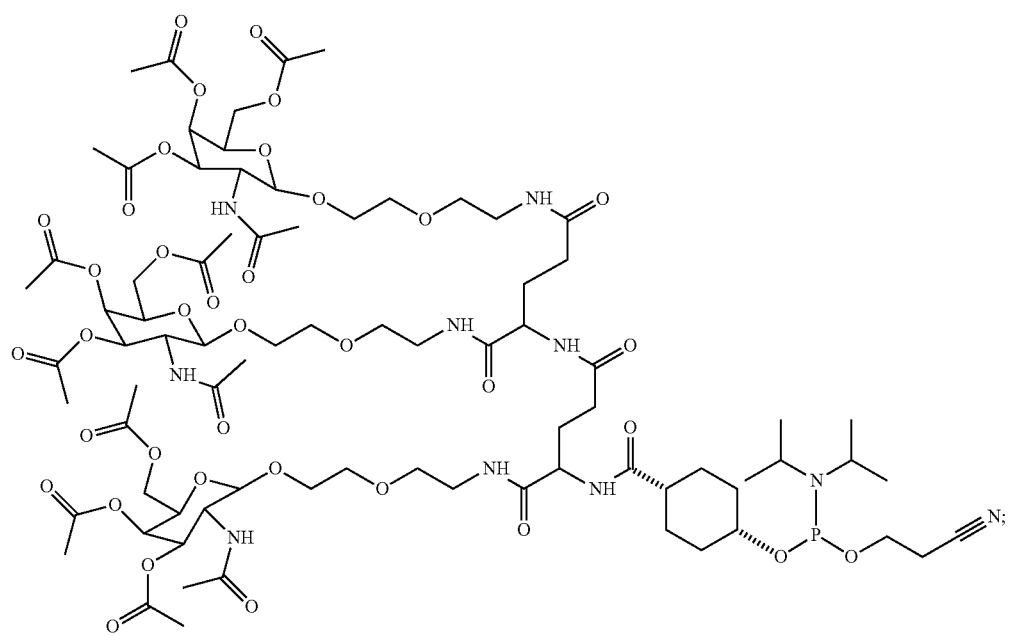

-continued
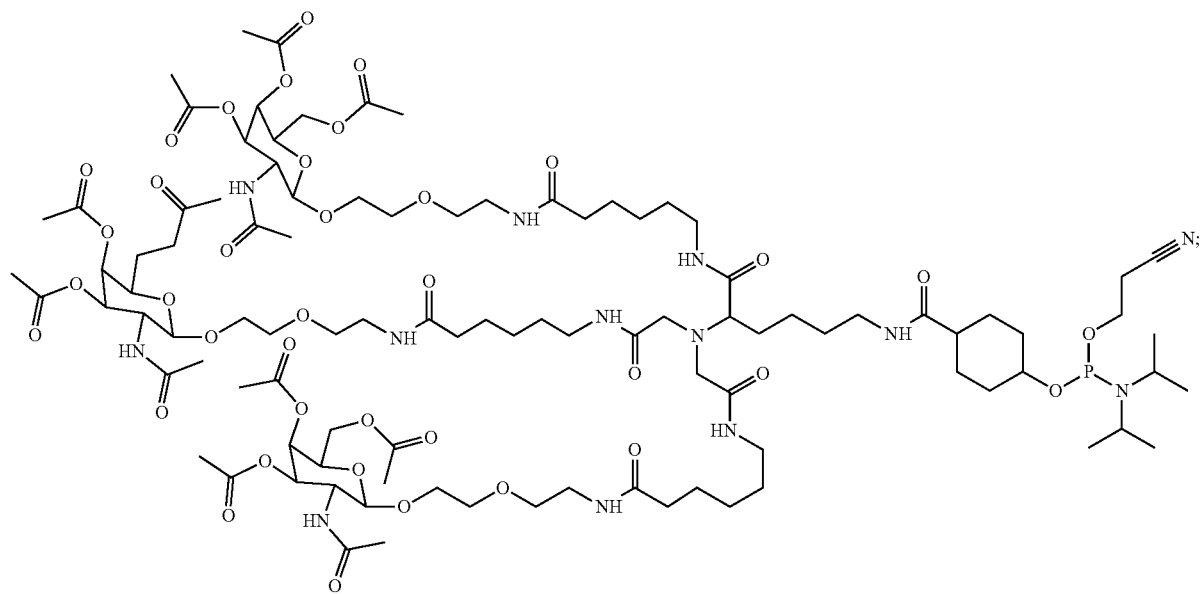
(Structure 1009b)
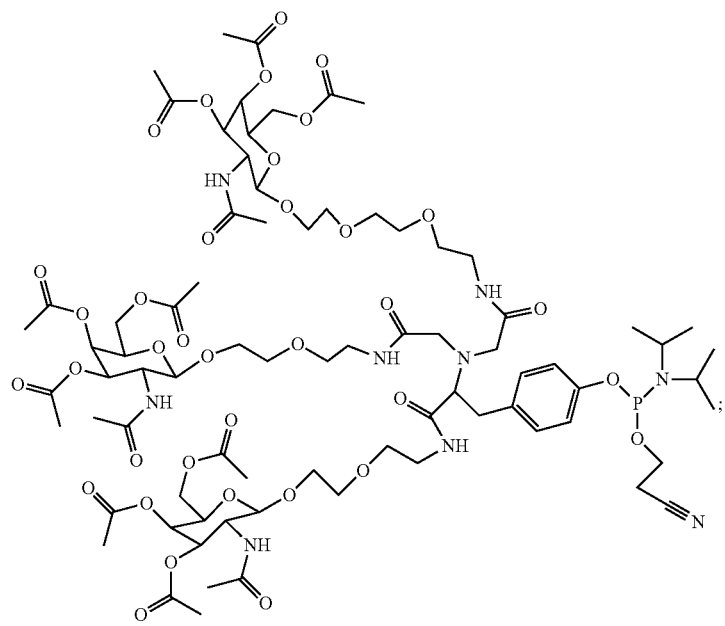
(Structure 1024b)

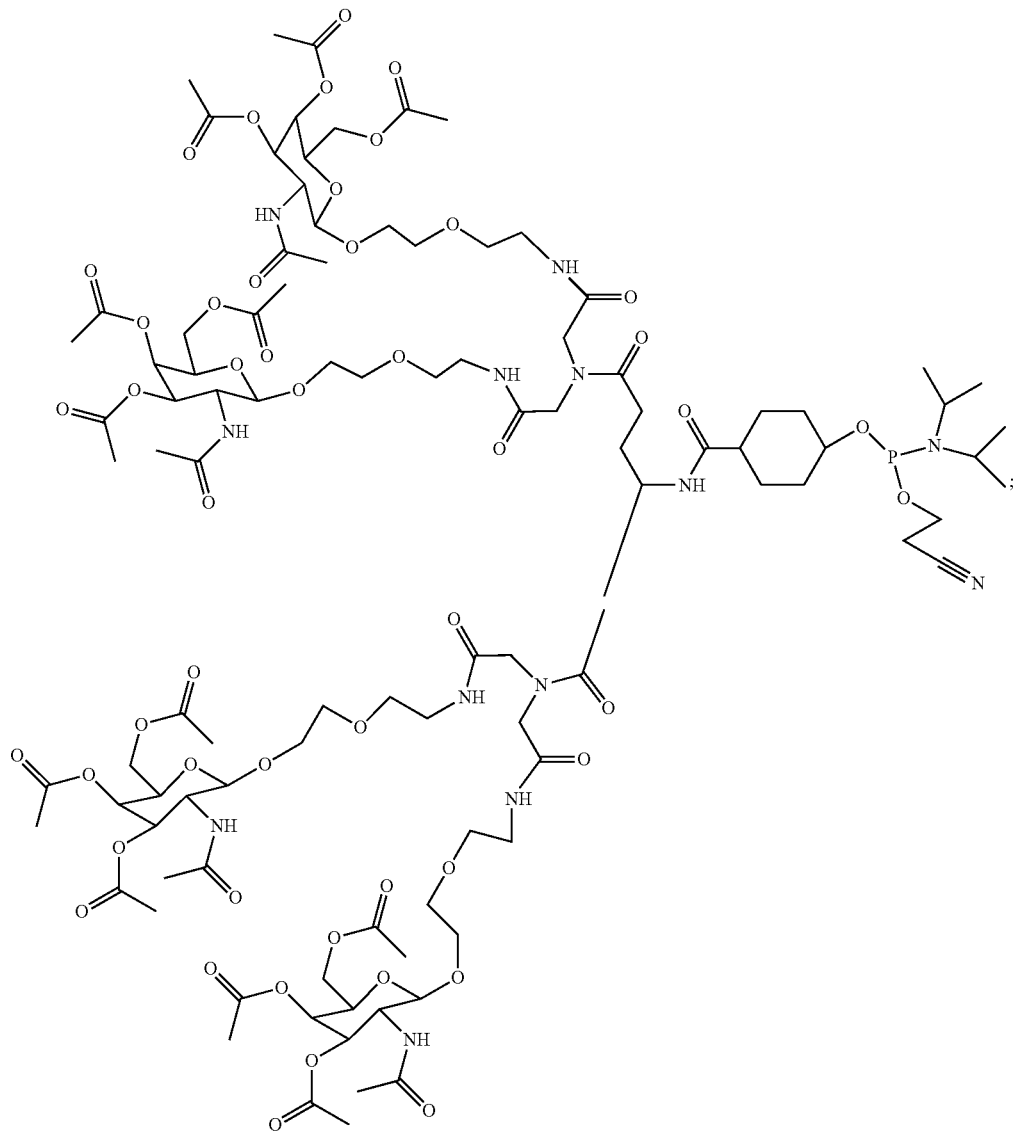
(Structure 1012b)

-continued
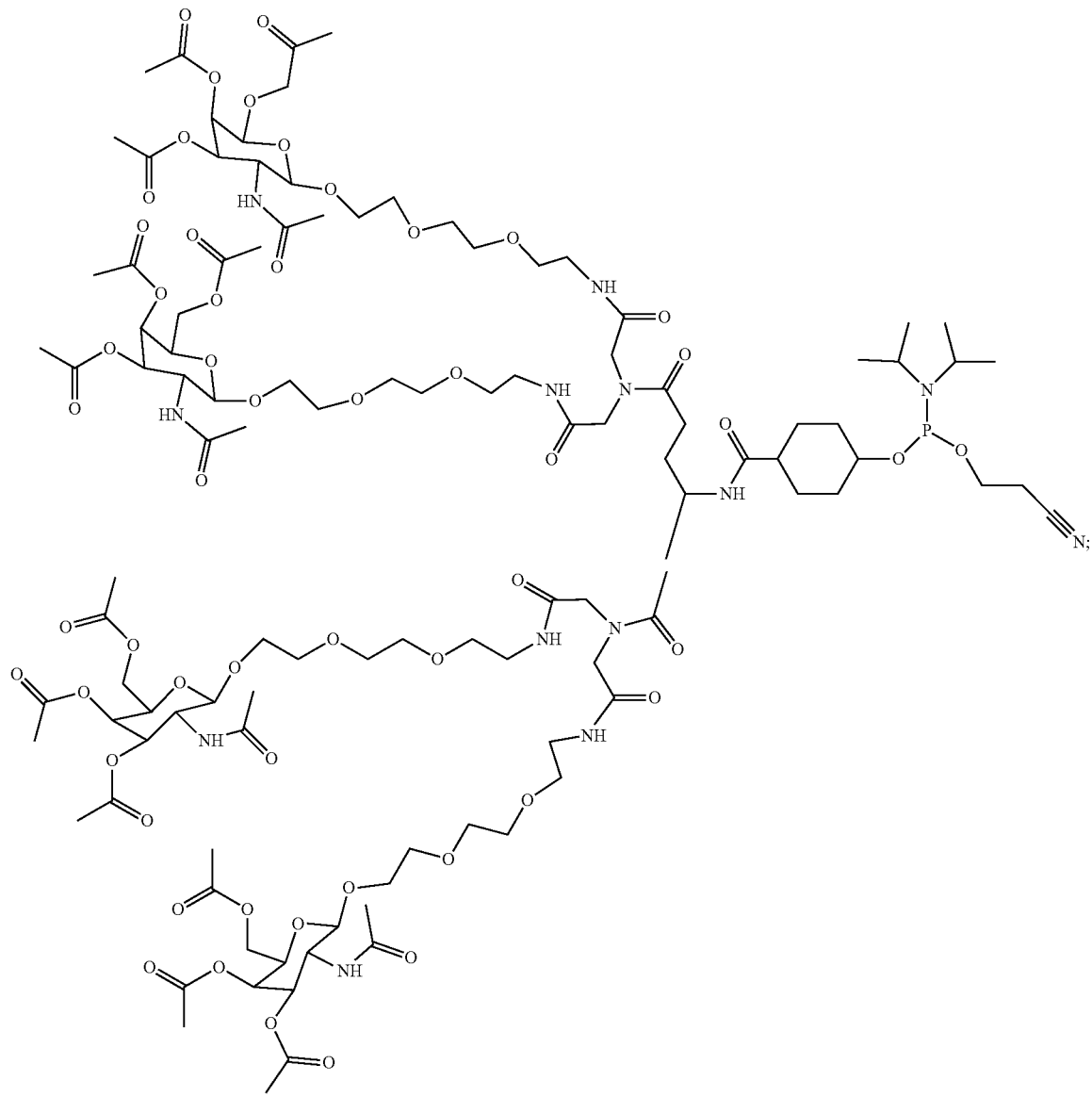
(Structure 1014b)

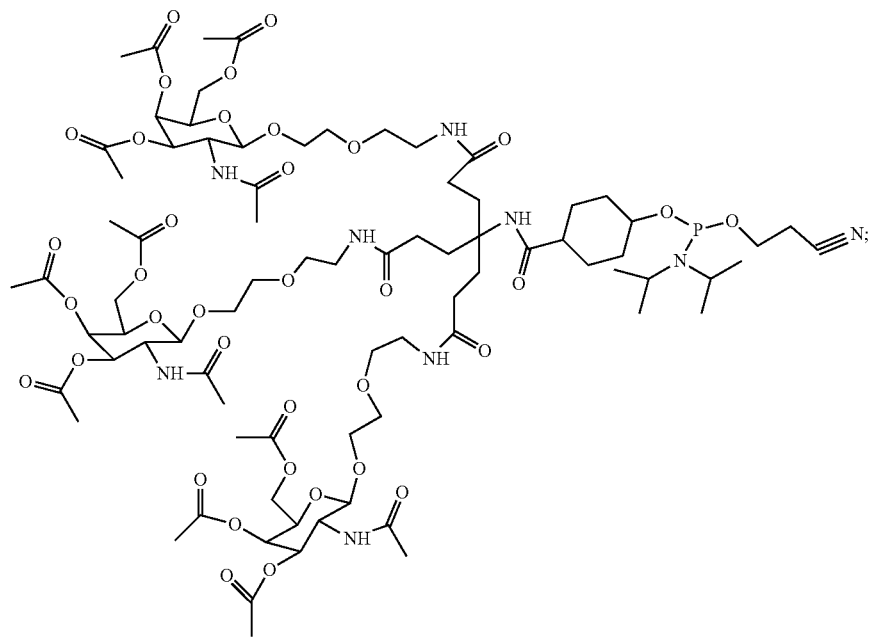
(Structure 1016b)
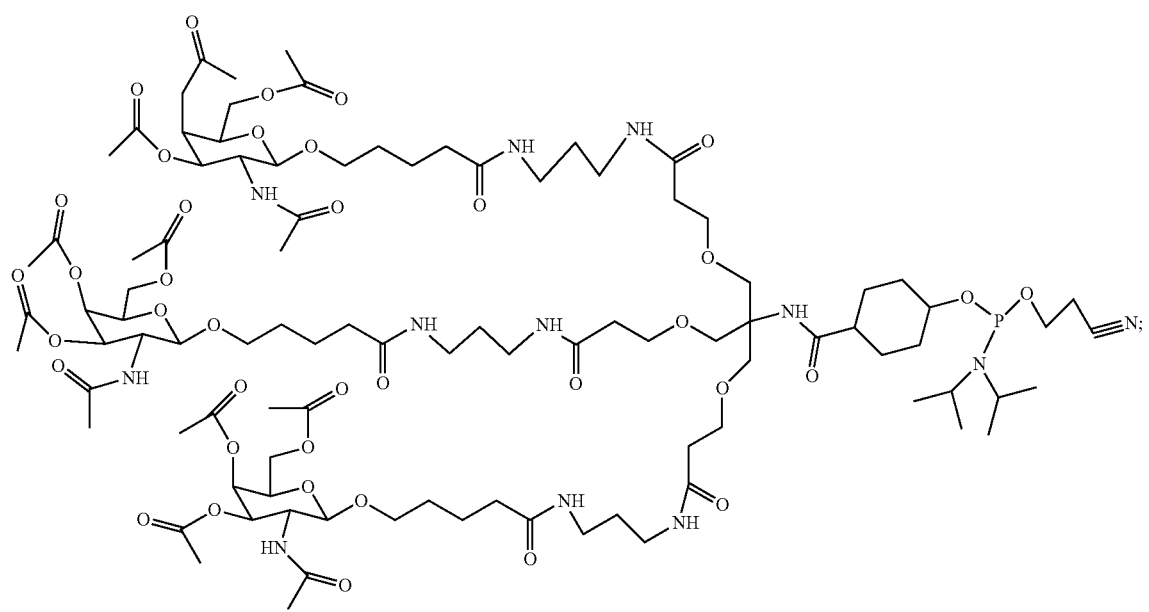
(Structure 1018b)

-continued
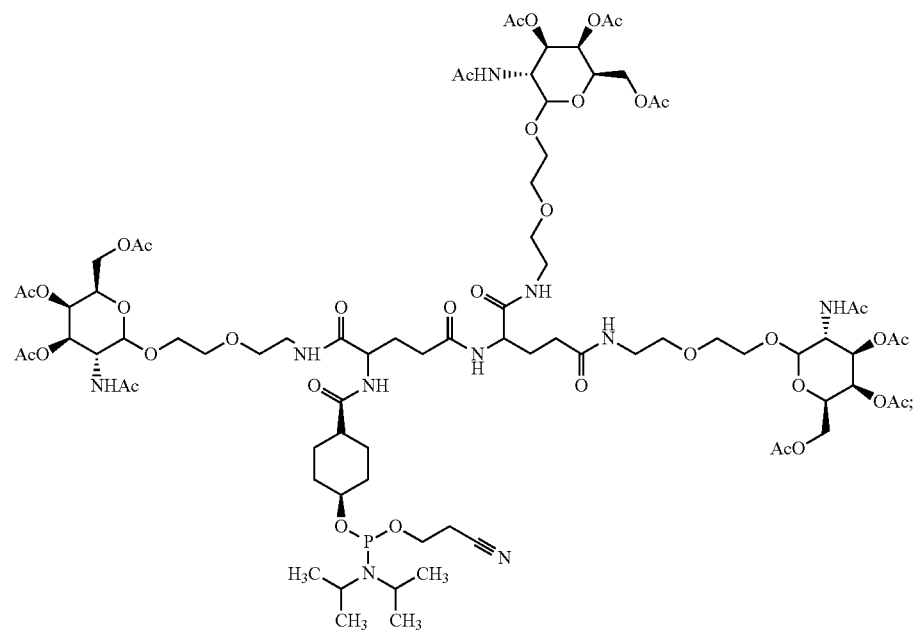
(Structure 1019b)
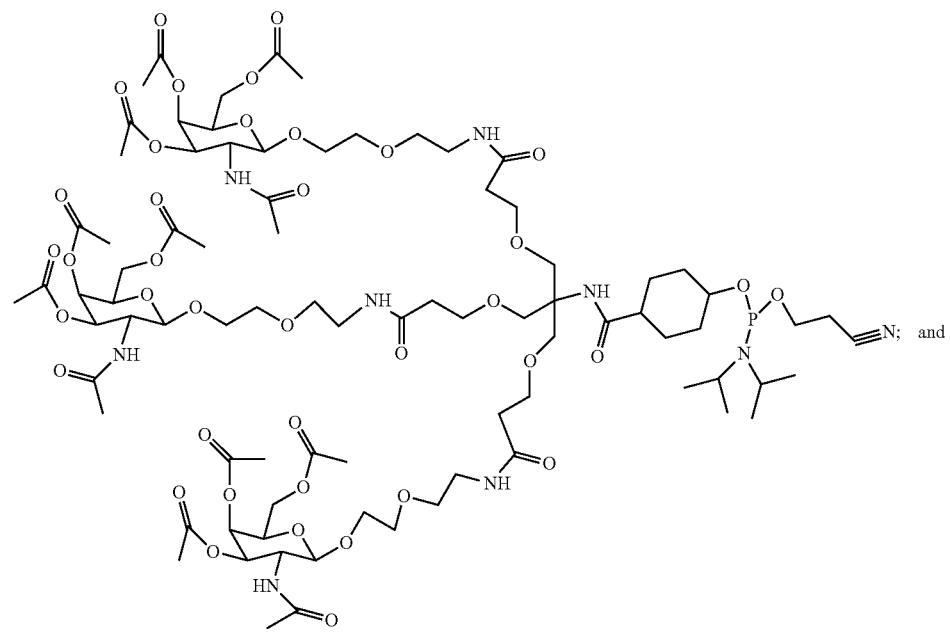
(Structure 1021b)

-continued
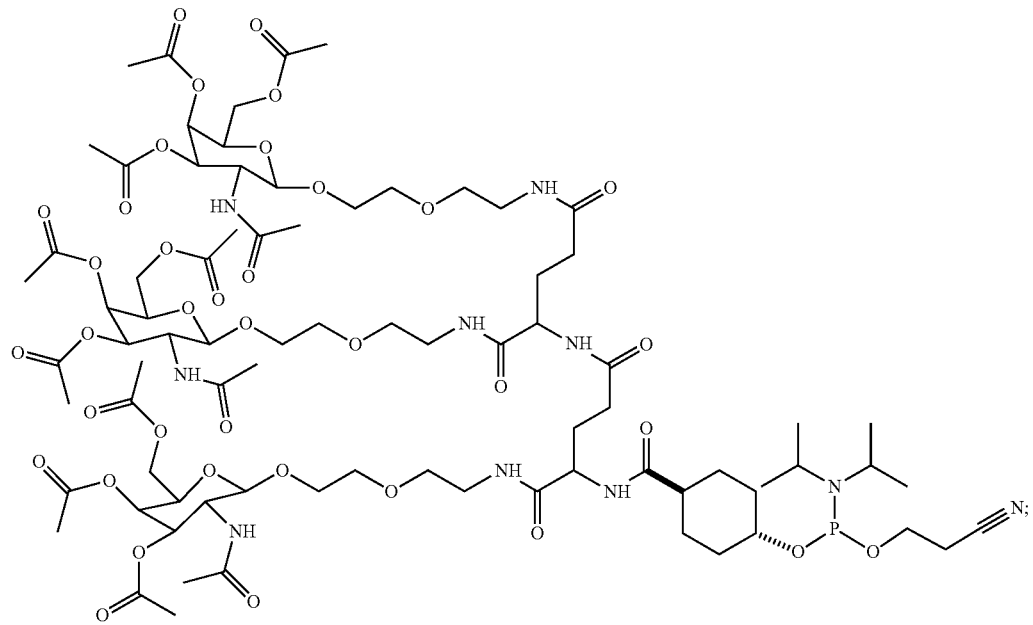
(Structure 1023b)
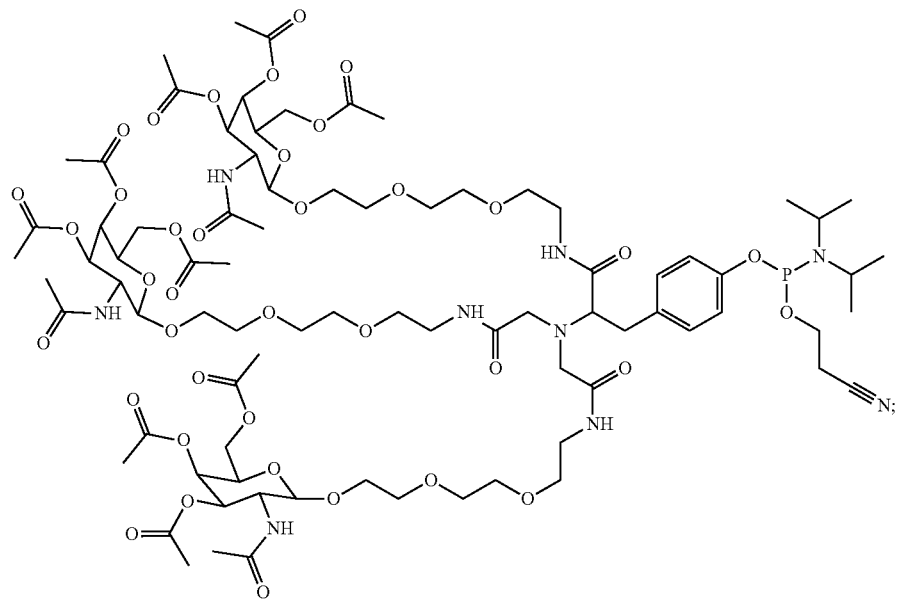
(Structure 1025b)

-continued
(Structure 1026b)
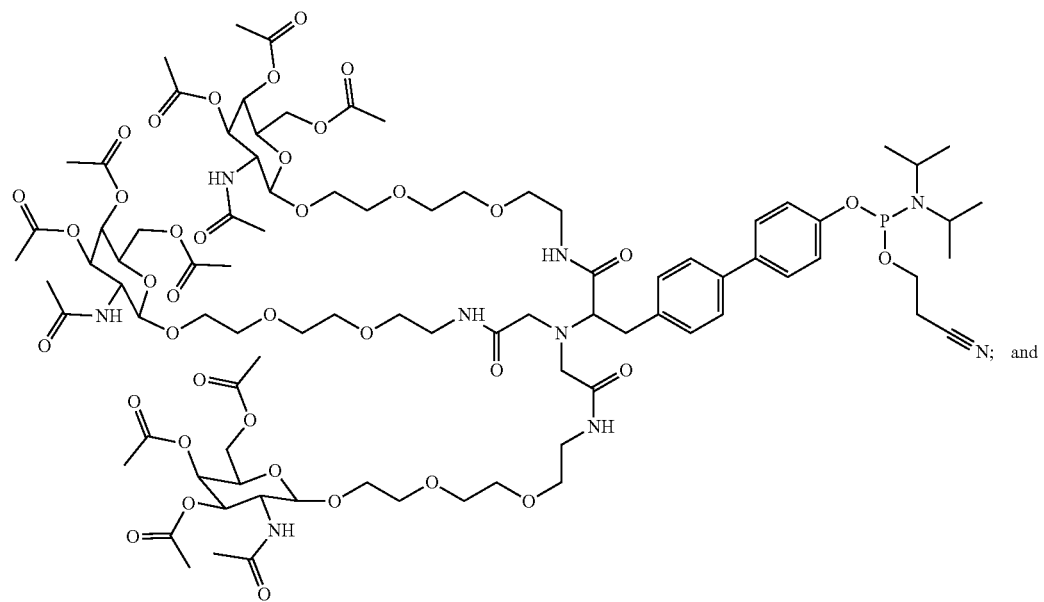
; and
(Structure 1027b)
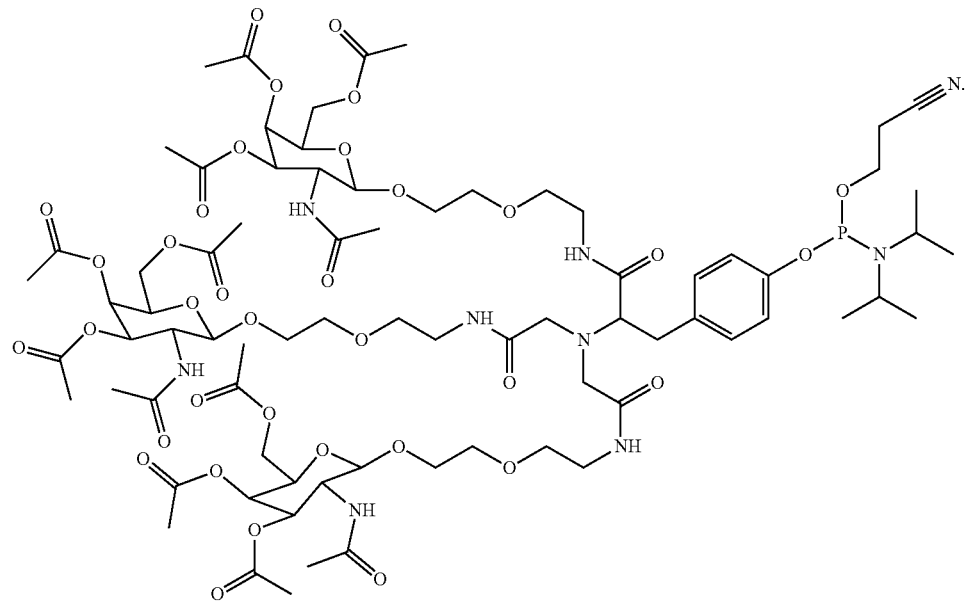
.
11. A targeting ligand comprising a structure selected from the group consisting of:

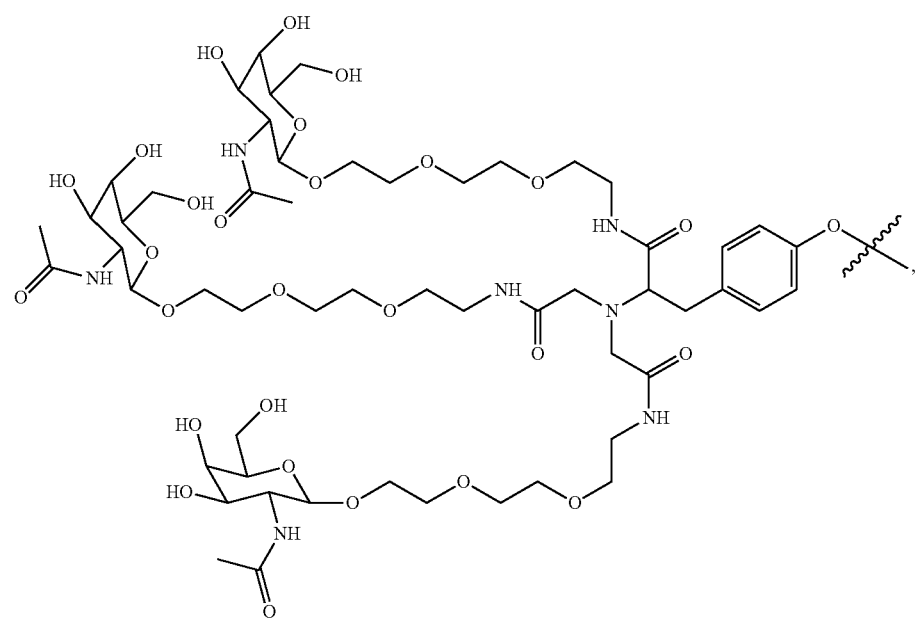
(Structure 1025)
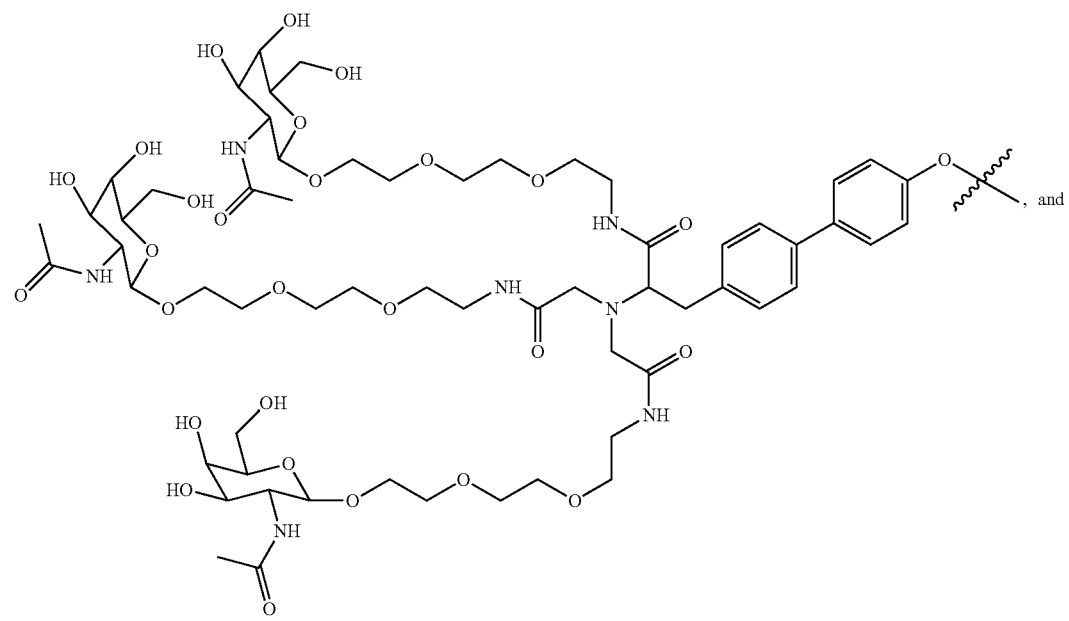
(Structure 1026)
, and (Structure 1027)

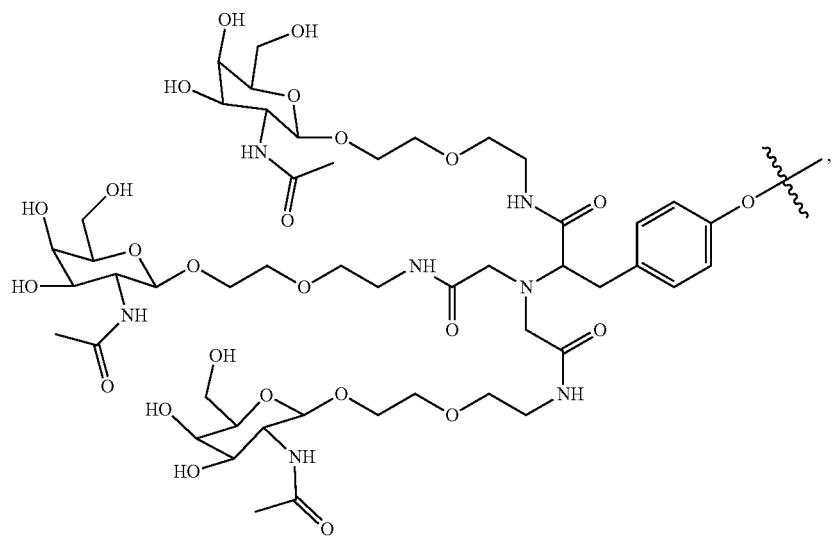

wherein the targeting ligand is linked to an RNAi agent.

12. The targeting ligand of claim 11, wherein the targeting ligand linked to the RNAi agent has the following structure:

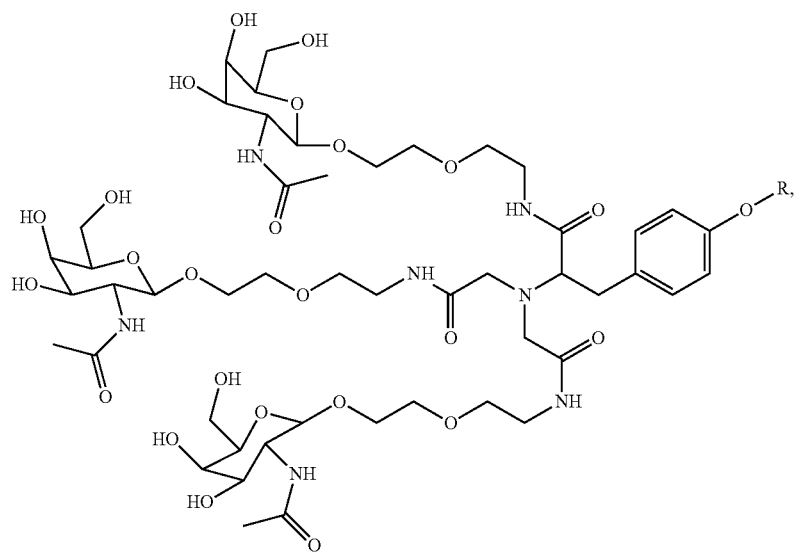

wherein R comprises the RNAi agent (Structure 1027a).

13. The targeting ligand of claim 11, wherein the RNAi agent is double stranded.

14. The targeting ligand of claim 13, wherein the RNAi agent includes one or more modified nucleotides.

15. A method of inhibiting expression of a target nucleic acid in a subject, the method comprising administering to the subject a therapeutic amount of the targeting ligand of claim 1.

16. A method of inhibiting expression of a target nucleic acid in a subject, the method comprising administering to the subject a therapeutic amount of the targeting ligand of claim 11.

17. A method of introducing a therapeutic agent into a mammalian cell, the method comprising contacting a mammalian cell with the targeting ligand of claim 1, wherein the therapeutic agent comprises the RNAi agent.

18. The method of claim 17, wherein the cell is present in a subject.

19. The method of claim 18, wherein the subject is a human.

20. The method of claim 19, wherein the therapeutic agent is a double-stranded RNAi agent.

21. A method of introducing a therapeutic agent into a mammalian cell, the method comprising contacting a mammalian cell with the targeting ligand of claim 11, wherein the therapeutic agent comprises the RNAi agent.

22. The method of claim 21, wherein the cell is present in a subject.

23. The method of claim 22, wherein the subject is a human.

24. The method of claim 23, wherein the therapeutic agent is a double-stranded RNAi agent.

25. A method of treating a disease or disorder that would benefit from administration of a therapeutic compound, the method comprising administering a therapeutic amount of the targeting ligand of claim 1 to a subject in need of treatment thereof.

26. A method of treating a disease or disorder that would benefit from administration of a therapeutic compound, the method comprising administering a therapeutic amount of the targeting ligand of claim 11 to a subject in need of treatment thereof.

27. A method of treating a disease or disorder that would benefit from administration of a therapeutic compound, the method comprising administering a therapeutic amount of the composition of claim 7 to a subject in need of treatment thereof.

28. A method of manufacturing a phosphoramidite compound including a compound of claim 10, the method comprising:
    (i) covalently linking the carboxylic acid moiety, or its activated ester, of the linker to a terminal amine located on the branch point group, and
    (ii) linking the linker to a phosphorus atom of a phosphoramidite through a phosphitylation reaction with a phosphoramidite forming reagent; thereby forming a phosphoramidite compound that includes a targeting ligand.

29. The method of claim 28, wherein the phosphoramidite reagent is selected from the group consisting of:

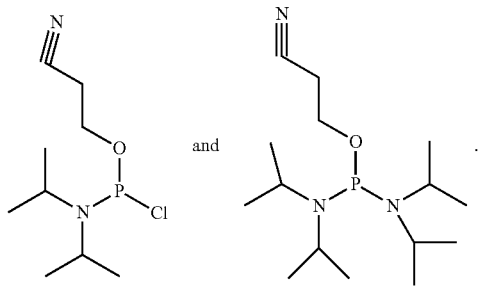 [SMILES: CC(C)N(C(C)C)P(Cl)OCCC#N ; CC(C)N(C(C)C)P(OCCC#N)N(C(C)C)C(C)C]

30. The targeting ligand of claim 2, comprising Structure 1003.

31. The targeting ligand of claim 2, comprising Structure 1008.

32. The targeting ligand of claim 2, comprising Structure 1023.

33. The targeting ligand of claim 5, comprising Structure 1003.

34. The targeting ligand of claim 5, comprising Structure 1008.

35. The targeting ligand of claim 5, comprising Structure 1023.

36. The targeting ligand of claim 6, comprising Structure 1003.

37. The targeting ligand of claim 6, comprising Structure 1008.

38. The targeting ligand of claim 6, comprising Structure 1023.

39. The composition of claim 7, comprising Structure 1003a.

40. The composition of claim 7, comprising Structure 1008a.

41. The composition of claim 7, comprising Structure 1023a.

42. The composition of claim 8, comprising Structure 1003a.

43. The composition of claim 8, comprising Structure 1008a.

44. The composition of claim 8, comprising Structure 1023a.

45. The composition of claim 9, comprising Structure 1003a.

46. The composition of claim 9, comprising Structure 1008a.

47. The composition of claim 9, comprising Structure 1023a.

48. The compound of claim 10, comprising Structure 1003b.

49. The compound of claim 10, comprising Structure 1008b.

50. The compound of claim 10, comprising Structure 1023b.

* * * * *

SEQUENCE LISTING

<160> NUMBER OF SEQ ID NOS: 38

<210> SEQ ID NO 1
<211> LENGTH: 26
<212> TYPE: RNA
<213> ORGANISM: artificial sequence
<220> FEATURE:

<223> OTHER INFORMATION: RNAi agent sense strand

<400> SEQUENCE: 1
uauaugccca agaaagugaa agacca         26

<210> SEQ ID NO 2
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 2
uggucuuuca cuuucuuggg cucuau         26

<210> SEQ ID NO 3
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA    Molecule"

<400> SEQUENCE: 3
uauaugccca agaaagugaa agacca         26

<210> SEQ ID NO 4
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 4
uggucuuuca cuuucuuggg cucuau         26

<210> SEQ ID NO 5
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA    Molecule"

<400> SEQUENCE: 5
uauaugccca agaaagugaa agacca         26

<210> SEQ ID NO 6
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 6
uggucuuuca cuuucuuggg cucuau         26

<210> SEQ ID NO 7
<211> LENGTH: 26
<212> TYPE: RNA
<213> ORGANISM: artificial sequence
<220> FEATURE:
<223> OTHER INFORMATION: RNAi agent sense strand

<400> SEQUENCE: 7
uauaugccca agaaagugaa agacca                                              26

<210> SEQ ID NO 8
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 8
uggucuuuca cuuucuuggg cucuau                                              26

<210> SEQ ID NO 9
<211> LENGTH: 26
<212> TYPE: RNA
<213> ORGANISM: artificial sequence
<220> FEATURE:
<223> OTHER INFORMATION: RNAi agent sense strand

<400> SEQUENCE: 9
uauauaauua ucgaggcuca uucuca                                              26

<210> SEQ ID NO 10
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 10
ugagaaugag ccucgauaau uauaua                                              26

<210> SEQ ID NO 11
<211> LENGTH: 26
<212> TYPE: RNA
<213> ORGANISM: artificial sequence
<220> FEATURE:
<223> OTHER INFORMATION: RNAi agent sense strand

<400> SEQUENCE: 11
uauauaauua ucgaggcuca uucuca                                              26

<210> SEQ ID NO 12
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 12
ugagaaugag ccucgauaau uauaua                                              26

<210> SEQ ID NO 13
<211> LENGTH: 21
<212> TYPE: RNA
<213> ORGANISM: artificial sequence
<220> FEATURE:
<223> OTHER INFORMATION: RNAi agent sense strand

<400> SEQUENCE: 13
gccccuuauu guuauacgau u                                                   21

<210> SEQ ID NO 14

```
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 14
ucguauaaca auaaggggcu u                                              21

<210> SEQ ID NO 15
<211> LENGTH: 21
<212> TYPE: RNA
<213> ORGANISM: artificial sequence
<220> FEATURE:
<223> OTHER INFORMATION: RNAi agent sense strand

<400> SEQUENCE: 15
gccccuuauu guuauacgau u                                              21

<210> SEQ ID NO 16
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 16
ucguauaaca auaaggggcu u                                              21

<210> SEQ ID NO 17
<211> LENGTH: 21
<212> TYPE: RNA
<213> ORGANISM: artificial sequence
<220> FEATURE:
<223> OTHER INFORMATION: RNAi agent sense strand

<400> SEQUENCE: 17
gccccuuauu guuauacgau u                                              21

<210> SEQ ID NO 18
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 18
ucguauaaca auaaggggcu u                                              21

<210> SEQ ID NO 19
<211> LENGTH: 21
<212> TYPE: RNA
<213> ORGANISM: artificial sequence
<220> FEATURE:
<223> OTHER INFORMATION: RNAi agent sense strand

<400> SEQUENCE: 19
gccccuuauu guuauacgau u                                              21

<210> SEQ ID NO 20
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 20
```
ucguauaaca auaaggggcu u                                              21

<210> SEQ ID NO 21
<211> LENGTH: 21
<212> TYPE: RNA
<213> ORGANISM: artificial sequence
<220> FEATURE:
<223> OTHER INFORMATION: RNAi agent sense strand

<400> SEQUENCE: 21
gccccuuauu guuauacgau u                                              21

<210> SEQ ID NO 22
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 22
ucguauaaca auaaggggcu u                                              21

<210> SEQ ID NO 23
<211> LENGTH: 21
<212> TYPE: RNA
<213> ORGANISM: artificial sequence
<220> FEATURE:
<223> OTHER INFORMATION: RNAi agent sense strand

<400> SEQUENCE: 23
gccccuuauu guuauacgau u                                              21

<210> SEQ ID NO 24
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 24
ucguauaaca auaaggggcu u                                              21

<210> SEQ ID NO 25
<211> LENGTH: 21
<212> TYPE: RNA
<213> ORGANISM: artificial sequence
<220> FEATURE:
<223> OTHER INFORMATION: RNAi agent sense strand

<400> SEQUENCE: 25
gccccuuauu guuauacgau u                                              21

<210> SEQ ID NO 26
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 26
ucguauaaca auaaggggcu u                                              21

<210> SEQ ID NO 27
<211> LENGTH: 21
<212> TYPE: RNA

```
<213> ORGANISM: artificial sequence
<220> FEATURE:
<223> OTHER INFORMATION: RNAi agent sense strand

<400> SEQUENCE: 27
gccccuuauu guuauacgau u                                              21

<210> SEQ ID NO 28
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 28
ucguauaaca auaaggggcu u                                              21

<210> SEQ ID NO 29
<211> LENGTH: 21
<212> TYPE: RNA
<213> ORGANISM: artificial sequence
<220> FEATURE:
<223> OTHER INFORMATION: RNAi agent sense strand

<400> SEQUENCE: 29
ucguauaaca auaaggggcu u                                              21

<210> SEQ ID NO 30
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 30
ucguauaaca auaaggggcu u                                              21

<210> SEQ ID NO 31
<211> LENGTH: 21
<212> TYPE: RNA
<213> ORGANISM: artificial sequence
<220> FEATURE:
<223> OTHER INFORMATION: RNAi agent sense strand

<400> SEQUENCE: 31
gccccuuauu guuauacgau u                                              21

<210> SEQ ID NO 32
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 32
ucguauaaca auaaggggcu u                                              21

<210> SEQ ID NO 33
<211> LENGTH: 21
<212> TYPE: RNA
<213> ORGANISM: artificial sequence
<220> FEATURE:
<223> OTHER INFORMATION: RNAi agent sense strand

<400> SEQUENCE: 33
gccccuuauu guuauacgau u                                              21
```

<210> SEQ ID NO 34
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 34
ucguauaaca auaaggggcu u                                              21

<210> SEQ ID NO 35
<211> LENGTH: 21
<212> TYPE: RNA
<213> ORGANISM: artificial sequence
<220> FEATURE:
<223> OTHER INFORMATION: RNAi agent sense strand

<400> SEQUENCE: 35
gccccuuauu guuauacgau u                                              21

<210> SEQ ID NO 36
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 36
ccguauaaca auaaggggcu u                                              21

<210> SEQ ID NO 37
<211> LENGTH: 19
<212> TYPE: RNA
<213> ORGANISM: artificial sequence
<220> FEATURE:
<223> OTHER INFORMATION: RNAi agent sense strand

<400> SEQUENCE: 37
ucaacaaacc cuuugucuu                                                 19

<210> SEQ ID NO 38
<211> LENGTH: 21
<212> TYPE: RNA
<213> ORGANISM: artificial sequence
<220> FEATURE:
<223> OTHER INFORMATION: RNAi agent antisense strand

<400> SEQUENCE: 38
aagacaaagg guuguugau u                                               21